(12) United States Patent
Kalra et al.

(10) Patent No.: US 11,464,800 B2
(45) Date of Patent: Oct. 11, 2022

(54) METHODS FOR MANUFACTURING T CELLS

(71) Applicant: Immatics US, Inc., Houston, TX (US)

(72) Inventors: Mamta Kalra, Houston, TX (US); Zoe Coughlin, Houston, TX (US); Amir Alpert, Houston, TX (US); Steffen Walter, Houston, TX (US); Ali Mohamed, Houston, TX (US); Agathe Bourgogne, Houston, TX (US)

(73) Assignee: Immatics US, Inc., Houston, TX (US)

( * ) Notice: Subject to any disclaimer, the term of this patent is extended or adjusted under 35 U.S.C. 154(b) by 616 days.

(21) Appl. No.: 16/271,393

(22) Filed: Feb. 8, 2019

(65) Prior Publication Data

US 2019/0247433 A1    Aug. 15, 2019

Related U.S. Application Data

(60) Provisional application No. 62/726,350, filed on Sep. 3, 2018, provisional application No. 62/647,571, filed on Mar. 23, 2018, provisional application No. 62/633,113, filed on Feb. 21, 2018, provisional application No. 62/628,521, filed on Feb. 9, 2018.

(30) Foreign Application Priority Data

Feb. 9, 2018   (DE) .................... 10 2018 102 971.3
Feb. 28, 2018  (DE) .................... 10 2018 104 628.6
Apr. 16, 2018  (DE) .................... 10 2018 108 996.1

(51) Int. Cl.
| | | |
|---|---|---|
| *A61K 35/17* | (2015.01) | |
| *C12N 5/0783* | (2010.01) | |
| *C07K 16/28* | (2006.01) | |
| *C12N 15/86* | (2006.01) | |
| *A61P 31/00* | (2006.01) | |
| *A61P 35/00* | (2006.01) | |

(52) U.S. Cl.
CPC .............. *A61K 35/17* (2013.01); *A61P 31/00* (2018.01); *A61P 35/00* (2018.01); *C07K 16/2809* (2013.01); *C07K 16/2818* (2013.01); *C12N 5/0636* (2013.01); *C12N 5/0637* (2013.01); *C12N 5/0638* (2013.01); *C12N 15/86* (2013.01); *C12N 2501/2302* (2013.01); *C12N 2501/2307* (2013.01); *C12N 2501/2312* (2013.01); *C12N 2501/2315* (2013.01); *C12N 2501/2321* (2013.01); *C12N 2501/51* (2013.01); *C12N 2501/515* (2013.01); *C12N 2510/00* (2013.01)

(58) Field of Classification Search
None
See application file for complete search history.

(56) References Cited

U.S. PATENT DOCUMENTS

| | | |
|---|---|---|
| 4,690,915 A | 9/1987 | Rosenberg |
| 6,040,177 A | 3/2000 | Riddell et al. |
| 6,410,319 B1 | 6/2002 | Raubitschek et al. |
| 7,763,243 B2 | 7/2010 | Lum et al. |
| 9,629,877 B2 | 4/2017 | Cooper et al. |
| 2003/0017023 A1 | 1/2003 | Bisping et al. |
| 2003/0017527 A1 | 1/2003 | Shinjo et al. |
| 2003/0170238 A1* | 9/2003 | Gruenberg ........... A61K 39/395 424/144.1 |
| 2003/0175272 A1 | 9/2003 | Gruenberg |
| 2009/0263421 A1* | 10/2009 | Spetz-Holmgren ..... A61P 31/18 424/209.1 |
| 2016/0122782 A1 | 5/2016 | Crisman et al. |
| 2016/0187351 A1 | 6/2016 | Weinschenk et al. |
| 2016/0280759 A1 | 9/2016 | Mahr et al. |
| 2016/0287687 A1 | 10/2016 | Mahr et al. |
| 2016/0346371 A1 | 12/2016 | Schoor et al. |
| 2016/0368965 A1 | 12/2016 | Mahr et al. |
| 2017/0002055 A1 | 1/2017 | Mahr et al. |
| 2017/0005125 A1 | 1/2017 | Itonaga et al. |
| 2017/0022251 A1 | 1/2017 | Rammensee et al. |
| 2017/0029486 A1 | 2/2017 | Mahr et al. |
| 2017/0035807 A1 | 2/2017 | Schuster et al. |
| 2017/0037089 A1 | 2/2017 | Mahr et al. |
| 2017/0051252 A1* | 2/2017 | Morgan .................. A61P 29/00 |

(Continued)

FOREIGN PATENT DOCUMENTS

| | | |
|---|---|---|
| EP | 1 760 088 B1 | 3/2008 |
| WO | 2007/028574 A2 | 3/2007 |

(Continued)

OTHER PUBLICATIONS

Written Opinion received in counterpart application No. PCT/US2019/017237, dated Aug. 11, 2020.

(Continued)

*Primary Examiner* — Michail A Belyavskyi

(74) *Attorney, Agent, or Firm* — McBee Moore & Vanik IP, LLC

(57) ABSTRACT

The disclosure relates to methods of manufacturing T cells for adoptive immunotherapy. The disclosure further provides for methods of genetically transducing T cells, methods of using T cells, and T cell populations thereof. In an aspect, the disclosure provides for methods of thawing frozen peripheral blood mononuclear cells (PBMC), resting the thawed PBMC, activating the T cell in the cultured PBMC with an anti-CD3 antibody and an anti-CD28 antibody immobilized on a solid phase, transducing the activated T cell with a viral vector, expanding the transduced T cell, and obtaining expanded T cells.

20 Claims, 81 Drawing Sheets

Specification includes a Sequence Listing.

(56) References Cited

U.S. PATENT DOCUMENTS

| | | | |
|---|---|---|---|
| 2017/0096461 A1 | 4/2017 | Mahr et al. | |
| 2017/0101473 A1 | 4/2017 | Mahr et al. | |
| 2017/0136108 A1 | 5/2017 | Mahr et al. | |
| 2017/0165335 A1 | 6/2017 | Weinschenk et al. | |
| 2017/0165337 A1 | 6/2017 | Mahr et al. | |
| 2017/0173132 A1 | 6/2017 | Mahr et al. | |
| 2017/0189505 A1 | 7/2017 | Mahr et al. | |
| 2017/0253633 A1 | 9/2017 | Mahr et al. | |
| 2017/0260249 A1 | 9/2017 | Mahr et al. | |
| 2017/0296640 A1 | 10/2017 | Schoor et al. | |
| 2018/0051080 A1 | 2/2018 | Alten et al. | |
| 2018/0164315 A1 | 6/2018 | Alten et al. | |
| 2019/0032011 A1* | 1/2019 | Better | A61P 35/00 |
| 2020/0330519 A1* | 10/2020 | Li | A61P 35/00 |

FOREIGN PATENT DOCUMENTS

| | | |
|---|---|---|
| WO | 2008/153742 A2 | 12/2008 |
| WO | 2015/164745 A1 | 10/2015 |
| WO | 2016/014789 A2 | 1/2016 |
| WO | 2016/113369 A1 | 7/2016 |
| WO | 2017/068419 A3 | 4/2017 |
| WO | 2017/176932 A1 | 10/2017 |
| WO | 2017/211900 A1 | 12/2017 |

OTHER PUBLICATIONS

Babad.J. et al.."Generation of ß cell-specific human cytotoxic T cells by lentiviral transduction and their survival in immunodeficient human leucocyte antigen-transgenic mice", Clinical and Experimental Immunology, 179, 2014, S.398-413. DOI: 10.1111/cei.12465.

Hubner et al. Molecular Therapy vol. 24 No. 7 Jul. 2016.

Ye et al. Journal of Immunology Research vol. 2017, Article ID 5210459.

Adair et al. Nature Communications | 7:13173, 2016.

Bajgain et al. Molecular Therapy—Methods & Clinical Development (2014) 1, 14015.

Wang et al. Molecular Therapy—Oncolytics (2016) 3, 16015.

Zhu et al. Cytotherapy. Mar. 2018;20(3):394-406 (abstract).

Fekete et al. vol. 00, Month 2018 Transfusion.

Sadelain et al. Nature. May 2, 20174; 545(7655): 423-431.

Search report for German Patent Application No. 10 2018 108 996.1, dated Jul. 24, 2018.

Petersen, Christopher T. et al. (2019). "Improving T-cell expansion andfunction for adoptive T-cell therapy using ex vivo treatment with PI3Kd inhibitors and VIP antagonists". Blood Advances, Jan. 31, 2018 (Jan. 31, 2018). XP055586570. https://www.ncbi.nlm.nih.gov/pmc/articles/PMC5812323/pdf/advances011254.pdf. [Retrieved May 8, 2019].

Xiao-Yi Tang et al. (2016). "Third-generation CD28/4-1BB chimeric antigen receptor cells for chemotherapy relapsed or refractory acute lymphoblastic leukaemia: a non-randomised, open-label phase I trial protocol". BMJ Open, vol. 6, No. 12, Dec. 30, 2016 (Dec. 30, 2016), p. e013904. XP055449362. ISSN: 2044-6055. DOI: 10.1136/bmjopen-2016-013904.

Kutscher, Sara et al. (2013). "Overnight resting of PBMC changes functional signatures of antigen specific T-cell responses: impact for immune monitoring within clinical trials". Plos One, vol. 8, No. 10. Oct. 11, 2013 (Oct. 11, 2013). p. e76215. XP05586241. DOI: 10.1371/journal.pone.0076215.

International Search Report for PCT/US2019/017237, dated May 21, 2019.

* cited by examiner

Naive
- Least differentiated ("young")
- Antigen-inexperienced

Central Memory ($T_{cm}$)
- Antigen-experienced
- Lymph-node homing; longer lasting in tissue
- Expand into $T_{em}$ upon subsequent recognition of antigen Effector Memory ($T_{em}$)
- Rapid effector (killing) function
- Short-lived $T_{emRA}$
- Terminally differentiated ("old")

SEQUENCE LISTING

```
<160> NUMBER OF SEQ ID NOS: 157

<210> SEQ ID NO 1
<211> LENGTH: 10
<212> TYPE: PRT
<213> ORGANISM: Homo sapiens

<400> SEQUENCE: 1

Tyr Leu Tyr Asp Ser Glu Thr Lys Asn Ala
1               5                   10

<210> SEQ ID NO 2
<211> LENGTH: 9
<212> TYPE: PRT
<213> ORGANISM: Homo sapiens

<400> SEQUENCE: 2

His Leu Met Asp Gln Pro Leu Ser Val
1               5

<210> SEQ ID NO 3
<211> LENGTH: 9
<212> TYPE: PRT
<213> ORGANISM: Homo sapiens

<400> SEQUENCE: 3

Gly Leu Leu Lys Lys Ile Asn Ser Val
1               5

<210> SEQ ID NO 4
<211> LENGTH: 9
<212> TYPE: PRT
<213> ORGANISM: Homo sapiens
```

```
<400> SEQUENCE: 4

Phe Leu Val Asp Gly Ser Ser Ala Leu
1               5

<210> SEQ ID NO 5
<211> LENGTH: 10
<212> TYPE: PRT
<213> ORGANISM: Homo sapiens

<400> SEQUENCE: 5

Phe Leu Phe Asp Gly Ser Ala Asn Leu Val
1               5                   10

<210> SEQ ID NO 6
<211> LENGTH: 9
<212> TYPE: PRT
<213> ORGANISM: Homo sapiens

<400> SEQUENCE: 6

Phe Leu Tyr Lys Ile Ile Asp Glu Leu
1               5

<210> SEQ ID NO 7
<211> LENGTH: 11
<212> TYPE: PRT
<213> ORGANISM: Homo sapiens

<400> SEQUENCE: 7

Phe Ile Leu Asp Ser Ala Glu Thr Thr Thr Leu
1               5                   10

<210> SEQ ID NO 8
<211> LENGTH: 9
<212> TYPE: PRT
<213> ORGANISM: Homo sapiens

<400> SEQUENCE: 8

Ser Val Asp Val Ser Pro Pro Lys Val
1               5

<210> SEQ ID NO 9
<211> LENGTH: 8
<212> TYPE: PRT
<213> ORGANISM: Homo sapiens

<400> SEQUENCE: 9

Val Ala Asp Lys Ile His Ser Val
1               5

<210> SEQ ID NO 10
<211> LENGTH: 9
<212> TYPE: PRT
<213> ORGANISM: Homo sapiens

<400> SEQUENCE: 10

Ile Val Asp Asp Leu Thr Ile Asn Leu
1               5

<210> SEQ ID NO 11
<211> LENGTH: 9
<212> TYPE: PRT
<213> ORGANISM: Homo sapiens

<400> SEQUENCE: 11
```

Gly Leu Leu Glu Glu Leu Val Thr Val
1               5

<210> SEQ ID NO 12
<211> LENGTH: 10
<212> TYPE: PRT
<213> ORGANISM: Homo sapiens

<400> SEQUENCE: 12

Thr Leu Asp Gly Ala Ala Val Asn Gln Val
1               5                   10

<210> SEQ ID NO 13
<211> LENGTH: 10
<212> TYPE: PRT
<213> ORGANISM: Homo sapiens

<400> SEQUENCE: 13

Ser Val Leu Glu Lys Glu Ile Tyr Ser Ile
1               5                   10

<210> SEQ ID NO 14
<211> LENGTH: 9
<212> TYPE: PRT
<213> ORGANISM: Homo sapiens

<400> SEQUENCE: 14

Leu Leu Asp Pro Lys Thr Ile Phe Leu
1               5

<210> SEQ ID NO 15
<211> LENGTH: 9
<212> TYPE: PRT
<213> ORGANISM: Homo sapiens

<400> SEQUENCE: 15

Tyr Thr Phe Ser Gly Asp Val Gln Leu
1               5

<210> SEQ ID NO 16
<211> LENGTH: 9
<212> TYPE: PRT
<213> ORGANISM: Homo sapiens

<400> SEQUENCE: 16

Tyr Leu Met Asp Asp Phe Ser Ser Leu
1               5

<210> SEQ ID NO 17
<211> LENGTH: 9
<212> TYPE: PRT
<213> ORGANISM: Homo sapiens

<400> SEQUENCE: 17

Lys Val Trp Ser Asp Val Thr Pro Leu
1               5

<210> SEQ ID NO 18
<211> LENGTH: 11
<212> TYPE: PRT
<213> ORGANISM: Homo sapiens

<400> SEQUENCE: 18

Leu Leu Trp Gly His Pro Arg Val Ala Leu Ala
1               5                   10

```
<210> SEQ ID NO 19
<211> LENGTH: 11
<212> TYPE: PRT
<213> ORGANISM: Homo sapiens

<400> SEQUENCE: 19

Lys Ile Trp Glu Glu Leu Ser Val Leu Glu Val
1               5                   10

<210> SEQ ID NO 20
<211> LENGTH: 9
<212> TYPE: PRT
<213> ORGANISM: Homo sapiens

<400> SEQUENCE: 20

Leu Leu Ile Pro Phe Thr Ile Phe Met
1               5

<210> SEQ ID NO 21
<211> LENGTH: 9
<212> TYPE: PRT
<213> ORGANISM: Homo sapiens

<400> SEQUENCE: 21

Phe Leu Ile Glu Asn Leu Leu Ala Ala
1               5

<210> SEQ ID NO 22
<211> LENGTH: 11
<212> TYPE: PRT
<213> ORGANISM: Homo sapiens

<400> SEQUENCE: 22

Leu Leu Trp Gly His Pro Arg Val Ala Leu Ala
1               5                   10

<210> SEQ ID NO 23
<211> LENGTH: 9
<212> TYPE: PRT
<213> ORGANISM: Homo sapiens

<400> SEQUENCE: 23

Phe Leu Leu Glu Arg Glu Gln Leu Leu
1               5

<210> SEQ ID NO 24
<211> LENGTH: 9
<212> TYPE: PRT
<213> ORGANISM: Homo sapiens

<400> SEQUENCE: 24

Ser Leu Ala Glu Thr Ile Phe Ile Val
1               5

<210> SEQ ID NO 25
<211> LENGTH: 9
<212> TYPE: PRT
<213> ORGANISM: Homo sapiens

<400> SEQUENCE: 25

Thr Leu Leu Glu Gly Ile Ser Arg Ala
1               5
```

```
<210> SEQ ID NO 26
<211> LENGTH: 9
<212> TYPE: PRT
<213> ORGANISM: Homo sapiens

<400> SEQUENCE: 26

Ile Leu Gln Asp Gly Gln Phe Leu Val
1               5

<210> SEQ ID NO 27
<211> LENGTH: 10
<212> TYPE: PRT
<213> ORGANISM: Homo sapiens

<400> SEQUENCE: 27

Val Ile Phe Glu Gly Glu Pro Met Tyr Leu
1               5                   10

<210> SEQ ID NO 28
<211> LENGTH: 9
<212> TYPE: PRT
<213> ORGANISM: Homo sapiens

<400> SEQUENCE: 28

Ser Leu Phe Glu Ser Leu Glu Tyr Leu
1               5

<210> SEQ ID NO 29
<211> LENGTH: 9
<212> TYPE: PRT
<213> ORGANISM: Homo sapiens

<400> SEQUENCE: 29

Ser Leu Leu Asn Gln Pro Lys Ala Val
1               5

<210> SEQ ID NO 30
<211> LENGTH: 9
<212> TYPE: PRT
<213> ORGANISM: Homo sapiens

<400> SEQUENCE: 30

Gly Leu Ala Glu Phe Gln Glu Asn Val
1               5

<210> SEQ ID NO 31
<211> LENGTH: 9
<212> TYPE: PRT
<213> ORGANISM: Homo sapiens

<400> SEQUENCE: 31

Lys Leu Leu Ala Val Ile His Glu Leu
1               5

<210> SEQ ID NO 32
<211> LENGTH: 9
<212> TYPE: PRT
<213> ORGANISM: Homo sapiens

<400> SEQUENCE: 32

Thr Leu His Asp Gln Val His Leu Leu
1               5

<210> SEQ ID NO 33
<211> LENGTH: 11
```

```
<212> TYPE: PRT
<213> ORGANISM: Homo sapiens

<400> SEQUENCE: 33

Thr Leu Tyr Asn Pro Glu Arg Thr Ile Thr Val
1               5                   10

<210> SEQ ID NO 34
<211> LENGTH: 9
<212> TYPE: PRT
<213> ORGANISM: Homo sapiens

<400> SEQUENCE: 34

Lys Leu Gln Glu Lys Ile Gln Glu Leu
1               5

<210> SEQ ID NO 35
<211> LENGTH: 10
<212> TYPE: PRT
<213> ORGANISM: Homo sapiens

<400> SEQUENCE: 35

Ser Val Leu Glu Lys Glu Ile Tyr Ser Ile
1               5                   10

<210> SEQ ID NO 36
<211> LENGTH: 11
<212> TYPE: PRT
<213> ORGANISM: Homo sapiens

<400> SEQUENCE: 36

Arg Val Ile Asp Asp Ser Leu Val Val Gly Val
1               5                   10

<210> SEQ ID NO 37
<211> LENGTH: 9
<212> TYPE: PRT
<213> ORGANISM: Homo sapiens

<400> SEQUENCE: 37

Val Leu Phe Gly Glu Leu Pro Ala Leu
1               5

<210> SEQ ID NO 38
<211> LENGTH: 9
<212> TYPE: PRT
<213> ORGANISM: Homo sapiens

<400> SEQUENCE: 38

Gly Leu Val Asp Ile Met Val His Leu
1               5

<210> SEQ ID NO 39
<211> LENGTH: 9
<212> TYPE: PRT
<213> ORGANISM: Homo sapiens

<400> SEQUENCE: 39

Phe Leu Asn Ala Ile Glu Thr Ala Leu
1               5

<210> SEQ ID NO 40
<211> LENGTH: 9
<212> TYPE: PRT
```

```
<400> SEQUENCE: 40

Ala Leu Leu Gln Ala Leu Met Glu Leu
1               5

<210> SEQ ID NO 41
<211> LENGTH: 9
<212> TYPE: PRT
<213> ORGANISM: Homo sapiens

<400> SEQUENCE: 41

Ala Leu Ser Ser Ser Gln Ala Glu Val
1               5

<210> SEQ ID NO 42
<211> LENGTH: 11
<212> TYPE: PRT
<213> ORGANISM: Homo sapiens

<400> SEQUENCE: 42

Ser Leu Ile Thr Gly Gln Asp Leu Leu Ser Val
1               5                   10

<210> SEQ ID NO 43
<211> LENGTH: 9
<212> TYPE: PRT
<213> ORGANISM: Homo sapiens

<400> SEQUENCE: 43

Gln Leu Ile Glu Lys Asn Trp Leu Leu
1               5

<210> SEQ ID NO 44
<211> LENGTH: 9
<212> TYPE: PRT
<213> ORGANISM: Homo sapiens

<400> SEQUENCE: 44

Leu Leu Asp Pro Lys Thr Ile Phe Leu
1               5

<210> SEQ ID NO 45
<211> LENGTH: 9
<212> TYPE: PRT
<213> ORGANISM: Homo sapiens

<400> SEQUENCE: 45

Arg Leu His Asp Glu Asn Ile Leu Leu
1               5

<210> SEQ ID NO 46
<211> LENGTH: 9
<212> TYPE: PRT
<213> ORGANISM: Homo sapiens

<400> SEQUENCE: 46

Tyr Thr Phe Ser Gly Asp Val Gln Leu
1               5

<210> SEQ ID NO 47
<211> LENGTH: 9
<212> TYPE: PRT
<213> ORGANISM: Homo sapiens

<400> SEQUENCE: 47
```

Gly Leu Pro Ser Ala Thr Thr Thr Val
1               5

<210> SEQ ID NO 48
<211> LENGTH: 11
<212> TYPE: PRT
<213> ORGANISM: Homo sapiens

<400> SEQUENCE: 48

Gly Leu Leu Pro Ser Ala Glu Ser Ile Lys Leu
1               5                   10

<210> SEQ ID NO 49
<211> LENGTH: 9
<212> TYPE: PRT
<213> ORGANISM: Homo sapiens

<400> SEQUENCE: 49

Lys Thr Ala Ser Ile Asn Gln Asn Val
1               5

<210> SEQ ID NO 50
<211> LENGTH: 9
<212> TYPE: PRT
<213> ORGANISM: Homo sapiens

<400> SEQUENCE: 50

Ser Leu Leu Gln His Leu Ile Gly Leu
1               5

<210> SEQ ID NO 51
<211> LENGTH: 9
<212> TYPE: PRT
<213> ORGANISM: Homo sapiens

<400> SEQUENCE: 51

Tyr Leu Met Asp Asp Phe Ser Ser Leu
1               5

<210> SEQ ID NO 52
<211> LENGTH: 9
<212> TYPE: PRT
<213> ORGANISM: Homo sapiens

<400> SEQUENCE: 52

Leu Met Tyr Pro Tyr Ile Tyr His Val
1               5

<210> SEQ ID NO 53
<211> LENGTH: 9
<212> TYPE: PRT
<213> ORGANISM: Homo sapiens

<400> SEQUENCE: 53

Lys Val Trp Ser Asp Val Thr Pro Leu
1               5

<210> SEQ ID NO 54
<211> LENGTH: 11
<212> TYPE: PRT
<213> ORGANISM: Homo sapiens

<400> SEQUENCE: 54

Leu Leu Trp Gly His Pro Arg Val Ala Leu Ala

```
1               5                  10
```

<210> SEQ ID NO 55
<211> LENGTH: 9
<212> TYPE: PRT
<213> ORGANISM: Homo sapiens

<400> SEQUENCE: 55

```
Val Leu Asp Gly Lys Val Ala Val Val
1               5
```

<210> SEQ ID NO 56
<211> LENGTH: 9
<212> TYPE: PRT
<213> ORGANISM: Homo sapiens

<400> SEQUENCE: 56

```
Gly Leu Leu Gly Lys Val Thr Ser Val
1               5
```

<210> SEQ ID NO 57
<211> LENGTH: 9
<212> TYPE: PRT
<213> ORGANISM: Homo sapiens

<400> SEQUENCE: 57

```
Lys Met Ile Ser Ala Ile Pro Thr Leu
1               5
```

<210> SEQ ID NO 58
<211> LENGTH: 11
<212> TYPE: PRT
<213> ORGANISM: Homo sapiens

<400> SEQUENCE: 58

```
Gly Leu Leu Glu Thr Thr Gly Leu Leu Ala Thr
1               5                   10
```

<210> SEQ ID NO 59
<211> LENGTH: 9
<212> TYPE: PRT
<213> ORGANISM: Homo sapiens

<400> SEQUENCE: 59

```
Thr Leu Asn Thr Leu Asp Ile Asn Leu
1               5
```

<210> SEQ ID NO 60
<211> LENGTH: 9
<212> TYPE: PRT
<213> ORGANISM: Homo sapiens

<400> SEQUENCE: 60

```
Val Ile Ile Lys Gly Leu Glu Glu Ile
1               5
```

<210> SEQ ID NO 61
<211> LENGTH: 9
<212> TYPE: PRT
<213> ORGANISM: Homo sapiens

<400> SEQUENCE: 61

```
Tyr Leu Glu Asp Gly Phe Ala Tyr Val
1               5
```

```
<210> SEQ ID NO 62
<211> LENGTH: 11
<212> TYPE: PRT
<213> ORGANISM: Homo sapiens

<400> SEQUENCE: 62

Lys Ile Trp Glu Glu Leu Ser Val Leu Glu Val
1               5                   10

<210> SEQ ID NO 63
<211> LENGTH: 9
<212> TYPE: PRT
<213> ORGANISM: Homo sapiens

<400> SEQUENCE: 63

Leu Leu Ile Pro Phe Thr Ile Phe Met
1               5

<210> SEQ ID NO 64
<211> LENGTH: 10
<212> TYPE: PRT
<213> ORGANISM: Homo sapiens

<400> SEQUENCE: 64

Ile Ser Leu Asp Glu Val Ala Val Ser Leu
1               5                   10

<210> SEQ ID NO 65
<211> LENGTH: 10
<212> TYPE: PRT
<213> ORGANISM: Homo sapiens

<400> SEQUENCE: 65

Lys Ile Ser Asp Phe Gly Leu Ala Thr Val
1               5                   10

<210> SEQ ID NO 66
<211> LENGTH: 11
<212> TYPE: PRT
<213> ORGANISM: Homo sapiens

<400> SEQUENCE: 66

Lys Leu Ile Gly Asn Ile His Gly Asn Glu Val
1               5                   10

<210> SEQ ID NO 67
<211> LENGTH: 9
<212> TYPE: PRT
<213> ORGANISM: Homo sapiens

<400> SEQUENCE: 67

Ile Leu Leu Ser Val Leu His Gln Leu
1               5

<210> SEQ ID NO 68
<211> LENGTH: 9
<212> TYPE: PRT
<213> ORGANISM: Homo sapiens

<400> SEQUENCE: 68

Leu Asp Ser Glu Ala Leu Leu Thr Leu
1               5

<210> SEQ ID NO 69
```

```
<211> LENGTH: 13
<212> TYPE: PRT
<213> ORGANISM: Homo sapiens

<400> SEQUENCE: 69

Val Leu Gln Glu Asn Ser Ser Asp Tyr Gln Ser Asn Leu
1               5                   10

<210> SEQ ID NO 70
<211> LENGTH: 11
<212> TYPE: PRT
<213> ORGANISM: Homo sapiens

<400> SEQUENCE: 70

His Leu Leu Gly Glu Gly Ala Phe Ala Gln Val
1               5                   10

<210> SEQ ID NO 71
<211> LENGTH: 9
<212> TYPE: PRT
<213> ORGANISM: Homo sapiens

<400> SEQUENCE: 71

Ser Leu Val Glu Asn Ile His Val Leu
1               5

<210> SEQ ID NO 72
<211> LENGTH: 9
<212> TYPE: PRT
<213> ORGANISM: Homo sapiens

<400> SEQUENCE: 72

Tyr Thr Phe Ser Gly Asp Val Gln Leu
1               5

<210> SEQ ID NO 73
<211> LENGTH: 9
<212> TYPE: PRT
<213> ORGANISM: Homo sapiens

<400> SEQUENCE: 73

Ser Leu Ser Glu Lys Ser Pro Glu Val
1               5

<210> SEQ ID NO 74
<211> LENGTH: 10
<212> TYPE: PRT
<213> ORGANISM: Homo sapiens

<400> SEQUENCE: 74

Ala Met Phe Pro Asp Thr Ile Pro Arg Val
1               5                   10

<210> SEQ ID NO 75
<211> LENGTH: 9
<212> TYPE: PRT
<213> ORGANISM: Homo sapiens

<400> SEQUENCE: 75

Phe Leu Ile Glu Asn Leu Leu Ala Ala
1               5

<210> SEQ ID NO 76
<211> LENGTH: 9
<212> TYPE: PRT
```

-continued

<213> ORGANISM: Homo sapiens

<400> SEQUENCE: 76

Phe Thr Ala Glu Phe Leu Glu Lys Val
1               5

<210> SEQ ID NO 77
<211> LENGTH: 9
<212> TYPE: PRT
<213> ORGANISM: Homo sapiens

<400> SEQUENCE: 77

Ala Leu Tyr Gly Asn Val Gln Gln Val
1               5

<210> SEQ ID NO 78
<211> LENGTH: 9
<212> TYPE: PRT
<213> ORGANISM: Homo sapiens

<400> SEQUENCE: 78

Leu Phe Gln Ser Arg Ile Ala Gly Val
1               5

<210> SEQ ID NO 79
<211> LENGTH: 11
<212> TYPE: PRT
<213> ORGANISM: Homo sapiens

<400> SEQUENCE: 79

Ile Leu Ala Glu Glu Pro Ile Tyr Ile Arg Val
1               5                   10

<210> SEQ ID NO 80
<211> LENGTH: 9
<212> TYPE: PRT
<213> ORGANISM: Homo sapiens

<400> SEQUENCE: 80

Phe Leu Leu Glu Arg Glu Gln Leu Leu
1               5

<210> SEQ ID NO 81
<211> LENGTH: 10
<212> TYPE: PRT
<213> ORGANISM: Homo sapiens

<400> SEQUENCE: 81

Leu Leu Leu Pro Leu Glu Leu Ser Leu Ala
1               5                   10

<210> SEQ ID NO 82
<211> LENGTH: 9
<212> TYPE: PRT
<213> ORGANISM: Homo sapiens

<400> SEQUENCE: 82

Ser Leu Ala Glu Thr Ile Phe Ile Val
1               5

<210> SEQ ID NO 83
<211> LENGTH: 11
<212> TYPE: PRT
<213> ORGANISM: Homo sapiens

<400> SEQUENCE: 83

Ala Ile Leu Asn Val Asp Glu Lys Asn Gln Val
1               5                   10

<210> SEQ ID NO 84
<211> LENGTH: 9
<212> TYPE: PRT
<213> ORGANISM: Homo sapiens

<400> SEQUENCE: 84

Arg Leu Phe Glu Glu Val Leu Gly Val
1               5

<210> SEQ ID NO 85
<211> LENGTH: 9
<212> TYPE: PRT
<213> ORGANISM: Homo sapiens

<400> SEQUENCE: 85

Tyr Leu Asp Glu Val Ala Phe Met Leu
1               5

<210> SEQ ID NO 86
<211> LENGTH: 11
<212> TYPE: PRT
<213> ORGANISM: Homo sapiens

<400> SEQUENCE: 86

Lys Leu Ile Asp Glu Asp Glu Pro Leu Phe Leu
1               5                   10

<210> SEQ ID NO 87
<211> LENGTH: 9
<212> TYPE: PRT
<213> ORGANISM: Homo sapiens

<400> SEQUENCE: 87

Lys Leu Phe Glu Lys Ser Thr Gly Leu
1               5

<210> SEQ ID NO 88
<211> LENGTH: 11
<212> TYPE: PRT
<213> ORGANISM: Homo sapiens

<400> SEQUENCE: 88

Ser Leu Leu Glu Val Asn Glu Ala Ser Ser Val
1               5                   10

<210> SEQ ID NO 89
<211> LENGTH: 10
<212> TYPE: PRT
<213> ORGANISM: Homo sapiens

<400> SEQUENCE: 89

Gly Val Tyr Asp Gly Arg Glu His Thr Val
1               5                   10

<210> SEQ ID NO 90
<211> LENGTH: 10
<212> TYPE: PRT
<213> ORGANISM: Homo sapiens

<400> SEQUENCE: 90

```
Gly Leu Tyr Pro Val Thr Leu Val Gly Val
1               5                   10

<210> SEQ ID NO 91
<211> LENGTH: 9
<212> TYPE: PRT
<213> ORGANISM: Homo sapiens

<400> SEQUENCE: 91

Ala Leu Leu Ser Ser Val Ala Glu Ala
1               5

<210> SEQ ID NO 92
<211> LENGTH: 9
<212> TYPE: PRT
<213> ORGANISM: Homo sapiens

<400> SEQUENCE: 92

Thr Leu Leu Glu Gly Ile Ser Arg Ala
1               5

<210> SEQ ID NO 93
<211> LENGTH: 9
<212> TYPE: PRT
<213> ORGANISM: Homo sapiens

<400> SEQUENCE: 93

Ser Leu Ile Glu Glu Ser Glu Glu Leu
1               5

<210> SEQ ID NO 94
<211> LENGTH: 9
<212> TYPE: PRT
<213> ORGANISM: Homo sapiens

<400> SEQUENCE: 94

Ala Leu Tyr Val Gln Ala Pro Thr Val
1               5

<210> SEQ ID NO 95
<211> LENGTH: 10
<212> TYPE: PRT
<213> ORGANISM: Homo sapiens

<400> SEQUENCE: 95

Lys Leu Ile Tyr Lys Asp Leu Val Ser Val
1               5                   10

<210> SEQ ID NO 96
<211> LENGTH: 9
<212> TYPE: PRT
<213> ORGANISM: Homo sapiens

<400> SEQUENCE: 96

Ile Leu Gln Asp Gly Gln Phe Leu Val
1               5

<210> SEQ ID NO 97
<211> LENGTH: 9
<212> TYPE: PRT
<213> ORGANISM: Homo sapiens

<400> SEQUENCE: 97

Ser Leu Leu Asp Tyr Glu Val Ser Ile
1               5
```

<210> SEQ ID NO 98
<211> LENGTH: 9
<212> TYPE: PRT
<213> ORGANISM: Homo sapiens

<400> SEQUENCE: 98

Leu Leu Gly Asp Ser Ser Phe Phe Leu
1               5

<210> SEQ ID NO 99
<211> LENGTH: 10
<212> TYPE: PRT
<213> ORGANISM: Homo sapiens

<400> SEQUENCE: 99

Val Ile Phe Glu Gly Glu Pro Met Tyr Leu
1               5                   10

<210> SEQ ID NO 100
<211> LENGTH: 9
<212> TYPE: PRT
<213> ORGANISM: Homo sapiens

<400> SEQUENCE: 100

Ala Leu Ser Tyr Ile Leu Pro Tyr Leu
1               5

<210> SEQ ID NO 101
<211> LENGTH: 9
<212> TYPE: PRT
<213> ORGANISM: Homo sapiens

<400> SEQUENCE: 101

Phe Leu Phe Val Asp Pro Glu Leu Val
1               5

<210> SEQ ID NO 102
<211> LENGTH: 11
<212> TYPE: PRT
<213> ORGANISM: Homo sapiens

<400> SEQUENCE: 102

Ser Glu Trp Gly Ser Pro His Ala Ala Val Pro
1               5                   10

<210> SEQ ID NO 103
<211> LENGTH: 9
<212> TYPE: PRT
<213> ORGANISM: Homo sapiens

<400> SEQUENCE: 103

Ala Leu Ser Glu Leu Glu Arg Val Leu
1               5

<210> SEQ ID NO 104
<211> LENGTH: 9
<212> TYPE: PRT
<213> ORGANISM: Homo sapiens

<400> SEQUENCE: 104

Ser Leu Phe Glu Ser Leu Glu Tyr Leu
1               5

<210> SEQ ID NO 105
<211> LENGTH: 9
<212> TYPE: PRT
<213> ORGANISM: Homo sapiens

<400> SEQUENCE: 105

Lys Val Leu Glu Tyr Val Ile Lys Val
1               5

<210> SEQ ID NO 106
<211> LENGTH: 10
<212> TYPE: PRT
<213> ORGANISM: Homo sapiens

<400> SEQUENCE: 106

Val Leu Leu Asn Glu Ile Leu Glu Gln Val
1               5                   10

<210> SEQ ID NO 107
<211> LENGTH: 9
<212> TYPE: PRT
<213> ORGANISM: Homo sapiens

<400> SEQUENCE: 107

Ser Leu Leu Asn Gln Pro Lys Ala Val
1               5

<210> SEQ ID NO 108
<211> LENGTH: 9
<212> TYPE: PRT
<213> ORGANISM: Homo sapiens

<400> SEQUENCE: 108

Lys Met Ser Glu Leu Gln Thr Tyr Val
1               5

<210> SEQ ID NO 109
<211> LENGTH: 11
<212> TYPE: PRT
<213> ORGANISM: Homo sapiens

<400> SEQUENCE: 109

Ala Leu Leu Glu Gln Thr Gly Asp Met Ser Leu
1               5                   10

<210> SEQ ID NO 110
<211> LENGTH: 11
<212> TYPE: PRT
<213> ORGANISM: Homo sapiens

<400> SEQUENCE: 110

Val Ile Ile Lys Gly Leu Glu Glu Ile Thr Val
1               5                   10

<210> SEQ ID NO 111
<211> LENGTH: 9
<212> TYPE: PRT
<213> ORGANISM: Homo sapiens

<400> SEQUENCE: 111

Lys Gln Phe Glu Gly Thr Val Glu Ile
1               5

<210> SEQ ID NO 112
<211> LENGTH: 9

<212> TYPE: PRT
<213> ORGANISM: Homo sapiens

<400> SEQUENCE: 112

Lys Leu Gln Glu Glu Ile Pro Val Leu
1               5

<210> SEQ ID NO 113
<211> LENGTH: 9
<212> TYPE: PRT
<213> ORGANISM: Homo sapiens

<400> SEQUENCE: 113

Gly Leu Ala Glu Phe Gln Glu Asn Val
1               5

<210> SEQ ID NO 114
<211> LENGTH: 9
<212> TYPE: PRT
<213> ORGANISM: Homo sapiens

<400> SEQUENCE: 114

Asn Val Ala Glu Ile Val Ile His Ile
1               5

<210> SEQ ID NO 115
<211> LENGTH: 9
<212> TYPE: PRT
<213> ORGANISM: Homo sapiens

<400> SEQUENCE: 115

Ala Leu Ala Gly Ile Val Thr Asn Val
1               5

<210> SEQ ID NO 116
<211> LENGTH: 12
<212> TYPE: PRT
<213> ORGANISM: Homo sapiens

<400> SEQUENCE: 116

Asn Leu Leu Ile Asp Asp Lys Gly Thr Ile Lys Leu
1               5                   10

<210> SEQ ID NO 117
<211> LENGTH: 10
<212> TYPE: PRT
<213> ORGANISM: Homo sapiens

<400> SEQUENCE: 117

Val Leu Met Gln Asp Ser Arg Leu Tyr Leu
1               5                   10

<210> SEQ ID NO 118
<211> LENGTH: 9
<212> TYPE: PRT
<213> ORGANISM: Homo sapiens

<400> SEQUENCE: 118

Lys Val Leu Glu His Val Val Arg Val
1               5

<210> SEQ ID NO 119
<211> LENGTH: 9
<212> TYPE: PRT
<213> ORGANISM: Homo sapiens

<400> SEQUENCE: 119

Leu Leu Trp Gly Asn Leu Pro Glu Ile
1               5

<210> SEQ ID NO 120
<211> LENGTH: 9
<212> TYPE: PRT
<213> ORGANISM: Homo sapiens

<400> SEQUENCE: 120

Ser Leu Met Glu Lys Asn Gln Ser Leu
1               5

<210> SEQ ID NO 121
<211> LENGTH: 9
<212> TYPE: PRT
<213> ORGANISM: Homo sapiens

<400> SEQUENCE: 121

Lys Leu Leu Ala Val Ile His Glu Leu
1               5

<210> SEQ ID NO 122
<211> LENGTH: 10
<212> TYPE: PRT
<213> ORGANISM: Homo sapiens

<400> SEQUENCE: 122

Ala Leu Gly Asp Lys Phe Leu Leu Arg Val
1               5                   10

<210> SEQ ID NO 123
<211> LENGTH: 11
<212> TYPE: PRT
<213> ORGANISM: Homo sapiens

<400> SEQUENCE: 123

Phe Leu Met Lys Asn Ser Asp Leu Tyr Gly Ala
1               5                   10

<210> SEQ ID NO 124
<211> LENGTH: 10
<212> TYPE: PRT
<213> ORGANISM: Homo sapiens

<400> SEQUENCE: 124

Lys Leu Ile Asp His Gln Gly Leu Tyr Leu
1               5                   10

<210> SEQ ID NO 125
<211> LENGTH: 12
<212> TYPE: PRT
<213> ORGANISM: Homo sapiens

<400> SEQUENCE: 125

Gly Pro Gly Ile Phe Pro Pro Pro Pro Gln Pro
1               5                   10

<210> SEQ ID NO 126
<211> LENGTH: 9
<212> TYPE: PRT
<213> ORGANISM: Homo sapiens

<400> SEQUENCE: 126

```
Ala Leu Asn Glu Ser Leu Val Glu Cys
1               5

<210> SEQ ID NO 127
<211> LENGTH: 9
<212> TYPE: PRT
<213> ORGANISM: Homo sapiens

<400> SEQUENCE: 127

Gly Leu Ala Ala Leu Ala Val His Leu
1               5

<210> SEQ ID NO 128
<211> LENGTH: 9
<212> TYPE: PRT
<213> ORGANISM: Homo sapiens

<400> SEQUENCE: 128

Leu Leu Leu Glu Ala Val Trp His Leu
1               5

<210> SEQ ID NO 129
<211> LENGTH: 9
<212> TYPE: PRT
<213> ORGANISM: Homo sapiens

<400> SEQUENCE: 129

Ser Ile Ile Glu Tyr Leu Pro Thr Leu
1               5

<210> SEQ ID NO 130
<211> LENGTH: 9
<212> TYPE: PRT
<213> ORGANISM: Homo sapiens

<400> SEQUENCE: 130

Thr Leu His Asp Gln Val His Leu Leu
1               5

<210> SEQ ID NO 131
<211> LENGTH: 9
<212> TYPE: PRT
<213> ORGANISM: Homo sapiens

<400> SEQUENCE: 131

Ser Leu Leu Met Trp Ile Thr Gln Cys
1               5

<210> SEQ ID NO 132
<211> LENGTH: 11
<212> TYPE: PRT
<213> ORGANISM: Homo sapiens

<400> SEQUENCE: 132

Phe Leu Leu Asp Lys Pro Gln Asp Leu Ser Ile
1               5                   10

<210> SEQ ID NO 133
<211> LENGTH: 10
<212> TYPE: PRT
<213> ORGANISM: Homo sapiens

<400> SEQUENCE: 133

Tyr Leu Leu Asp Met Pro Leu Trp Tyr Leu
```

```
<210> SEQ ID NO 134
<211> LENGTH: 9
<212> TYPE: PRT
<213> ORGANISM: Homo sapiens

<400> SEQUENCE: 134

Gly Leu Leu Asp Cys Pro Ile Phe Leu
1               5

<210> SEQ ID NO 135
<211> LENGTH: 9
<212> TYPE: PRT
<213> ORGANISM: Homo sapiens

<400> SEQUENCE: 135

Val Leu Ile Glu Tyr Asn Phe Ser Ile
1               5

<210> SEQ ID NO 136
<211> LENGTH: 11
<212> TYPE: PRT
<213> ORGANISM: Homo sapiens

<400> SEQUENCE: 136

Thr Leu Tyr Asn Pro Glu Arg Thr Ile Thr Val
1               5                   10

<210> SEQ ID NO 137
<211> LENGTH: 9
<212> TYPE: PRT
<213> ORGANISM: Homo sapiens

<400> SEQUENCE: 137

Ala Val Pro Pro Pro Pro Ser Ser Val
1               5

<210> SEQ ID NO 138
<211> LENGTH: 9
<212> TYPE: PRT
<213> ORGANISM: Homo sapiens

<400> SEQUENCE: 138

Lys Leu Gln Glu Glu Leu Asn Lys Val
1               5

<210> SEQ ID NO 139
<211> LENGTH: 11
<212> TYPE: PRT
<213> ORGANISM: Homo sapiens

<400> SEQUENCE: 139

Lys Leu Met Asp Pro Gly Ser Leu Pro Pro Leu
1               5                   10

<210> SEQ ID NO 140
<211> LENGTH: 9
<212> TYPE: PRT
<213> ORGANISM: Homo sapiens

<400> SEQUENCE: 140

Ala Leu Ile Val Ser Leu Pro Tyr Leu
1               5
```

```
<210> SEQ ID NO 141
<211> LENGTH: 9
<212> TYPE: PRT
<213> ORGANISM: Homo sapiens

<400> SEQUENCE: 141

Phe Leu Leu Asp Gly Ser Ala Asn Val
1               5

<210> SEQ ID NO 142
<211> LENGTH: 10
<212> TYPE: PRT
<213> ORGANISM: Homo sapiens

<400> SEQUENCE: 142

Ala Leu Asp Pro Ser Gly Asn Gln Leu Ile
1               5                   10

<210> SEQ ID NO 143
<211> LENGTH: 9
<212> TYPE: PRT
<213> ORGANISM: Homo sapiens

<400> SEQUENCE: 143

Ile Leu Ile Lys His Leu Val Lys Val
1               5

<210> SEQ ID NO 144
<211> LENGTH: 9
<212> TYPE: PRT
<213> ORGANISM: Homo sapiens

<400> SEQUENCE: 144

Val Leu Leu Asp Thr Ile Leu Gln Leu
1               5

<210> SEQ ID NO 145
<211> LENGTH: 9
<212> TYPE: PRT
<213> ORGANISM: Homo sapiens

<400> SEQUENCE: 145

His Leu Ile Ala Glu Ile His Thr Ala
1               5

<210> SEQ ID NO 146
<211> LENGTH: 9
<212> TYPE: PRT
<213> ORGANISM: Homo sapiens

<400> SEQUENCE: 146

Ser Met Asn Gly Gly Val Phe Ala Val
1               5

<210> SEQ ID NO 147
<211> LENGTH: 9
<212> TYPE: PRT
<213> ORGANISM: Homo sapiens

<400> SEQUENCE: 147

Met Leu Ala Glu Lys Leu Leu Gln Ala
1               5

<210> SEQ ID NO 148
```

```
<211> LENGTH: 9
<212> TYPE: PRT
<213> ORGANISM: Homo sapiens

<400> SEQUENCE: 148

Tyr Met Leu Asp Ile Phe His Glu Val
1               5

<210> SEQ ID NO 149
<211> LENGTH: 11
<212> TYPE: PRT
<213> ORGANISM: Homo sapiens

<400> SEQUENCE: 149

Ala Leu Trp Leu Pro Thr Asp Ser Ala Thr Val
1               5                   10

<210> SEQ ID NO 150
<211> LENGTH: 9
<212> TYPE: PRT
<213> ORGANISM: Homo sapiens

<400> SEQUENCE: 150

Gly Leu Ala Ser Arg Ile Leu Asp Ala
1               5

<210> SEQ ID NO 151
<211> LENGTH: 9
<212> TYPE: PRT
<213> ORGANISM: Homo sapiens

<400> SEQUENCE: 151

Ser Tyr Val Lys Val Leu His His Leu
1               5

<210> SEQ ID NO 152
<211> LENGTH: 9
<212> TYPE: PRT
<213> ORGANISM: Homo sapiens

<400> SEQUENCE: 152

Val Tyr Leu Pro Lys Ile Pro Ser Trp
1               5

<210> SEQ ID NO 153
<211> LENGTH: 9
<212> TYPE: PRT
<213> ORGANISM: Homo sapiens

<400> SEQUENCE: 153

Asn Tyr Glu Asp His Phe Pro Leu Leu
1               5

<210> SEQ ID NO 154
<211> LENGTH: 9
<212> TYPE: PRT
<213> ORGANISM: Homo sapiens

<400> SEQUENCE: 154

Val Tyr Ile Ala Glu Leu Glu Lys Ile
1               5

<210> SEQ ID NO 155
<211> LENGTH: 12
<212> TYPE: PRT
```

```
<213> ORGANISM: Homo sapiens

<400> SEQUENCE: 155

Val His Phe Glu Asp Thr Gly Lys Thr Leu Leu Phe
1               5                   10

<210> SEQ ID NO 156
<211> LENGTH: 9
<212> TYPE: PRT
<213> ORGANISM: Homo sapiens

<400> SEQUENCE: 156

Val Leu Ser Pro Phe Ile Leu Thr Leu
1               5

<210> SEQ ID NO 157
<211> LENGTH: 9
<212> TYPE: PRT
<213> ORGANISM: Homo sapiens

<400> SEQUENCE: 157

His Leu Leu Glu Gly Ser Val Gly Val
1               5
```

METHODS FOR MANUFACTURING T CELLS

CROSS REFERENCE TO RELATED APPLICATIONS

This application is a U.S. provisional application, which claims priority to U.S. Provisional application No. 62/726,350, filed on Sep. 3, 2018, U.S. provisional application No. 62/647,571, filed on Mar. 23, 2018, U.S. provisional application No. 62/633,113, filed on Feb. 21, 2018, U.S. provisional application No. 62/628,521, filed on Feb. 9, 2018, German Patent Application number 10 2018 108 996.1, filed Apr. 16, 2018; German Patent Application number 10 2018 104 628.6, filed Feb. 28, 2018; and German Patent Application number 10 2018 102 971.3, filed Feb. 9, 2018, the contents of each are hereby incorporated by reference in their entireties.

FIELD

The present disclosure generally relates to methods of manufacturing T cells for adoptive immunotherapy. The disclosure further provides for methods of genetically transducing T cells, methods of using T cells, and T cell populations thereof.

BACKGROUND

Redirecting the specificity of T cells against tumor-associated antigens by genetically enforced expression of T cell receptors (TCRs) or chimeric antigen receptor (CARs) has recently boosted the field of adoptive T cell transfer. The use of second- and third-generation CARs has helped to resolve the long-standing problem of insufficient in vivo T cell persistence after transfer that was severely hampering its efficacy. Nevertheless, important obstacles for a wider application remain, such as the necessity to produce T cell products on an individualized basis, making this promising treatment approach hardly economically feasible. Although the use of T cells, for example autologous T cells, has shown promise, it can be difficult to obtain a suitable numbers of autologous cells in heavily pretreated patients.

U.S. 2003/0170238 and U.S. 2003/0175272 describe methods for adoptive immunotherapy, in which T cells are allowed to rest by removing them from activation stimuli for at least 48-72 hours, typically at least about 72-120 hours, and then reactivating them prior to infusion by labeling cells, for example, with mitogenic monoclonal antibodies (mAbs), such as soluble anti-CD3 and anti-CD28 mAbs, and then mixing the labeled cells with autologous mononuclear cells that are optionally enhanced in monocytes and granulocytes.

U.S. 2017/0051252 describes methods for manufacturing T cell therapeutics including the steps of obtaining a population of cells containing T cells and antigen presenting cells (APCs); culturing the population of cells in a cell culture medium comprising (i) one or more cytokines, (ii) an anti-CD3 antibody or CD3-binding fragment thereof, and (iii) an anti-CD28 antibody or a CD28-binding fragment thereof, B7-1 or a CD28-binding fragment thereof, or B7-2 or a CD28-binding fragment thereof, in which the culture activates and stimulates the T cells; transducing the population of activated cells with a viral vector; and culturing the population of cells in a cell growth medium to expand the transduced T cells; thereby manufacturing T cell therapeutics.

Improved strategies are needed for transducing cell populations in vitro that could generate enough T cells for research, diagnostic, and therapeutic purposes. A solution to this technical problem is provided herein.

BRIEF SUMMARY

In an aspect, the present disclosure relates to a method of transducing a T cell including thawing frozen peripheral blood mononuclear cells (PBMC), resting the thawed PBMC, activating the T cell in the cultured PBMC with an anti-CD3 antibody and an anti-CD28 antibody, transducing the activated T cell with a viral vector, expanding the transduced T cell, and obtaining the expanded T cells.

In an aspect, the T cell is activated in cultured PBMC with an anti-CD3 antibody and an anti-CD28 antibody immobilized on a solid phase support.

In another aspect, the resting step may be carried out within a period of no more than about 1 hour, no more than about 2 hours, no more than about 3 hours, no more than about 4 hours, no more than about 5 hours, no more than about 6 hours, no more than about 7 hours, no more than about 8 hours, no more than about 9 hours, no more than about 10 hours, no more than about 11 hours, no more than about 12 hours, no more than about 18 hours, no more than about 24 hours, no more than about 48 hours, no more than about 36 hours, no more than about 48 hours, no more than about 60 hours, no more than about 72 hours, no more than about 84 hours, no more than about 96 hours, no more than about 108 hours, or no more than about 120 hours.

In another aspect, resting may be carried out within a period of from about 0.5 hour to about 48 hours, about 0.5 hour to about 36 hours, about 0.5 hour to about 24 hours, about 0.5 hour to about 18 hours, about 0.5 hour to about 12 hours, about 0.5 hour to about 6 hours, about 1 hour to about 6 hours, about 2 hours to about 5 hours, about 3 hours to about 5 hours, about 3 hours to about 4 hours, about 4 to about 5 hours, or about 1 hours to about 24 hours, about 2 to about 24 hours, about 12 to about 48 hours, about 0.5 hour to about 120 hours, about 0.5 hour to about 108 hours, about 0.5 hour to about 96 hours, about 0.5 hour to about 84 hours, about 0.5 hour to about 72 hours, or about 0.5 hour to about 60 hours.

In another aspect, the resting step may be carried out within a period of about 1 hour, about 2 hours, about 3 hours, about 4 hours, about 5 hours, about 6 hours, about 7 hours, about 8 hours, about 9 hours, or about 10 hours.

In an aspect, the fold expansion of T cells produced with a resting step of about 1 hour, about 2 hours, about 3 hours, about 4 hours, about 5 hours, about 6 hours, about 7 hours, about 8 hours, about 9 hours, about 10 hours, about 2 hours to about 5 hours, about 3 hours to about 5 hours, about 3 hours to about 4 hours, or about 4 to about 5 hours is about equal to (about 1:1); about at least 1.1 times, about at least 1.2 times, about at least 1.3 times, about at least 1.5 times, about at least 1.7 times, or about at least 2.0 times greater than the fold expansion of T cells produced with a resting step of about 16 hours, about 17 hours, about 18 hours, about 19 hours, about 20 hours, about 24 hours, or about 16 to about 20 hours. In a preferred aspect, the fold expansion of T cells produced with a resting step of about 4 hours is about at least 1.5 times greater than the fold expansion of T cells produced with a resting step of about 16 hours (for example, overnight). In an aspect, the only difference between the production of the T cells is the reduced resting time.

In an aspect, the number of T cells produced with a resting step of about 1 hour, about 2 hours, about 3 hours, about 4 hours, about 5 hours, about 6 hours, about 7 hours, about 8 hours, about 9 hours, about 10 hours, about 2 hours to about 5 hours, about 3 hours to about 5 hours, about 3 hours to about 4 hours, or about 4 to about 5 hours is about equal to (about 1:1); about at least 1.1 times, about at least 1.2 times, about at least 1.3 times, about at least 1.5 times, about at least 1.7 times, or about at least 2.0 times greater than the number of T cells produced with a resting step of about 16 hours, about 17 hours, about 18 hours, about 19 hours, about 20 hours, about 24 hours, or about 16 to about 20 hours. In a preferred aspect, the number of T cells produced with a resting step of about 4 hours is about at least 1.5 times or about 1.3 times to about 2.0 times greater than the fold expansion of T cells produced with a resting step of about 16 hours (for example, overnight). In an aspect, the only difference between the production of the T cells is the reduced resting time.

In yet another aspect, anti-CD3 antibody and the anti-CD28 antibody each may have a concentration of no more than about 0.1 µg/ml, no more than about 0.2 µg/ml, no more than about 0.3 µg/ml, no more than about 0.4 µg/ml, no more than about 0.5 µg/ml, no more than about 0.6 µg/ml, no more than about 0.7 µg/ml, no more than about 0.8 µg/ml, no more than about 0.9 µg/ml, no more than about 1.0 µg/ml, no more than about 2.0 µg/ml, no more than about 4.0 µg/ml, no more than about 6.0 µg/ml, no more than about 8.0 µg/ml, or no more than about 10.0 µg/ml.

In yet another aspect, anti-CD3 antibody and the anti-CD28 antibody each may have a concentration of from about 0.1 µg/ml to about 1.0 µg/ml, about 0.1 µg/ml to about 0.8 µg/ml, about 0.1 µg/ml to about 0.6 µg/ml, about 0.1 µg/ml to about 0.5 µg/ml, about 0.1 µg/ml to about 0.25 µg/ml, about 0.2 µg/ml to about 0.5 µg/ml, about 0.2 µg/ml to about 0.3 µg/ml, about 0.3 µg/ml to about 0.5 µg/ml, about 0.3 µg/ml to about 0.4 µg/ml, about 0.2 µg/ml to about 0.5 µg/ml, about 0.1 µg/ml to about 10.0 µg/ml, about 0.1 µg/ml to about 8.0 µg/ml, about 0.1 µg/ml to about 6.0 µg/ml, about 0.1 µg/ml to about 4.0 µg/ml, or about 0.1 µg/ml to about 2.0 µg/ml.

In an aspect, activation described herein may be carried out within a period of no more than about 1 hour, no more than about 2, hours, no more than about 3 hours, no more than about 4 hours, no more than about 5 hours, no more than about 6 hours, no more than about 7 hours, no more than about 8 hours, no more than about 9 hours, no more than about 10 hours, no more than about 11 hours, no more than about 12 hours, no more than about 14 hours, no more than about 16 hours, no more than about 18 hours, no more than about 20 hours, no more than about 22 hours, no more than about 24 hours, no more than about 26 hours, no more than about 28 hours, no more than about 30 hours, no more than about 36 hours, no more than about 48 hours, no more than about 60 hours, no more than about 72 hours, no more than about 84 hours, no more than about 96 hours, no more than about 108 hours, or no more than about 120 hours.

In another aspect, activation described herein may be carried out within a period of from about 1 hour to about 120 hours, about 1 hour to about 108 hours, about 1 hour to about 96 hours, about 1 hour to about 84 hours, about 1 hour to about 72 hours, about 1 hour to about 60 hours, about 1 hour to about 48 hours, about 1 hour to about 36 hours, about 1 hour to about 24 hours, about 2 hours to about 24 hours, about 4 hours to about 24 hours, about 6 hours to about 24 hours, about 8 hours to about 24 hours, about 10 hours to about 24 hours, about 12 hours to about 24 hours, about 12 hours to about 72 hours, about 24 hours to about 72 hours, about 6 hours to about 48 hours, about 24 hours to about 48 hours, about 6 hours to about 72 hours, or about 1 hours to about 12 hours.

In an aspect, T cells described herein are autologous to the patient or individual. In another aspect, T cells described herein are allogenic to the patient or individual.

In another aspect, a solid phase described herein may be a surface of a bead, a plate, a flask, or a bag.

In yet another aspect, a plate described herein may be a 6-well, 12-well, or 24-well plate.

In an aspect, a flask described herein may have a seeding surface area of at least about 25 $cm^2$, about 75 $cm^2$, about 92.6 $cm^2$, about 100 $cm^2$, about 150 $cm^2$, about 162 $cm^2$, about 175 $cm^2$, about 225 $cm^2$, about 235 $cm^2$, about 300 $cm^2$, about 1720 $cm^2$, about 25 $cm^2$ to about 75 $cm^2$, about 25 $cm^2$ to about 225 $cm^2$, or about 25 $cm^2$ to about 1720 $cm^2$.

In another aspect, a bag described herein may have a volume of from about 50 ml to about 100 liters, about 100 ml to about 100 liters, about 150 ml to about 100 liters, about 200 ml to about 100 liters, about 250 ml to about 100 liters, about 500 ml to about 100 liters, about 1 liter to about 100 liters, about 1 liter to about 75 liters, about 1 liter to about 50 liters, about 1 liter to about 25 liters, about 1 liter to about 20 liters, about 1 liter to about 15 liters, about 1 liter to about 10 liters, about 1 liter to about 5 liters, about 1 liter to about 2.5 liters, or about 1 liter to about 2 liters.

In yet another aspect, activation described herein may be carried out in the presence of the T cell activation stimulus.

In an aspect, cytokines described herein may include interleukin 2 (IL-2), interleukin 7 (IL-7), interleukin 15 (IL-15), and/or interleukin 21 (IL-21).

In another aspect, the concentration of IL-7 may be no more than about 1 ng/ml, no more than about 2 ng/ml, no more than about 3 ng/ml, no more than about 4 ng/ml, no more than about 5 ng/ml, no more than about 6 ng/ml, no more than about 7 ng/ml, no more than about 8 ng/ml, no more than about 9 ng/ml, no more than about 10 ng/ml, no more than about 11 ng/ml, no more than about 12 ng/ml, no more than about 13 ng/ml, no more than about 14 ng/ml, no more than about 15 ng/ml, no more than about 16 ng/ml, no more than about 17 ng/ml, no more than about 18 ng/ml, no more than about 19 ng/ml, no more than about 20 ng/ml, no more than about 25 ng/ml, no more than about 30 ng/ml, no more than about 35 ng/ml, no more than about 40 ng/ml, no more than about 45 ng/ml, no more than about 50 ng/ml, no more than about 60 ng/ml, no more than about 70 ng/ml, no more than about 80 ng/ml, no more than about 90 ng/ml, or no more than about 100 ng/ml.

In another aspect, the concentration of IL-7 may be from about 1 ng/ml to 100 ng/ml, about 1 ng/ml to 90 ng/ml, about 1 ng/ml to 80 ng/ml, about 1 ng/ml to 70 ng/ml, about 1 ng/ml to 60 ng/ml, about 1 ng/ml to 50 ng/ml, about 1 ng/ml to 40 ng/ml, about 1 ng/ml to 30 ng/ml, about 1 ng/ml to 20 ng/ml, about 1 ng/ml to 15 ng/ml, about 1 ng/ml to 10 ng/ml, about 2 ng/ml to 10 ng/ml, about 4 ng/ml to 10 ng/ml, about 6 ng/ml to 10 ng/ml, or about 5 ng/ml to 10 ng/ml.

In yet another aspect, the concentration of IL-15 may be no more than about 5 ng/ml, no more than about 10 ng/ml, no more than about 15 ng/ml, no more than about 20 ng/ml, no more than about 25 ng/ml, no more than about 30 ng/ml, no more than about 35 ng/ml, no more than about 40 ng/ml, no more than about 45 ng/ml, no more than about 50 ng/ml, no more than about 60 ng/ml, no more than about 70 ng/ml, no more than about 80 ng/ml, no more than about 90 ng/ml, no more than about 100 ng/ml, no more than about 110 ng/ml, no more than about 120 ng/ml, no more than about 130 ng/ml, no more than about 140 ng/ml, no more than about 150 ng/ml, 200 ng/ml, 250 ng/ml, 300 ng/ml, 350 ng/ml, 400 ng/ml, 450 ng/ml, or 500 ng/ml.

In another aspect, the concentration of IL-15 may be from about 5 ng/ml to 500 ng/ml, about 5 ng/ml to 400 ng/ml, about 5 ng/ml to 300 ng/ml, about 5 ng/ml to 200 ng/ml, about 5 ng/ml to 150 ng/ml, about 5 ng/ml to 100 ng/ml, about 10 ng/ml to 100 ng/ml, about 20 ng/ml to 100 ng/ml, about 30 ng/ml to 100 ng/ml, about 40 ng/ml to 100 ng/ml, about 50 ng/ml to 100 ng/ml, about 60 ng/ml to 100 ng/ml, about 70 ng/ml to 100 ng/ml, about 80 ng/ml to 100 ng/ml, about 90 ng/ml to 100 ng/ml, about 1 ng/ml to 50 ng/ml, about 5 ng/ml to 50 ng/ml, about 10 ng/ml to 50 ng/ml, or about 20 ng/ml to 50 ng/ml.

In another aspect, the concentration of IL-2 may be no more than about 1000 IU/ml, no more than about 950 IU/ml, no more than about 900 IU/ml, no more than about 850 IU/ml, no more than about 800 IU/ml, no more than about 750 IU/ml, no more than about 700 IU/ml, no more than about 650 IU/ml, no more than about 600 IU/ml, no more than about 550 IU/ml, no more than about 500 IU/ml, no more than about 450 IU/ml, no more than about 400 IU/ml, no more than about 350 IU/ml, no more than about 300 IU/ml, no more than about 250 IU/ml, no more than about 200 IU/ml, no more than about 150 IU/ml, no more than about 100 IU/ml, no more than about 90 IU/ml, no more than about 80 IU/ml, no more than about 70 IU/ml, no more than about 65 IU/ml, no more than about 60 IU/ml, no more than about 55 IU/ml, no more than about 50 IU/ml, no more than about 40 IU/ml, no more than about 30 IU/ml, no more than about 20 IU/ml, no more than about 10 IU/ml, or no more than about 5 IU/ml.

In another aspect, the concentration of IL-2 may be from about 10 IU/ml to 1000 IU/ml, about 20 IU/ml to 900 IU/ml, about 30 IU/ml to 800 IU/ml, about 40 IU/ml to 700 IU/ml, about 50 IU/ml to 600 IU/ml, about 50 IU/ml to 550 IU/ml, about 50 IU/ml to 500 IU/ml, about 50 IU/ml to 450 IU/ml, about 50 IU/ml to 400 IU/ml, about 50 IU/ml to 350 IU/ml, about 50 IU/ml to 300 IU/ml, about 50 IU/ml to 250 IU/ml, about 50 IU/ml to 200 IU/ml, about 50 IU/ml to 150 IU/ml, or about 50 IU/ml to 100 IU/ml.

In another aspect, the concentration of IL-21 may be no more than about 1 ng/ml, no more than about 2 ng/ml, no more than about 3 ng/ml, no more than about 4 ng/ml, no more than about 5 ng/ml, no more than about 6 ng/ml, no more than about 7 ng/ml, no more than about 8 ng/ml, no more than about 9 ng/ml, no more than about 10 ng/ml, no more than about 11 ng/ml, no more than about 12 ng/ml, no more than about 13 ng/ml, no more than about 14 ng/ml, no more than about 15 ng/ml, no more than about 16 ng/ml, no more than about 17 ng/ml, no more than about 18 ng/ml, no more than about 19 ng/ml, no more than about 20 ng/ml, no more than about 25 ng/ml, no more than about 30 ng/ml, no more than about 35 ng/ml, no more than about 40 ng/ml, no more than about 45 ng/ml, no more than about 50 ng/ml, no more than about 60 ng/ml, no more than about 70 ng/ml, no more than about 80 ng/ml, no more than about 90 ng/ml, or no more than about 100 ng/ml.

In another aspect, the concentration of IL-21 may be from about 1 ng/ml to 100 ng/ml, about 1 ng/ml to 90 ng/ml, about 1 ng/ml to 80 ng/ml, about 1 ng/ml to 70 ng/ml, about 1 ng/ml to 60 ng/ml, about 1 ng/ml to 50 ng/ml, about 1 ng/ml to 40 ng/ml, about 1 ng/ml to 30 ng/ml, about 1 ng/ml to 20 ng/ml, about 1 ng/ml to 15 ng/ml, about 1 ng/ml to 10 ng/ml, about 2 ng/ml to 10 ng/ml, about 4 ng/ml to 10 ng/ml, about 6 ng/ml to 10 ng/ml, about 5 ng/ml to 10 ng/ml, about 10 ng/ml to 20 ng/ml, about 10 ng/ml to 30 ng/ml, about 10 ng/ml to 40 ng/ml, about 10 ng/ml to 50 ng/ml, about 10 ng/ml to 60 ng/ml, about 10 ng/ml to 70 ng/ml, about 10 ng/ml to 80 ng/ml, about 10 ng/ml to 90 ng/ml, or about 10 ng/ml to 100 ng/ml.

In an aspect, transducing described herein may be carried out within a period of no more than about 1 hour, no more than about 2 hours, no more than about 3 hours, no more than about 4 hours, no more than about 5 hours, no more than about 6 hours, no more than about 7 hours, no more than about 8 hours, no more than about 9 hours, no more than about 10 hours, no more than about 11 hours, no more than about 12 hours, no more than about 14 hours, no more than about 16 hours, no more than about 18 hours, no more than about 20 hours, no more than about 22 hours, no more than about 24 hours, no more than about 26 hours, no more than about 28 hours, no more than about 30 hours, no more than about 36 hours, no more than about 42 hours, no more than about 48 hours, no more than about 54 hours, no more than about 60 hours, no more than about 66 hours, no more than about 72 hours, no more than about 84 hours, no more than about 96 hours, no more than about 108 hours, or no more than about 120 hours.

In yet another aspect, transducing described herein may be carried out within a period of from about 1 hour to about 120 hours, about 1 hour to about 108 hours, about 1 hour to about 96 hours, about 1 hour to about 72 hours, about 1 hour to about 48 hours, about 1 hour to about 36 hours, about 1 hour to about 24 hours, about 1 hour to about 12 hours, about 2 hours to about 24 hours, about 4 hours to about 24 hours, about 12 hours to about 24 hours, about 12 hours to about 48 hours, about 12 hour to about 72 hours, about 24 hours to about 72 hours, or about 36 hours to about 72 hours.

In another aspect, viral vector described herein may be a γ-retroviral vector expressing a T cell receptor (TCR).

In yet another aspect, viral vector described herein may be a lentiviral vector expressing a TCR.

In an aspect, transducing described herein may be carried out in the presence of the T cell activation stimulus.

In an aspect, expanding described herein may be carried out in the presence of the T cell activation stimulus.

In an aspect, expanding described herein may be carried out within a period of no more than about 1 day, no more than about 2 days, no more than about 3 days, no more than about 4 days, no more than about 5 days, no more than about 6 days, no more than about 7 days, no more than about 8 days, no more than about 9 days, no more than about 10 days, no more than about 15 days, no more than about 20 days, no more than about 25 days, or no more than about 30 days.

In another aspect, expanding described herein may be carried out within a period of from about 1 day to about 30 days, about 1 day to about 25 days, about 1 day to about 20 days, about 1 day to about 15 days, about 1 day to about 10 days, about 2 days to about 10 days, about 3 days to about 10 days, about 4 days to about 10 days, about 4 days to about 30 days, about 6 days to about 25 days, about 10 days to about 30 days, or about 12 days to about 30 days.

In an aspect, the number of the obtained T cells may be at least about $1\times10^9$, may be at least about $2\times10^9$, may be at least about $3\times10^9$, may be at least about $4\times10^9$, may be at least about $5\times10^9$, may be at least about $6\times10^9$, may be at least about $7\times10^9$, may be at least about $8\times10^9$, may be at least about $9\times10^9$, may be at least about $1\times10^{10}$, may be at least about $5\times10^{19}$, may be at least about $1\times10^{11}$, may be at least about $5\times10^{11}$, may be at least about $1\times10^{12}$, may be at least about $5\times10^{12}$ or may be at least about $1\times10^{13}$ cells.

In another aspect, the number of the obtained T cells may be from about $1\times10^9$ to about $1\times10^{13}$, about $1\times10^9$ to about $5 \times 10^{12}$, about $1 \times 10^9$ to about $1 \times 10^{12}$, about $1 \times 10^9$ to about $5 \times 10^{11}$, about $1 \times 10^9$ to about $1 \times 10^{11}$, about $1 \times 10^9$ to about $5 \times 10^{10}$, about $1 \times 10^9$ to about $1 \times 10^{10}$, about $2 \times 10^9$ to about $1 \times 10^{10}$, about $3 \times 10^9$ to about $1 \times 10^{10}$, about $4 \times 10^9$ to about $1 \times 10^{10}$, about $5 \times 10^9$ to about $1 \times 10^{10}$, about $6 \times 10^9$ to about $1 \times 10^{10}$, about $7 \times 10^9$ to about $1 \times 10^{10}$, about $8 \times 10^9$ to about $1 \times 10^{10}$, or about $9 \times 10^9$ to about $1 \times 10^{10}$ cells.

In an aspect, the obtained T cells may be a CD3+CD8+ T cell and/or CD3+CD4+ T cells.

In another aspect, PBMC may be obtained from the patient.

In yet another aspect, the present disclosure relates to genetically transduced T cells produced by the method described herein.

In another aspect, the present disclosure relates to pharmaceutical compositions containing the genetically transduced T cells produced by the method described herein and pharmaceutically acceptable carriers.

In another aspect, the present disclosure relates to a method of preparing a T cell population, including thawing frozen peripheral blood mononuclear cells (PBMC), resting the thawed PBMC, activating the T cell in the rested PBMC with an anti-CD3 antibody and an anti-CD28 antibody immobilized on a solid phase, expanding the activated T cell, and obtaining the T cell population comprising the expanded T cell.

In yet another aspect, the present disclosure relates to a T cell population prepared by the method described herein.

In another aspect, the present disclosure relates to methods of treating a patient or individual having a cancer or in need of a treatment thereof, comprising administering to the patient an effective amount of the expanded T cells described herein. In an aspect, the patient or individual in need thereof is a cancer patient. In an aspect, the cancer to be treated is selected from one or more of hepatocellular carcinoma (HCC), colorectal carcinoma (CRC), glioblastoma (GB), gastric cancer (GC), esophageal cancer, non-small cell lung cancer (NSCLC), pancreatic cancer (PC), renal cell carcinoma (RCC), benign prostate hyperplasia (BPH), prostate cancer (PCA), ovarian cancer (OC), melanoma, breast cancer, chronic lymphocytic leukemia (CLL), Merkel cell carcinoma (MCC), small cell lung cancer (SCLC), Non-Hodgkin lymphoma (NHL), acute myeloid leukemia (AML), gallbladder cancer and cholangiocarcinoma (GBC, CCC), urinary bladder cancer (UBC), acute lymphocytic leukemia (ALL), and uterine cancer (UEC).

In another aspect, the expanding may be carried out in the presence of at least one cytokine selected from the group consisting of IL-2, IL-7, IL-12, IL-15, and IL-21. In an aspect, the expansion takes place in the presence of a combination IL-7 and IL-15.

In another aspect, the thawing, the resting, the activating, the transducing, the expanding, and/or the obtaining may be performed in a closed system.

In another aspect, the present disclosure relates to a method of preparing a T cell population, including obtaining fresh peripheral blood mononuclear cells (PBMC), i.e., PBMC is not obtained by thawing cryopreserved PBMC, activating the T cell in the fresh PBMC with an anti-CD3 antibody and an anti-CD28 antibody, transducing the activated T cell with a viral vector, expanding the transduced T cell, and harvesting the expanded T cell.

In an aspect, the obtaining and the activating may be performed for no more than 1 day.

In an aspect, the expanding may be performed for more than 1 day.

In another aspect, the expanding may be performed for from about 1 day to 2 days, from about 1 day to 3 days, from about 1 day to about 4 days, from about 1 day to about 5 days, from about 1 day to 6 days, from about 1 day to 7 days, from about 1 day to 8 days, from about 1 day to 9 days, from about 1 day to 10 days, from about 2 days to 3 days, from about 2 days to 4 days, from about 2 days to 5 days, from about 2 days to 6 days, from about 2 days to 7 days, from about 2 days to 8 days, from about 2 days to 9 days, from about 2 days to 10 days, from about 3 days to 4 days, from about 3 days to 5 days, from about 3 days to 6 days, from about 3 days to 7 days, from about 3 days to 8 days, from about 3 days to 9 days, from about 3 days to 10 days, from about 4 days to 5 days, from about 4 days to 6 days, from about 4 days to 7 days, from about 4 days to 8 days, from about 4 days to 9 days, from about 4 days to 10 days, from about 5 days to 6 days, from about 5 days to 7 days, from about 5 days to 8 days, from about 5 days to 9 days, or from about 5 days to 10 days.

In another aspect, the harvesting may be performed after the activating within from about 4 days to about 12 days, from about 4 days to about 11 days, from about 4 days to about 10 days, from about 4 days to about 9 days, from about 4 days to about 8 days, from about 4 days to about 7 days, from about 4 days to about 6 days, from about 4 days to about 5 days, from about 5 days to about 12 days, from about 5 days to about 11 days, from about 5 days to about 10 days, from about 5 days to about 9 days, from about 5 days to about 8 days, from about 5 days to about 7 days, or from about 5 days to about 6 days.

In another aspect, the number of the harvested T cells may be selected from the group consisting of from about $2 \times 10^9$ to about $5 \times 10^9$, about $5 \times 10^9$ to about $10 \times 10^9$, about $10 \times 10^9$ to about $15 \times 10^9$, about $5 \times 10^9$ to about $35 \times 10^9$, about $5 \times 10^9$ to about $30 \times 10^9$, about $10 \times 10^9$ to about $30 \times 10^9$, about $15 \times 10^9$ to about $20 \times 10^9$, about $20 \times 10^9$ to about $35 \times 10^9$, about $24 \times 10^9$ to about $33 \times 10^9$, and about $24.8 \times 10^9$ to about $32.2 \times 10^9$.

In another aspect, the activating, the transducing, the expanding, and the harvesting may be performed in a closed or semi-closed system.

In another aspect, the closed system may be CliniMACS, Prodigy™, WAVE (XURI™) Bioreactor, WAVE (XURI™) Bioreactor in combination with BioSafe Sepax™ II, G-Rex/GatheRex™ closed system, or G-Rex/GatheRex™ closed system in combination with BioSafe Sepax™ II.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

DETAILED DESCRIPTION

Figure 1A:
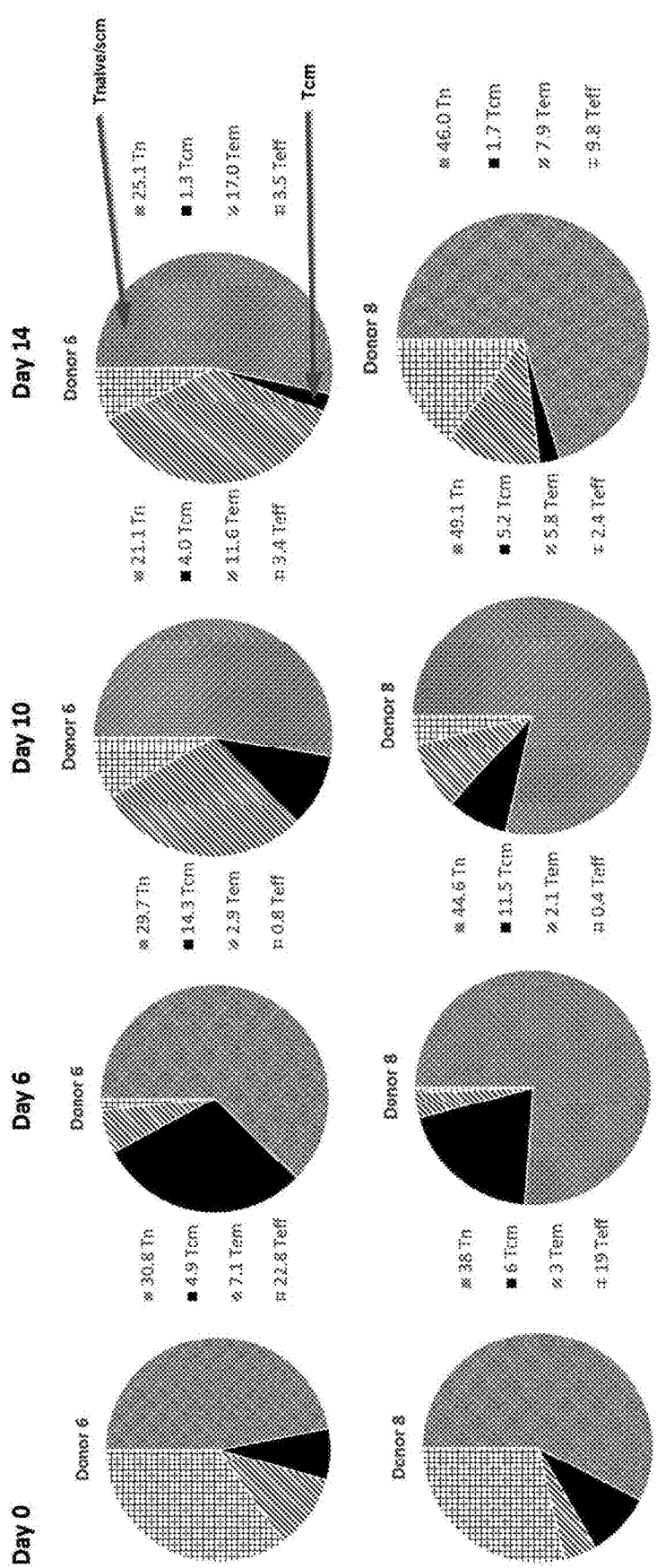
FIGS. 1A and 1B show loss of $T_{naive/scm}$ and $T_{cm}$ phenotype by prolonging ex vivo culturing of T cells obtained from different donors.

In an aspect, the disclosure provides for T cells populations produced by a method including thawing frozen peripheral blood mononuclear cells (PBMC), resting the thawed PBMC, activating the T cell in the rested PBMC with an anti-CD3 antibody and an anti-CD28 antibody immobilized on a solid phase, expanding the activated T cell, and obtaining the T cell population comprising the expanded T cell.

In an aspect, the disclosure provides for methods of transducing a T cell including thawing frozen peripheral blood mononuclear cells (PBMC), resting the thawed PBMC, activating the T cell in the cultured PBMC with an anti-CD3 antibody and an anti-CD28 antibody, transducing the activated T cell with a viral vector, expanding the transduced T cell, and obtaining the expanded T cells; method of preparing a T cell population, including thawing frozen peripheral blood mononuclear cells (PBMC), resting the thawed PBMC, activating the T cell in the rested PBMC with an anti-CD3 antibody and an anti-CD28 antibody immobilized on a solid phase, expanding the activated T cell, and obtaining the T cell population comprising the expanded T cell; and methods of treating a patient or individual having a cancer or in need of a treatment thereof, comprising administering to the patient an effective amount of the expanded T cells described herein. In an aspect, the patient or individual in need thereof is a cancer patient. In an aspect, the cancer to be treated is selected from one or more of hepatocellular carcinoma (HCC), colorectal carcinoma (CRC), glioblastoma (GB), gastric cancer (GC), esophageal cancer, non-small cell lung cancer (NSCLC), pancreatic cancer (PC), renal cell carcinoma (RCC), benign prostate hyperplasia (BPH), prostate cancer (PCA), ovarian cancer (OC), melanoma, breast cancer, chronic lymphocytic leukemia (CLL), Merkel cell carcinoma (MCC), small cell lung cancer (SCLC), Non-Hodgkin lymphoma (NHL), acute myeloid leukemia (AML), gallbladder cancer and cholangiocarcinoma (GBC, CCC), urinary bladder cancer (UBC), acute lymphocytic leukemia (ALL), and uterine cancer (UEC).

T-cell based immunotherapy targets peptide epitopes derived from tumor-associated or tumor-specific proteins, which are presented by molecules of the major histocompatibility complex (MHC). The antigens that are recognized by the tumor specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides. MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules. This non-classical way of class I presentation is referred to as cross-presentation. MHC class II molecules can be found predominantly on professional antigen presenting cells (APCs), and primarily present peptides of exogenous or transmembrane proteins that are taken up by APCs e.g., during endocytosis, and are subsequently processed.

Complexes of peptide and MHC class I are recognized by CD8-positive T-cells bearing the appropriate T-cell receptor (TCR), whereas complexes of peptide and MHC class II molecules are recognized by CD4-positive-helper-T-cells bearing the appropriate TCR. It is well known that the TCR, the peptide and the MHC are thereby present in a stoichiometric amount of 1:1:1.

CD4-positive helper T-cells play an important role in inducing and sustaining effective responses by CD8-positive cytotoxic T-cells. The identification of CD4-positive T-cell epitopes derived from tumor associated antigens (TAA) is of great importance for the development of pharmaceutical products for triggering anti-tumor immune responses. At the tumor site, T helper cells, support a cytotoxic T-cell-(CTL-) friendly cytokine milieu and attract effector cells, e.g., CTLs, natural killer (NK) cells, macrophages, and granulocytes.

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules. Elongated (longer) peptides of the description can function as MHC class II active epitopes.

T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T-cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T-cells are sufficient for inhibiting manifestation of tumors via inhibition of angiogenesis by secretion of interferon-gamma (IFN-γ). There is evidence for CD4-positive T-cells as direct anti-tumor effectors.

Since the constitutive expression of HLA class II molecules is usually limited to immune cells, the possibility of isolating class II peptides directly from primary tumors was previously not considered possible. However, Dengjel et al. were successful in identifying a number of MHC Class II epitopes directly from tumors (WO 2007/028574, EP 1 760 088 B1, the contents of which are herein incorporated by reference in their entirety).

Since both types of response, CD8 and CD4 dependent, contribute jointly and synergistically to the anti-tumor effect, the identification and characterization of tumor-associated antigens recognized by either CD8+ T-cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-class-1-binding peptides are usually 8-12 amino acid residues in length and usually contain two conserved residues ("anchors") in their sequence that interact with the corresponding binding groove of the MHC-molecule. In this way, each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T-cells bearing specific T-cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e., copy numbers of the respective peptide per cell). Tumor-specific and tumor-associated antigens are often derived from proteins directly involved in transformation of a normal cell to a tumor cell due to their function, e.g., in cell cycle control or suppression of apoptosis. Additionally, downstream targets of the proteins directly causative for a transformation may be up-regulated and thus may be indirectly tumor-associated. Such indirect tumor-associated antigens may also be targets of a vaccination approach. Epitopes are present in the amino acid sequence of the antigen, in order to ensure that such a peptide ("immunogenic peptide"), being derived from a tumor associated antigen, and leads to an in vitro or in vivo T-cell-response.

Therefore, TAAs are a starting point for the development of a T-cell based therapy including but not limited to tumor vaccines. The methods for identifying and characterizing the TAAs are usually based on the use of T-cells that can be isolated from patients or healthy subjects, or they are based on the generation of differential transcription profiles or differential peptide expression patterns between tumors and normal tissues. However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T-cell with a corresponding TCR has to be present and the immunological tolerance for this particular epitope needs to be absent or minimal.

In a very preferred embodiment of the description it is therefore important to select only those over- or selectively presented peptides against which a functional and/or a proliferating T-cell can be found. Such a functional T-cell is defined as a T-cell, which upon stimulation with a specific antigen can be clonally expanded and is able to execute effector functions ("effector T-cell").

The term "T-cell receptor (TCR)" as used herein refers to a protein receptor on T cells that is composed of a heterodimer of an alpha ($\alpha$) and beta ($\beta$) chain, although in some cells the TCR consists of gamma and delta ($\gamma/\delta$) chains. In embodiments of the disclosure, the TCR may be modified on any cell comprising a TCR, including a helper T cell, a cytotoxic T cell, a memory T cell, regulatory T cell, natural killer T cell, and gamma delta T cell, for example.

TCR is a molecule found on the surface of T lymphocytes (or T cells) that is generally responsible for recognizing antigens bound to major histocompatibility complex (MHC) molecules. It is a heterodimer consisting of an alpha and beta chain in 95% of T cells, while 5% of T cells have TCRs consisting of gamma and delta chains. Engagement of the TCR with antigen and MHC results in activation of its T lymphocyte through a series of biochemical events mediated by associated enzymes, co-receptors, and specialized accessory molecules. In immunology, the CD3 antigen (CD stands for cluster of differentiation) is a protein complex composed of four distinct chains (CD3-$\gamma$, CD3$\delta$, and two times CD3$\epsilon$) in mammals, that associate with molecules known as the T-cell receptor (TCR) and the $\zeta$-chain to generate an activation signal in T lymphocytes. The TCR, $\zeta$-chain, and CD3 molecules together comprise the TCR complex. The CD3-$\gamma$, CD3$\delta$, and CD3$\epsilon$ chains are highly related cell surface proteins of the immunoglobulin superfamily containing a single extracellular immunoglobulin domain. The transmembrane region of the CD3 chains is negatively charged, a characteristic that allows these chains to associate with the positively charged TCR chains (TCR$\alpha$ and TCR$\beta$). The intracellular tails of the CD3 molecules contain a single conserved motif known as an immunoreceptor tyrosine-based activation motif or ITAM for short, which is essential for the signalling capacity of the TCR.

CD28 is one of the molecules expressed on T cells that provide co-stimulatory signals, which are required for T cell activation. CD28 is the receptor for B7.1 (CD80) and B7.2 (CD86). When activated by Toll-like receptor ligands, the B7.1 expression is upregulated in antigen presenting cells (APCs). The B7.2 expression on antigen presenting cells is constitutive. CD28 is the only B7 receptor constitutively expressed on naive T cells. Stimulation through CD28 in addition to the TCR can provide a potent co-stimulatory signal to T cells for the production of various interleukins (IL-2 and IL-6 in particular).

In an aspect, expansion and/or activation of T cells take place in the presence of one or more of IL-2, IL-7, IL-10, IL-12, IL-15, IL-21. In another aspect, expansion and/or activation of T cells takes place with IL-2 alone, IL-7 alone, IL-15 alone, a combination of IL-2 and IL-15, or a combination of IL-7 and IL-15.

TCR constructs of the present disclosure may be applicable in subjects having or suspected of having cancer by reducing the size of a tumor or preventing the growth or re-growth of a tumor in these subjects. Accordingly, the present disclosure further relates to a method for reducing growth or preventing tumor formation in a subject by introducing a TCR construct of the present disclosure into an isolated T cell of the subject and reintroducing into the subject the transformed T cell, thereby effecting anti-tumor responses to reduce or eliminate tumors in the subject. Suitable T cells that can be used include cytotoxic lymphocytes (CTL) or any cell having a T cell receptor in need of disruption. As is well-known to one of skill in the art, various methods are readily available for isolating these cells from a subject. For example, using cell surface marker expression or using commercially available kits (e.g., ISO-CELL™ from Pierce, Rockford, Ill.).

It is contemplated that the TCR construct can be introduced into the subject's own T cells as naked DNA or in a suitable vector. Methods of stably transfecting T cells by electroporation using naked DNA in the art. See, e.g., U.S. Pat. No. 6,410,319, the content of which is incorporated by reference in its entirety. Naked DNA generally refers to the DNA encoding a TCR of the present disclosure contained in a plasmid expression vector in proper orientation for expression. Advantageously, the use of naked DNA reduces the time required to produce T cells expressing the TCR of the present disclosure.

Alternatively, a viral vector (e.g., a retroviral vector, adenoviral vector, adeno-associated viral vector, or lentiviral vector) can be used to introduce the TCR construct into T cells. Suitable vectors for use in accordance with the method of the present disclosure are non-replicating in the subject's T cells. A large number of vectors are known that are based on viruses, where the copy number of the virus maintained in the cell is low enough to maintain the viability of the cell. Illustrative vectors include the pFB-neo vectors (STRATAGENE®) as well as vectors based on HIV, SV40, EBV, HSV, or BPV.

Once it is established that the transfected or transduced T cell is capable of expressing the TCR construct as a surface membrane protein with the desired regulation and at a desired level, it can be determined whether the TCR is functional in the host cell to provide for the desired signal induction. Subsequently, the transduced T cells are reintroduced or administered to the subject to activate anti-tumor responses in the subject.

To facilitate administration, the transduced T cells according to the disclosure can be made into a pharmaceutical composition or made into an implant appropriate for administration in vivo, with appropriate carriers or diluents, which further can be pharmaceutically acceptable. The means of making such a composition or an implant have been described in the art (see, for instance, Remington's Pharmaceutical Sciences, 16th Ed., Mack, ed. (1980, the content which is herein incorporated by reference in its entirety)). Where appropriate, the transduced T cells can be formulated into a preparation in semisolid or liquid form, such as a capsule, solution, injection, inhalant, or aerosol, in the usual ways for their respective route of administration. Means known in the art can be utilized to prevent or minimize release and absorption of the composition until it reaches the target tissue or organ, or to ensure timed-release of the composition. Desirably, however, a pharmaceutically acceptable form is employed that does not hinder the cells from expressing the TCR. Thus, desirably the transduced T cells can be made into a pharmaceutical composition containing a balanced salt solution, preferably Hanks' balanced salt solution, or normal saline.

In certain aspects, the invention includes a method of making and/or expanding the antigen-specific redirected T cells that comprises transfecting T cells with an expression vector containing a DNA construct encoding TCR, then, optionally, stimulating the cells with antigen positive cells, recombinant antigen, or an antibody to the receptor to cause the cells to proliferate.

In another aspect, a method is provided of stably transfecting and re-directing T cells by electroporation, or other non-viral gene transfer (such as, but not limited to sonoporation) using naked DNA. Most investigators have used viral vectors to carry heterologous genes into T cells. By using naked DNA, the time required to produce redirected T cells can be reduced. "Naked DNA" means DNA encoding a TCR contained in an expression cassette or vector in proper orientation for expression. The electroporation method of this disclosure produces stable transfectants that express and carry on their surfaces the TCR.

In certain aspects, the T cells are primary human T cells, such as T cells derived from human peripheral blood mononuclear cells (PBMC), PBMC collected after stimulation with G-CSF, bone marrow, or umbilical cord blood. Conditions include the use of mRNA and DNA and electroporation. Following transfection, cells may be immediately infused or may be stored. In certain aspects, following transfection, the cells may be propagated for days, weeks, or months ex vivo as a bulk population within about 1, 2, 3, 4, 5 days or more following gene transfer into cells. In a further aspect, following transfection, the transfectants are cloned and a clone demonstrating presence of a single integrated or episomally maintained expression cassette or plasmid, and expression of the TCR is expanded ex vivo. The clone selected for expansion demonstrates the capacity to specifically recognize and lyse peptide-expressing target cells. The recombinant T cells may be expanded by stimulation with IL-2, or other cytokines that bind the common gamma-chain (e.g., IL-7, IL-12, IL-15, IL-21, and others). The recombinant T cells may be expanded by stimulation with artificial antigen presenting cells. The recombinant T cells may be expanded on artificial antigen presenting cell or with an antibody, such as OKT3, which cross links CD3 on the T cell surface. Subsets of the recombinant T cells may be deleted on artificial antigen presenting cell or with an antibody, such as Campath, which binds CD52 on the T cell surface. In a further aspect, the genetically modified cells may be cryopreserved.

A composition of the present invention can be provided in unit dosage form wherein each dosage unit, e.g., an injection, contains a predetermined amount of the composition, alone or in appropriate combination with other active agents. The term unit dosage form as used herein refers to physically discrete units suitable as unitary dosages for human and animal subjects, each unit containing a predetermined quantity of the composition of the present invention, alone or in combination with other active agents, calculated in an amount sufficient to produce the desired effect, in association with a pharmaceutically acceptable diluent, carrier, or vehicle, where appropriate. The specifications for the novel unit dosage forms of the present invention depend on the particular pharmacodynamics associated with the pharmaceutical composition in the particular subject.

Desirably an effective amount or sufficient number of the isolated transduced T cells is present in the composition and introduced into the subject such that long-term, specific, anti-tumor responses are established to reduce the size of a tumor or eliminate tumor growth or regrowth than would otherwise result in the absence of such treatment. Desirably, the amount of transduced T cells reintroduced into the subject causes an about 10%, about 20%, about 30%, about 40%, about 50%, about 60%, about 70%, about 80%, about 90%, about 95%, about 98%, or about 99% decrease in tumor size when compared to otherwise same conditions wherein the transduced T cells are not present.

Accordingly, the amount of transduced T cells administered should take into account the route of administration and should be such that a sufficient number of the transduced T cells will be introduced so as to achieve the desired therapeutic response. Furthermore, the amounts of each active agent included in the compositions described herein (e.g., the amount per each cell to be contacted or the amount per certain body weight) can vary in different applications. In general, the concentration of transduced T cells desirably should be sufficient to provide in the subject being treated at least from about $1 \times 10^6$ to about $1 \times 10^9$ transduced T cells/m$^2$ (or kg) of a patient, even more desirably, from about $1 \times 10^7$ to about $5 \times 10^8$ transduced T cells/m$^2$ (or kg) of a patient, although any suitable amount can be utilized either above, e.g., greater than $5 \times 10^8$ cells/m$^2$ (or kg) of a patient, or below, e.g., less than $1 \times 10^7$ cells/m$^2$ (or kg) of a patient. The dosing schedule can be based on well-established cell-based therapies (see, e.g., U.S. Pat. No. 4,690,915, the content which is herein incorporated by reference in its entirety), or an alternate continuous infusion strategy can be employed.

These values provide general guidance of the range of transduced T cells to be utilized by the practitioner upon optimizing the method of the present invention for practice of the invention. The recitation herein of such ranges by no means precludes the use of a higher or lower amount of a component, as might be warranted in a particular application. For example, the actual dose and schedule can vary depending on whether the compositions are administered in combination with other pharmaceutical compositions, or depending on interindividual differences in pharmacokinetics, drug disposition, and metabolism. One skilled in the art readily can make any necessary adjustments in accordance with the exigencies of the particular situation.

The terms "T cell" or "T lymphocyte" are art-recognized and are intended to include thymocytes, naïve T lymphocytes, immature T lymphocytes, mature T lymphocytes, resting T lymphocytes, or activated T lymphocytes. Illustrative populations of T cells suitable for use in particular embodiments include, but are not limited to, helper T cells (HTL; CD4+ T cell), a cytotoxic T cell (CTL; CD8+ T cell), CD4+CD8+ T cell, CD4−CD8− T cell, or any other subset of T cells. Other illustrative populations of T cells suitable for use in particular embodiments include, but are not limited to, T cells expressing one or more of the following markers: CD3, CD4, CD8, CD27, CD28, CD45RA, CD45RO, CD62L, CD127, CD197, and HLA-DR and if desired, can be further isolated by positive or negative selection techniques.

A peripheral blood mononuclear cell (PBMC) is defined as any blood cell with a round nucleus (i.e., a lymphocyte, a monocyte, or a macrophage). These blood cells are a critical component in the immune system to fight infection and adapt to intruders. The lymphocyte population consists of CD4+ and CD8+ T cells, B cells and Natural Killer cells, CD14+ monocytes, and basophils/neutrophils/eosinophils/dendritic cells. These cells are often separated from whole blood or from leukapheresis products using FICOLL™, a hydrophilic polysaccharide that separates layers of blood, with monocytes and lymphocytes forming a buffy coat under a layer of plasma. In one embodiment, "PBMCs" refers to a population of cells comprising at least T cells, and optionally NK cells, and antigen presenting cells.

The term "activation" refers to the state of a T cell that has been sufficiently stimulated to induce detectable cellular proliferation. In particular embodiments, activation can also be associated with induced cytokine production, and detectable effector functions. The term "activated T cells" refers to, among other things, T cells that are proliferating. Signals generated through the TCR alone are insufficient for full activation of the T cell and one or more secondary or costimulatory signals are also required. Thus, T cell activation comprises a primary stimulation signal through the TCR/CD3 complex and one or more secondary costimulatory signals. Co-stimulation can be evidenced by proliferation and/or cytokine production by T cells that have received a primary activation signal, such as stimulation through the CD3/TCR complex or through CD2.

As used herein, a resting T cell means a T cell that is not dividing or producing cytokines. Resting T cells are small (approximately 6-8 microns) in size compared to activated T cells (approximately 12-15 microns).

As used herein, a primed T cell is a resting T cell that has been previously activated at least once and has been removed from the activation stimulus for at least about 1 hour, at least about 2 hours, at least about 3 hours, at least about 4 hours, at least about 5 hours, at least about 6 hours, at least about 12 hours, at least about 24 hours, at least about 48 hours, at least about 60 hours, at least about 72 hours, at least about 84 hours, at least about 96 hours, at least about 108 hours, or at least about 120 hours. Alternatively, resting may be carried out within a period of from about 0.5 hour to about 120 hours, about 0.5 hour to about 108 hours, about 0.5 hour to about 96 hours, about 0.5 hour to about 84 hours, about 0.5 hour to about 72 hours, about 0.5 hour to about 60 hours, about 0.5 hour to about 48 hours, about 0.5 hour to about 36 hours, about 0.5 hour to about 24 hours, about 0.5 hour to about 18 hours, about 0.5 hour to about 12 hours, about 0.5 hour to about 6 hours, about 1 hour to about 6 hours, about 2 hours to about 5 hours, about 3 hours to about 5 hours, or about 4 hours to about 5 hours. Primed T cells usually have a memory phenotype.

A population of T cells may be induced to proliferate by activating T cells and stimulating an accessory molecule on the surface of T cells with a ligand, which binds the accessory molecule. Activation of a population of T cells may be accomplished by contacting T cells with a first agent which stimulates a TCR/CD3 complex-associated signal in the T cells. Stimulation of the TCR/CD3 complex-associated signal in a T cell may be accomplished either by ligation of the T cell receptor (TCR)/CD3 complex or the CD2 surface protein, or by directly stimulating receptor-coupled signalling pathways. Thus, an anti-CD3 antibody, an anti-CD2 antibody, or a protein kinase C activator in conjunction with a calcium ionophore may be used to activate a population of T cells.

To induce proliferation, an activated population of T cells may be contacted with a second agent, which stimulates an accessory molecule on the surface of the T cells. For example, a population of CD4+ T cells can be stimulated to proliferate with an anti-CD28 antibody directed to the CD28 molecule on the surface of the T cells. Alternatively, CD4+ T cells can be stimulated with a natural ligand for CD28, such as B7-1 and B7-2. The natural ligand can be soluble, on a cell membrane, or coupled to a solid phase surface. Proliferation of a population of CD8+ T cells may be accomplished by use of a monoclonal antibody ES5.2D8, which binds to CD9, an accessory molecule having a molecular weight of about 27 kD present on activated T cells. Alternatively, proliferation of an activated population of T cells can be induced by stimulation of one or more intracellular signals, which result from ligation of an accessory molecule, such as CD28.

The agent providing the primary activation signal and the agent providing the costimulatory agent can be added either in soluble form or coupled to a solid phase surface. In a preferred embodiment, the two agents may be coupled to the same solid phase surface.

Following activation and stimulation of an accessory molecule on the surface of the T cells, the progress of proliferation of the T cells in response to continuing exposure to the ligand or other agent, which acts intracellularly to simulate a pathway mediated by the accessory molecule, may be monitored. When the rate of T cell proliferation decreases, T cells may be reactivated and re-stimulated, such as with additional anti-CD3 antibody and a co-stimulatory ligand, to induce further proliferation. In one embodiment, the rate of T cell proliferation may be monitored by examining cell size. Alternatively, T cell proliferation may be monitored by assaying for expression of cell surface molecules in response to exposure to the ligand or other agent, such as B7-1 or B7-2. The monitoring and re-stimulation of T cells can be repeated for sustained proliferation to produce a population of T cells increased in number from about 100- to about 100,000-fold over the original T cell population.

The method of the present disclosure can be used to expand selected T cell populations for use in treating an infectious disease or cancer. The resulting T cell population can be genetically transduced and used for immunotherapy or can be used for in vitro analysis of infectious agents. Following expansion of the T cell population to sufficient numbers, the expanded T cells may be restored to the individual. The method of the present disclosure may also provide a renewable source of T cells. Thus, T cells from an individual can be expanded ex vivo, a portion of the expanded population can be re-administered to the individual and another portion can be frozen in aliquots for long term preservation, and subsequent expansion and administration to the individual. Similarly, a population of tumor-infiltrating lymphocytes can be obtained from an individual afflicted with cancer and the T cells stimulated to proliferate to sufficient numbers and restored to the individual.

The present disclosure may also pertain to compositions containing an agent that provides a costimulatory signal to a T cell for T cell expansion (e.g., an anti-CD28 antibody, B7-1 or B7-2 ligand), coupled to a solid phase surface which may additionally include an agent that provides a primary activation signal to the T cell (e.g., an anti-CD3 antibody) coupled to the same solid phase surface. These agents may be preferably attached to beads or flasks or bags. Compositions comprising each agent coupled to different solid phase surfaces (i.e., an agent that provides a primary T cell activation signal coupled to a first solid phase surface and an agent that provides a costimulatory signal coupled to a second solid phase surface) may also be within the scope of this disclosure.

In an aspect, TAA peptides that are capable of use with the methods and embodiments described herein include, for example, those TAA peptides described in U.S. Publication 20160187351, U.S. Publication 20170165335, U.S. Publication 20170035807, U.S. Publication 20160280759, U.S. Publication 20160287687, U.S. Publication 20160346371, U.S. Publication 20160368965, U.S. Publication 20170022251, U.S. Publication 20170002055, U.S. Publication 20170029486, U.S. Publication 20170037089, U.S. Publication 20170136108, U.S. Publication 20170101473, U.S. Publication 20170096461, U.S. Publication 20170165337, U.S. Publication 20170189505, U.S. Publication 20170173132, U.S. Publication 20170296640, U.S. Publication 20170253633, U.S. Publication 20170260249, U.S. Publication 20180051080, and U.S. Publication No. 20180164315, the contents of each of these publications and sequence listings described therein are herein incorporated by reference in their entireties.

In an aspect, T cells described herein selectively recognize cells which present a TAA peptide described in one of more of the patents and publications described above.

In another aspect, TAA that are capable of use with the methods and embodiments described herein include at least one selected from SEQ ID NO: 1 to SEQ ID NO: 157.

| SEQ ID NO: | Amino Acid Sequence |
|---|---|
| 1 | YLYDSETKNA |
| 2 | HLMDQPLSV |
| 3 | GLLKKINSV |
| 4 | FLVDGSSAL |
| 5 | FLFDGSANLV |
| 6 | FLYKIIDEL |
| 7 | FILDSAETTTL |
| 8 | SVDVSPPKV |
| 9 | VADKIHSV |
| 10 | IVDDLTINL |
| 11 | GLLEELVTV |
| 12 | TLDGAAVNQV |
| 13 | SVLEKEIYSI |
| 14 | LLDPKTIFL |
| 15 | YTFSGDVQL |
| 16 | YLMDDFSSL |
| 17 | KVWSDVTPL |
| 18 | LLWGHPRVALA |
| 19 | KIWEELSVLEV |
| 20 | LLIPFTIFM |
| 21 | FLIENLLAA |
| 22 | LLWGHPRVALA |
| 23 | FLLEREQLL |
| 24 | SLAETIFIV |
| 25 | TLLEGISRA |
| 26 | ILQDGQFLV |
| 27 | VIFEGEPMYL |
| 28 | SLFESLEYL |
| 29 | SLLNQPKAV |
| 30 | GLAEFQENV |
| 31 | KLLAVIHEL |
| 32 | TLHDQVHLL |
| 33 | TLYNPERTITV |
| 34 | KLQEKIQEL |
| 35 | SVLEKEIYSI |
| 36 | RVIDDSLVVGV |
| 37 | VLFGELPAL |
| 38 | GLVDIMVHL |
| 39 | FLNAIETAL |
| 40 | ALLQALMEL |
| 41 | ALSSSQAEV |
| 42 | SLITGQDLLSV |
| 43 | QLIEKNWLL |
| 44 | LLDPKTIFL |
| 45 | RLHDENILL |
| 46 | YTFSGDVQL |
| 47 | GLPSATTTV |
| 48 | GLLPSAESIKL |
| 49 | KTASINQNV |
| 50 | SLLQHLIGL |
| 51 | YLMDDFSSL |
| 52 | LMYPYIYHV |
| 53 | KVWSDVTPL |
| 54 | LLWGHPRVALA |
| 55 | VLDGKVAVV |
| 56 | GLLGKVTSV |
| 57 | KMISAIPTL |
| 58 | GLLETTGLLAT |
| 59 | TLNTLDINL |
| 60 | VIIKGLEEI |
| 61 | YLEDGFAYV |
| 62 | KIWEELSVLEV |
| 63 | LLIPFTIFM |
| 64 | ISLDEVAVSL |
| 65 | KISDFGLATV |
| 66 | KLIGNIHGNEV |
| 67 | ILLSVLHQL |
| 68 | LDSEALLTL |
| 69 | VLQENSSDYQSNL |
| 70 | HLLGEGAFAQV |
| 71 | SLVENIHVL |
| 72 | YTFSGDVQL |
| 73 | SLSEKSPEV |

-continued

| SEQ ID NO: | Amino Acid Sequence |
|---|---|
| 74 | AMFPDTIPRV |
| 75 | FLIENLLAA |
| 76 | FTAEFLEKV |
| 77 | ALYGNVQQV |
| 78 | LFQSRIAGV |
| 79 | ILAEEPIYIRV |
| 80 | FLLEREQLL |
| 81 | LLLPLELSLA |
| 82 | SLAETIFIV |
| 83 | AILNVDEKNQV |
| 84 | RLFEEVLGV |
| 85 | YLDEVAFML |
| 86 | KLIDEDEPLFL |
| 87 | KLFEKSTGL |
| 88 | SLLEVNEASSV |
| 89 | GVYDGREHTV |
| 90 | GLYPVTLVGV |
| 91 | ALLSSVAEA |
| 92 | TLLEGISRA |
| 93 | SLIEESEEL |
| 94 | ALYVQAPTV |
| 95 | KLIYKDLVSV |
| 96 | ILQDGQFLV |
| 97 | SLLDYEVSI |
| 98 | LLGDSSFFL |
| 99 | VIFEGEPMYL |
| 100 | ALSYILPYL |
| 101 | FLFVDPELV |
| 102 | SEWGSPHAAVP |
| 103 | ALSELERVL |
| 104 | SLFESLEYL |
| 105 | KVLEYVIKV |
| 106 | VLLNEILEQV |
| 107 | SLLNQPKAV |
| 108 | KMSELQTYV |
| 109 | ALLEQTGDMSL |
| 110 | VIIKGLEEITV |
| 111 | KQFEGTVEI |

-continued

| SEQ ID NO: | Amino Acid Sequence |
|---|---|
| 112 | KLQEEIPVL |
| 113 | GLAEFQENV |
| 114 | NVAEIVIHI |
| 115 | ALAGIVTNV |
| 116 | NLLIDDKGTIKL |
| 117 | VLMQDSRLYL |
| 118 | KVLEHVVRV |
| 119 | LLWGNLPEI |
| 120 | SLMEKNQSL |
| 121 | KLLAVIHEL |
| 122 | ALGDKFLLRV |
| 123 | FLMKNSDLYGA |
| 124 | KLIDHQGLYL |
| 125 | GPGIFPPPPPQP |
| 126 | ALNESLVEC |
| 127 | GLAALAVHL |
| 128 | LLLEAVWHL |
| 129 | SIIEYLPTL |
| 130 | TLHDQVHLL |
| 131 | SLLMWITQC |
| 132 | FLLDKPQDLSI |
| 133 | YLLDMPLWYL |
| 134 | GLLDCPIFL |
| 135 | VLIEYNFSI |
| 136 | TLYNPERTITV |
| 137 | AVPPPPSSV |
| 138 | KLQEELNKV |
| 139 | KLMDPGSLPPL |
| 140 | ALIVSLPYL |
| 141 | FLLDGSANV |
| 142 | ALDPSGNQLI |
| 143 | ILIKHLVKV |
| 144 | VLLDTILQL |
| 145 | HLIAEIHTA |
| 146 | SMNGGVFAV |
| 147 | MLAEKLLQA |
| 148 | YMLDIFHEV |
| 149 | ALWLPTDSATV |

-continued

| SEQ ID NO: | Amino Acid Sequence |
|---|---|
| 150 | GLASRILDA |
| 151 | SYVKVLHHL |
| 152 | VYLPKIPSW |
| 153 | NYEDHFPLL |
| 154 | VYIAELEKI |
| 155 | VHFEDTGKTLLF |
| 156 | VLSPFILTL |
| 157 | HLLEGSVGV |

EXAMPLES

Example 1

Autologous T Cell Manufacturing Process

Figure 1B:
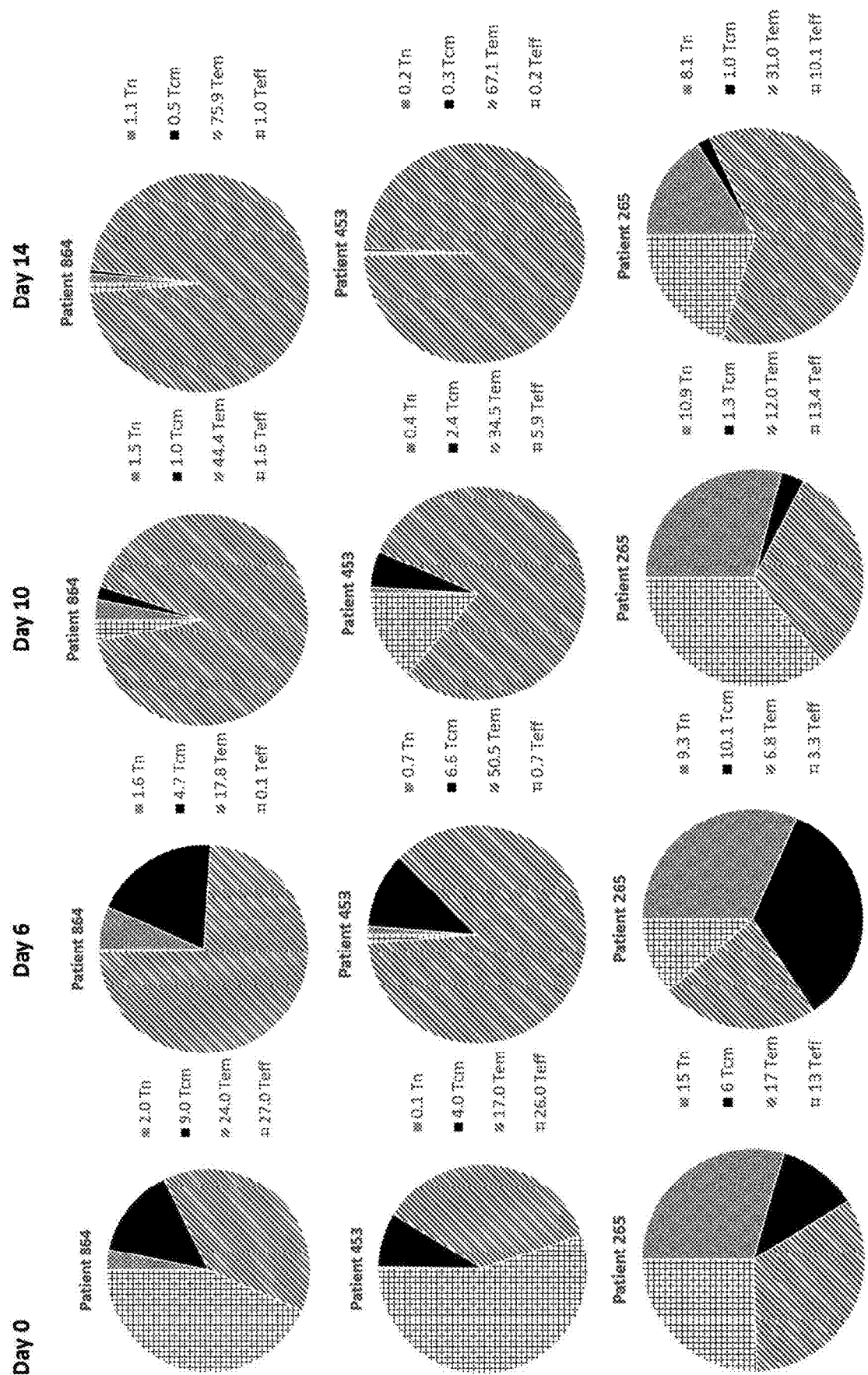

Adoptive cell transfer of purified naïve ($T_n$), stem cell memory ($T_{scm}$), and central memory ($T_{cm}$) T cell subsets causes superior tumor regression compared with transfer of the more-differentiated effector memory ($T_{em}$) and effector ($T_{eff}$) T cells. Traditional manufacturing process for an engineered T cell product may take 10-15 days long. However, a process longer than about 12 days, e.g., 14 days, may result in reduced potency of the cells, e.g., fewer more-effective $T_n$, $T_{scm}$, and $T_{cm}$ T cell subsets and more less-effective $T_{em}$ and $T_{eff}$ T cell subsets. For example, FIG. 1A shows prolonging ex vivo culturing of T cells, e.g., 14 days, from two healthy donors, e.g., donor 6 and donor 8, in which the desirable $T_{cm}$ T cell subsets were reduced from that cultured for 0, 6, or 10 days. On the other hand, the more differentiated and less persistent $T_{em}$ T cell subsets were increased from that cultured for 0, 6, or 10 days. FIG. 1B shows prolonging ex vivo culturing of T cells, e.g., 14 days, from three patients, e.g., patient 864, patient 453, and patient 265, in which the desirable $T_{cm}$ T cell subsets were reduced from that cultured for 0, 6, or 10 days. On the other hand, the more differentiated and less persistent $T_{em}$ T cell subsets were increased from that cultured for 0, 6, or 10 days.

Figure 2:
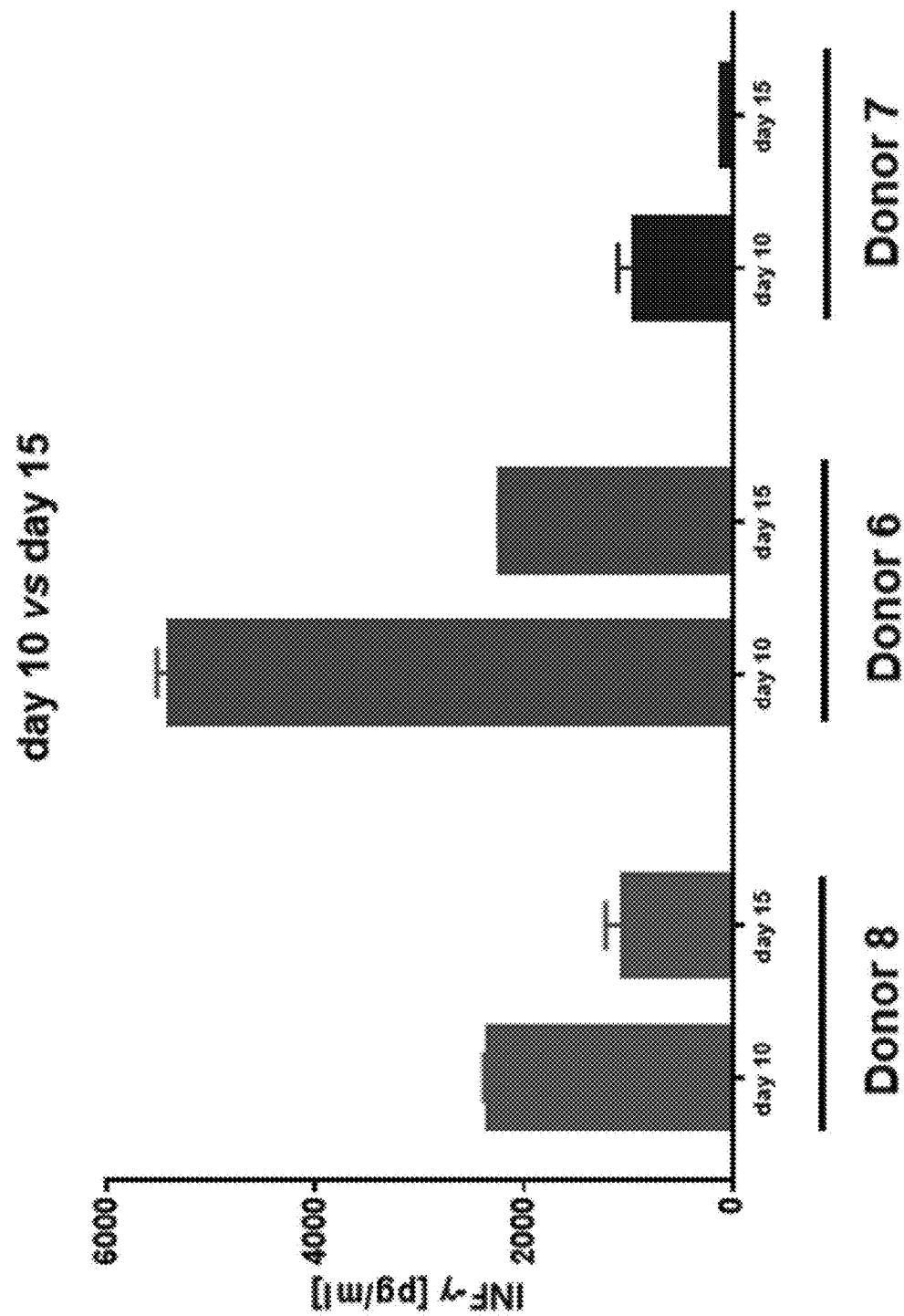
FIG. 2 shows reduction of IFN-γ secretion in cells grown on Day 15 as compared with that grown on Day 10 from different donors.

Fewer more-effective $T_n$, $T_{scm}$, and $T_{cm}$ T cell subsets may result in fewer effectively activated T cells that secret cytokines, e.g., interferon gamma (IN F-γ). FIG. 2 shows reduced INF-γ secretion by peripheral blood mononuclear cells (PBMC) obtained from three healthy donors, e.g., donor 6 (D 6), donor 7 (D7), and donor 8 (D8), activated and cultured for 15 days as compared with that activated and cultured for 10 days.

To shorten the manufacturing process, embodiments of the present disclosure include an about 7 to about 10-day process leading to the manufacturing of over 10 billion ($10 \times 10^9$) cells without the loss of potency. In addition, the concentrations of several raw materials may be optimized to reduce the cost of good by 30%.

Figure 3:
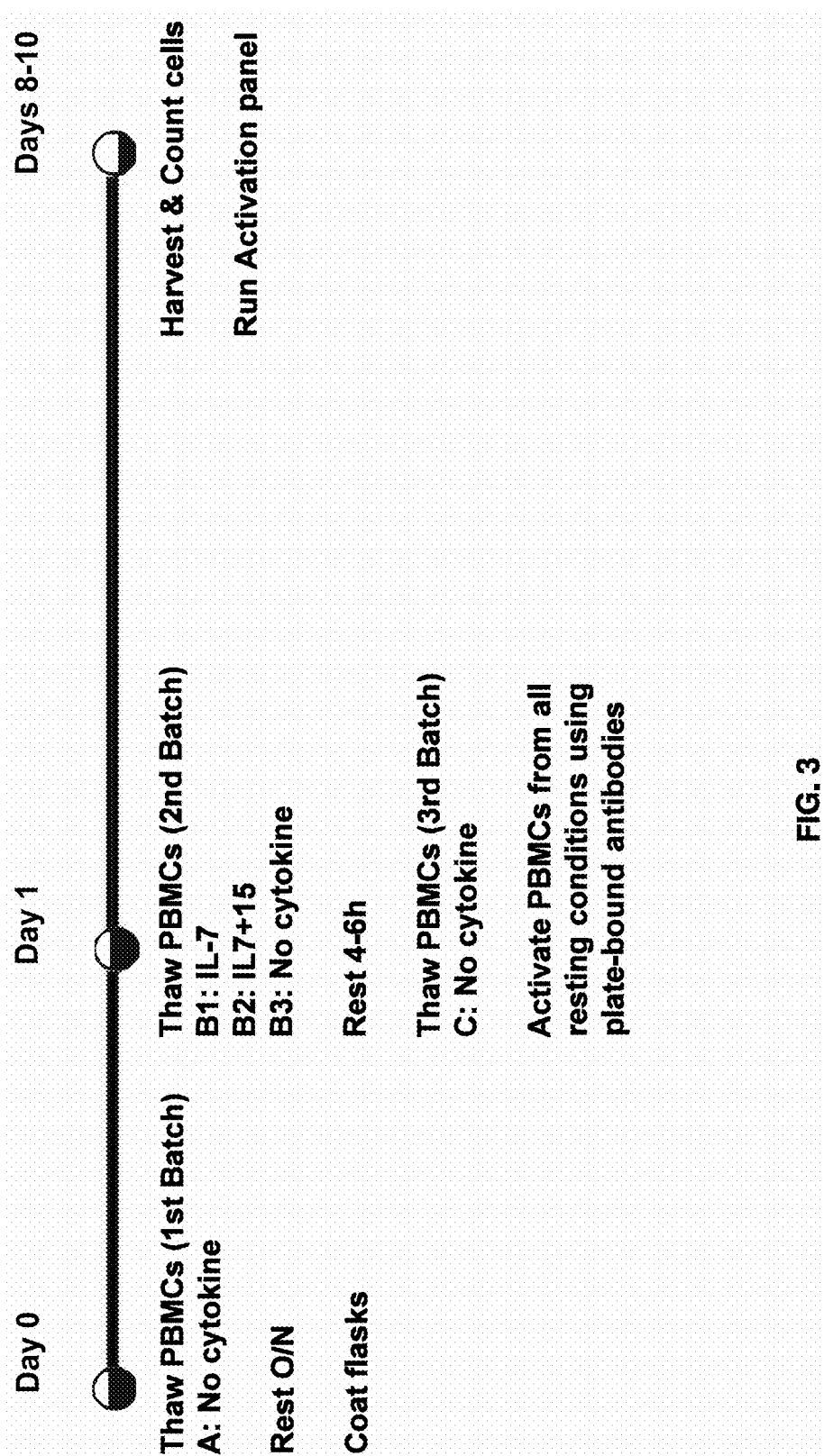
FIG. 3 shows an experimental design to test the effect of resting conditions on T cell activation and expansion.

Effect of Eliminating or Modifying Resting Conditions in Autologous T Cell Manufacturing Process on T Cell Activation FIG. 3 shows an experimental design used to test the effect of resting conditions on T cell activation and expansion. Briefly, group A represents a first batch of PBMC that were thawed on Day 0, followed by resting without cytokines overnight (O/N), i.e., 24 hours, followed by activating the rested PBMC with anti-CD3 and anti-CD28 antibodies immobilized on non-tissue culture treated plates. IL-7 is a homeostatic cytokine that promotes survival of T cells by preventing apoptosis. IL-7 may be added to PBMC during resting. Groups B1-B3 represent a second batch of PBMC that were thawed on Day 1, followed by resting in the presence of IL-7 (group B1) or in the presence of IL-7+IL-15 (group B2) or without cytokine (group B3) for 4-6 hours, followed by activating the rested PBMC with anti-CD3 and anti-CD28 antibodies immobilized on non-tissue culture treated plates. Group C represents a third batch of PBMC that were thawed on Day 1 (without resting and without cytokine), followed by activating the thawed PBMC with anti-CD3 and anti-CD28 antibodies immobilized on tissue culture plates. Cells may be harvested and counted on Day 8-10, followed by activation panel analysis.

CD25 and CD69 are activation markers on the surface of cytokine- or mitogen-activated lymphocytes. The binding and entry of the VSV-G pseudotyped lentiviral vectors, such as LV-R73, has been shown to be mediated by interaction of the VSV-G envelop protein with low density lipoprotein receptor (LDL-R) on the host cells. Resting T cells do not express LDL-R, however activation with anti-CD3 and anti-CD28 antibodies induces LDL-R expression on T cells and permits efficient lentiviral transduction. This suggests that kinetics of LDL-R expression regulated by level of activation can impact transduction efficiency with VSV-G lentiviral vector.

Figure 4:
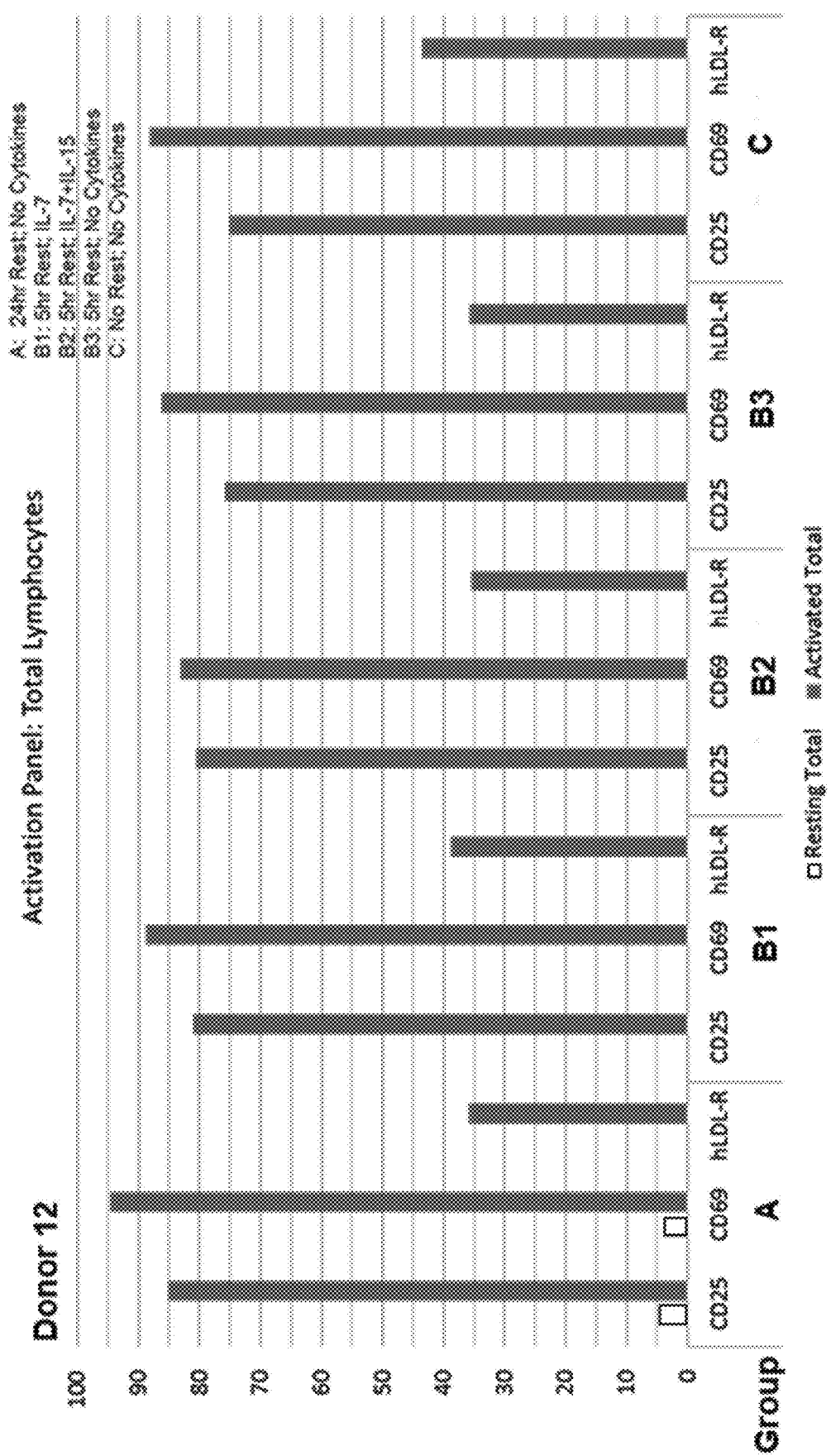
FIG. 4 shows CD25, CD69, and hLDL-R expression levels in different experimental groups.

FIG. 4 shows CD25, CD69, and hLDL-R expression levels among groups A, B1-B3, and C are comparable, indicating that the time for resting may be shortened, e.g., from 24 hours to 4-6 hours, without significantly reducing T cell activation.

Figure 5A:
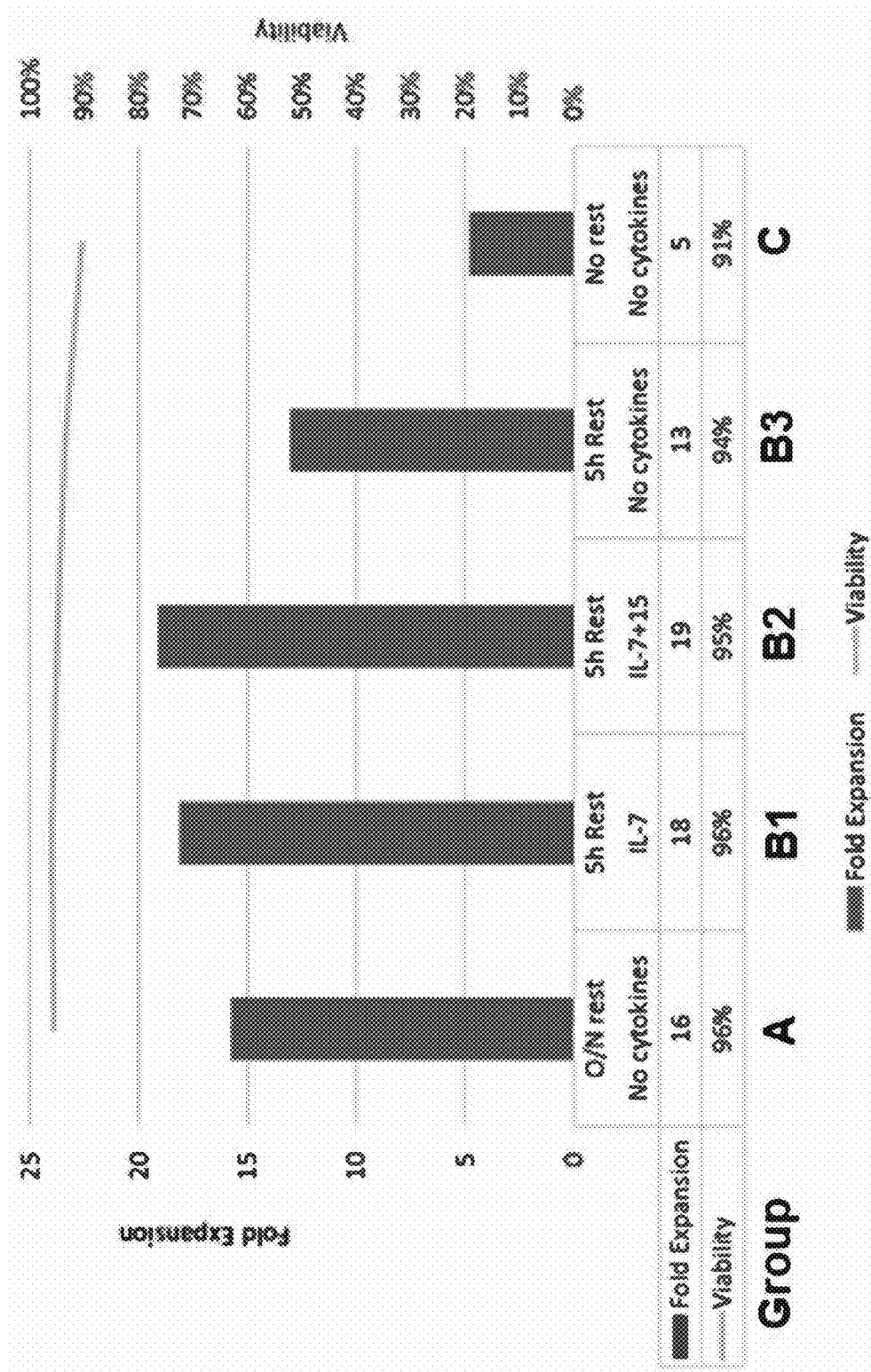
FIGS. 5A and 5B show fold expansion and cell viability in different experimental groups on Day 7 expansion and Day 10 expansion, respectively.
Figure 5B:
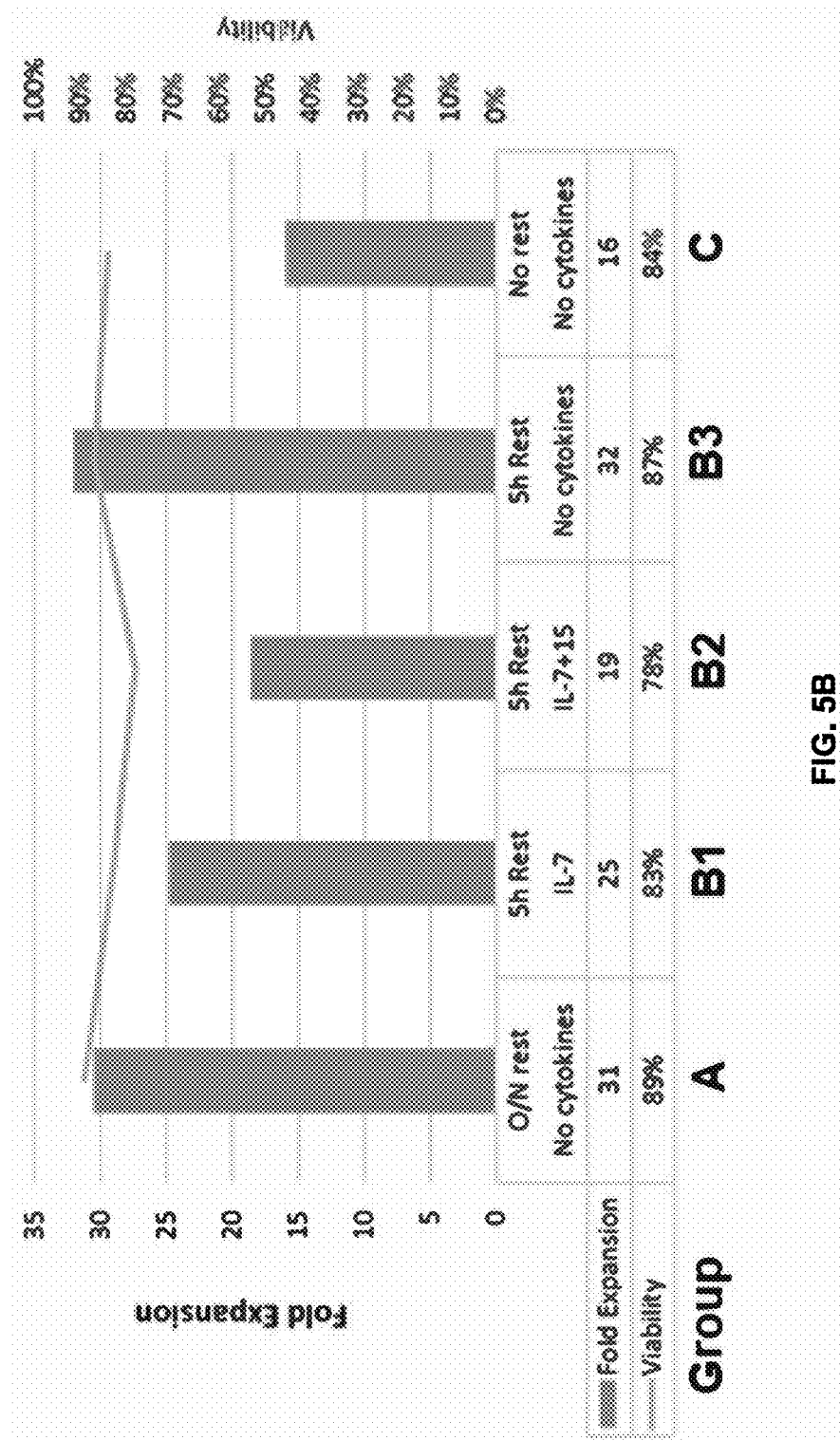

Effect of Eliminating or Modifying Resting Conditions in Autologous T Cell Manufacturing Process on T Cell Expansion FIGS. 5A and 5B show fold expansion and cell viability in groups A and B1-B3 are comparable on Day 7 expansion and Day 10 expansion, respectively. Group C, which is without resting, however, has the least fold expansion on Day 7 expansion (5-fold) (FIG. 5A) and Day 10 expansion (16-fold) (FIG. 5B). These results suggest that the time for resting may be shortened, e.g., from 24 hours to 4-6 hours, without significantly reducing T cell expansion.

Figure 6:
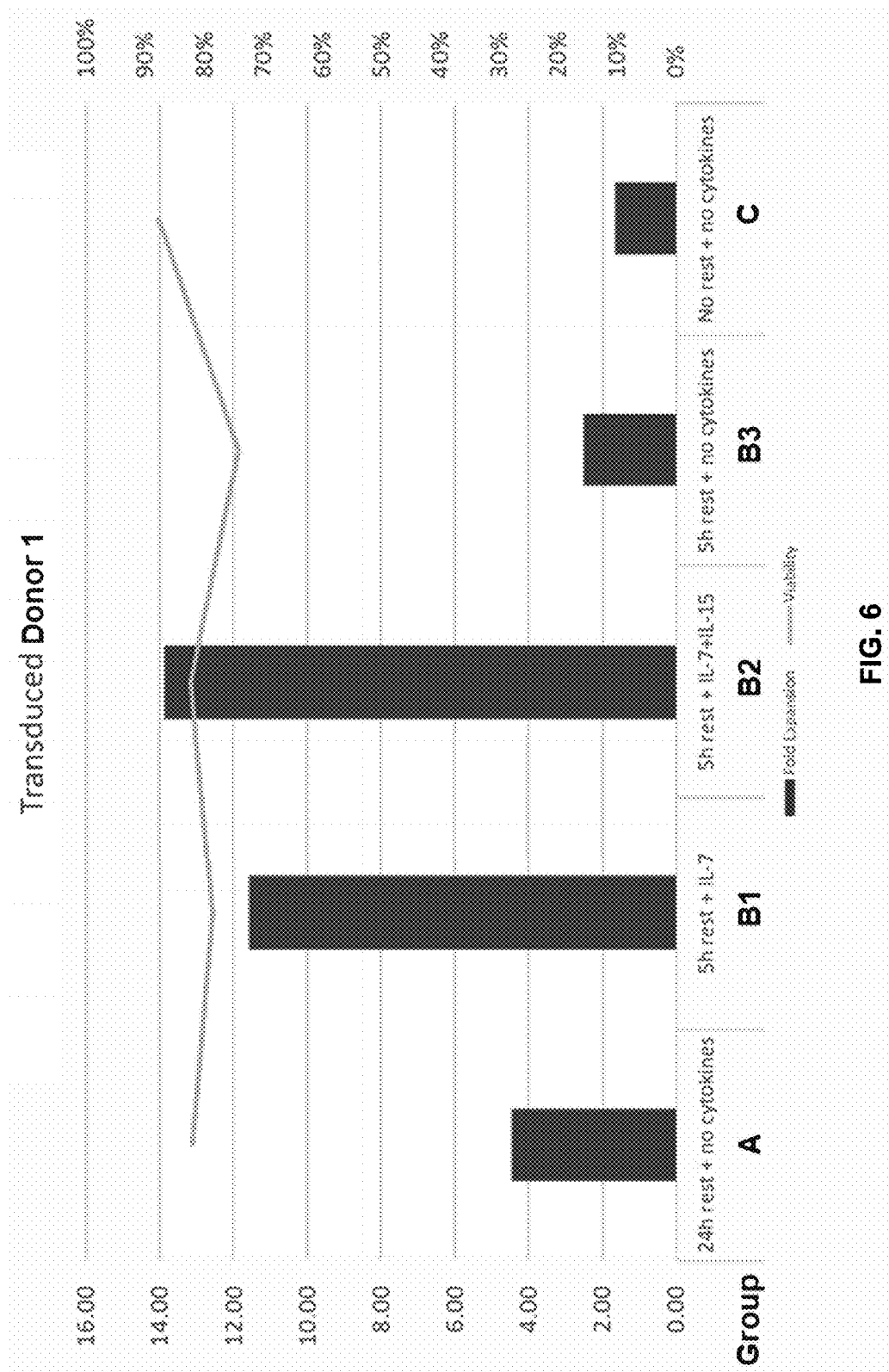
FIG. 6 shows fold expansion and viability of activated T cells transduced with a viral vector in different experimental groups on Day 9.
Figure 7:
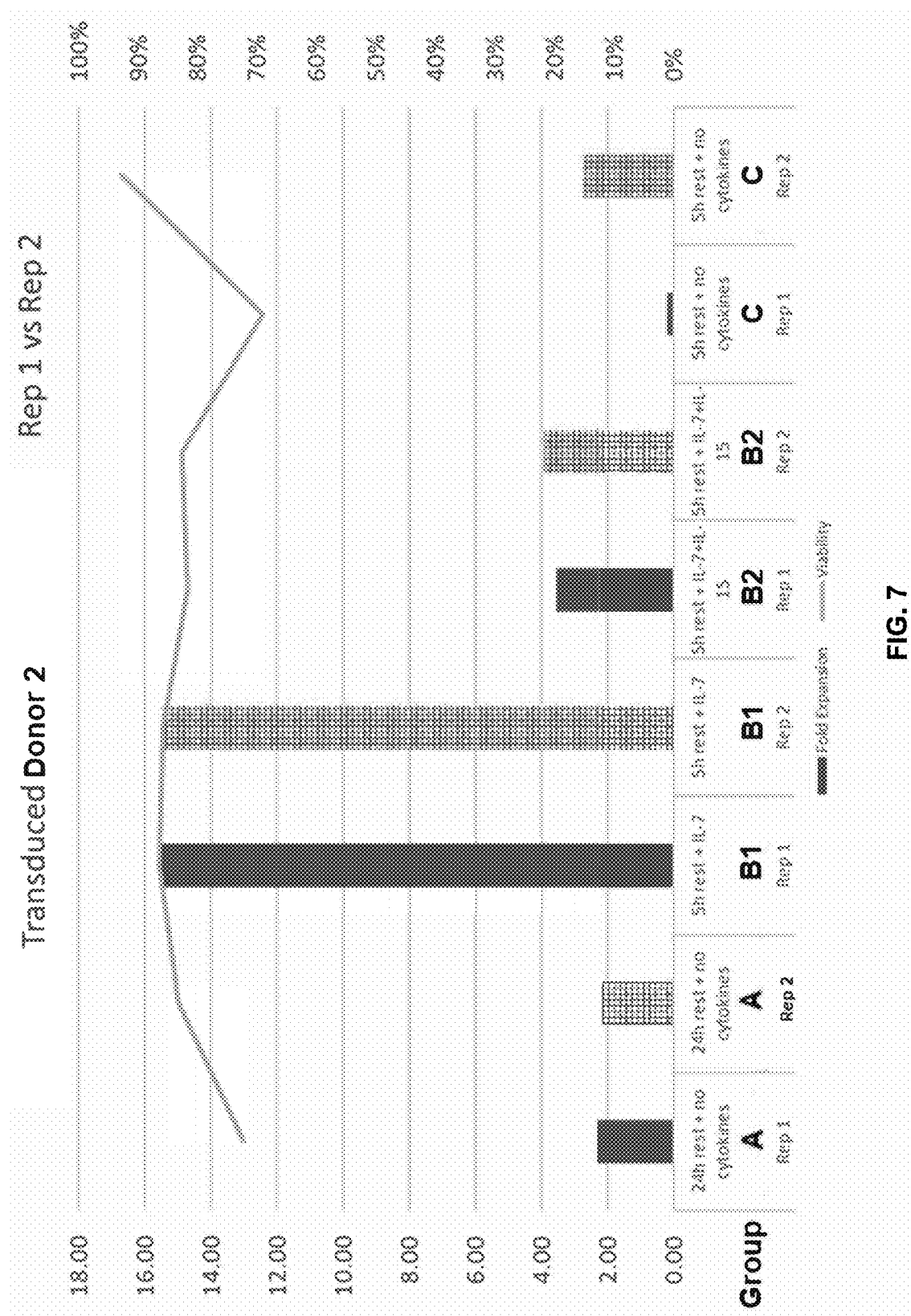
FIG. 7 shows fold expansion and viability of activated T cells transduced with a viral vector in different experimental groups on Day 9.

FIGS. 6 and 7 show fold expansion and viability of activated T cells transduced with a viral vector expressing TCR, e.g., LV-R73, in 2 donors, i.e., donor 1 (FIG. 6) or donor 2 (FIG. 7), in groups A, B1-B3, and C on Day 9 expansion. Groups B1 and B2 show better cell expansion than groups A, B3, and C, indicating that brief resting time, e.g., 5 hours, in the presence of cytokines, e.g., IL-7 or IL-7+IL-15, may increase expansion of transduced T cells. Rep1 and Rep2 represent two replicates. These results support use of shortened resting time, e.g., from 24 hours to 4-6 hours, in autologous T cell manufacturing process in the presence of cytokines, e.g., IL-7 and/or IL-15, without significantly reducing T cell expansion.

Figure 8:
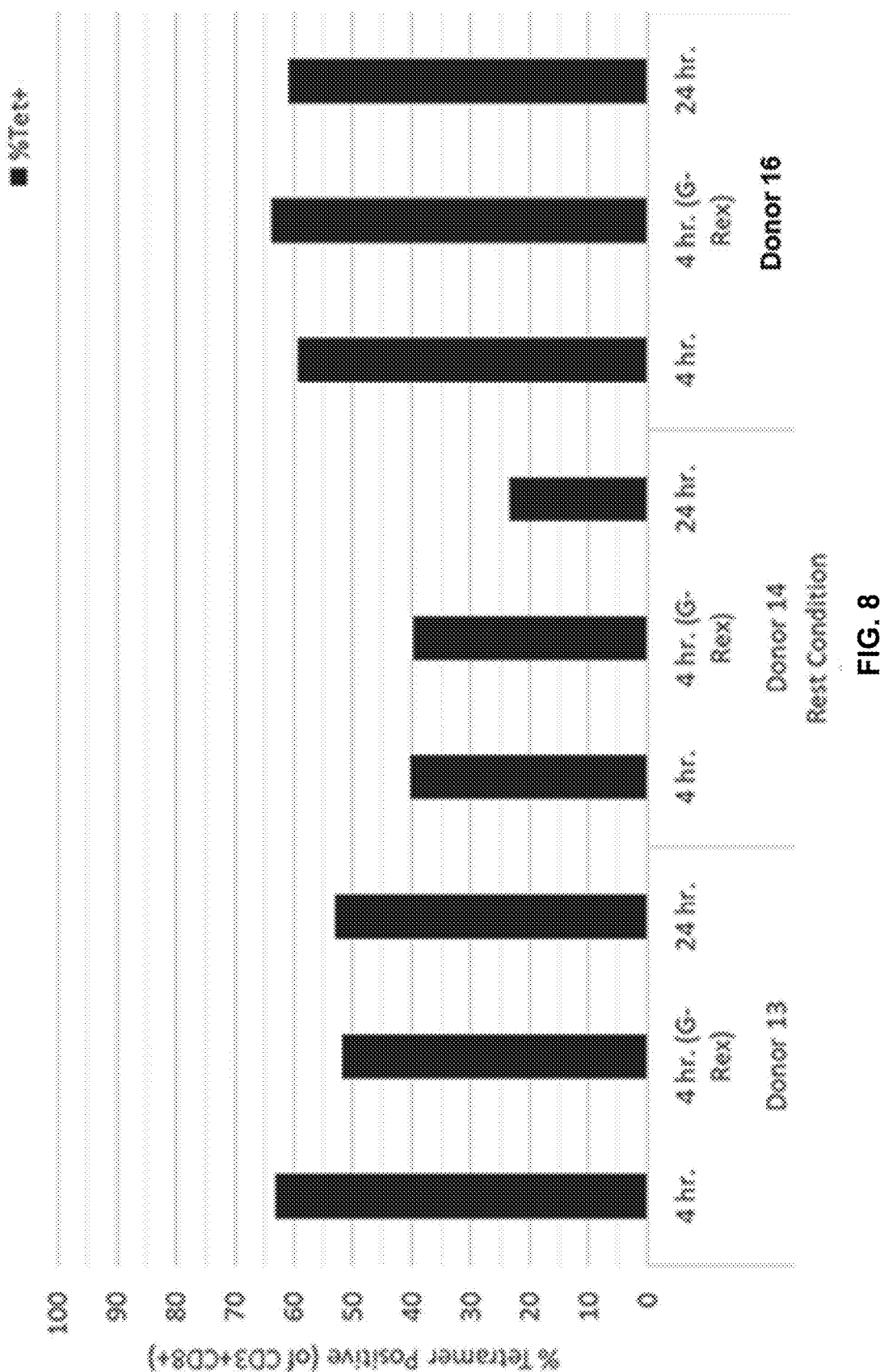
FIG. 8 shows transgene expression in T cells resulting from different resting time and in different scale production.

Effect of Eliminating or Modifying Resting Conditions in Autologous T Cell Manufacturing Process on Transgene Expression in T Cells Using peptide/MHC complex-loaded tetramers to detect T cells expressing transduced TCR that specifically binds peptide/MHC complex, FIG. 8 shows comparable transgene expression, e.g., recombinant TCR expression, in T cells rested for 4 hours (with IL-7) and 24 h (without cytokine) in a T75 tissue culture flask or 4 hours (with IL-7) in G-Rex 100 flask in a large-scale production run for donor 13, donor 14, and donor 16. These results suggest that the resting time may be shortened, e.g., from 24 hours to 4-6 hours in a scale-up manufacturing process, without significantly reducing transgene expression in transduced T cells. In addition, use of one G-Rex 100 flask can simplify the resting process further by replacing multiple T75 flasks.

Figure 9:
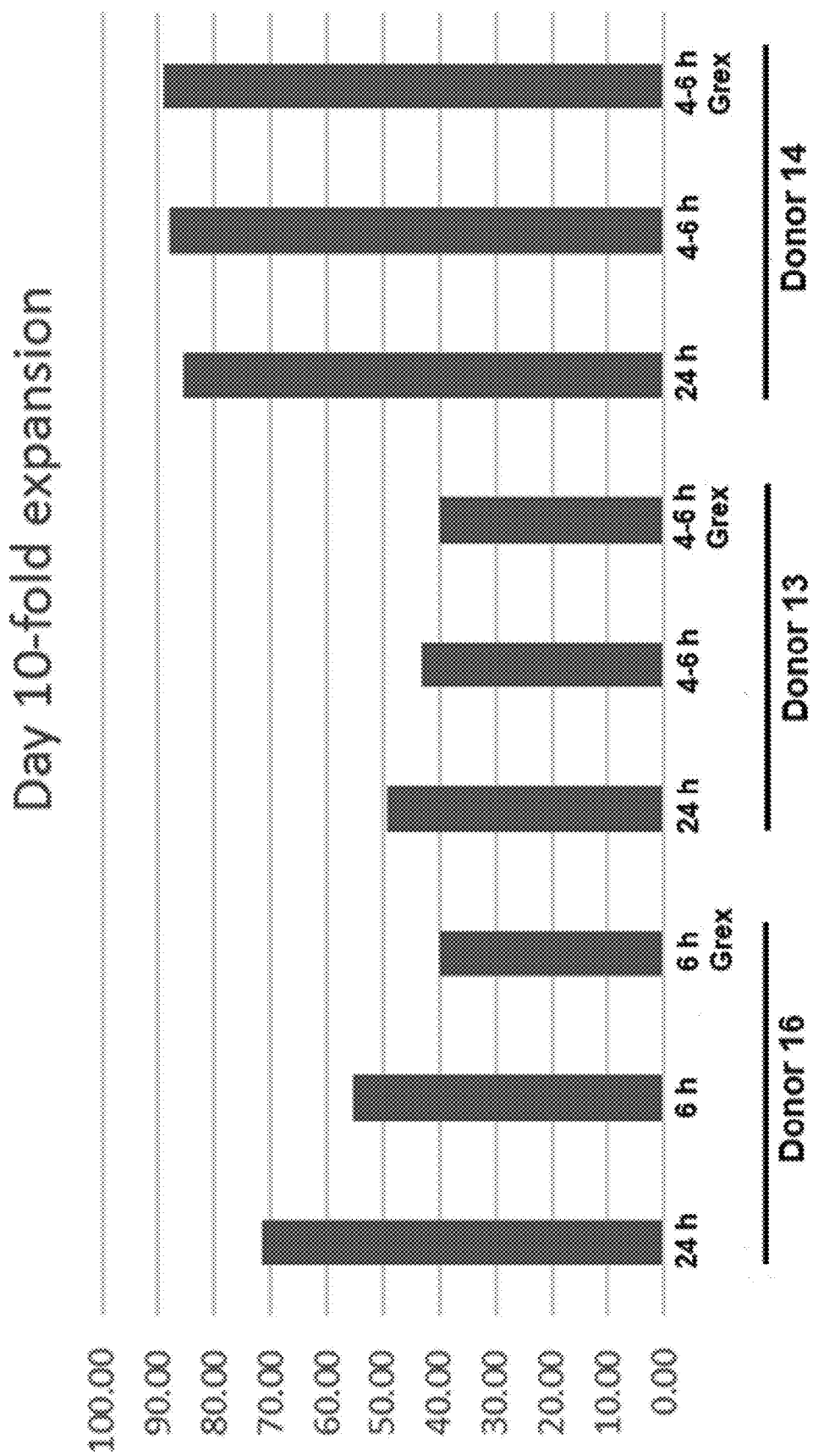
FIG. 9 shows fold expansion on Day 10 resulting from different resting time and in different scale production.

FIG. 9 shows comparable fold expansion on Day 10 expansion in T cells rested for 4-6 hours, 6 hours, or 24 hours in small scale or large-scale production for donor 13, donor 14, and donor 16. These results suggest that the resting time may be shortened, e.g., from 24 hours to 4-6 hours in a scale-up manufacturing process, without significantly impacting the expansion of transduced T cells.

Effect of Concentration of Anti-CD3 and Anti-CD28 Antibodies in Autologous T Cell Manufacturing Process on T Cell Activation Activation is an important step in autologous T cell manufacturing processes because both transduction efficiency and rate of expansion rely on T cell activation. Stimulation of T cells via engagement of CD3 receptor and a co-receptor, such as CD28, using antibodies is a common method of activating T cells. T cell activation serves as a preparatory step for transduction with viral vectors, such as lentiviral vector.

Figure 10:
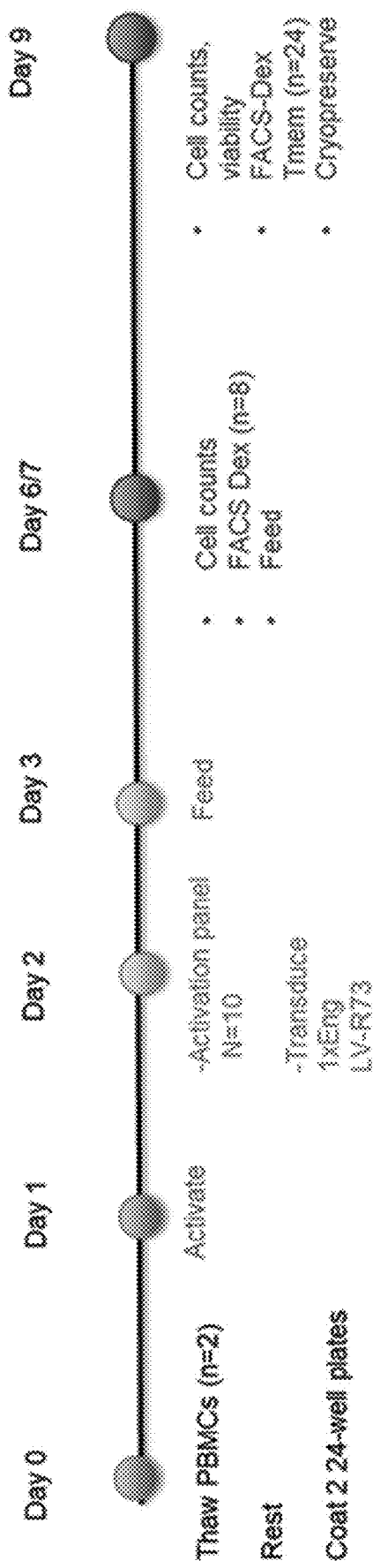
FIG. 10 shows an experimental design to test the effect of concentration of anti-CD3 and anti-CD28 antibodies on T cell activation.

FIG. 10 shows an experimental design used to test the effect of concentration of anti-CD3 and anti-CD28 antibodies on T cell activation. Briefly, on Day 0, PBMC were thawed and cultured or rested without activation cytokines overnight or 24 hours. On Day 1, the rested PBMC were activated by incubating them in two 24-well plates coated with different concentrations, e.g., 0.1 µg/ml, 0.25 µg/ml, 0.5 µg/ml, 1.0 µg/ml, of anti-CD3 and anti-CD28 antibodies in the presence of IL-7+IL-15. On Day 2, the activated T cells were analyzed for CD25, CD69, and hLDL-R expression and transduced with VSV-G pseudotyped lentiviral vectors, e.g., 1xEng LV-R73. On Day 6/7 and 9, analyses, such as cell counts, viability, and fluorescence-activated cell sorting (FACS) with dextramers (Dex), which are multimers based on a dextran backbone bearing multiple fluorescein and peptide/MHC complexes for detecting T cells expressing recombinant TCR, were performed.

Figure 11:
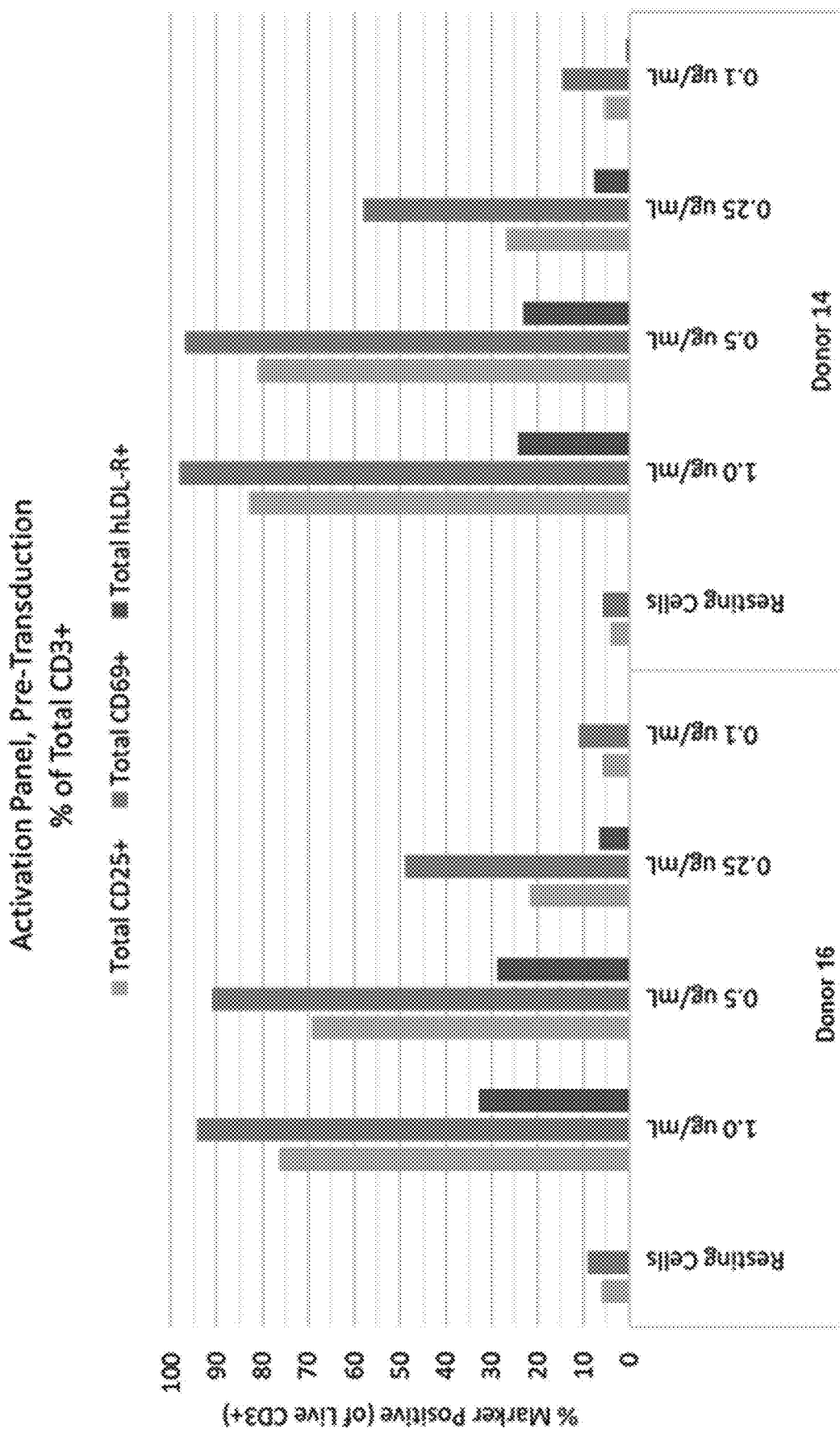
FIG. 11 shows CD25, CD69, and hLDL-R expression in T cells activated by different concentrations of anti-CD3 and anti-CD28 antibodies.

FIG. 11 shows, prior to viral transduction, T cells activated with 0.5 µg/ml and 1.0 µg/ml of anti-CD3 and anti-CD28 antibodies have comparable levels of CD25, CD69, and hLDL-R expression within each donor 16 and donor 14. However, these expression levels are significantly higher than those from T cells activated with lower concentrations, e.g., 0.1 µg/ml and 0.25 µg/ml, of anti-CD3 and anti-CD28 antibodies. These results suggest that the concentration of anti-CD3 and anti-CD28 antibodies may be reduced, e.g., from 1.0 µg/ml to 0.5 µg/ml, without significantly reducing T cell activation.

Figure 12:
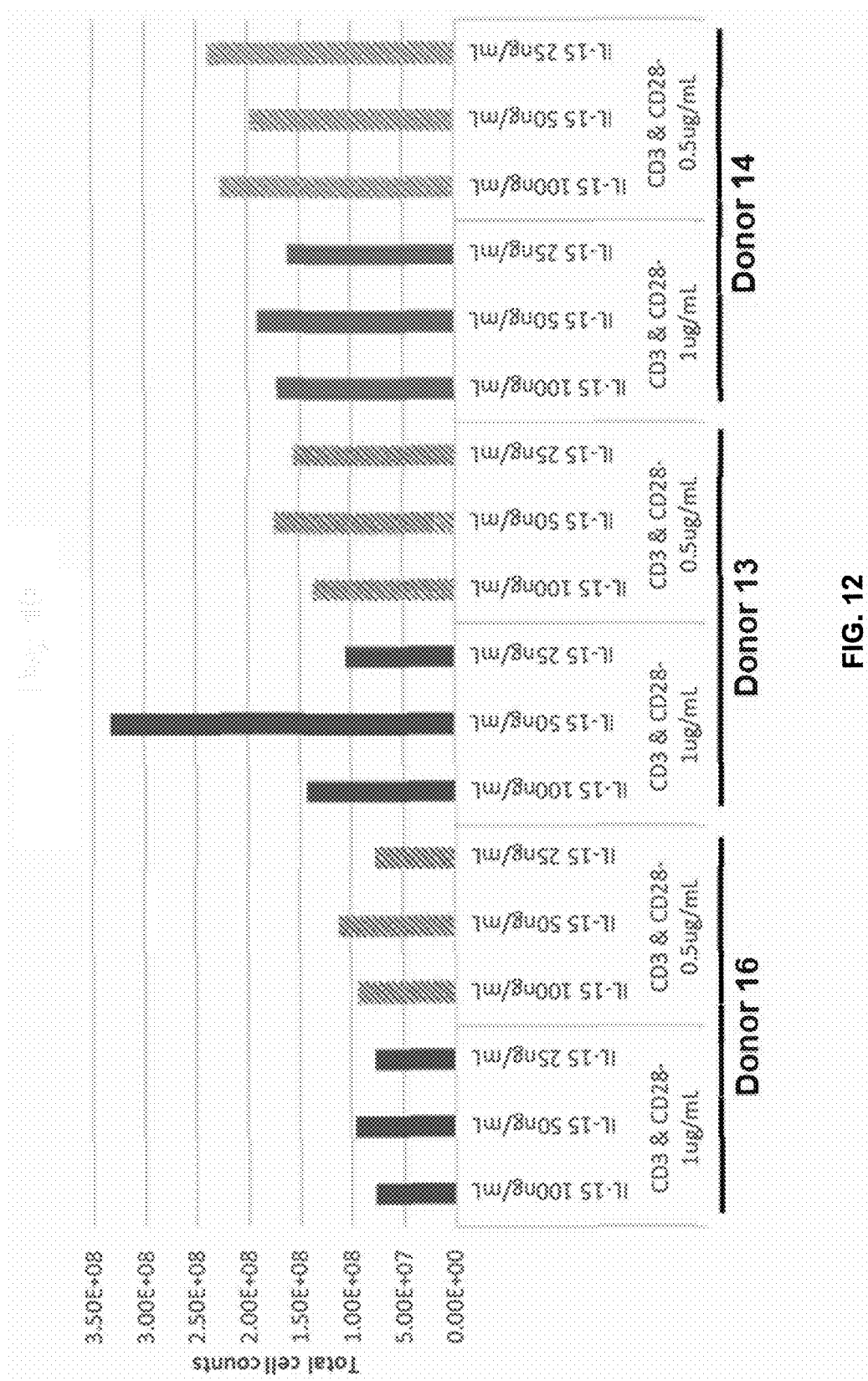
FIG. 12 shows, on Day 10 expansion, cell counts of T cells activated by different concentrations of anti-CD3 and anti-CD28 antibodies in the presence of different concentrations of IL-15.

Effect of Concentration of Anti-CD3 and Anti-CD28 Antibodies and Cytokines in Autologous T Cell Manufacturing Process on T Cell Expansion FIG. 12 shows, on Day 10 expansion, cell counts of T cells activated by 0.5 µg/ml or 1.0 µg/ml of anti-CD3 and anti-CD28 antibodies in the presence of different concentrations, e.g., 25 ng/ml, 50 ng/ml, or 100 ng/ml, of IL-15 are comparable within each donor 16, donor 13, and donor 14. These results suggest that the concentration of anti-CD3 and anti-CD28 antibodies may be reduced, e.g., from 1.0 µg/ml to 0.5 µg/ml, and the concentration of IL-15 may be reduced, e.g., from 100 ng/ml to 25 ng/ml, without significantly reducing T cell expansion.

Figure 13:
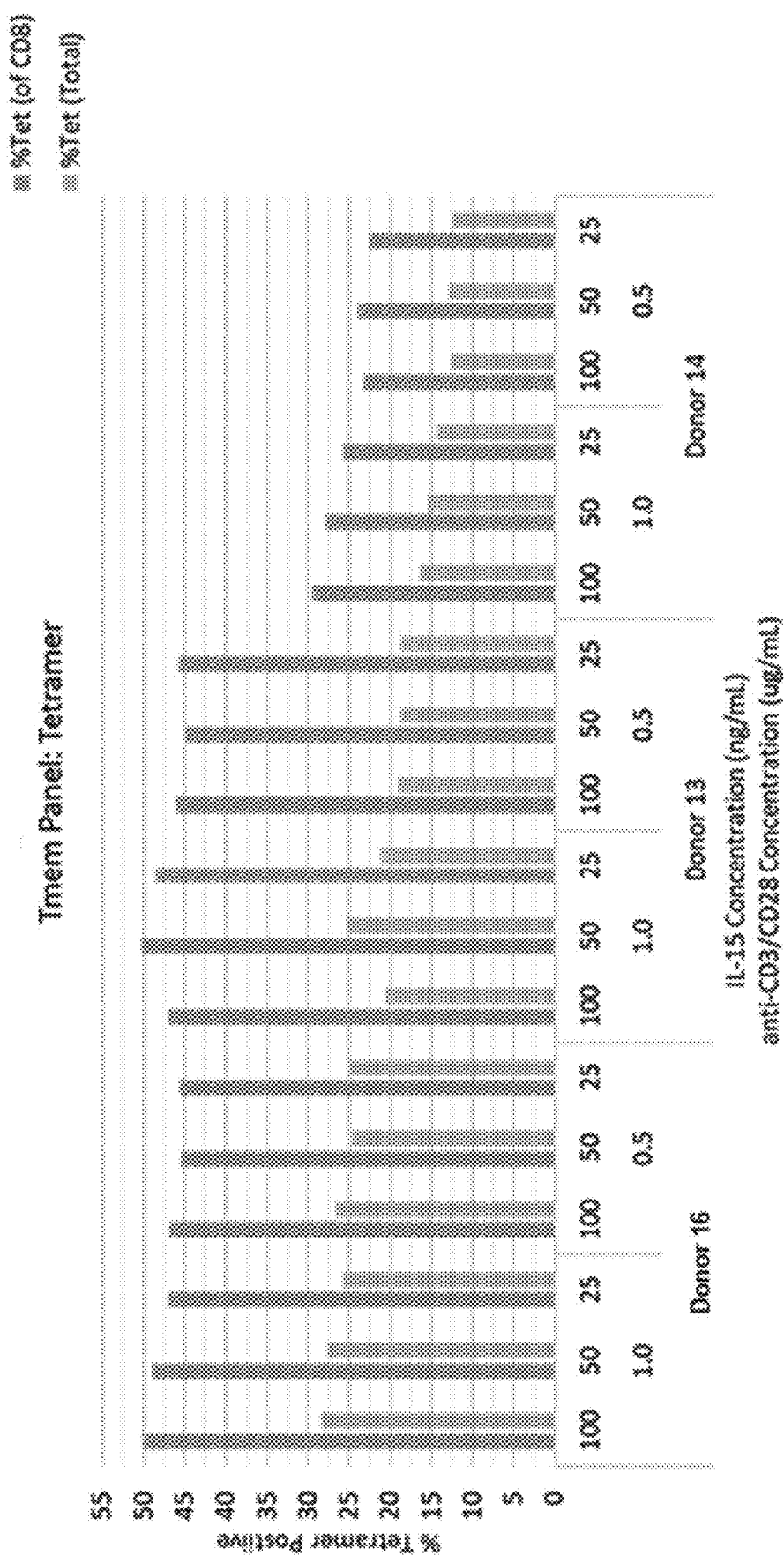
FIG. 13 shows tetramer staining of recombinant TCR-transduced T cells activated by different concentrations of anti-CD3 and anti-CD28 antibodies in the presence of different concentrations of IL-15.

FIG. 13 shows tetramer staining of recombinant TCR-transduced T cells activated by 0.5 µg/ml or 1.0 µg/ml of anti-CD3 and anti-CD28 antibodies in the presence of different concentrations, e.g., 25 ng/ml, 50 ng/ml, or 100 ng/ml, of IL-15 are comparable within each donor 16, donor 13, and donor 14. These results suggest that the concentration of anti-CD3 and anti-CD28 antibodies may be reduced, e.g., from 1.0 µg/ml to 0.5 µg/ml, and the concentration of IL-15 may be reduced, e.g., from 100 ng/ml to 25 ng/ml, without significantly reducing viral transduction of T cells.

Together, these results suggest that (1) resting time after thawing PBMC can be shortened, e.g., from 24 hours to 4-6 hours, without significantly reducing T cell activation, transgene expression, and T cell expansion; and (2) concentrations of anti-CD3 and anti-CD28 antibodies can be reduced, e.g., from 1.0 µg/ml to 0.5 µg/ml, and concentrations of cytokines can be reduced, such as IL-15, e.g., from 100 ng/ml to 25 ng/ml, without significantly reducing T cell activation, transgene expression, and T cell expansion.

Effect of Duration of Activation in Autologous T Cell Manufacturing Process on Transduction Efficiency with Lentiviral Vector One of the major goals of developing an autologous T cell manufacturing process is to improve the rate of transduction achieved in primary human T cells with the lentiviral construct encoding TCR. Unlike gamma retroviruses that can transduce only dividing cells, lentiviruses, in theory, can transduce both dividing and non-dividing cells. However, transducing resting T cells with lentiviruses have yielded poor transduction efficiencies. Activation of T cells has been shown to facilitate their transduction with a lentivirus. Thus, stimulation of T cells with anti-CD3 and anti-CD28 antibodies in immobilized, beads or soluble form, has become a pre-requisite for performing lentiviral transduction and is a standard part of manufacturing genetically modified T cells for adoptive cell therapy.

Because the T cell activation step plays a critical role in preparing T cells for transduction, the effective duration of activation with anti-CD3 and anti-CD28 antibodies may need to be optimized.

To determine the optimal duration of activation, a time course study evaluating the effect of different duration of activation on transduction efficiency was performed. The results show that optimal window for transducing T cells may be after 16-24 h of activation with anti-CD3 and anti-CD28 antibodies. Thus, time for T-cell activation prior to transduction may be reduced from 48 h to 16-24 h for all further process development and clinical manufacturing.

In another embodiment of the present disclosure, for fresh PBMC, i.e., not frozen, resting may not be needed. Thus, fresh PBMC, without resting, may be activated by anti-CD3 antibody and anti-CD28 antibody, followed by viral vector transduction to obtain transduced T cells.

Although methods of transducing T cells may involve sequential steps of activating T cells in tissue culture, followed by transferring the activated T cells to different tissue culture, in which transducing activated T cells with viral vectors takes place, activating and transducing steps, however, may be carried out concurrently. For example, while T cells are being activated by anti-CD3 and anti-CD28 antibodies, transducing activated T cells may be carried out simultaneously in the same culture. By doing so, the entire T cell transducing process, i.e., from providing PBMC to obtaining transduced T cells, may be shortened to, for example, 3-4 days.

Example 2

Determine Optimal Duration of T Cell Activation for the Improvement of Transduction Efficiency with Lentiviral Construct PBMC from healthy donors were activated using anti-CD3 and anti-CD28 antibodies for different time intervals in preparation for transduction. Activated T cells from PBMC were treated with concentrated supernatants generated using different lentiviral constructs expressing TAA targeting R7P1 D5 TCR. Transduced cells were expanded in the presence of IL-7 and IL-15. The products were compared based on R7P1 D5 TCR transgene expression as determined by flow cytometry using specific dextramer/tetramer.

Representative Materials and Methods

| Supplies | Manufacturer | Catalog # |
| --- | --- | --- |
| TexMACS media | Miltenyi Biotec | 130-097-196 |
| Human AB Serum | Gemini | 100-512 |
| PBS/EDTA | Lonza | BE02-017F |
| IL-7 | Peprotech | 200-07 |
| IL-15 | Peprotech | 200-15 |
| Anti-CD3 antibody | Ebioscience | 16-0037-85 |
| Anti-CD28 antibody | Ebioscience | 16-0289-85 |
| 24-well non-tissue culture plates | Co-star | 3738 |
| G-Rex 24-well plate | Wilson Wolf | 80192M |
| 15 mL Conical Tube | Falcon | 352097 |
| 50 ml conical tube | Corning | 430290 |
| 5 mL serological Pipet | BD | 53300-421 |
| 10 mL serological Pipet | BD | 53300-523 |
| 25 ml serological pipet | BD | 53300-567 |
| 1000 ul pipet tips | Rainin | 17007954 |
| 200 ul pipet tips | Rainin | 17007961 |
| 20 µL pipet tips | Rainin | 17007957 |
| 1.5 mL Microcentrifuge Tube | Fisher | 02-681-5 |
| AOPI Staining Solution | Nexcelom | CS2-0106 |
| PBS without Mg and Ca | Lonza | 17-516F/24 |
| 96 well plate | Corning | 3799 |
| P-20 Micropipettor | Rainin | 17014382 |
| P-200 Micropipettor | Rainin | 17014391 |
| P-1000 Micropipettor | Rainin | 17017382 |
| Pipettaid | Drummond | 193970L |
| T75 flasks | BD Falcon | BD353136 |
| T25 flask | Corning | 430372 |
| Benzonase | Sigma | E1014 |
| Protamine sulfate | McKesson | 804514 |
| Lentivirus | Lentigen | LV-R73, R78, R72, R22 |
| Live/Dead Aqua dye | Thermo Fisher | L-34966 |
| ABC Comp Beads | Thermo Fisher | A10497 |
| CD3-BV421 | BD | 562426 |
| CD8-APC | Biolegend | 301014 |
| TAA Tetramer-PE | Immatics | N/A |

Representative Methods

To compare different durations of T cell activation, representative experiments described herein were carried out following standard small-scale T cells generation process involving, for example, 4 steps: thaw/rest, activation, transduction and expansion.

Thaw and Rest

Frozen PBMC from healthy donors (n=3, D3, D4, D9) were thawed in warm TexMACS media supplemented with 5% human AB serum. Cells were treated with benzonase nuclease (50 U/ml) for 15 minutes at 37° C., washed, counted, and put to overnight rest in complete TexMACS media.

Activation

On a day when cells are thawed, 24-well non-tissue culture plates were coated with anti-CD3 and anti-CD28 antibodies diluted in PBS (1 µg/mL), sealed and incubated overnight at 4° C. Next day, rested PBMCs were harvested, counted, washed and resuspended at the concentration of $1 \times 10^6$/ml. Antibody solution was aspirated, and wells were washed with complete media followed by addition of $2 \times 10^6$ cells to each well. Activation was carried out at 37° C. for the specified time intervals.

Transduction

Activated T cells were harvested, washed and counted. Transduction mixtures containing concentrated virus supernatants, protamine sulfate (10 µg/ml), IL-7 (10 ng/ml) and IL-15 (100 ng/ml) were prepared. For each transduction, $1.0 \times 10^6$ cells were separated in a sterile microcentrifuge tube and centrifuged at 400×g for 5 minutes. Each cell pellet was resuspended in 0.5 ml of the transduction mixture corresponding to a specific MOI. Cell suspension was placed in an appropriately labelled well of a 24-well G-Rex plate. After 24 hours of incubation at 37° C. and 5% $CO_2$, 1.5 ml media supplemented with IL-7 (10 ng/ml) and IL-15 (100 ng/ml) was added to each well. Ninety-six-hour post-transduction, transgene expression was determined by flow cytometry. Multimeric MHC-peptide complexes (Dextramer or Tetramer) were used to monitor surface expression of transgenic TCR by FACS.

Flow Cytometry

Briefly, $1.0 \times 10^6$ cells transduced at given lentiviral Multiplicity of Infection (MOI) were stained following the work instructions. For tetramer staining, cells were incubated with 1 µl of TAA tetramer in 50 µl of Flow buffer for 15 minutes at RT in the dark. Tetramer staining was followed by staining with antibodies for T cells surface markers (e.g., CD3, CD4, CD8, etc). Samples were acquired with auto-compensation matrix derived from compensation beads.

Results

PBMC obtained from 2 donors (D3 and D4) were activated for 16, 24 and 48 hours using plate-bound anti-CD3 and CD28 antibodies. Cells were transduced with 3 different lentiviral constructs (R72, R21, and R22).

Figure 14A:
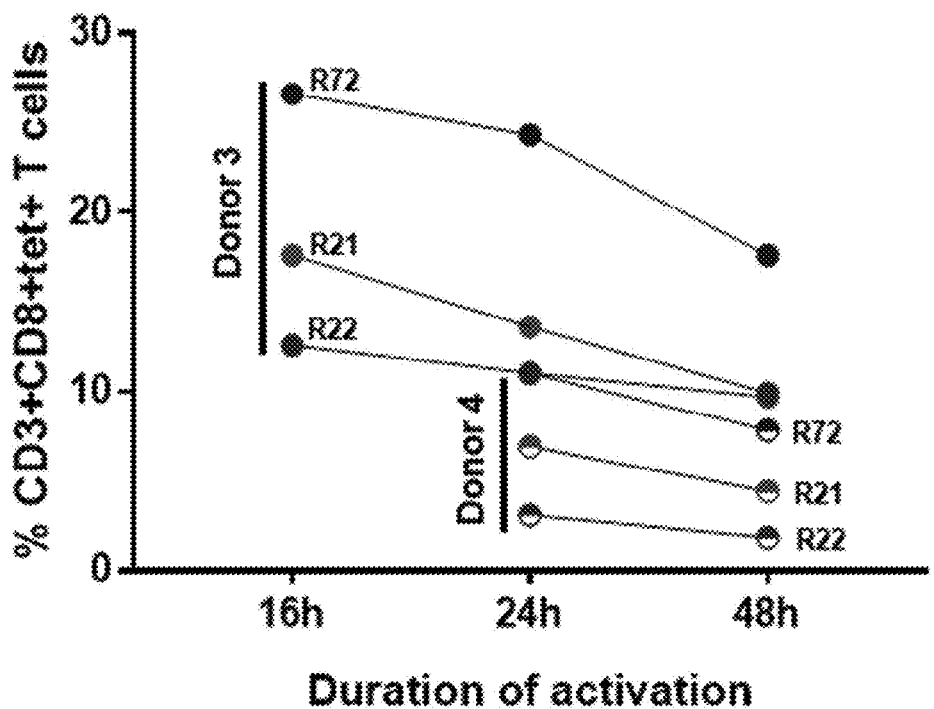
FIG. 14A shows the percentage of $CD3^+CD8^+Tetramer^+$ T cells resulting from different durations of activation.

FIG. 14A shows % $CD3^+CD8^+Tetramer^+$ T cells gradually decrease with the increase in the duration of activation in the order of 16 h>24 h>48 h. This order was consistently observed for both tested constructs and donors.

A time course study was performed to determine the optimal duration of activation for viral transduction that may result in high transgene expression. PBMC from one donor (D9) were activated with plate-bound anti-CD3 and anti-CD28 antibodies for the specified duration of activation, e.g., from 0 to 48 hours, and transduced with each of two different lentiviral constructs encoding R7P1 D5 TCR, i.e., LV-R73 and LV-R78.

Figure 14B:
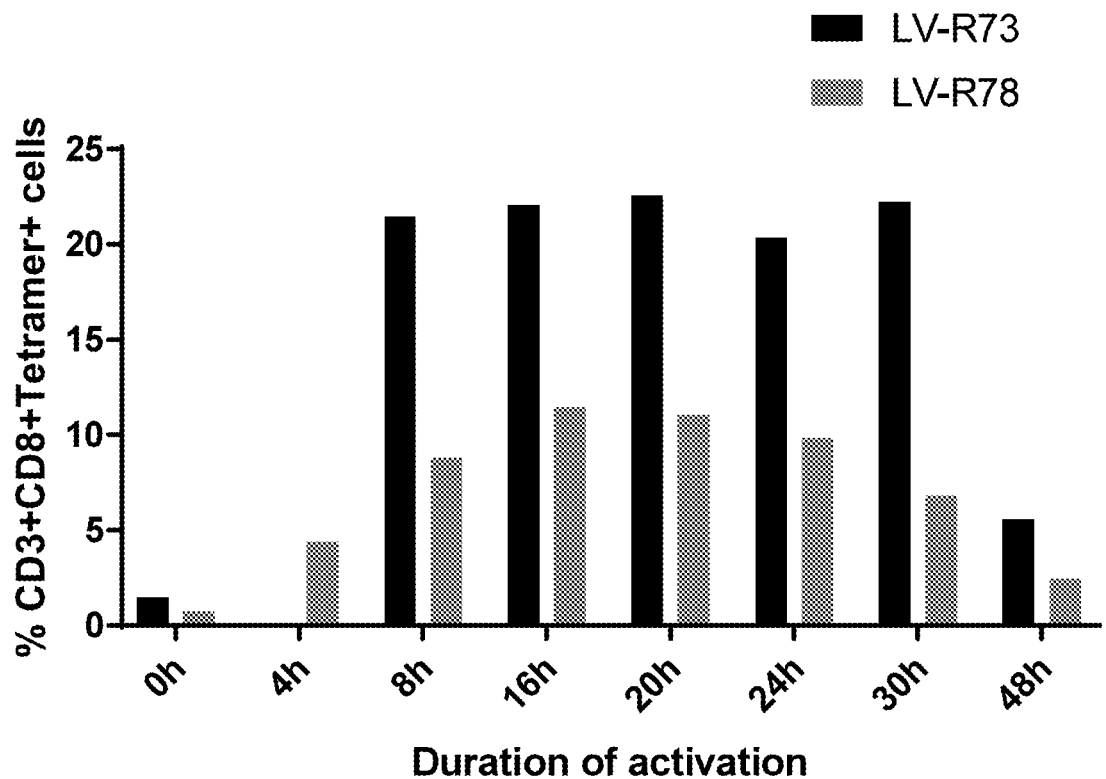
FIG. 14B shows transgene expression resulting from different durations of activation.

FIG. 14B shows transgene expression to be highest in cells activated for 16-20 hours. Results represent level of transgene expression measured as % $CD3^+CD8^+Tetramer^+$ T cells by flow cytometry 96-hour post transduction. The window for optimal activation was determined to be about 16 to about 20 hours and may be extended to the maximum for 24 hours to add flexibility to GMP manufacturing.

Overall, these results may explain one of the causes of low transduction rates observed in T cells activated for 48 hours and show that shorter activation for 16 to 24 hours may be optimal for performing lentiviral transduction. Although, robust expansion achieved by 48-hour activation may be impacted by limiting the activation time to 16 to 24 hours, this change can be considered highly beneficial for the product and implemented for all further process development and into the clinical manufacturing.

Example 3

Like all bioprocesses, scaling up of T cell manufacturing is a challenging part of the process development. Maintaining T cell function and quality to preserve product efficacy is of prime importance through all stages of scale up. For autologous T cell manufacturing process, the present inventors identified the critical steps and divided the scale-up into two parts: scale up of activation may be carried out on a non-tissue culture surface and scale up of transduction and expansion may be carried out in a G-Rex device.

Although beads or soluble antibodies present simpler methods to activate cells that are easily scalable, autologous T cell manufacturing processes which use immobilized antibodies on a non-tissue culture surface (24-well plate) for activation yielded the best transduction and expansion rates with the lentivirus. However, harvesting activated cells from multiple 24-well non-tissue culture antibody coated plates posed to be a laborious, time-consuming step that added complexity to an otherwise simple process. Considering activating up to $1 \times 10^9$ PBMC, for example, approximately 20 plates and 480 manipulations may be required to harvest activated cells in each manufacturing run.

Conventional methods of activating T cells may include an open-system and a labor-intensive process using either commercially available beads or non-tissue culture treated 24-well or 6-well plates coated with anti-CD3 and anti-CD28 antibodies ("plate-bound") at a concentration of 1 ug/mL each. Open system methods, however, may take a relatively long time, e.g., about 8 hours, to complete. To simplify the open-system and the labor-intensive process, embodiments of the present disclosure may include a straightforward process adaptable to a closed-system that can be combined with containers, e.g., bags, of commercially available closed system, e.g., G-Rex™ system and Xuri™ cell expansion system, resulting in comparable T cell activation profile, transducibility of T cells, and functionality of the end-product with that of T cells activated using the conventional methods. In addition, methods of the present disclosure, e.g., flask-bound method, may take a relatively short time, e.g., about 1 hour, to complete, which is about 8 times faster than the conventional methods.

Optimizations for developing the autologous T cell manufacturing process were performed at a small scale using 24-well non-tissue culture plates for activation and 24-well G-Rex plates for transduction and expansion. At this scale, 1-2 million T cells transduced on Day 2 underwent from 30-fold to 40-fold expansion until Day 10 to yield 30-80 million cells at the time of harvest. However, the goal of the final process may be to transduce 250-400 million activated cells and expand them to over 10 billion viable $CD3^+$ T cells keeping the manufacturing timeline of 10 days. Therefore, in an aspect, scaling up of entire process is provided herein.

For embodiments of the present disclosure including methods of activating larger number of cells, non-tissue culture treated T175 cm² flasks provide a larger surface area and simpler platform requiring very few manipulations. After optimization, use of flask-bound antibodies for activating T cells resulted in expansion and transduction comparable to plate-bound antibodies. Thus, scale up of the activation step was a major development in simplifying the autologous T cell manufacturing process for clinical manufacturing. Based on greater cell numbers, transduction and expansion were scaled up from G-Rex-24 well plate to G-Rex 100. Use of G-Rex devices may facilitate nearly linear scale up of post-activation steps especially in terms of seeding density. Other parameters, such as number of feeds and splits, may be standardized to achieve maximum expansion rates and viability. Validation of the entire scaled up process in full scale PD runs ensure successful technology transfer of the T Cell Product #1 process in GMP.

Plate-Bound Versus Flask-Bound

T cell activation followed by transduction and expansion are critical steps of T cell manufacturing. To optimize the conditions for scaling up of these steps, use of T175 cm² flasks presented a suitable platform for activation with larger surface area and fewer manipulations to replace 24-well plates coated with anti-CD3 and anti-CD28 antibodies. In a comparative study following optimization of critical parameters in T175 cm² flasks, cells activated using antibodies coated on a flask (flask-bound) showed comparable levels of activation, transduction, and expansion to cells activated using antibodies coated on 24-well plates (plate-bound) in multiple donors.

Further, transduction and expansion steps were scaled up from small scale (G-Rex-24 well plate) to mid-scale (2-6 G-Rex10 or 1 G-Rex100) to full scale (5-8 G-Rex100). The entire scaled-up process may be validated in 2 full scale Process Development (PD) runs. All products generated using the final process passed the clinical release criteria in terms of % $Dex^+$ $CD3^+CD8^+$ cells and generated cell numbers sufficient to meet the clinical doses.

Comparison Between T Cells Activated by the Plate-Bound Method and the Flask-Bound Method (a Non-Tissue Culture Treated Flask is Coated with Anti-CD3 and Anti-CD28 Antibodies) with Respect to Activation Level (Flow Cytometry), Transducibility (Dextramer Staining, FACS), Expansion (Cell Counts), and Functionality (IFN-γ ELISA)

PBMC from healthy donors were activated using anti-CD3 and anti-CD28 antibodies using non-tissue culture treated T175 cm² flasks or 24-well plates in preparation for transduction. Activated T cells were transduced with a lentiviral construct encoding R7P1 D5 TCR and seeded in G-Rex 24-well plates or G-Rex10/G-Rex100 flasks. Transduced T cells were expanded in the presence of IL-7 and IL-15 and harvested on Day 10 of the process. In-process and final testing were performed on the products to determine cell counts, viability and percentage of transduced $CD8^+$ T cells.

Representative Materials and Methods

| Supplies | Manufacturer | Catalog # |
|---|---|---|
| TexMACS media | Miltenyi Biotec | 130-097-196 |
| Human AB Serum | Gemini | 100-512 |
| IL-7 | Peprotech | 200-07 |
| IL-15 | Peprotech | 200-15 |
| Anti-CD3 antibody | Ebioscience | 16-0037-85 |
| Anti-CD28 antibody | Ebioscience | 16-0289-85 |
| 24-well non-tissue culture plates | Co-star | 3738 |
| T175 cm² non-tissue culture plates | Corning | 431466 |
| G-Rex 24-well plate | Wilson Wolf | 80192M |
| G-Rex10 | Wilson Wolf | 80040S |
| G-Rex100 | Wilson Wolf | 80500S |
| 15 mL Conical Tube | Falcon | 352097 |
| 50 ml conical tube | Corning | 430290 |
| 5 mL serological Pipet | BD | 53300-421 |
| 10 mL serological Pipet | BD | 53300-523 |
| 25 ml serological pipet | BD | 53300-567 |
| 1000 ul pipet tips | Rainin | 17007954 |
| 200 ul pipet tips | Rainin | 17007961 |
| 20 μL pipet tips | Rainin | 17007957 |
| 1.5 mL Microcentrifuge Tube | Fisher | 02-681-5 |
| AOPI Staining Solution | Nexcelom | CS2-0106 |
| PBS without Mg and Ca | Lonza | 17-516F/24 |
| 96 well plate | Corning | 3799 |
| P-20 Micropipettor | Rainin | 17014382 |
| P-200 Micropipettor | Rainin | 17014391 |
| P-1000 Micropipettor | Rainin | 17017382 |
| Pipettaid | Drummond | 193970L |
| T75 flasks | BD Falcon | BD353136 |
| Benzonase | Sigma | E1014 |

-continued

| Supplies | Manufacturer | Catalog # |
|---|---|---|
| Protamine sulfate | McKesson | 804514 |
| Lentivirus | Lentigen | LV-R73, R78 |
| Live/Dead Aqua dye | Thermo Fisher | L-34966 |
| ABC Comp Beads | Thermo Fisher | A10497 |
| CD3-BV421 | BD | 562426 |
| CD8-APC | Biolegend | 301014 |
| CD4-PerCPCy5.5 | BD | 560650 |
| TAA Dextramer-PE | Immudex | N/A |

Methods

Experiments were carried out following the standard autologous T cell manufacturing process involving 4 steps: thaw/rest, activation, transduction, and expansion, however at different scales.

Thaw and Rest

Frozen PBMC from healthy donors were thawed in warm TexMACS media supplemented with 5% human AB serum (complete media). Cells were treated with benzonase nuclease (50 U/ml) for 15 minutes at 37° C., washed, counted and put to overnight rest in complete TexMACS media.

Activation

On the day of thawing cells, 24-well non-tissue culture plates or T175 cm$^2$ flasks were coated with anti-CD3 and anti-CD28 antibodies diluted in PBS (1 µg/mL), sealed and incubated overnight at 4° C. Next day, rested PBMCs were harvested, counted, washed and resuspended at the concentration of 1×10$^6$/ml. Antibody solution was aspirated, and wells were washed with complete media followed by addition of 2×10$^6$ cells to each well. Activation was carried out at 37° C. for the specified time intervals.

Transduction

Activated T cells were harvested, washed and counted. Transduction mixtures containing preclinical lentiviral supernatants (calculated based on a specified MOI), protamine sulfate (10 µg/ml) and IL-7 (10 ng/mL) and IL-15 (100 ng/mL). For each transduction, activated cells were separated and centrifuged at 400×g for 5 minutes. Each cell pellet was resuspended in the transduction mixture (1 ml per 2×10$^6$ cells) and seeded in an appropriately sized G-Rex flask. After 24 hours of incubation at 37° C. and 5% $CO_2$, culture volume in each G-Rex flask was brought to half or full capacity as specified using media supplemented with IL-7 (10 ng/ml) and IL-15 (100 ng/ml). Cell counts and viability were monitored regularly up to Day 10 of the process. Multimeric MHC-peptide complexes (Dextramer or Tetramer) were used to monitor surface expression of transgenic TCR by FACS.

Flow Cytometry

Briefly, 1.0×10$^6$ transduced cells were stained following the work instructions. Tetramer staining was followed by staining with antibodies for T cells surface markers. Samples were acquired with auto-compensation matrix derived from compensation beads.

Results

To evaluate non-tissue culture treated T175 cm$^2$ flasks as an alternative to 24-well plates for coating anti-CD3 and anti-CD28 antibodies to activate T cells, the antibody concentration was kept the same as in small scale, other parameters such as coating volume, cell density, and seeding volume were optimized for a larger area in a flask.

To compare viability and expression of activation markers CD25 and CD69 and LDL-R in plate-bound (PB) and flask-bound (FB) activated PBMC, FACS staining and acquisition were performed 16-24 hours post-activation using FB or PB anti-CD3 and CD28 antibodies. Unstimulated PBMC were used as negative controls.

Figure 15:
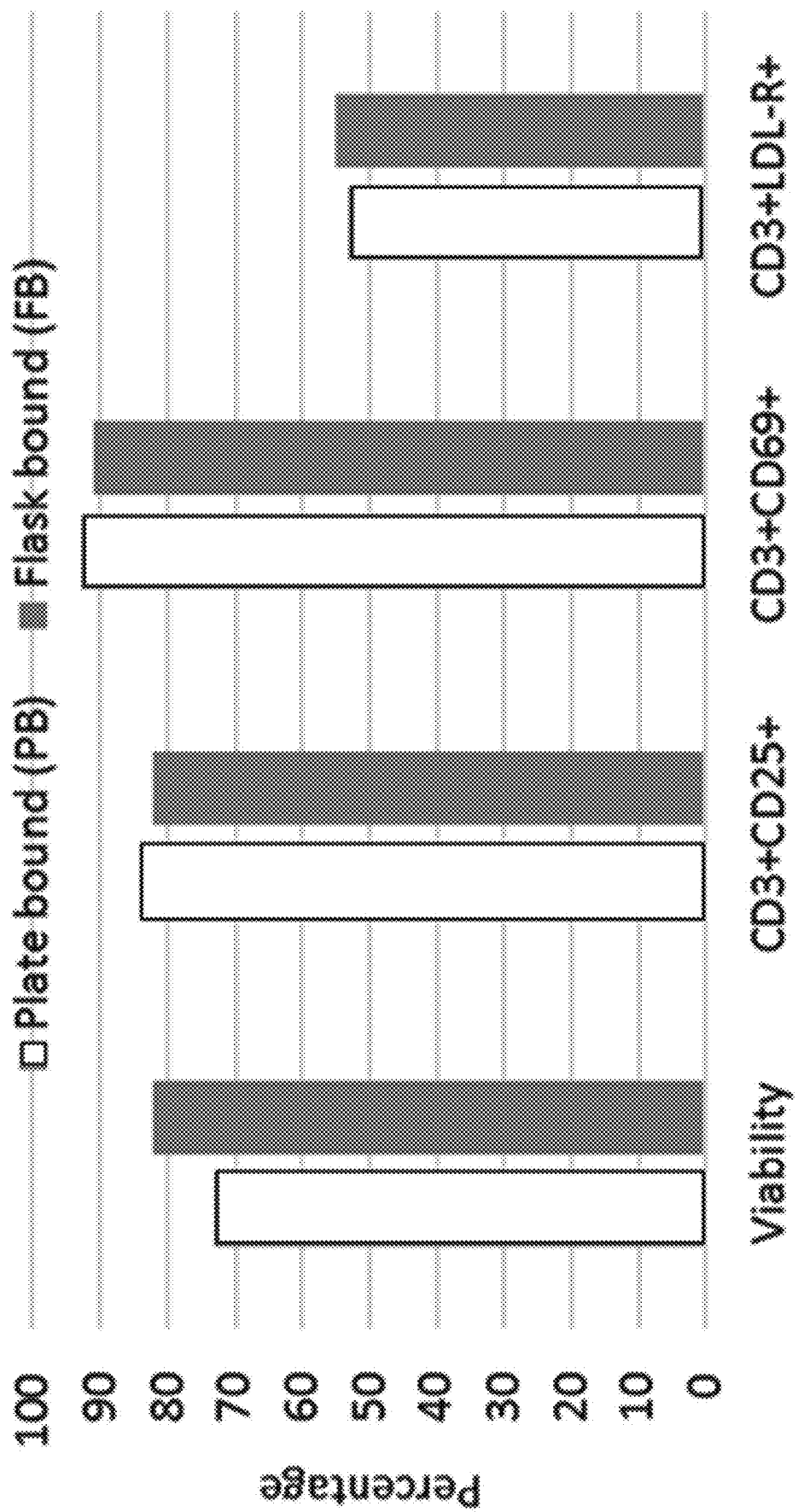
FIG. 15 shows CD25, CD69, and LDL-R expression in T cells activated by plate-bound or flask-bound anti-CD3 and anti-CD28 antibodies.

FIG. 15 shows, under optimized conditions, T cells activated in T175 cm$^2$ flasks (flask-bound, FB) exhibit comparable expression levels of activation markers CD25 and CD69 and LDL-R to that of T cells activated under plate-bound (PB) conditions. These results suggest scale-up activation using FB antibodies may be feasible in view of the comparable levels of activation resulting from FB and PB activated T cells.

Figure 16A:
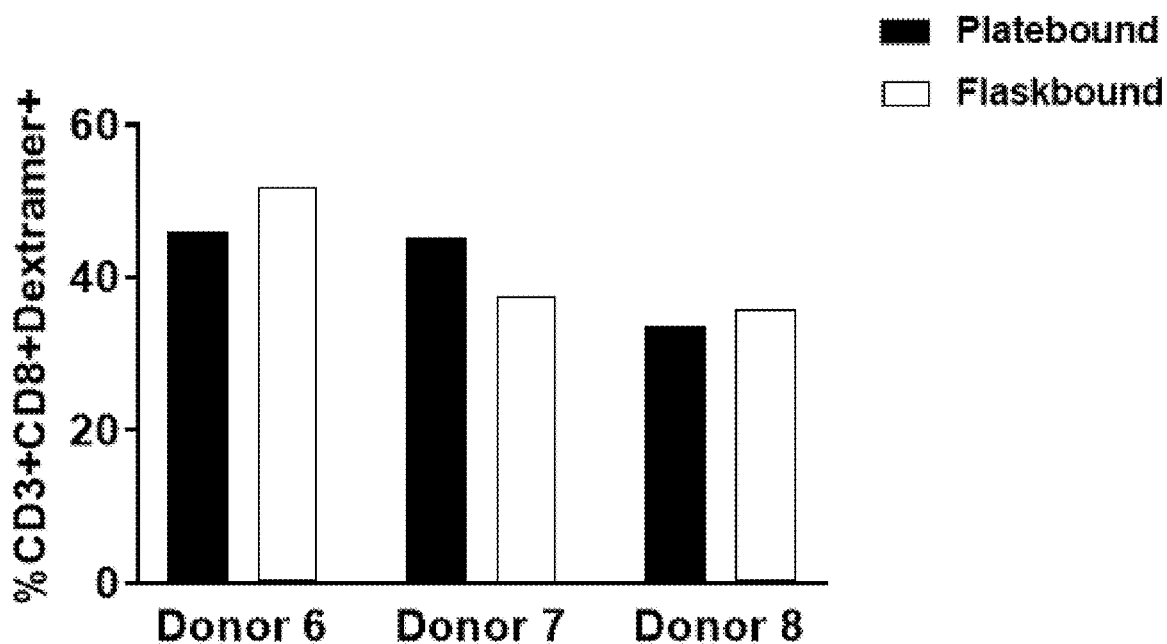
FIG. 16A shows levels of transduction in flask-bound (FB) and plate-bound (PB) activated T cells.
Figure 16B:
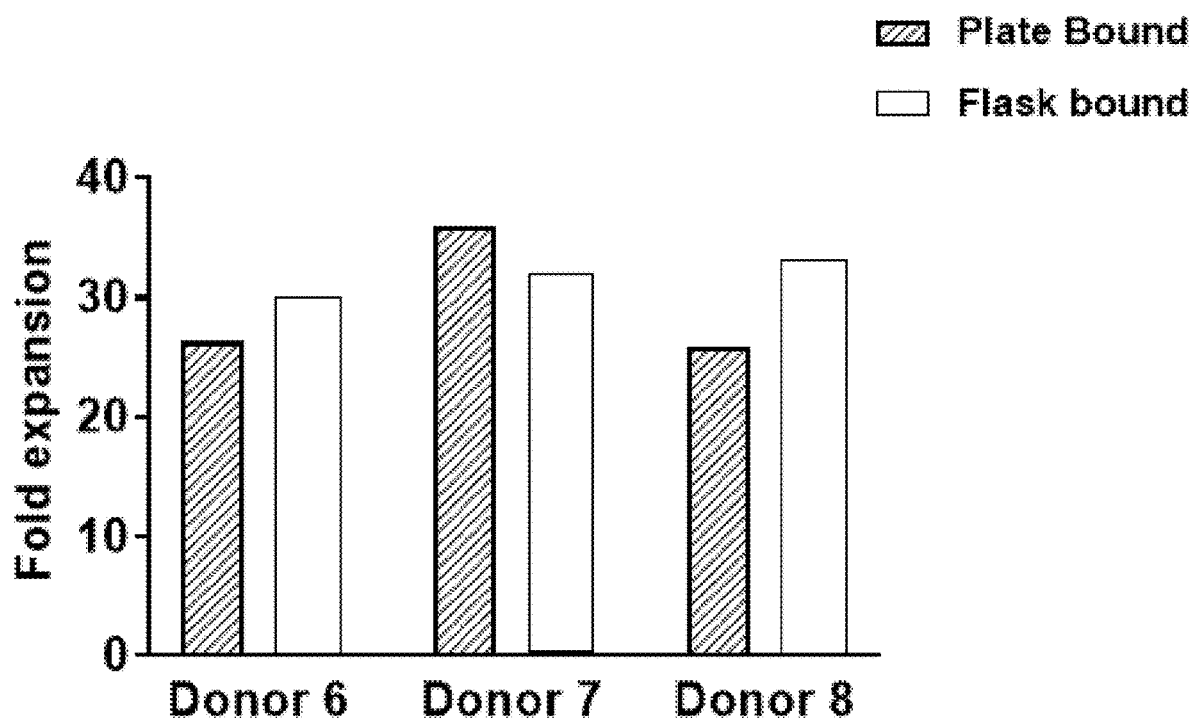
FIG. 16B shows fold expansion in flask-bound (FB) and plate-bound (PB) activated T cells.

To compare transgene expression and expansion in Day 10 harvested T cell products (from donor 6, donor 7, and donor 8) using PB or FB antibodies for activation, surface expression of R7P1 D5 TCR was determined by flow cytometry using TAA specific dextramer or transgenic TCR β chain specific antibody. Fold expansion was calculated on the basis of viable cell number seeded in the G-Rex plate or flask at the time of transduction (Day 2) and the day of harvest (Day 10). FIGS. 16A and 16B show comparable levels of transduction and fold expansion, respectively, in FB and PB activated T cells. These results suggest scale-up transduction and expansion using FB antibodies may be feasible in view of the comparable levels of transduction and expansion resulting from FB and PB activated T cells.

For further validation of successful scale up of activation, functionality of T cell products generated by FB and PB activation methods were compared. To evaluate induction of antigen specific IFN-γ by LV-R73 transduced T cell products generated using PB or FB antibodies for activation, IFN-γ released in the supernatant of T cell co-cultured with tumor cell lines (Target+ve, Target−ve) was quantitated using a commercially available ELISA kit.

Figure 17:
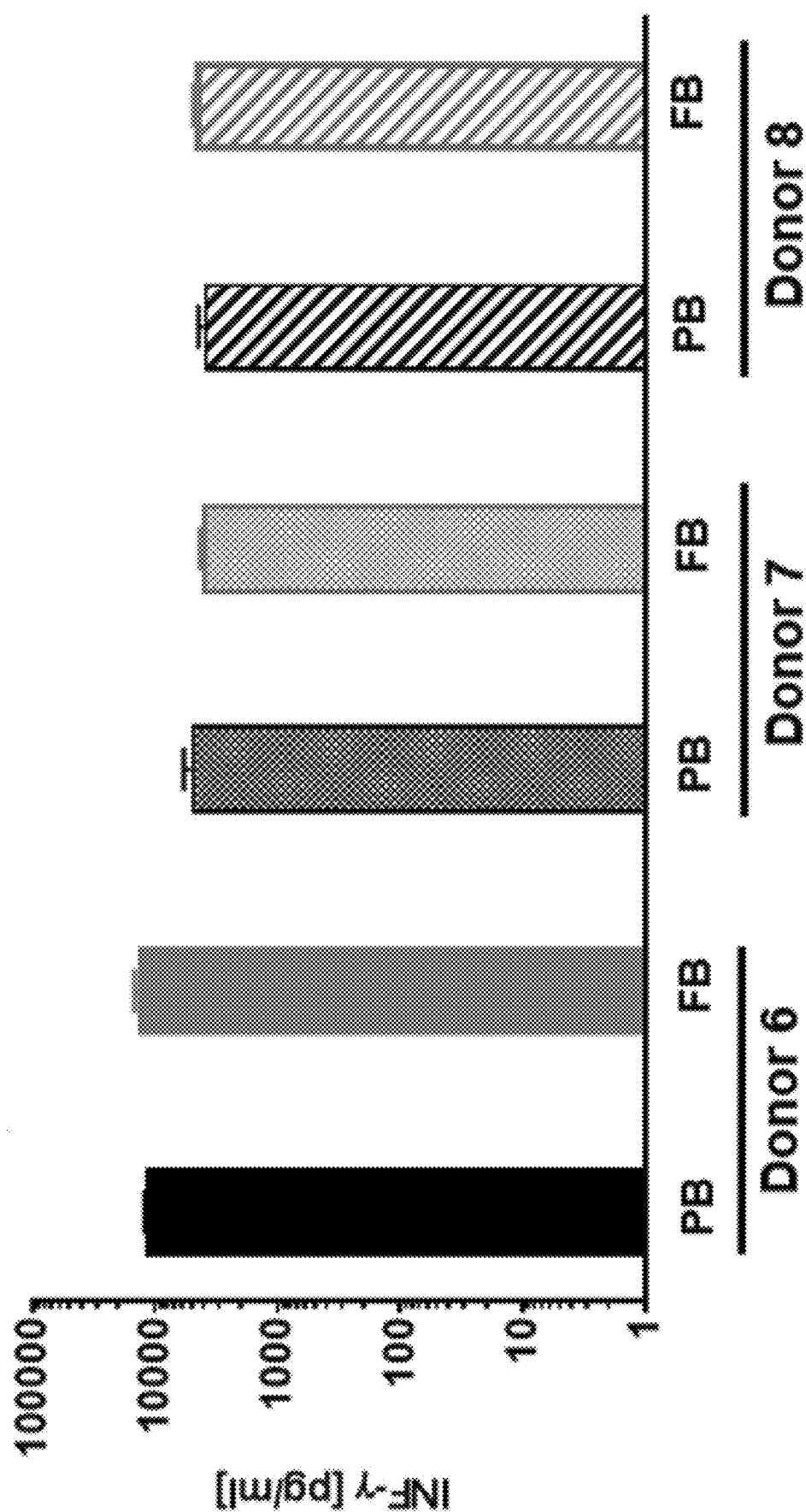
FIG. 17 shows antigen specific IFN-γ levels elicited by flask-bound (FB) activated LV-R73 (a lentiviral vector expressing a T cell receptor) transduced T cells and plate-bound (PB) activated transduced T cells in response to tumor cells expressing a tumor associated antigen (TAA) in different donors.

FIG. 17 shows FB activated LV-R73 transduced T cells secreted comparable levels of antigen specific IFN-γ to that of PB activated transduced T cells in response to tumor cells expressing TAA in each donor 6, donor, 7, and donor 8. These results suggest scale-up of IFN-γ-secreting T cells using FB antibodies may be feasible in view of the comparable levels of IFN-γ secretion resulting from FB and PB activated T cells.

For scale up of the remaining process, 2.5×10$^8$–4.0×10$^8$ activated T cells were transduced and seeded at optimal seeding density of 0.5×10$^6$ per cm$^2$ of surface area of the G-Rex100 flask. Multiple G-Rex100 flasks were used to seed the transduced cells at the optimal density. Additional parameters, such as conditions for feeding and splitting the cells, were also optimized to achieve maximum expansion. The final manufacturing process was tested in 2 full scale Process Development (PD) runs. All products generated using the final process passed the % Dextramer and integration copy number release criteria. Cell numbers generated in these manufacturing runs met clinical dose at all cohort levels. Results of PD scale up runs are summarized in the Table 1 below.

TABLE 1

Summary of product characterization from 2 full scale PD runs performed

| Scale up Run# | Donor | % CD3 | % CD8 | % Dextramer+ | Integration Copy# | Cell # |
|---|---|---|---|---|---|---|
| 1 | Donor 6 | 99.5% | 66.9% | 21.6% | 0.96 | $1.01 \times 10^{10}$ |
| 2 | Donor 9 | 96.2% | 57.7% | 23.1% | 1.21 | $1.05 \times 10^{10}$ |

GMP manufacturing with the above process have yielded over 20 billion cells for a few donors.

Flask-Bound Versus Bag-Bound

Comparison Between T Cells Activated by Flask-Bound Method and Bag-Bound Method (e.g., Saint-Gobain Vue-Life AC Bag Coated with Anti-CD3 and Anti-CD28 Antibodies) with Respect to Activation Level (Flowcytometry), Transducibility (Dextramer Staining, FACS), and Expansion (Cell Counts)

Figure 18:
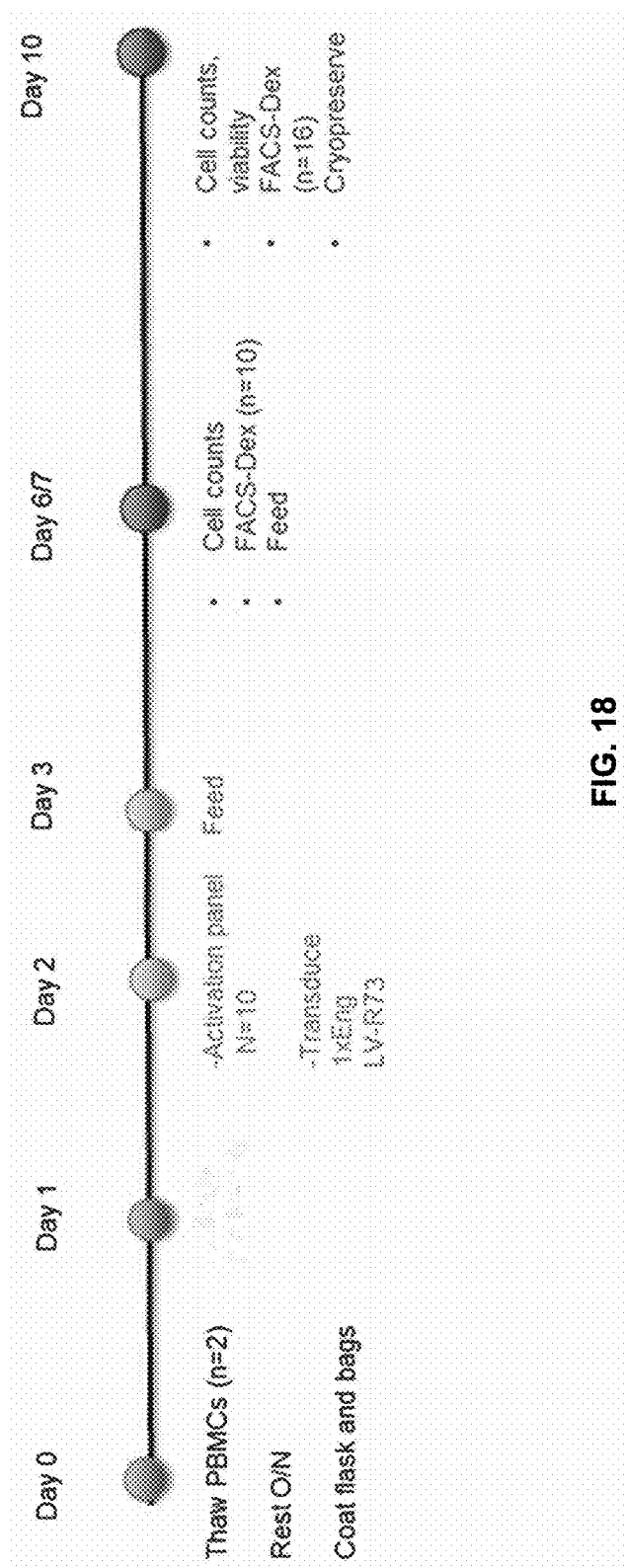
FIG. 18 shows an experimental design to test the effect of using bags and plates coated with anti-CD3 and anti-CD28 antibodies on T cell activation.

To compare activation of T cells using anti-CD3 and anti-CD28 antibody coated bags versus plates, FIG. 18 shows the experimental design used to test the effect of anti-CD3 and anti-CD28 antibody coated bags and plates on T cell activation. Briefly, on Day 0, PBMC were thawed and rested overnight (24 hours). On Day 1, the rested PBMC were activated by seeding them on flasks, e.g., T175 cm² flasks, or bags, e.g., Saint-Gobain VueLife AC Bags, coated with anti-CD3 and anti-CD28 antibodies for 16-20 hours. On Day 2, activated T cells were analyzed for CD25, CD69, and hLDL-R expression and transduced with VSV-G pseudotyped lentiviral vectors, e.g., 1xEng LV-R73. On Day 6/7 and 10, analyses, such as cell counts, viability, and fluorescence-activated cell sorting (FACS) with dextramers (Dex), were performed.

Figure 19:
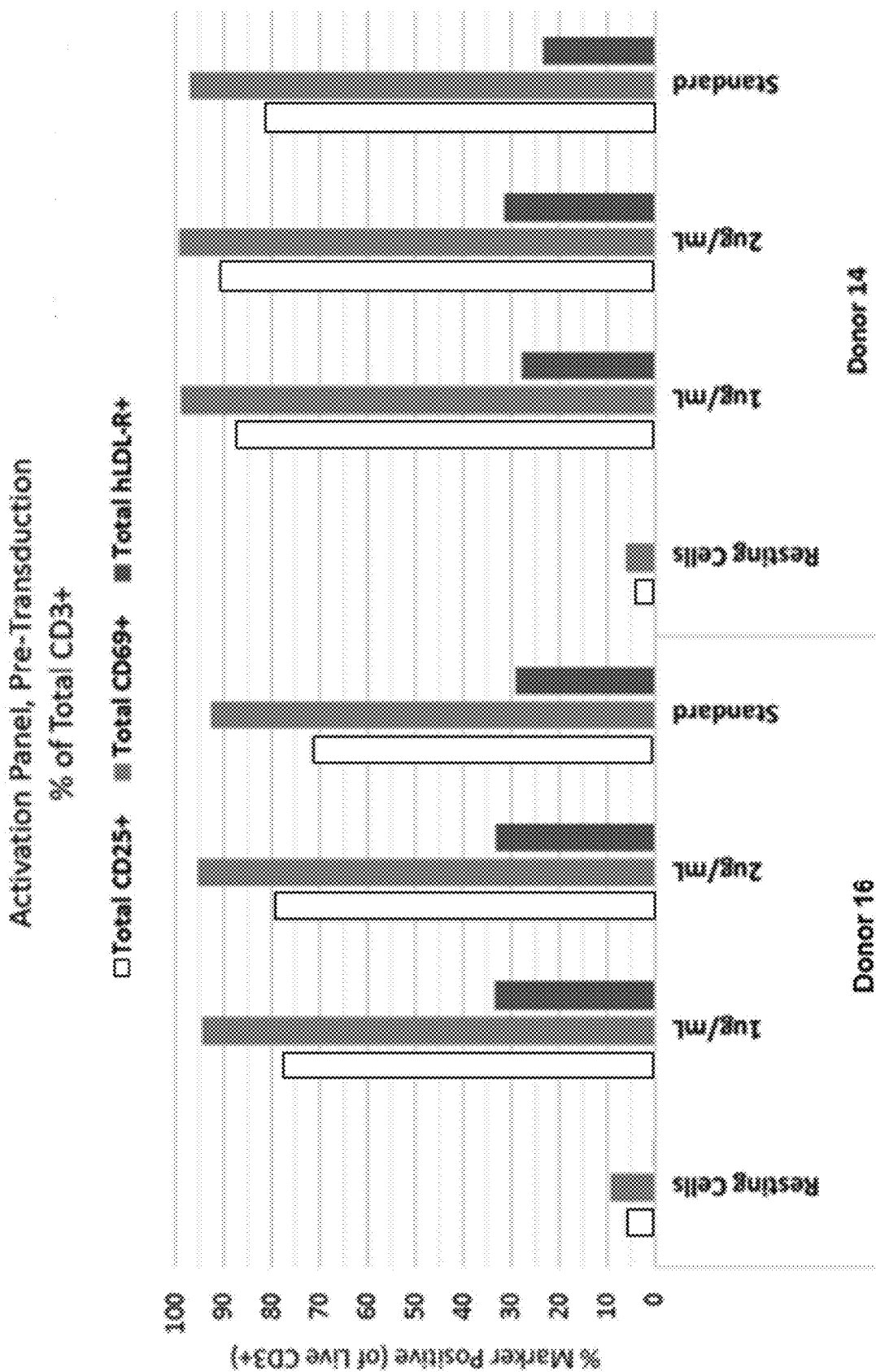
FIG. 19 shows CD25, CD69, and LDL-R expression in T cells activated in bag-bound or flask-bound anti-CD3 and anti-CD28 antibodies.

FIG. 19 shows, under optimized conditions, T cells (from donor 16 and donor 14) activated in bags bound with antibodies at concentrations of 1 µg/ml or 2 µg/ml exhibit comparable expression of activation markers CD25 and CD69 and hLDL-R expression to those activated under flask-bound (T175 cm² flask, labelled as "standard") conditions. These results suggest scale-up activation using bag-bound (Bag) antibodies may be feasible in view of the comparable levels of activation resulted from bag-bound (Bag) and flask-bound (FB) activated T cells.

Figure 20:
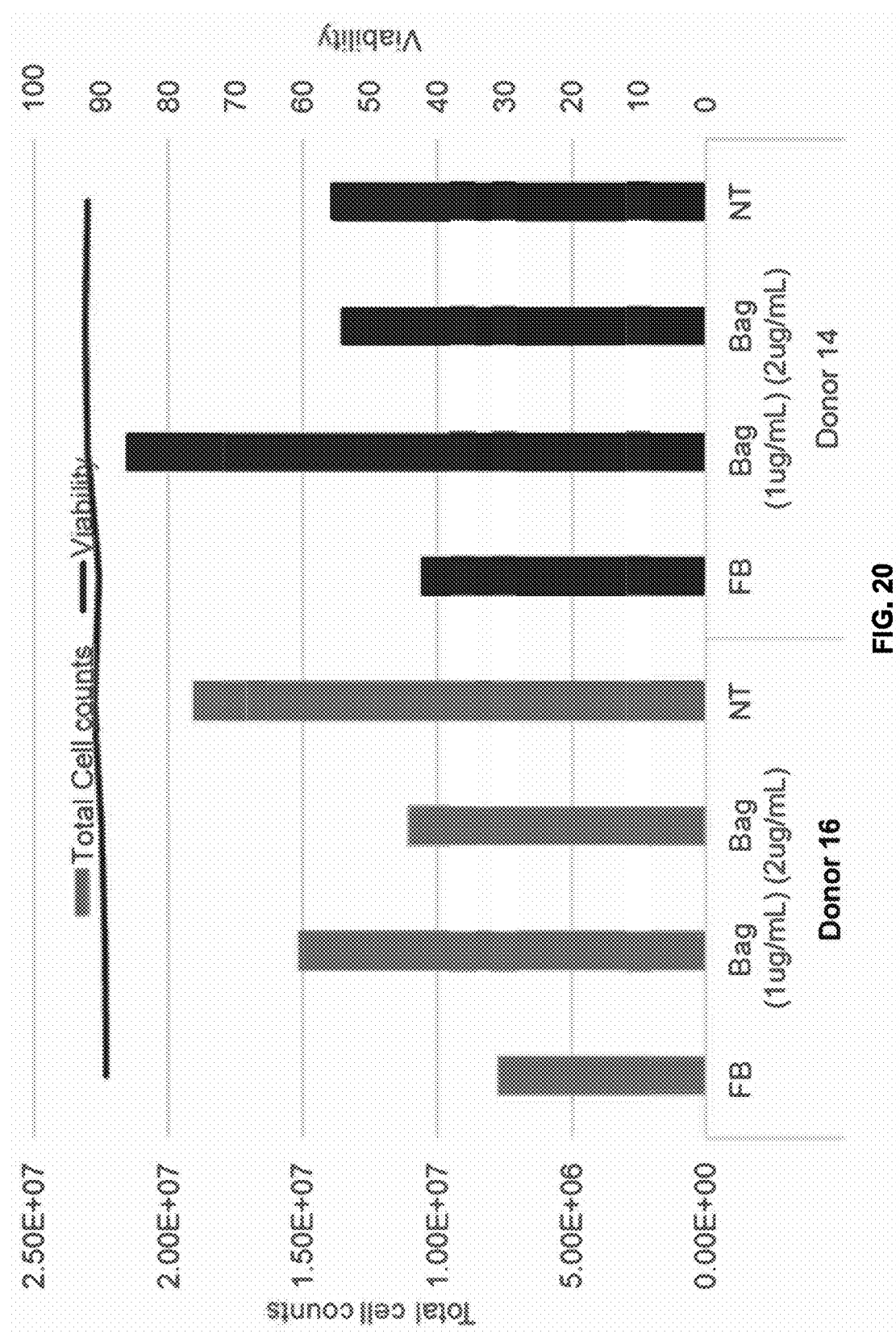
FIG. 20 shows, on Day 6 expansion, cell expansion resulting from T cells activated by bag-bound antibodies at different concentrations and that of T cells activated under FB conditions.
Figure 21:
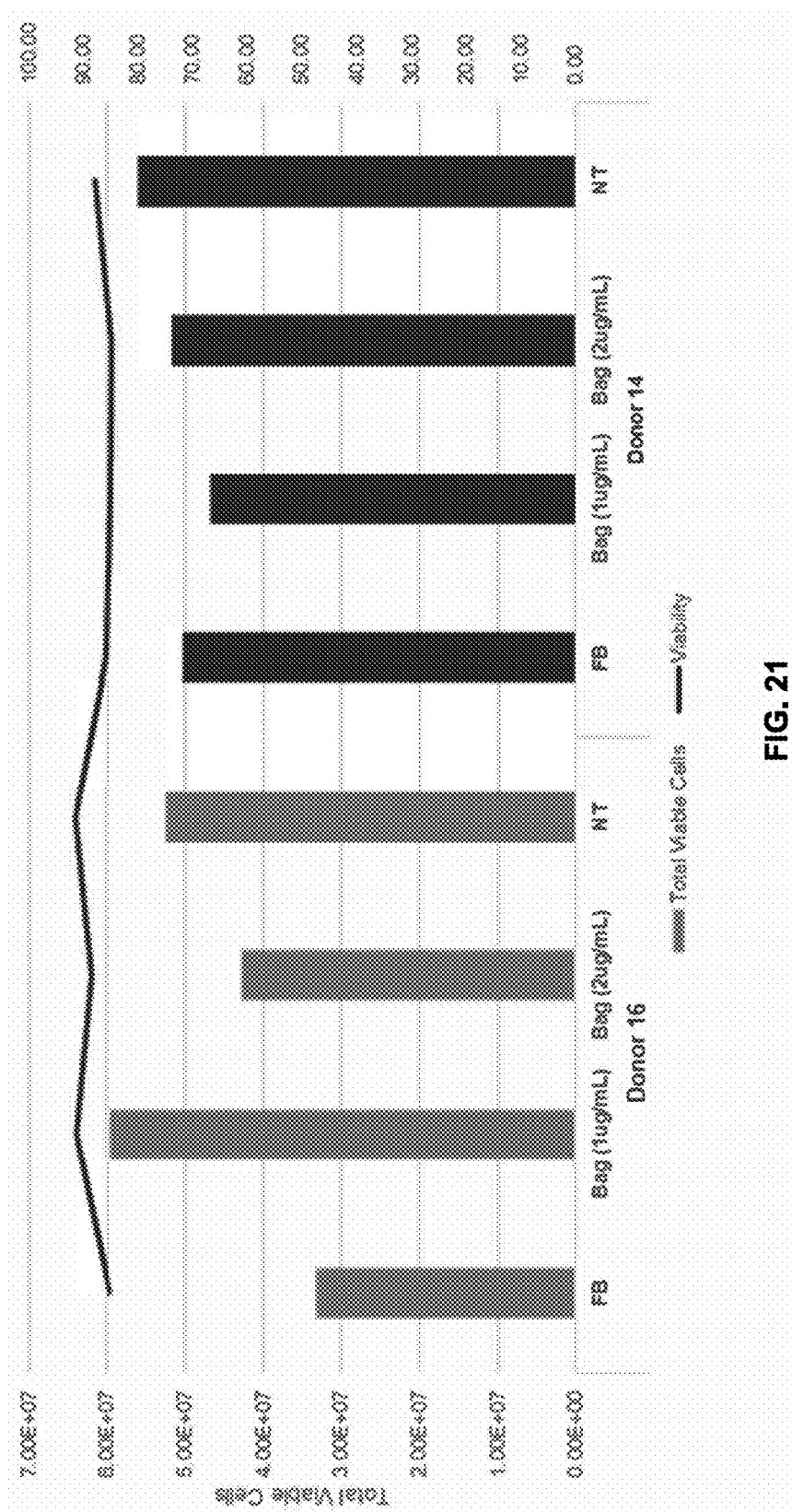
FIG. 21 shows, on Day 10 expansion, cell expansion resulting from T cells activated by bag-bound antibodies at different concentrations and that of T cells activated under FB conditions.

FIGS. 20 and 21 shows, on Day 6 and Day 10 of expansion, respectively, T cells (from donor 16 and donor 14) activated in bags bound with antibodies at concentrations of 1 µg/ml or 2 µg/ml exhibit comparable T cell counts, i.e., cell expansion, with that of T cells activated under FB conditions. These results suggest scale-up expansion using bag-bound antibodies may be feasible in view of the comparable levels of expansion resulting from bag-bound and flask-bound activated T cells.

Example 4

Short Rest Versus Overnight Rest in T Cell Manufacturing Process

Figure 22:
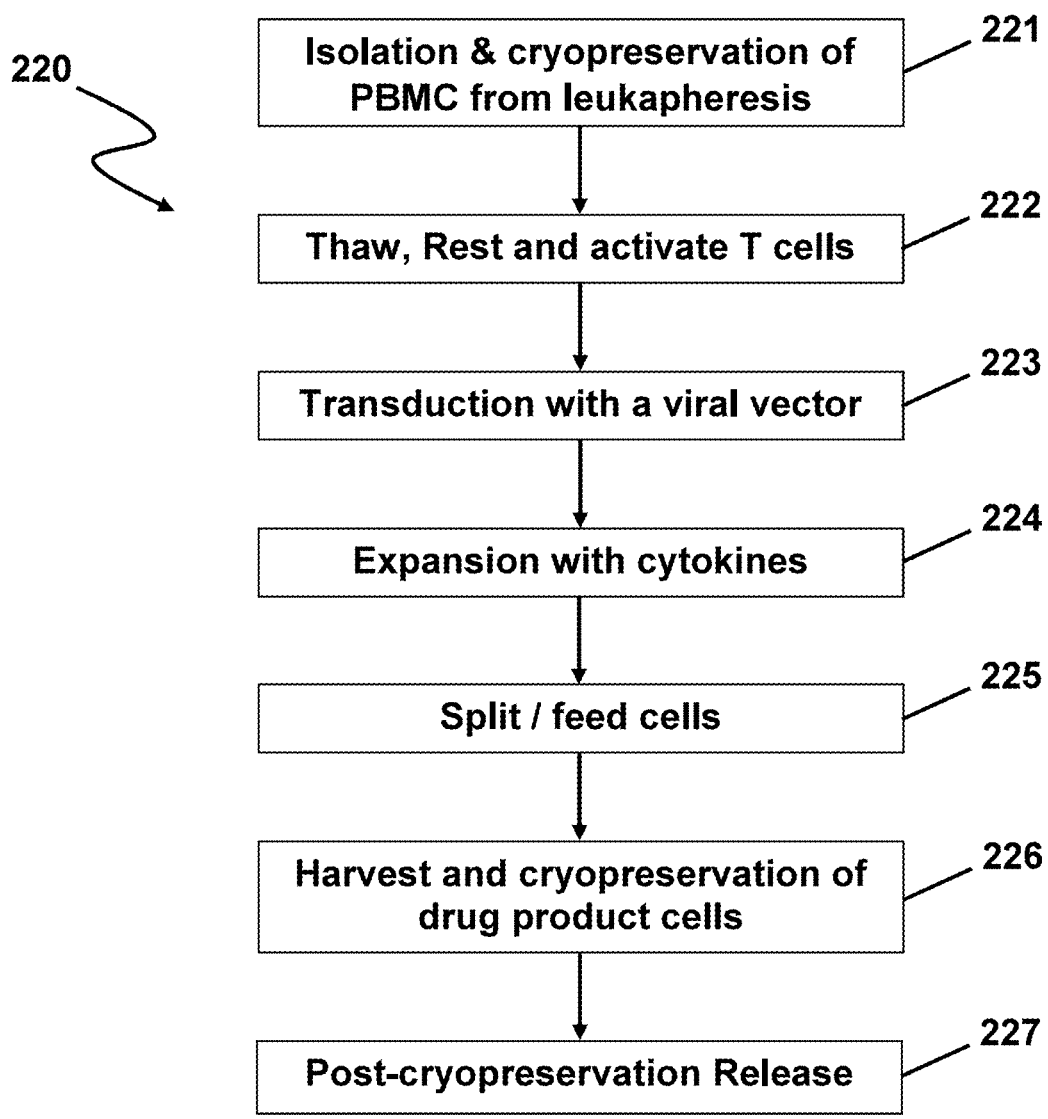
FIG. 22 shows a T cell manufacturing process according to one embodiment of the present disclosure.

FIG. 22 shows a T cell manufacturing process 220 by resting PBMC for a period of time of about 4 hours according to one embodiment of the present disclosure. For example, a T cell manufacturing process 220 may include Isolation and cryopreservation of PBMC from leukapheresis (221), in which sterility may be tested; thaw, rest (e.g., about 4 hours) and activate T cells (222); transduction with a viral vector (223); expansion with cytokines (224); split/feed cells (225), in which cell count and immunophenotyping may be tested; harvest and cryopreservation of drug product cells (226), in which cell count and mycoplasma may be tested, and post-cryopreservation release (227), in which viability, sterility, endotoxin, immunophenotyping, copy number of integrated vector, and vesicular stomatitis virus glycoprotein G (VSV-g) may be tested.

Table 2 shows characteristics of T cells manufactured by three different qualification runs of T cell manufacturing process 220 by resting PBMC for a short period of time, e.g., about 4 to about 6 hours, in the presence of IL-7 according to one embodiment of the present disclosure.

TABLE 2

Qualification runs (QR) of T cell manufacturing process 220 by resting PBMC for a short period of time, e.g., about 4 to about 6 hours, preferably about 4 hours (in GMP cleanroom)

| | QR1 | QR2 | QR3 | Average |
|---|---|---|---|---|
| % CD3+ | 99.6 | 99.7 | 99.8 | 99.7 |
| % CD8+ | 33.5 | 51.5 | 75.2 | 53.4 |
| % Dex+/CD3+CD8+ | 35.5 | 72.7 | 83.0 | 63.7 |
| % Viability | 92.0 | 92.2 | 91.7 | 92.0 |
| Residual VSV-g | <50 copies/µg | <50 copies/µg | <50 copies/µg | <50 copies/µg |
| Average copy number (per cell) | 1.0 | 3.0 | 4.2 | 2.7 |
| Total viable cells | $24.8 \times 10^9$ | $32.2 \times 10^9$ | $26.8 \times 10^9$ | $28.0 \times 10^9$ |
| Transduced cells | $2.95 \times 10^9$ | $12.1 \times 10^9$ | $16.73 \times 10^9$ | $10.6 \times 10^9$ |
| Days manufacturing | 10 | 8 | 8 | 8.7 |
| Cells at transduction | $281 \times 10^6$ | $400 \times 10^6$ (max) | $400 \times 10^6$ (max) | $360 \times 10^6$ |
| Fold expansion | 88-fold | 81-fold | 67-fold | 78.7-fold |
| LV batch | ENG | ENG | GMP | NA |

Figure 23A:
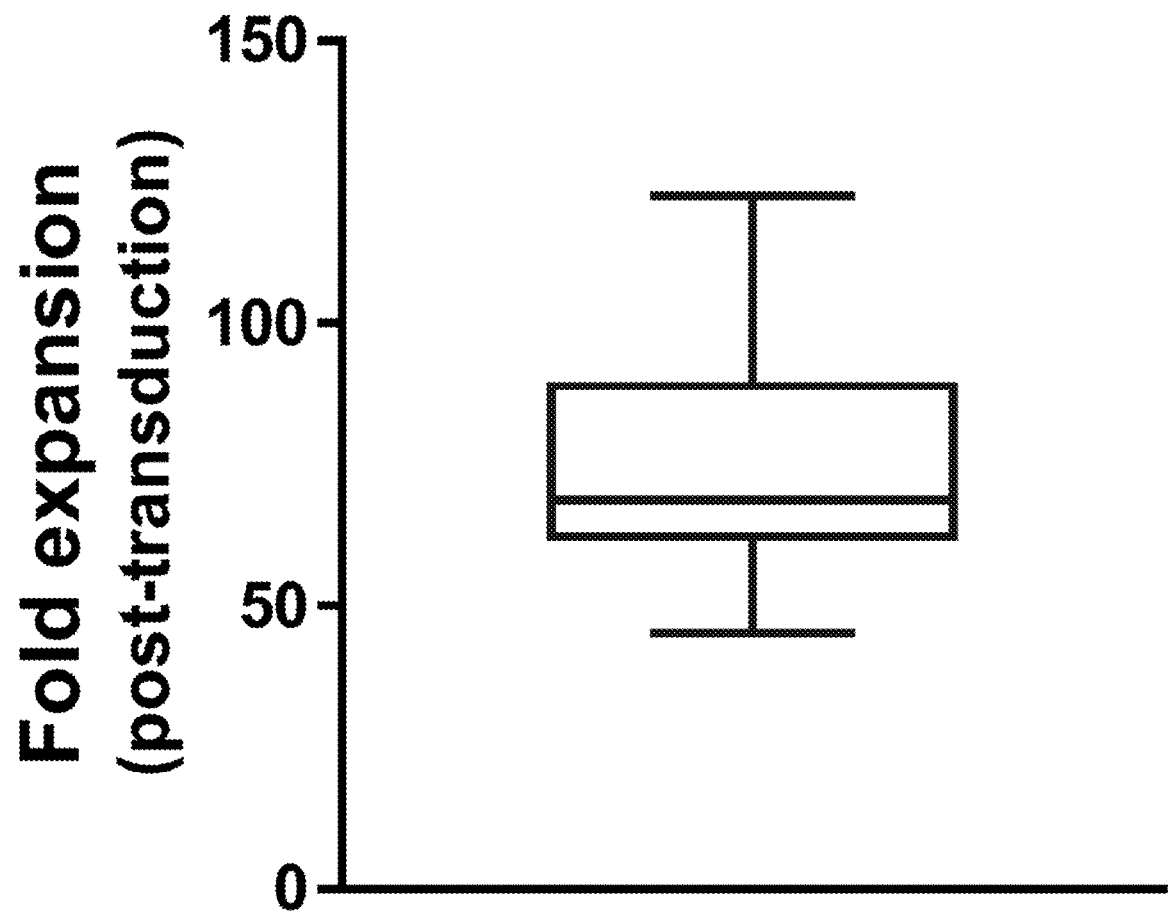
FIG. 23A shows fold expansion of T cells manufactured according to one embodiment of the present disclosure.

FIG. 23A and Table 2 show average fold expansion of T cells (n=7) manufactured by resting PBMC overnight is about 78.7-fold.

Figure 23B:
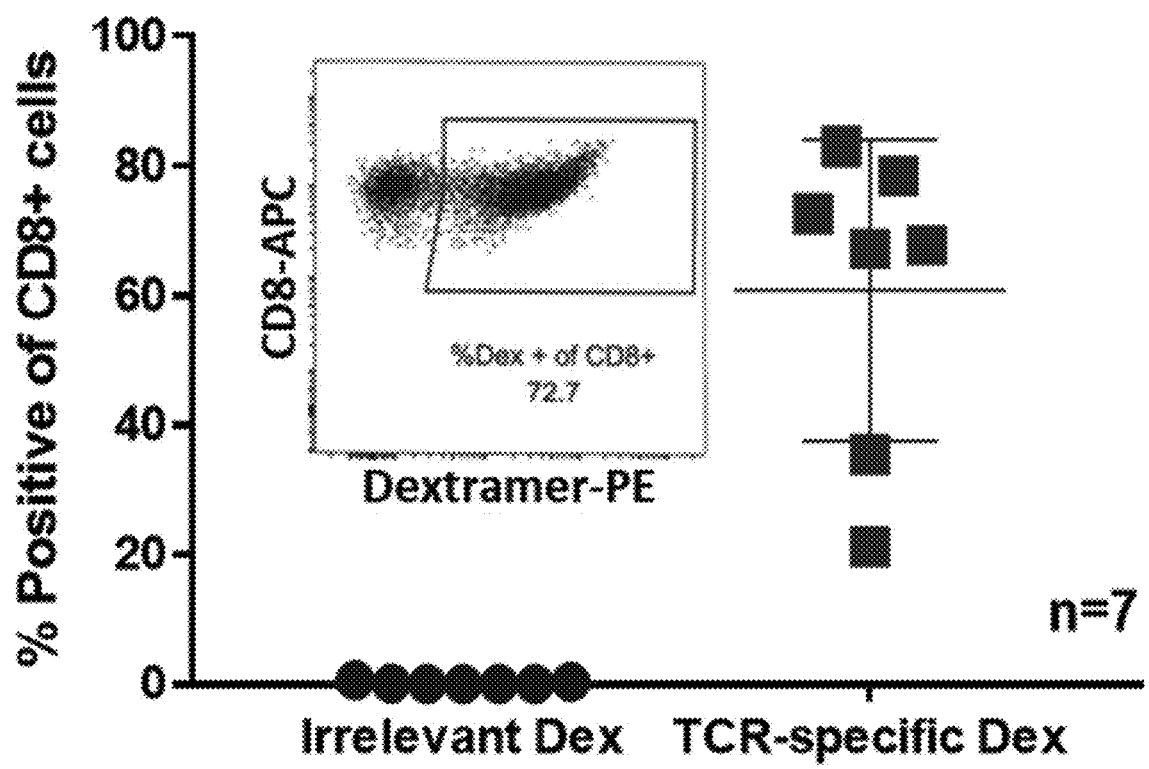
FIG. 23B shows transduced TCR expression of T cells manufactured according to one embodiment of the present disclosure.

To determine whether transduced TCR is expressed on the cell surface of expanded T cells, expanded T cells were stained with peptide/MHC complex-loaded dextramers that specifically bind to transduced TCR, followed by flow cytometry to identify CD8+ T cells expressing transduced TCR. FIG. 23B and Table 2 show average % Dex+/CD8+ T cells (n=7) manufactured by short rest is about 53.4%, indicating that transduced TCR is expressed on the cell surface of expanded T cells.

Figure 23C:
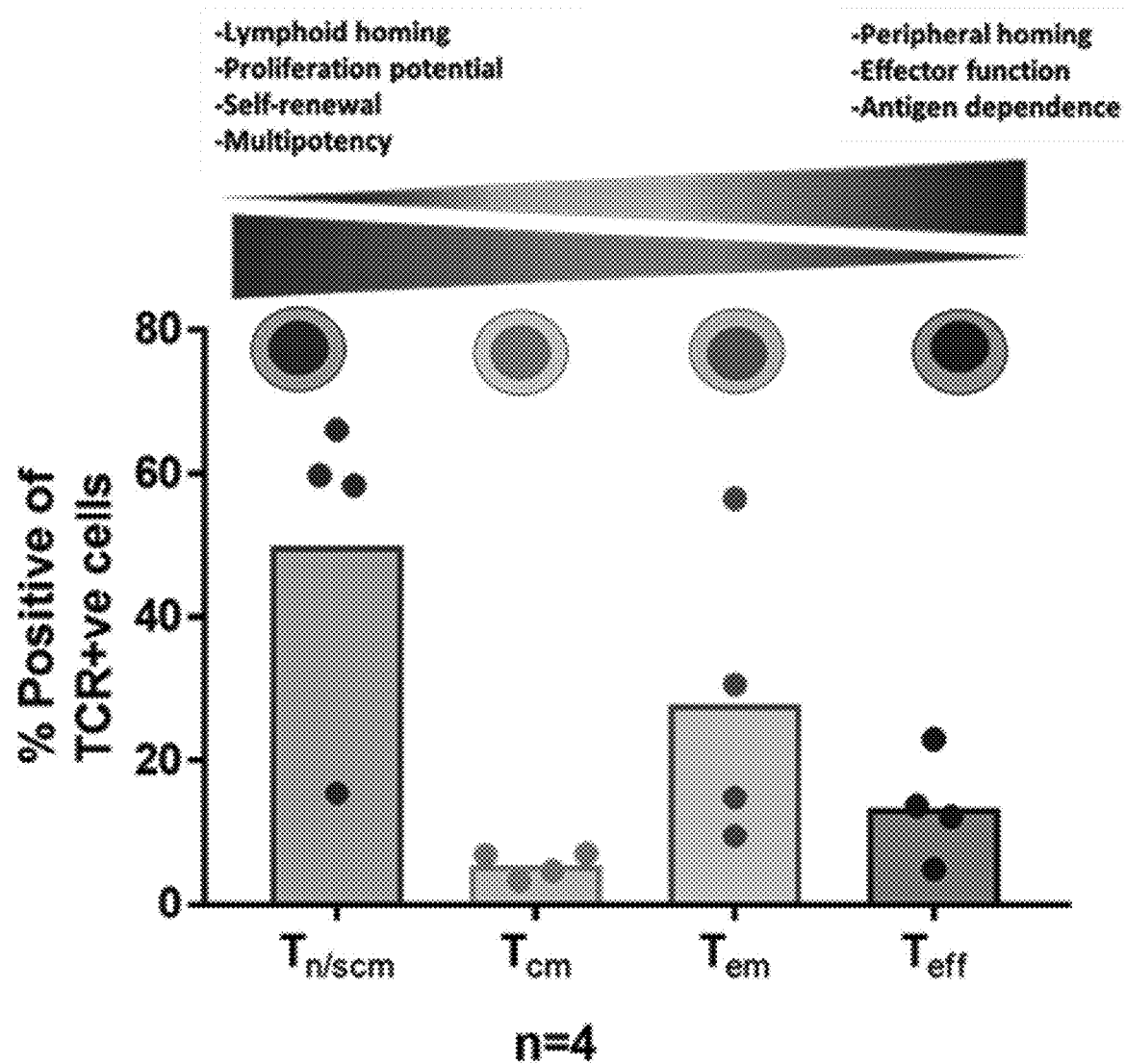
FIG. 23C shows phenotypes of T cells manufactured according to one embodiment of the present disclosure.

To determine what T cell phenotypes are present in expanded T cells expressing transduced TCR, cells were stained with various immune cell surface markers, followed by flow cytometry to identify T cell phenotypes, e.g., $T_{n/scm}$, $T_{cm}$, $T_{em}$, and $T_{eff}$. Among them, $T_{n/scm}$ may be more desirable for immunotherapy than others because $T_{n/scm}$ may have properties of lymphoid homing, proliferation potential, self-renewal, and multipotency. FIG. 23C shows average about 50% of expanded T cells expressing transduced TCR (n=4) exhibiting $T_{n/scm}$ phenotypes.

Figure 23D:
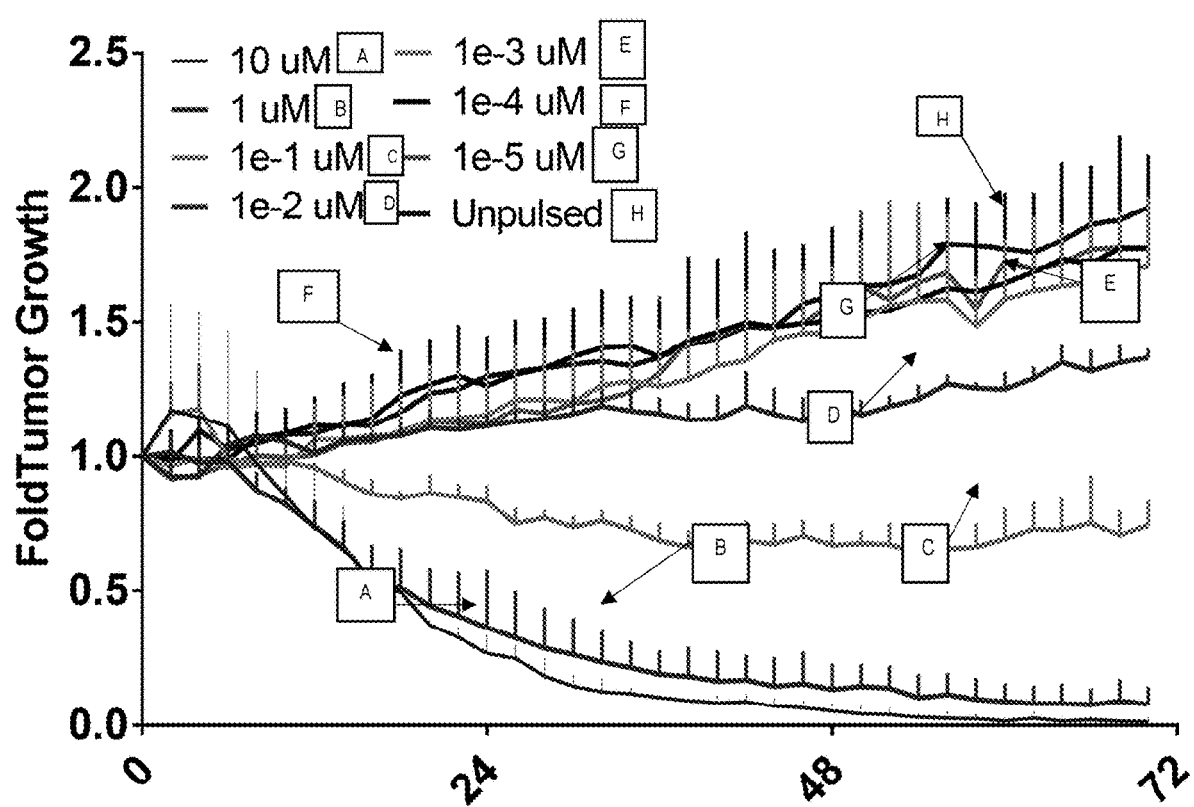
FIG. 23D shows tumor cell growth inhibitory activity of T cells manufactured according to one embodiment of the present disclosure.

To determine cytotoxic activity of expanded T cells expressing transduced TCR, tumor cells pulsed with different concentration of target peptide were incubated with expanded T cells expressing transduced TCR that specifically recognizes target peptide/MHC complex, followed by measuring tumor cell growth. FIG. 23D shows expanded T cells expressing transduced TCR inhibit tumor cell growth in a peptide concentration dependent manner.

Figure 23E:
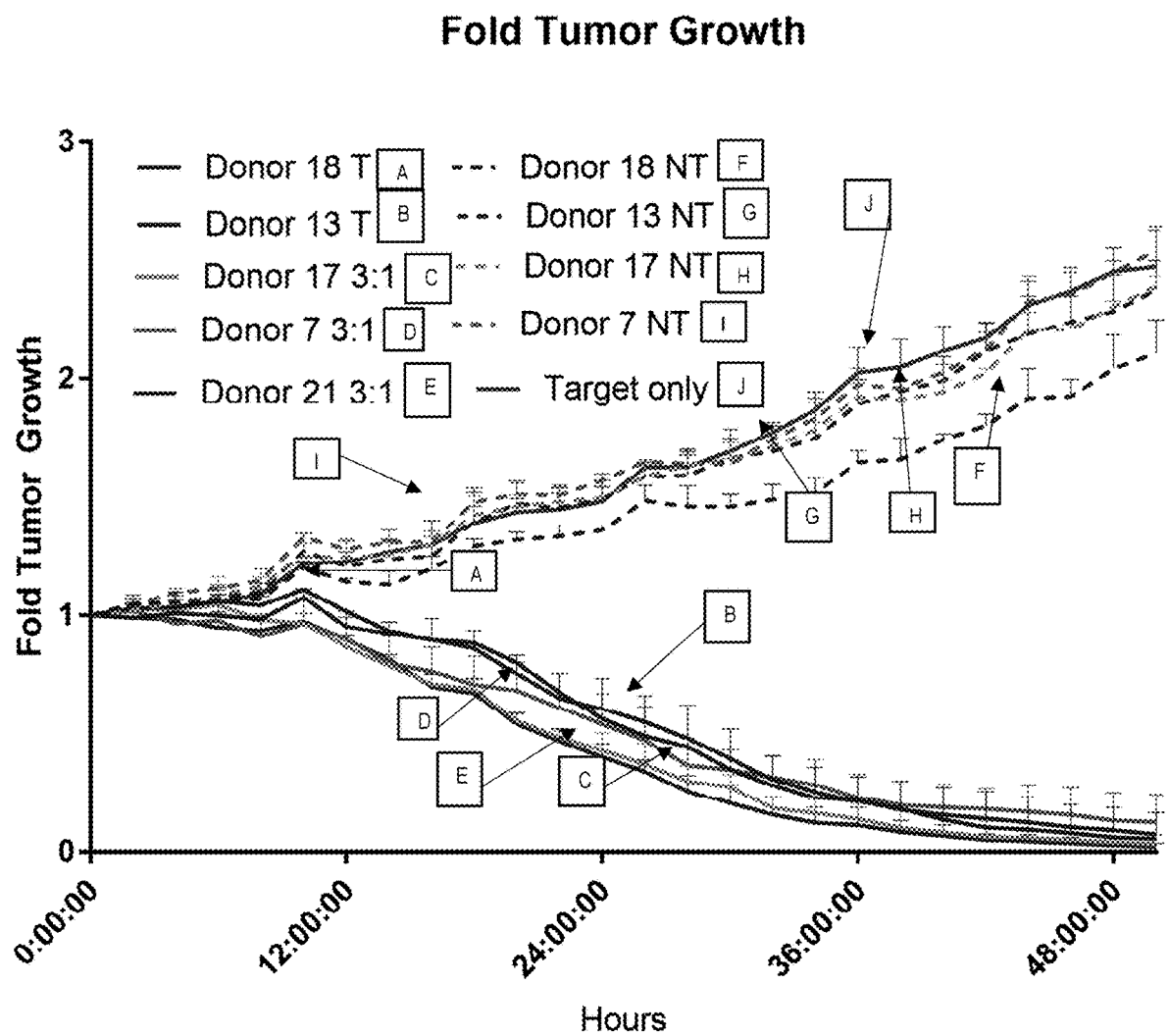
FIG. 23E shows tumor cell growth inhibitory activity of T cells manufactured according to another embodiment of the present disclosure.
Figure 23F:
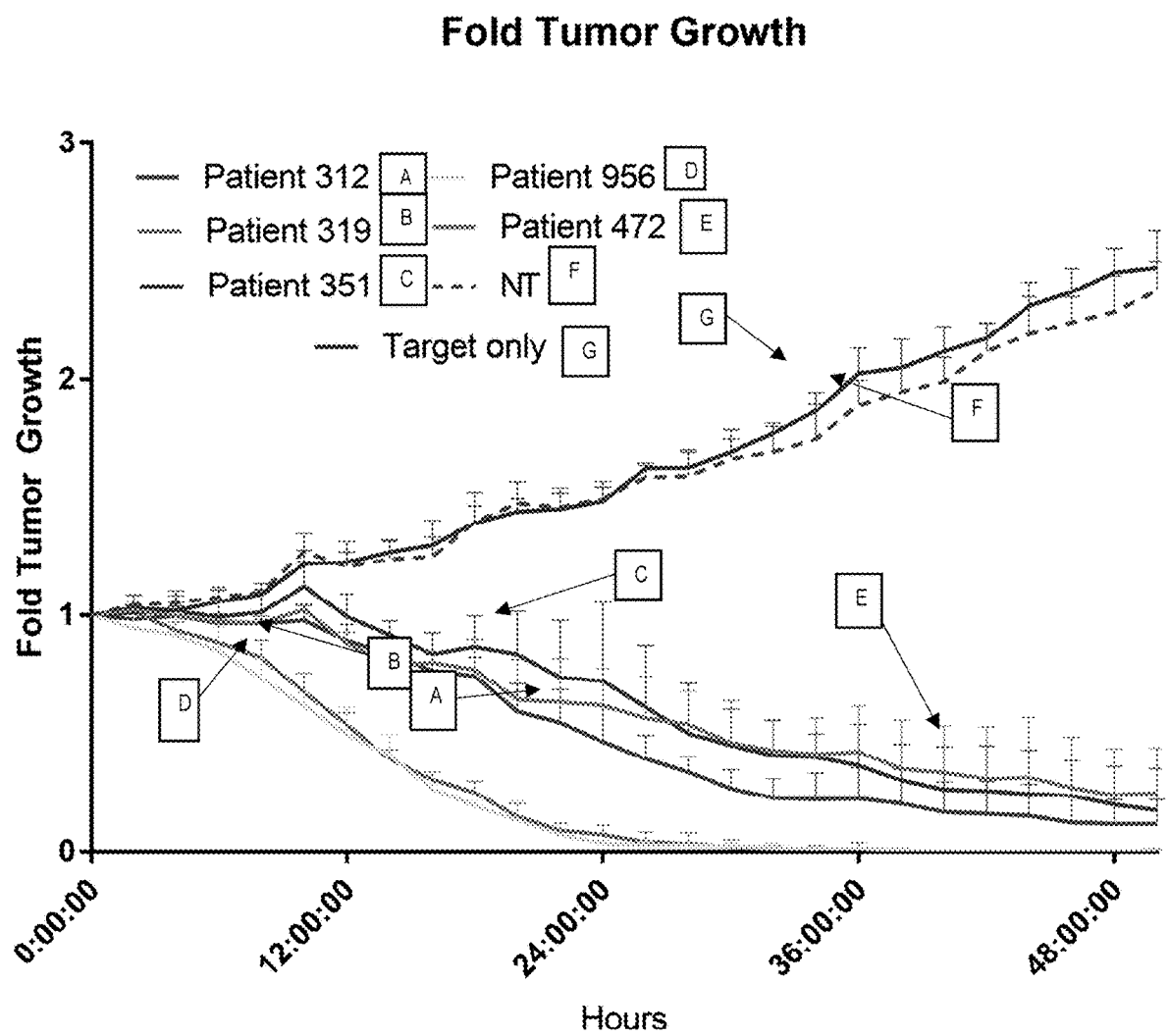
FIG. 23F shows tumor cell growth inhibitory activity of T cells manufactured according to another embodiment of the present disclosure.

Cytotoxic activities of expanded T cells expressing transduced TCR appear comparable between PBMC obtained from different healthy donors, e.g., Donors 7, 13, 17, 18, and 21 (FIG. 23E), and that obtained from different patients, e.g., Patients 312, 319, 351, 472, and 956 (FIG. 23F).

Figure 23G:
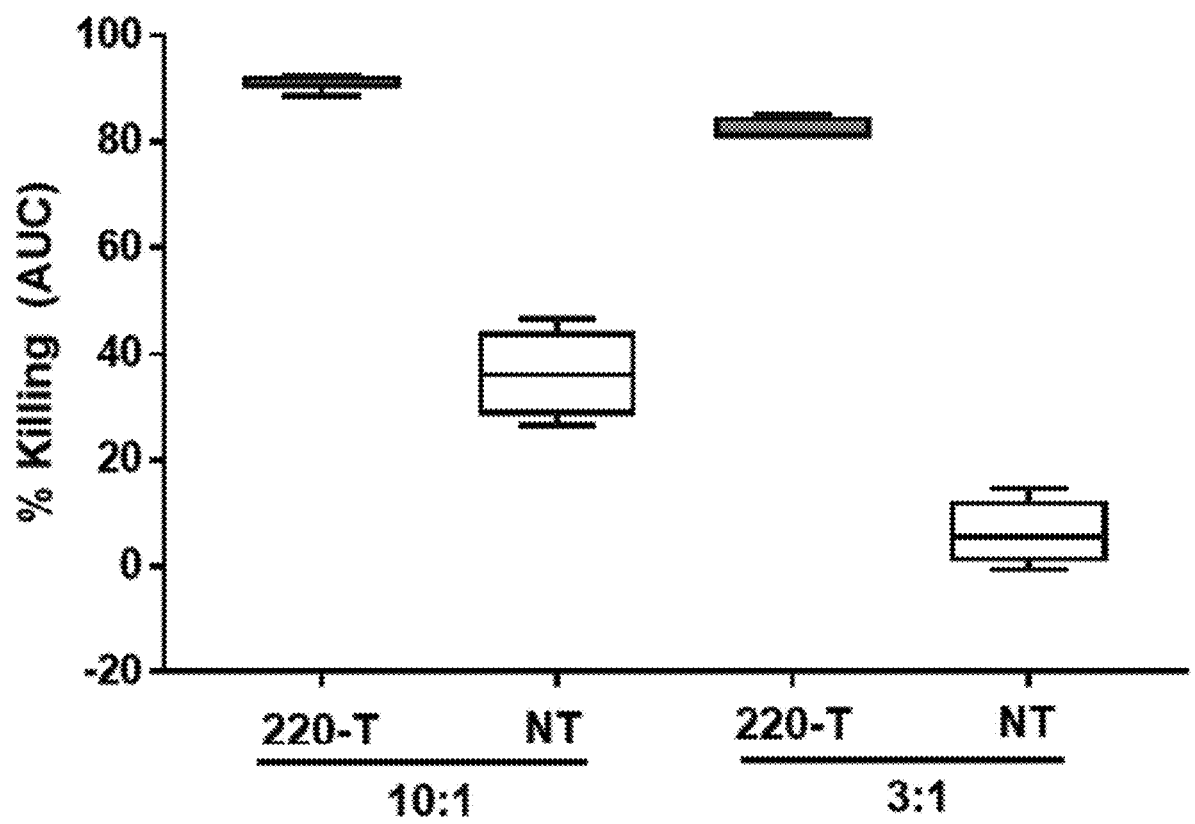
FIG. 23G shows tumor cell killing activity of T cells manufactured according to another embodiment of the present disclosure.
Figure 23H:
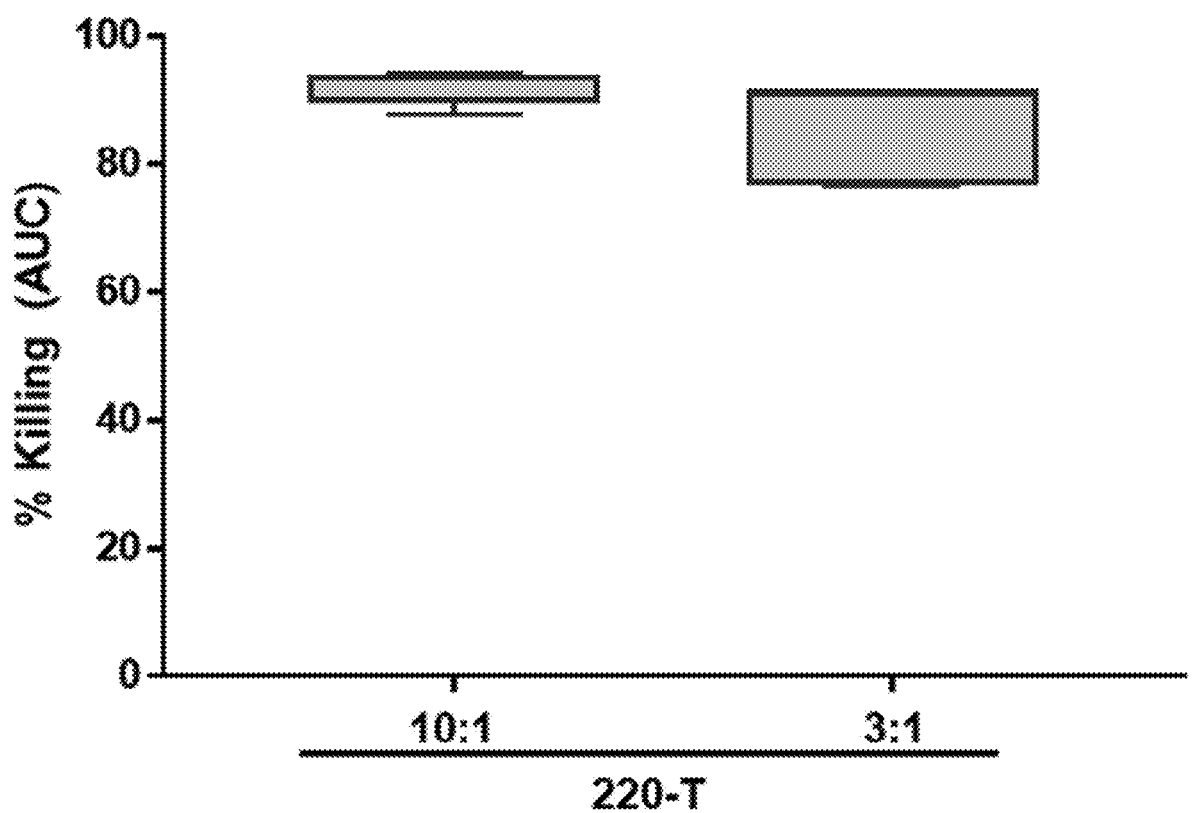
FIG. 23H shows tumor cell killing activity of T cells manufactured according to another embodiment of the present disclosure.

To determine cytotoxic potential of the expanded T cells expressing transduced TCR, tumor cells expressing target peptide were incubated with expanded T cells expressing transduced TCR (220-T) that specifically recognize target peptide/MHC complex, followed by measuring fold growth of tumor cells. FIG. 23G and FIG. 23H show increased regression or suppression of tumor growth by incubation with expanded T cells expressing transduced TCR (220-T) (effectors) at effectors to tumor cells ratios of 10:1 and 3:1 as compared with that of the non-transduced T cells lacking target-specific TCR (NT).

Figure 24:
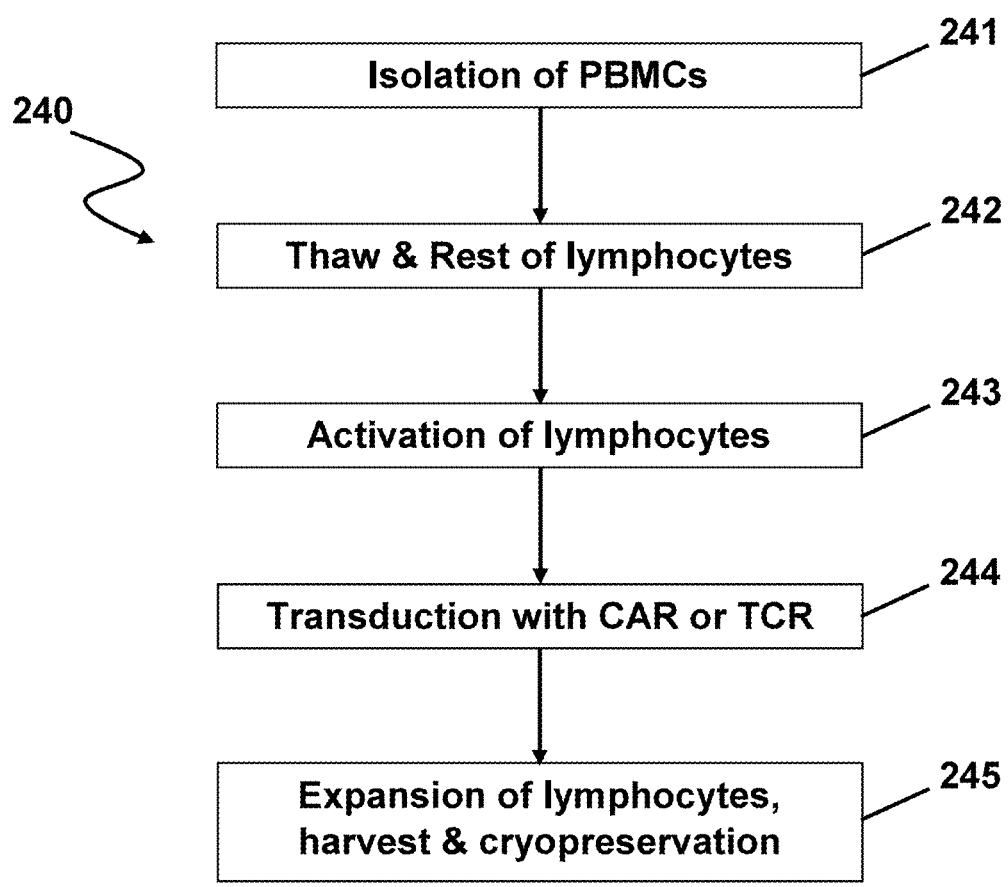
FIG. 24 shows T cell manufacturing process with overnight rest (about 16 hours).

FIG. 24 shows a T cell manufacturing process 240 by resting PBMC overnight (about 16 hours). For example, T cell manufacturing process 240 may include isolation of PBMC (241), in which PBMC may be used fresh or stored frozen till ready for use, or may be used as starting materials for T cell manufacturing and selection of lymphocyte populations (e.g., CD8, CD4, or both) may also be possible; thaw and rest lymphocytes overnight, e.g., about 16 hours, (242), which may allow apoptotic cells to die off and restore T cell functionality (this step may not be necessary, if fresh materials are used); activation of lymphocytes (243), which may use anti-CD3 and anti-CD28 antibodies (soluble or surface bound, e.g., magnetic or biodegradable beads); transduction with CAR or TCR (244), which may use lentiviral or retroviral constructs encoding CAR or TCR or may use non-viral methods; and expansion of lymphocytes, harvest, and cryopreservation (245), which may be carried out in the presence of cytokine(s), serum (ABS or FBS), and/or cryopreservation media.

Table 3 shows characteristics of T cells manufactured by three different qualification runs of a T cell manufacturing process (240) by resting PBMC overnight, e.g., about 16 hours.

TABLE 3

| Qualification runs (QR) of a T cell manufacturing process by resting PBMC overnight (in GMP cleanroom) | | | | |
|---|---|---|---|---|
| | QR1 | QR2 | QR3 | Average |
| % CD3+ | 99.2 | 99.6 | 99.7 | 99.5 |
| % CD8+ | 47.9 | 46.9 | 60.9 | 51.9 |
| % Dex+/CD3+CD8+ | 36.7 | 57.3 | 64.9 | 53.0 |
| % Viability | 85.6 | 86.8 | 85.5 | 86.0 |
| Residual VSV-g | <50 copies/µg | <50 copies/µg | <50 copies/µg | <50 copies/µg |
| Average copy number (per cell) | 2.7 | 3.2 | 3.6 | 3.2 |
| Total viable cells | $8.7 \times 10^9$ | $24.3 \times 10^9$ | $14.2 \times 10^9$ | $15.7 \times 10^9$ |
| Transduced cells | $1.3 \times 10^9$ | $5.65 \times 10^9$ | $4.8 \times 10^9$ | $3.9 \times 10^9$ |
| Days manufacturing | 8 | 9 | 8 | 8.3 |
| Cells at transduction | $231 \times 10^6$ | $400 \times 10^6$ | $400 \times 10^6$ | $344 \times 10^6$ |
| Fold expansion | 38-fold | 61-fold | 36-fold | 45-fold |
| LV batch | ENG | ENG | GMP | NA |

Figure 25A:
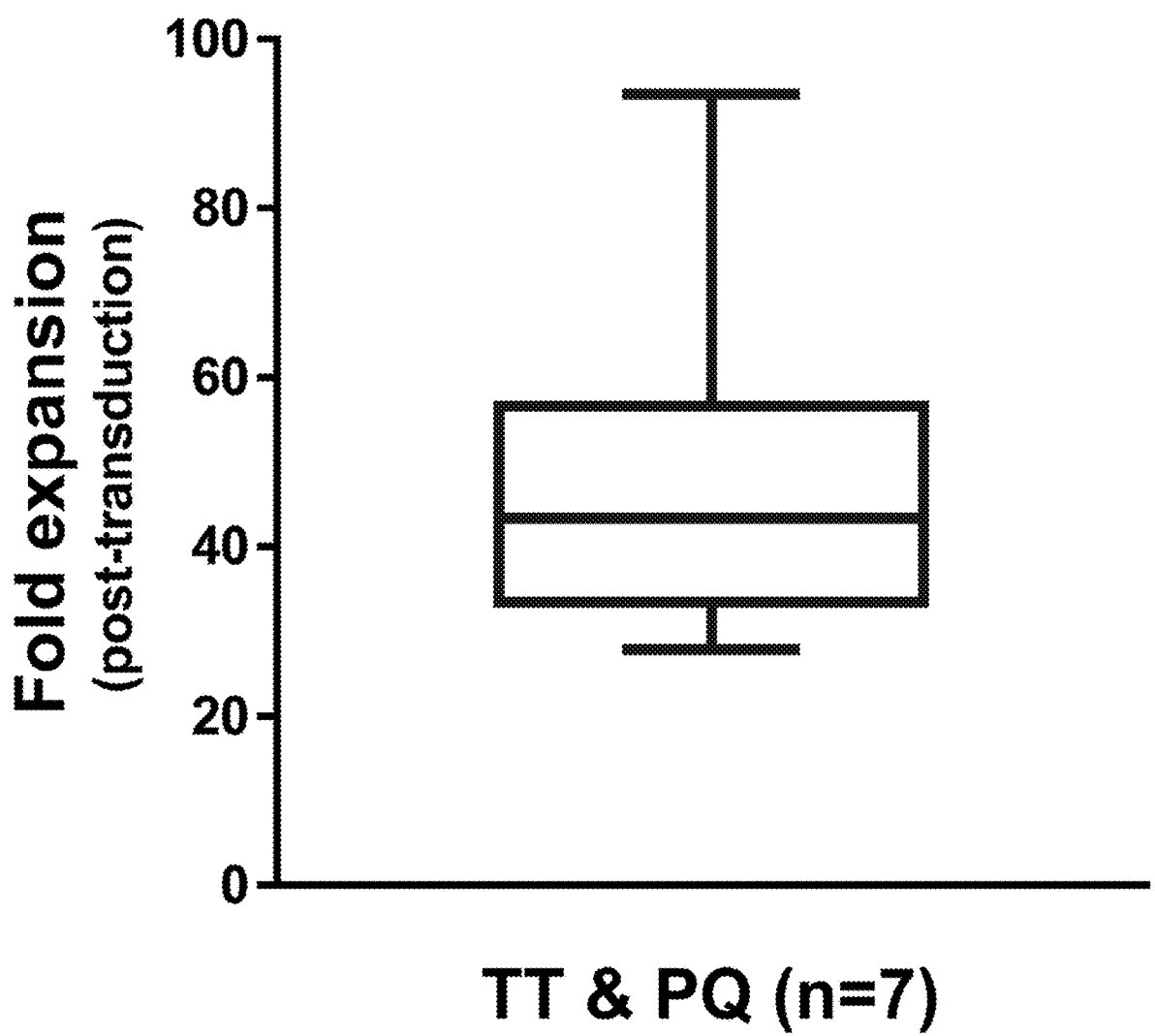
FIG. 25A shows fold expansion of T cells manufactured with overnight rest (about 16 hours).

In contrast to T cell manufacturing process with short rest, e.g., about 4 hours, T cells manufactured with rest of about 16 hours yielded less fold expansion of T cells. FIG. 25A and Table 3 show average fold expansion of T cells (n=7) manufactured by resting PBMC for about 16 hours is about 45-fold, as compared with about 78.7-fold with short rest of about 4 hours (Table 2). TT and PQ stand for Technology Transfer and Process Qualification runs, respectively.

Figure 25B:
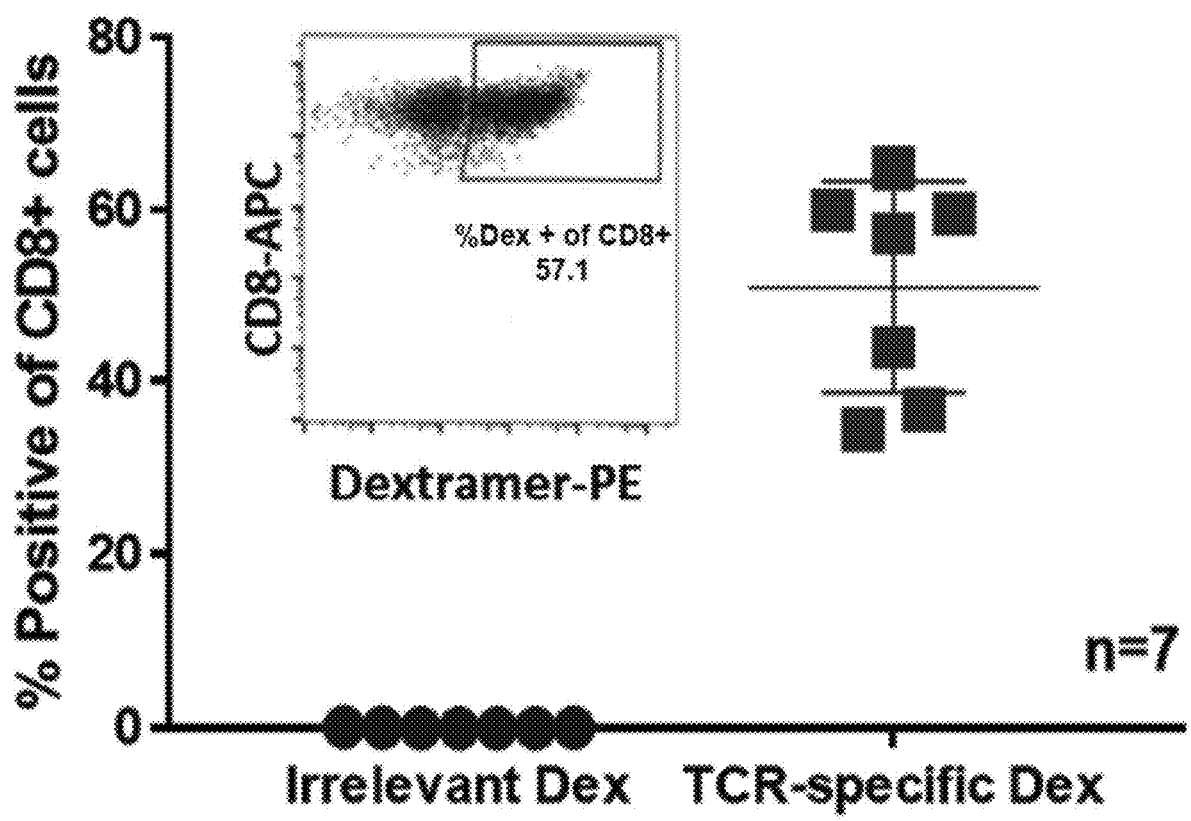
FIG. 25B shows transduced TCR expression of T cells manufactured with overnight rest (about 16 hours).

Overnight rest (about 16 hours) yielded less expanded T cells expressing transduced TCR than rest of about 4 hours. FIG. 25B and Table 3 show average % Dex+/CD8+ T cells (n=7) manufactured by resting PBMC overnight for about 16 hours is about 51.9%, as compared with about 53.4% with rest of about 4 hours (Table 2).

Figure 25C:
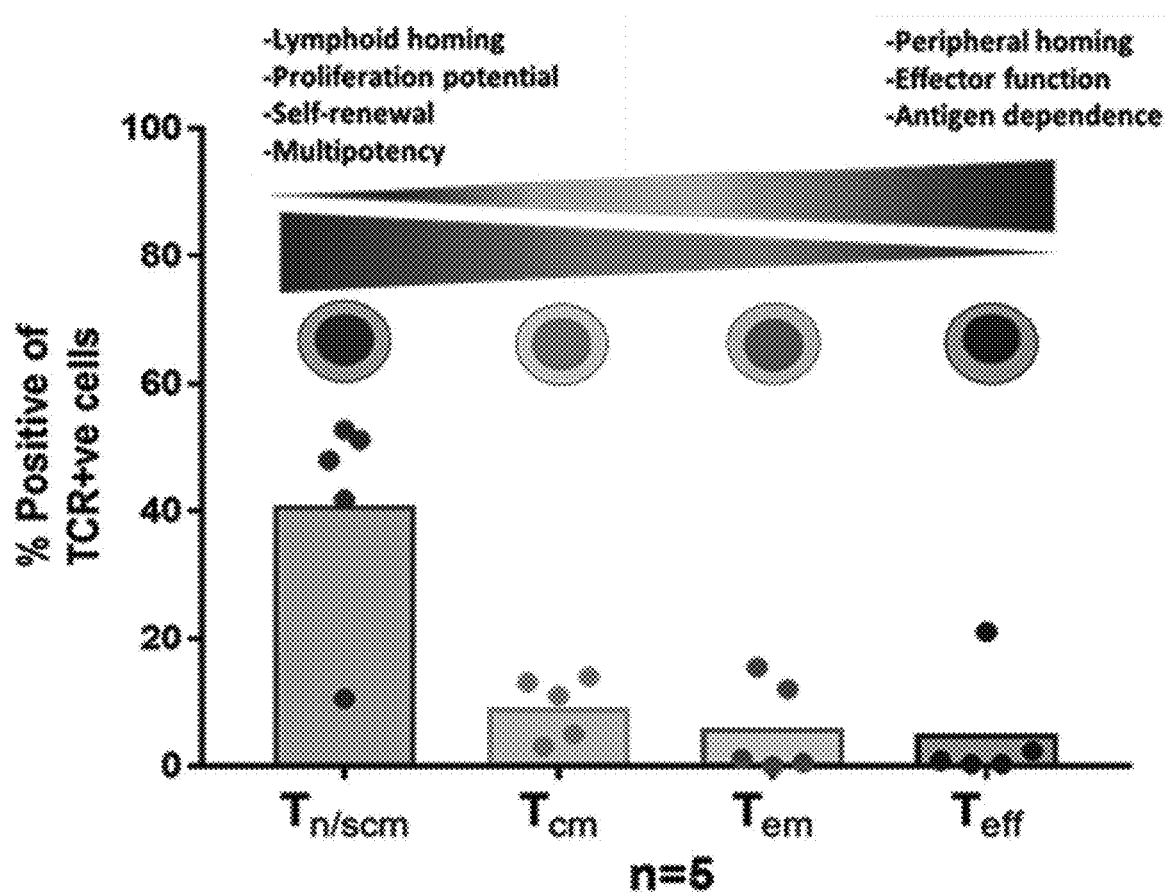
FIG. 25C shows phenotypes of T cells manufactured with overnight rest (about 16 hours).

Overnight rest of about 16 hours yielded less expanded T cells expressing transduced TCR with $T_{n/scm}$ phenotype than rest of about 4 hours. FIG. 25C shows average about 40% of expanded T cells (n=5) having $T_{n/scm}$ phenotypes, as compared with about 50% with rest of about 4 hours (FIG. 23C).

Figure 25D:
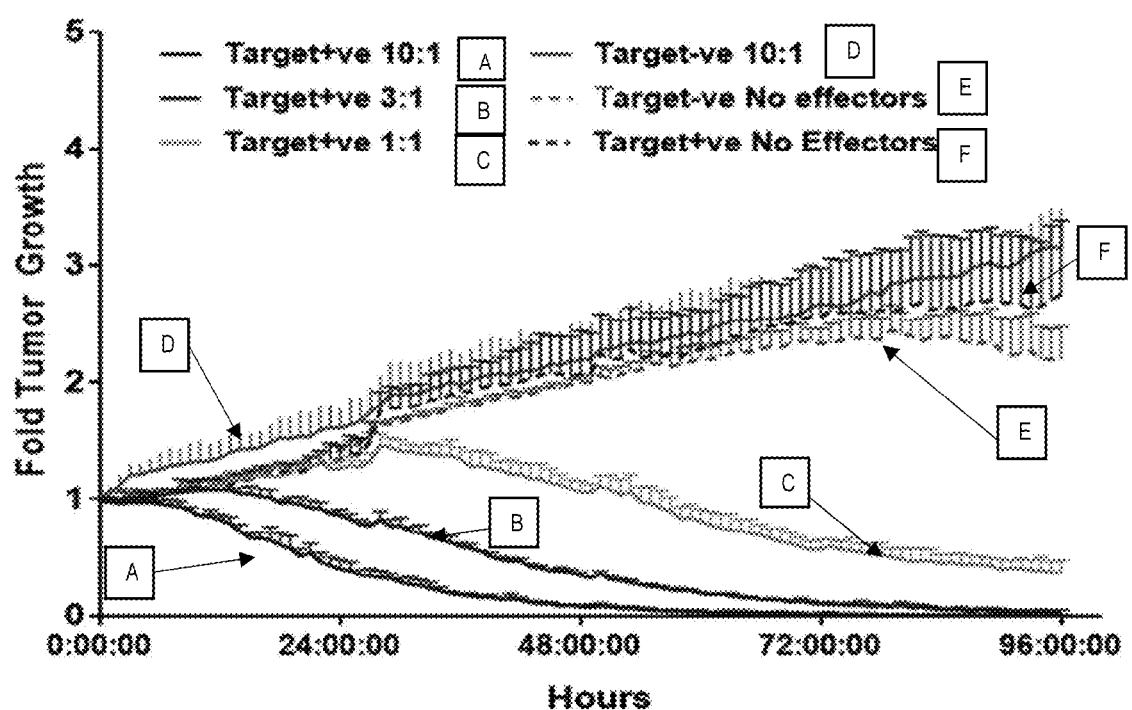
FIG. 25D shows tumor cell growth inhibitory activity of T cells manufactured with overnight rest (about 16 hours).
Figure 25E:
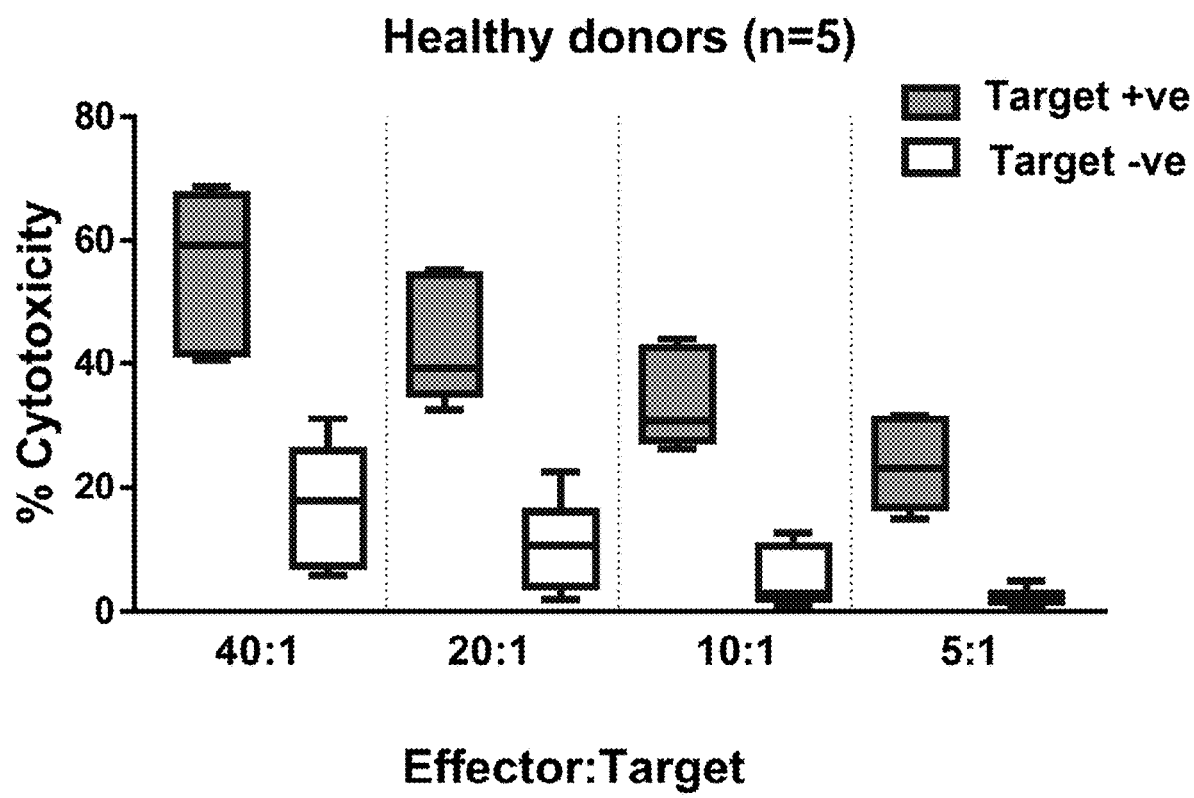
FIGS. 25E and 25F show cytotoxic activity of T cells manufactured with overnight rest (about 16 hours).
Figure 25F:
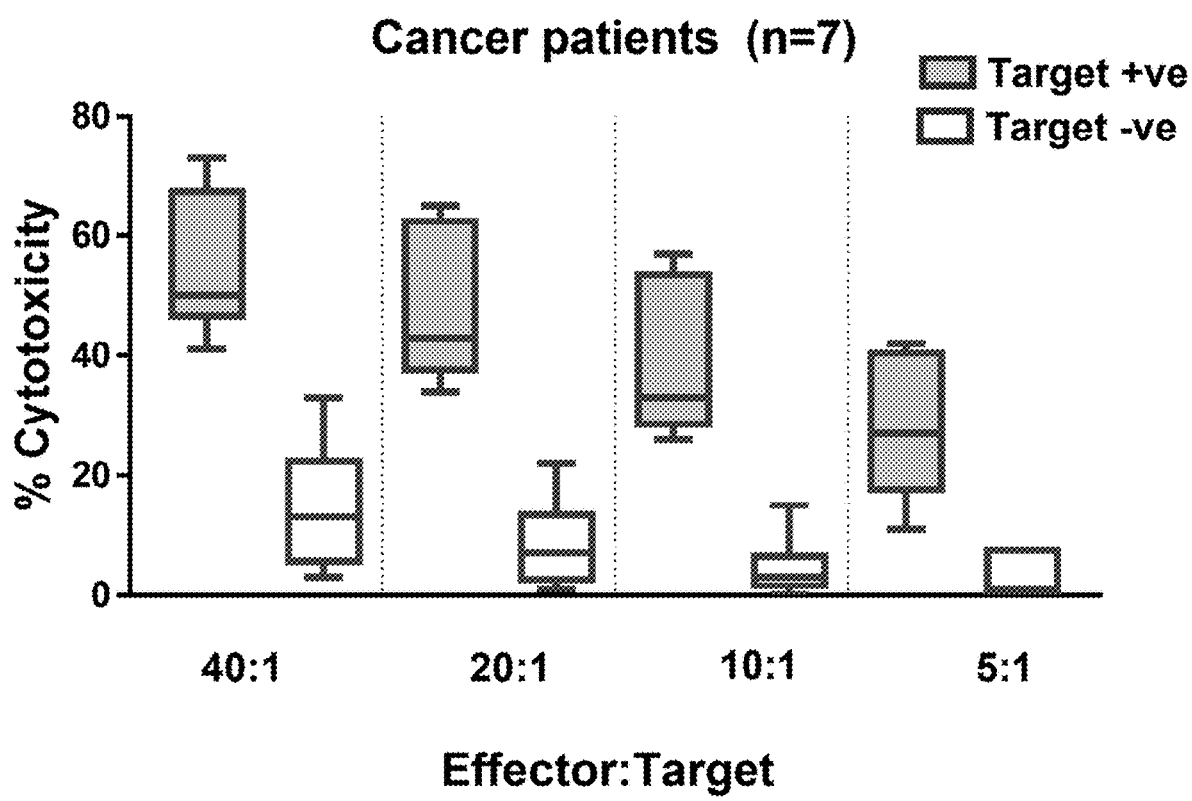

FIG. 25D shows significantly more inhibition of tumor cell growth by incubation of tumor cells with expanded T cells expressing transduced TCR (effectors) at effectors to tumor cells ratios of 10:1, 3:1, and 1:1 than that of the negative controls, e.g., tumor cells incubated with either expanded T cells that do not express transduced TCR (Target-ve) or no effectors. In addition, cytotoxic activities of expanded T cells expressing transduced TCR appear comparable between PBMC obtained from healthy donors (n=5) (FIG. 25E) and that obtained from cancer patients (n=7) (FIG. 25F).

Table 4 summarizes characteristics of T cells manufactured with short rest of about 4 hours according to one embodiment of the present disclosure (process 220) and that with overnight rest of about 16 hours (process 240).

TABLE 4

| Process | Fold Expansion | Harvest Count | Viability ≥70% | % Live CD3+ ≥80% | % CD8+ of CD3+ | % Dex+ of CD8+ ≥10% |
|---|---|---|---|---|---|---|
| 220 | 78.7 | $28.0 \times 10^9$ | 92.0 | 99.7 | 53.4 | 63.7 |
| 240 | 45.0 | $15.7 \times 10^9$ | 86.0 | 99.5 | 51.9 | 53.0 |

Table 4 shows process with short rest 220 (about 4-6 hours) may allow an extra day in expansion, e.g., Day 8 of process 240 is Day 9 for process 220, thus, resulting in more cells.

Example 5

T Cell Manufacturing in Closed System

As noted above, processes 220 and 240 may be carried out in open systems, such as G-Rex™. Ex vivo manipulation of haematopoietic cells, e.g., T cells, in open systems, however, may introduce risk of contamination with infectious agents and may reduce engraftment potential and haematopoietic fitness. In manufacturing clinical cell products, closed cell culture systems may be preferred due to the assurance of sterility throughout culture processes.

Figure 26:
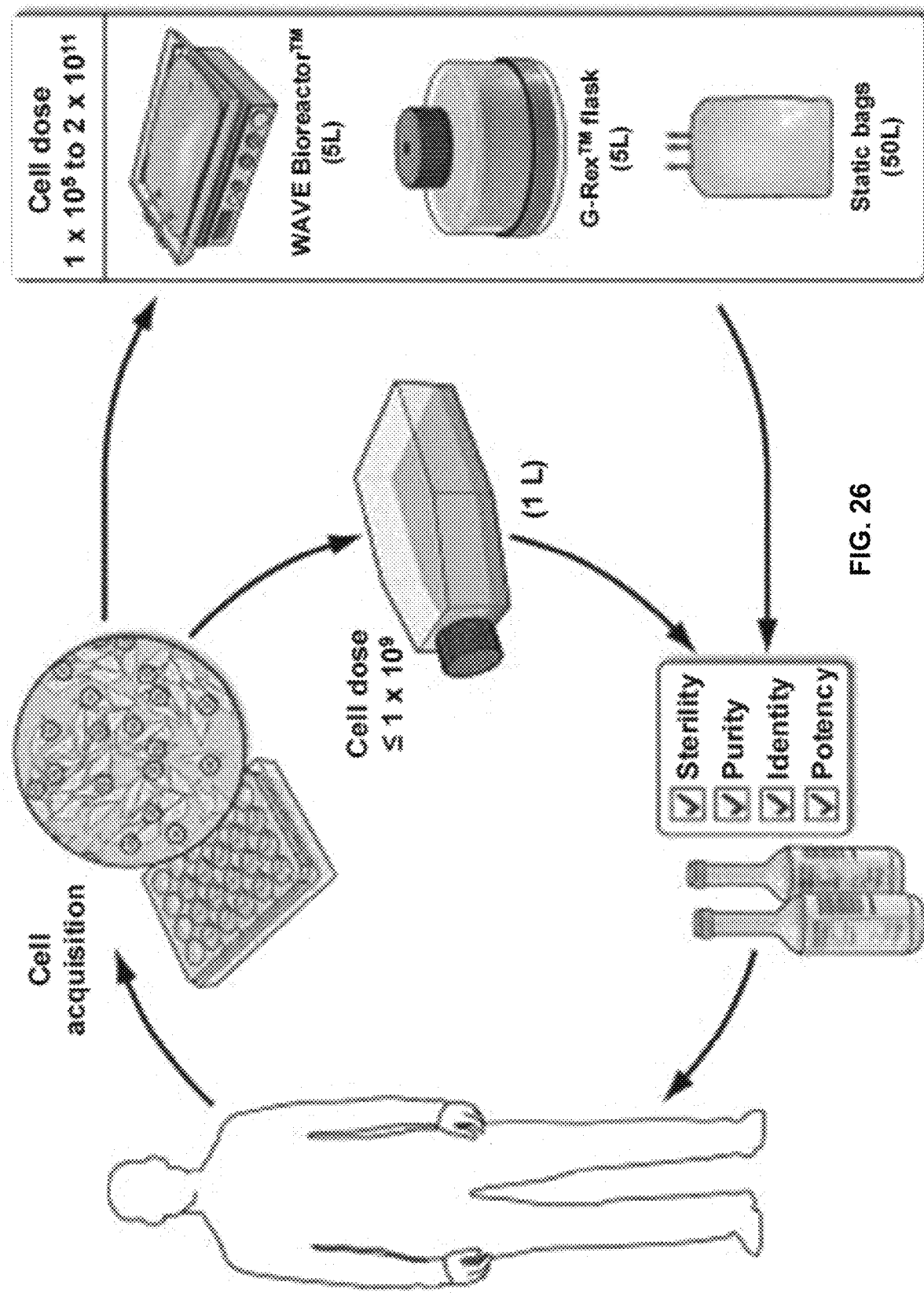
FIG. 26 shows ex vivo manipulation protocol in open and closed systems.

FIG. 26 shows ex vivo manipulation protocol in open and closed systems. Closed systems not only can mitigate external processing risks and contamination, but also promote product robustness and quality, and increase product security, thus, can reduce challenges for downstream processing, final product analysis, and testing. While relatively small numbers of cells, e.g., $\leq 1 \times 10^9$, may be cultured in a relatively small volume in open system, e.g., 1 liter, relatively large numbers of cells, e.g., from about $1 \times 10^9$ to about $2 \times 10^{11}$, may be cultured in a relatively large volume in closed system, e.g., from 5 liters (e.g., WAVE (XURI™) Bioreactor bag and G-Rex™ flask) to 50 liters (e.g., static bag). These closed system cell culturing technologies may deliver high quality, individualized cell therapies as a regulated, faster, and cost-effective route of cell manufacturing.

T cell manufacturing process of the present disclosure may be carried out in any cell culture closed systems including commercially available systems, e.g., CliniMACS Prodigy™ (Miltenyi), WAVE (XURI™) Bioreactor (GE Biosciences) alone or in combination with BioSafe Sepax™ II, and G-Rex/GatheRex™ closed system (Wilson Wolf) alone or in combination with BioSafe Sepax™ II. G-Rex™-closed system is the expansion vessel and GatheRex™ is the pump for concentrating and harvesting.

CliniMACS Prodigy™ (Miltenyi)

CliniMACS Prodigy™ with TCT process software and the TS520 tubing set may allow closed-system processing for cell enrichment, transduction, washing and expansion. For example, MACS-CD4 and CD8-MicroBeads may be used for enrichment, TransACT beads, e.g., CD3/CD28 reagents, may be used for activation, lentiviral vectors expressing a recombinant TCR may be used for transduction, TexMACS medium-3%-HS-IL2 for culture and phosphate-buffered saline/ethylenediaminetetraacetic acid buffer for washing. This system may yield about $4-5 \times 10^9$ cells, contain automated protocols for manufacturing with chamber maximum ~300 mL fill volume, and perform selection and activation (TransACT beads), transduction, and expansion over a 10 to 14-day process.

WAVE (Xuri™) Bioreactor (GE Biosciences)

WAVE (Xuri™) Bioreactor allows T cells to be cultured in culture bags, e.g., Xuri Cellbags, with and/or without perfusion. Medium bag for feeding may be 5-liter Hyclone Labtainer. Waste bag may be Mbag (purchased from GE Healthcare). This system may yield about $15-30 \times 10^9$ cells, use unicorn software that allows for culture control and monitoring, contain rocking tray that may hold from about 0.3-liter to about 25 liters, and perform perfusion function to maintain culture volume while mediating gas exchange and introducing fresh media and cytokines to cell culture.

WAVE (Xuri™) Bioreactor may include Xuri Bags for expansion, Saint Gobain's VueLife bags for thawing and resting, and VueLife AC bags for activation. WAVE (Xuri™) Bioreactor may be used in combination with other technologies, e.g., Sepax™ cell separation system (GE Biosciences) for culture washing and volume reduction steps. Sterile welder (Terumo BCT™) may be used for connecting sterile bags for solution transfer and heat sealer for sealing tubing.

Sepax™ cell separation system relies on a separation chamber that provides both separation through rotation of the syringe chamber (centrifugation) and component transfer through displacement of the syringe piston. An optical sensor measures the light absorbency of the separated components and manages the flow direction of each of them in the correct output container, for example, plasma, buffy coat, and red blood cells may be thus separated and collected from blood samples.

Figure 27:
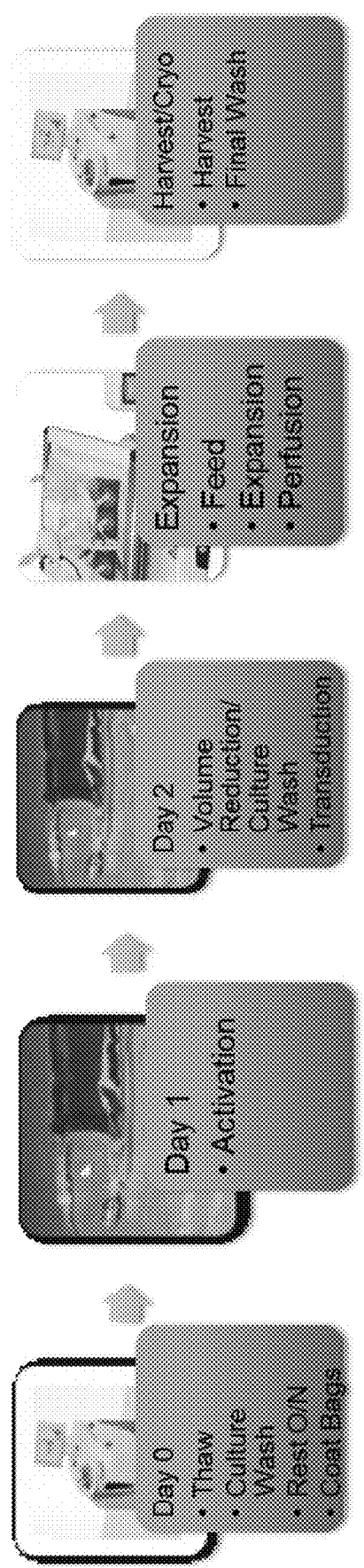
FIG. 27 shows ex vivo manipulation protocol in closed system in accordance with one embodiment of the present disclosure.

FIG. 27 shows, on Day 0, frozen PBMC isolated by Sepax™ cell separation system may be thawed, washed, rested, e.g., overnight (O/N), and culture bags, e.g., VueLife AC cell bags, may be coated with anti-CD3 antibody and anti-CD28 antibody; on Day 1, rested PBMC may be transferred to culture bags coated with anti-CD3 antibody and anti-CD28 antibody for activation; on Day 2, cells may be washed and media may be reduced by Sepax™ cell separation system to an appropriate volume suitable for viral transduction, e.g., transduced with lentiviral vector expressing TCR. Cell expansion can be performed in Xuri™ culture bags on a rocking tray with perfusion function to maintain culture volume while mediating gas exchange and introducing fresh media and cytokines to cell culture. Expanded transduced T cells may be harvested and washed using Sepax™ cell separation system.

G-Rex/GatheRex™ Closed System (Wilson Wolf)

G-Rex/GatheRex™ closed system comprises a gas-exchange vessel (G-Rex-CS) for cell expansion and an automated pump (GatheRex) that may allow the operator to drain the excess media present in the culture and collect cells without risk of contamination. The harvesting process may be divided into two stages: cell concentrating and cell harvesting. In cell concentrating process, GatheRex™ closed system may operate via an air pump, which pressurizes the G-Rex™ device, e.g., flasks, with sterile air, allowing 90% of the medium residing above the cells to be displaced into a medium collection bag. Once this process is complete, a first optical detector senses the presence of air in the medium collection line, automatically stopping the pump. Prior to beginning the harvest process, the operator may resuspend the cells using the residual 10% of the medium by manually swirling the G-Rex™ device to dislodge cells from the gas-permeable membrane. The air pump is then reactivated, and the resuspended cells are drawn into the cell collection bag. This phase may automatically end once a second optical detector detects air in the cell collection line. This system may yield about 15-20×10$^9$ cells and hold 5-liters per vessel.

G-Rex/GatheRex™ closed system may support transduction and expansion in the vessel and harvest with the pump. Thawing, resting, and activation steps may be carried out in VueLife™ bags. GatheRex™ closed system may be used in combination with other technologies, e.g., Sepax™ cell separation system for culture washing and volume reduction steps Sterile welder (Terumo BCT™) may be used for connecting sterile bag for solution transfer and heat sealer for sealing tubing.

Figure 28:
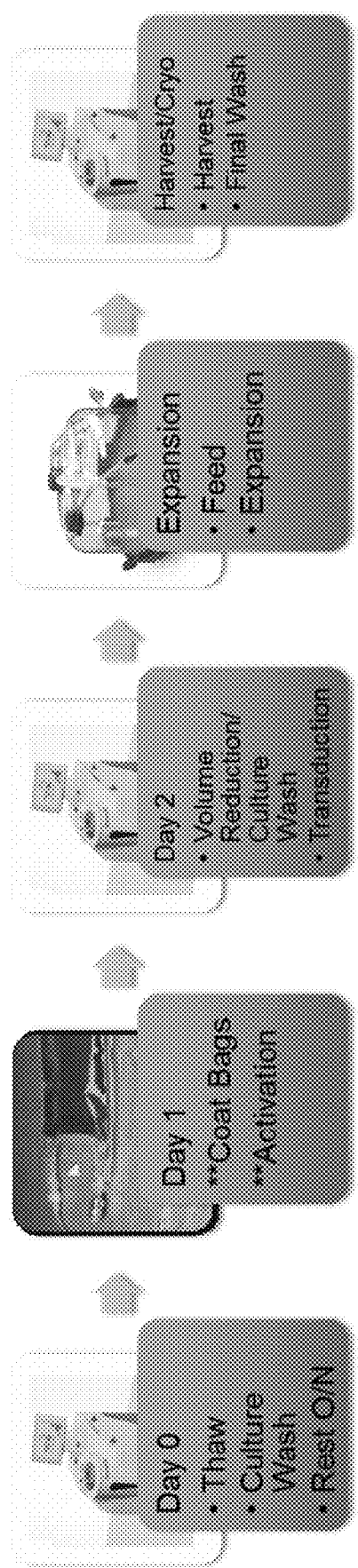
FIG. 28 shows ex vivo manipulation protocol in closed system in accordance with another embodiment of the present disclosure.

FIG. 28 shows on Day 0, frozen PBMC isolated by Sepax™ cell separation system may be thawed, washed, rested, e.g., overnight (O/N); on Day 1, culture bags may be coated with anti-CD3 antibody and anti-CD28 antibody and rested PBMC may be transferred to the coated culture bags for activation; on Day 2, cells may be washed and media may be reduced by Sepax™ cell separation system to an appropriate volume suitable for viral transduction, e.g., transduced with lentiviral vector expressing TCR. Cell expansion and feeding may be performed in G-Rex™ closed system devices. Expanded transduced T cells may then be harvested using the GatheRex™ pump and washed using Sepax™ cell separation system.

Table 5 shows comparison between T cells obtained by open systems, e.g., G-Rex™, as shown in Table 4, i.e., processes 220 and 240, and T cells obtained by closed systems, e.g., CliniMACS Prodigy™, WAVE (XURI™) Bioreactor in combination with BioSafe Sepax™ II, and G-Rex/GatheRex™ closed system in combination with BioSafe Sepax™ II.

TABLE 5

| Process | Fold Expansion | Harvest Count | Viability ≥ 70% | % Live CD3+ ≥ 80% | % CD8+ of CD3+ | % Dex+ of CD8+ ≥ 10% |
|---|---|---|---|---|---|---|
| 220 | 78.7 | 28.0 × 10$^9$ | 92.0 | 99.7 | 53.4 | 63.7 |
| 240 | 45.0 | 15.7 × 10$^9$ | 86.0 | 99.5 | 51.9 | 53.0 |
| CliniMACS Prodigy ™ | 55.0 | 4.4 × 10$^9$ | 95.4 | 98.5 | 55.0 | 39.7 |
| WAVE (XURI ™) Bioreactor in combination with BioSafe Sepax ™ II | 40.3 | 16.1 × 10$^9$ | 92.0 | 99.6 | 60.8 | 41.7 |
| G-Rex/ GatheRex ™ in combination with BioSafe Sepax ™ II | 46.3 | 18.5 × 10$^9$ | 89.7 | 99.4 | 62.8 | 49.5 |

These results show T cell manufacturing process of the present disclosure can be readily performed in closed systems to produce T cells with comparable characteristics to that produced in open systems, while mitigating external processing risks and contamination, promoting product robustness and quality, and increasing product security, and thus, reducing challenges for downstream processing, final product analysis, and testing.

To further compare functional characteristics of engineered T cells manufactured in closed systems with that manufactured in open systems, PBMCs obtained from donor 17 were processed to produce expanded transduced T cells according to the process of the present disclosure. The expanded transduced T cells expressing TCR were then measured for IFN-γ release in the present or absence of TCR-specific peptide/MHC complex (target).

Figure 29:
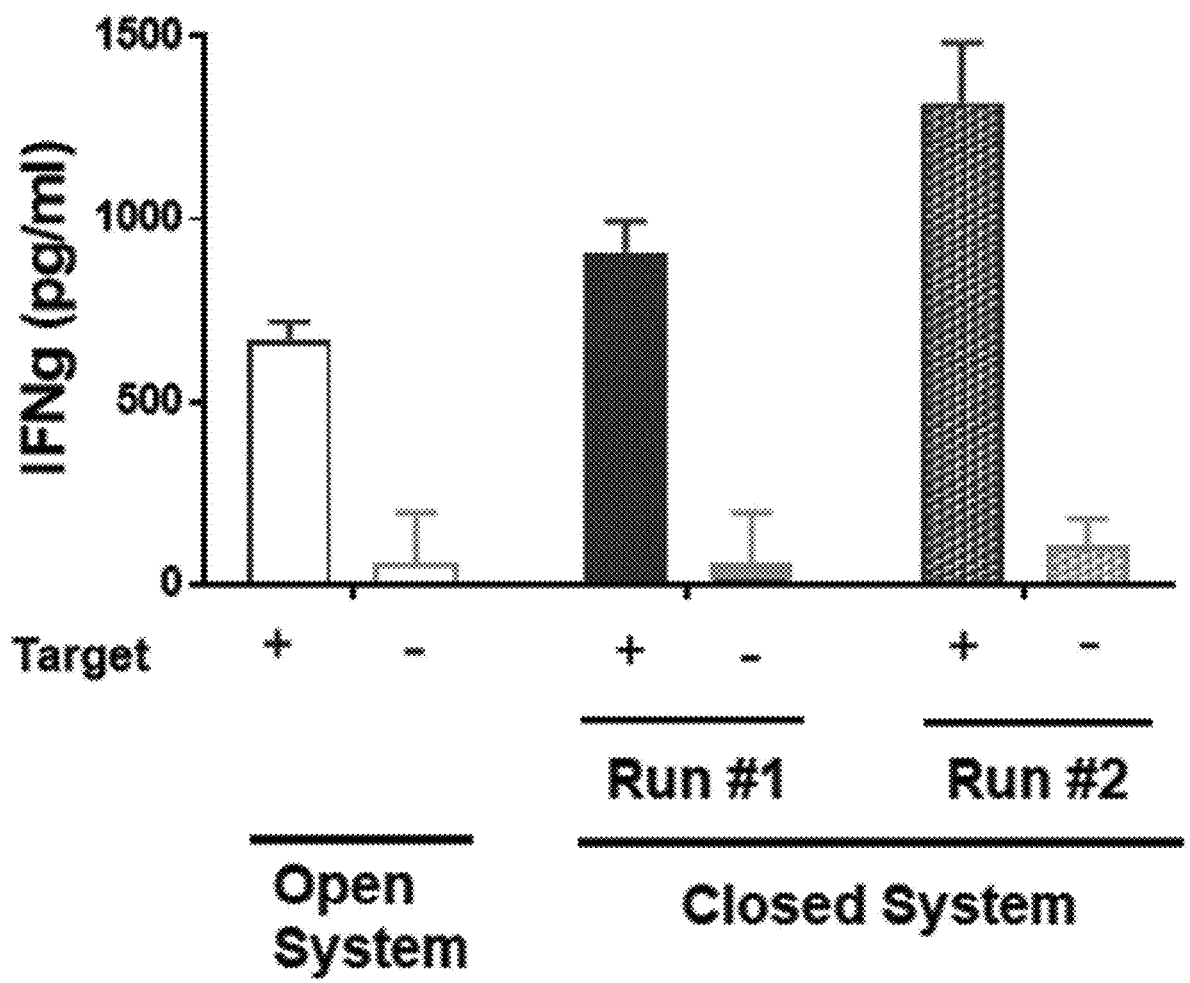
FIG. 29 shows IFN-γ release from T cells manufactured in open and closed systems.

FIG. 29 shows that engineered T cells manufactured in closed systems as measured by two runs, Run #1 and Run #2, released significantly more IFN-γ in the presence of target than that manufactured in open system, e.g., process 220. These results suggest that engineered T cells manufactured in closed systems may exhibit greater cytotoxic activity than that manufactured in open systems.

Example 6

GMP Manufacturing of TCR-Engineered T Cells in about 5 to 6 Days

Adoptive cellular therapy with autologous engineered T cells approach capitalizes on translational development of safe and effective targets and their cognate TCRs. These TCRs are genetically engineered into patients' own (autologous) T-cells for the immunotherapy of solid tumors.

Figure 30:
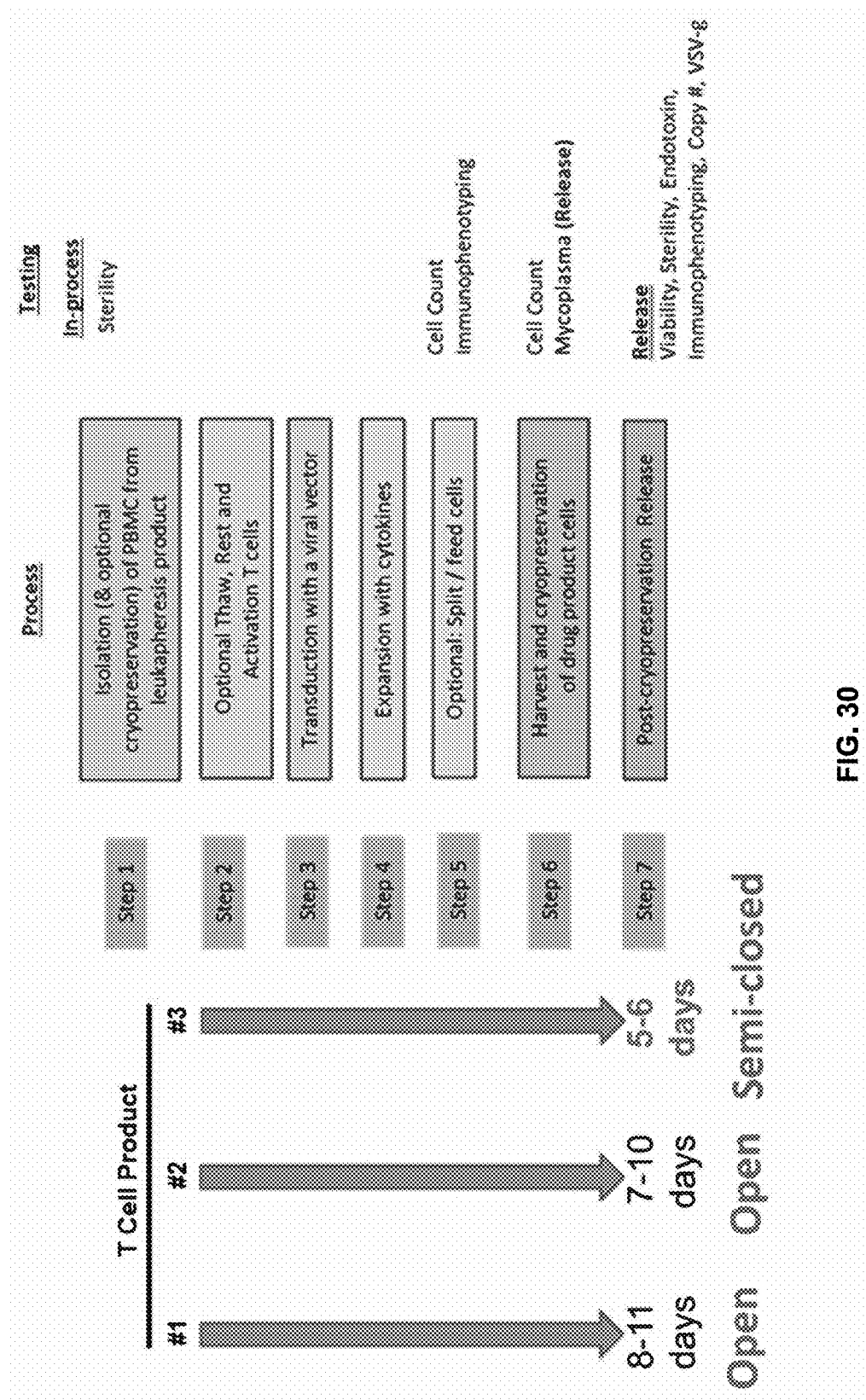
FIG. 30 shows a schematic of T cell manufacturing in accordance with some embodiments of the present disclosure.

FIG. 30 shows manufacturing outline of three T-cell products (T Cell Product #1, T Cell Product #2, and T Cell Product #3) each expressing a transgenic TCR against its own respective HLA-A*02:01 restricted tumor targeted antigen. T Cell Product #1 and T Cell Product #2 were manufactured in about 8-11 days and about 7-10 days, respectively, from thawing frozen PBMC, resting the thawed PBMC, and activating the rested PBMC (Step 2), transducing the activated T cells (Step 3), to "harvest and cryopreservation of drug product cells" (Step 6), using open systems for IND driven phase 1 first in man trials.

T Cell Product #3 may be manufactured by shortening the expansion phase from about 5-8 days (T Cell Products #1 and #2) to about 3-4 days. In addition, T Cell Product #3 may be manufactured by activating fresh PBMC, i.e., PBMC is not cryopreserved and then thawed, on Day 0. This is in contrast to the manufacturing T Cell Products #1 by thawing the cryopreserved PBMC on Day 0 and then activating the thawed PBMC on Day 1 and the manufacturing T Cell Products #2 by thawing the cryopreserved PBMC and activating the thawed PBMC on Day 0.

In contrast to T Cell Products #1 and #2, which are manufactured by using open systems, T Cell Product #3 may be manufactured by using a complete closed system or a semi-closed system, in which some steps may be performed by using open systems, e.g., from T cell activation to volume reduction for transduction and/or from harvest to washing, concentration, and cryopreservation.

Figure 31:
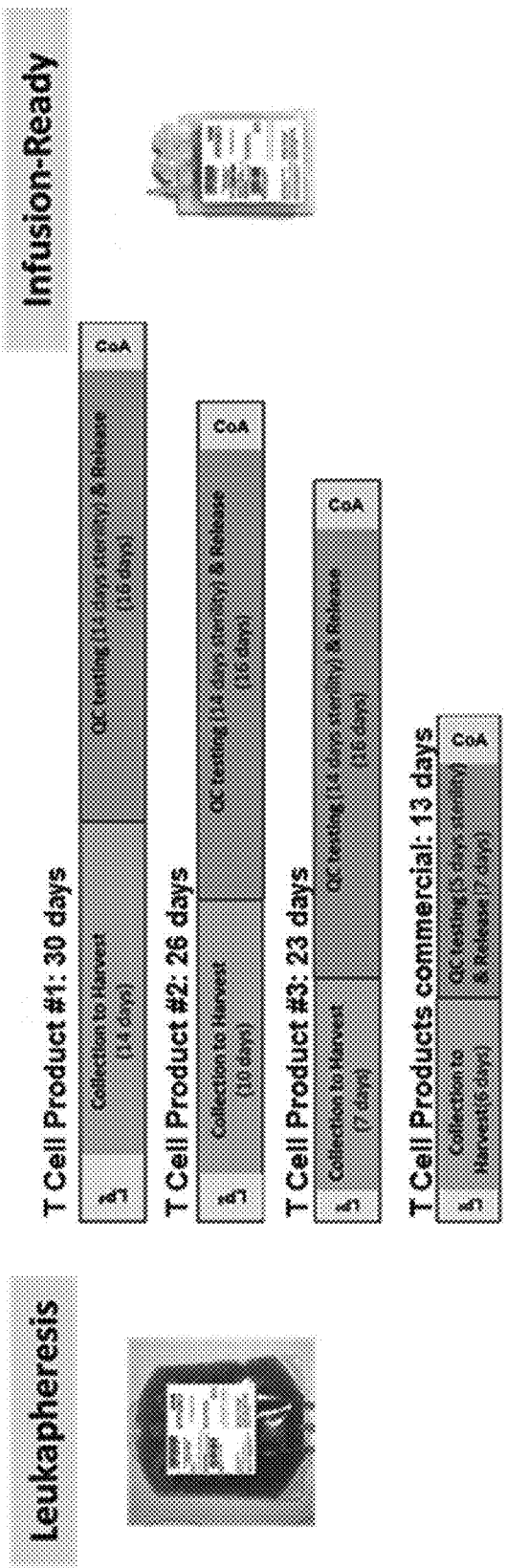
FIG. 31 shows a representative turnaround time from leukapheresis collection to infusion-ready in accordance with one embodiment of the present disclosure.
$LP^\#$:Leukapheresis collection, processing & freeze (optional). CoA: Additional time required for issuance of Certificate of Analysis.

FIG. 31 shows the turnaround time from leukapheresis collection to infusion-ready TCR T Cell Product #1 may take about 30 days, e.g., about 14 days from sample collection to harvest and about 16 days from quality control (QC) to product release; and the turnaround time for manufacturing TCR T Cell Product #2 may take about 26 days, e.g., about 10 days from sample collection to harvest and about 16 days from QC to product release.

There is, however, a need for fast turnaround. FIG. 30 shows, T Cell Product #3 was manufactured using shorter manufacturing process, e.g., 5-6 days, from "optional thaw, rest, and activation" (Step 2) to "harvest and cryopreservation of drug product cells" (Step 6), using semi-closed system. FIG. 31 shows TCR T Cell Product #3 may take about 23 days to manufacture, e.g., about 7 days from sample collection to harvest and about 16 days from QC to product release. For commercial manufacturing, for example, TCR T cell products, e.g., T Cell Product #1, T Cell Product #2, and T Cell Product #3, may take about 13 days to manufacture, e.g., about 6 days from sample collection to harvest and about 7 days from QC to product release.

Figure 32:
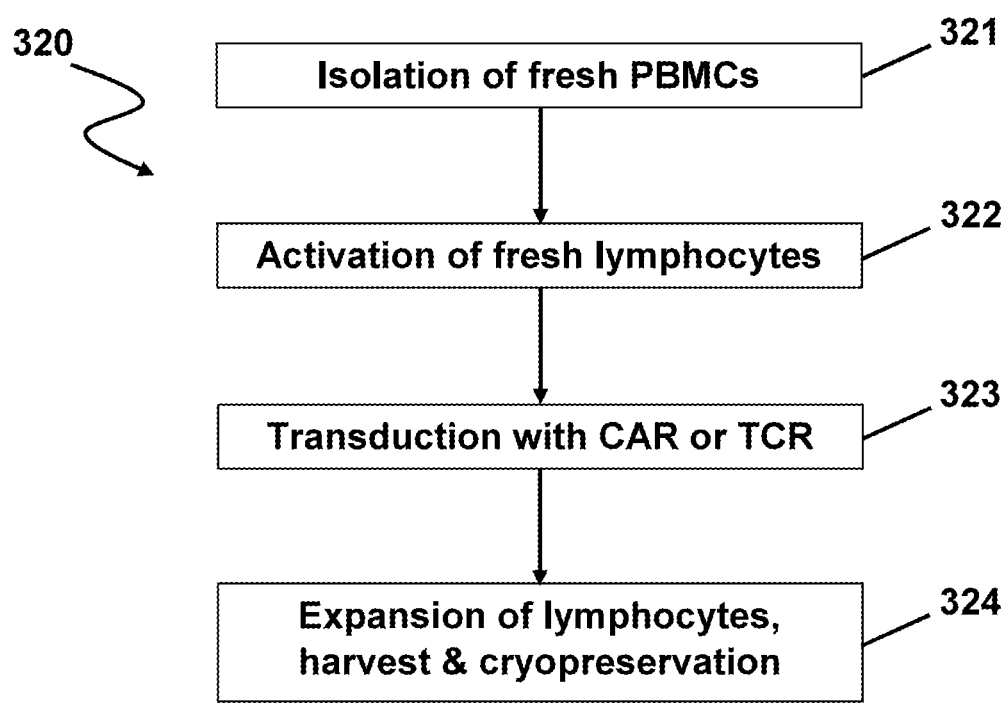
FIG. 32 shows a T cell manufacturing process in accordance with one embodiment of the present disclosure.

FIG. 32 shows a T cell manufacturing process 320 using fresh PBMCs, which is not obtained by thawing cryopreserved PBMC, thus, minimizing cell loss due to freezing, thawing, and/or resting PBMCs and maximizing cell numbers at the beginning of manufacturing process. For example, T cell manufacturing process 320 may include Day 0, isolation of fresh PBMC (321), activation of fresh lymphocytes (322) using, for example, anti-CD3 and anti-CD28 antibodies (soluble or surface bound, e.g., magnetic or biodegradable beads) in bags, e.g., Saint-Gobain VueLife AC Bags, coated with anti-CD3 and anti-CD28 antibodies; Day 1, transduction with CAR or TCR (323) using, for example, lentiviral or retroviral constructs encoding CAR or TCR or non-viral methods, e.g., liposomes; and Day 2, expansion of lymphocytes, Day 5/6, harvest, and cryopreservation (324) in the presence of cytokine(s), serum (ABS or FBS), and/or cryopreservation media.

Improved Product Profile with Shorter Expansion

The quality, efficacy, longevity, and location of T cell immunity may result from the diversification of naive T cells ($T_n$) into various phenotypically distinct subsets with specific roles in protective immunity. These include memory stem ($T_{scm}$), central memory ($T_{cm}$), effector memory ($T_{em}$), and highly differentiated effector ($T_{eff}$) T cells. The antigen-specific $T_n$ give rise to long-lived $T_{scm}$ and $T_{cm}$ that self-renew and provide proliferating populations of shorter-lived $T_{em}$ and $T_{eff}$ cells. Therefore, selecting less differentiated $T_n$, $T_{scm}$ or $T_{cm}$ subsets for genetic modification may provide cells with greater therapeutic efficacy.

To evaluate the differentiation status of T cell products harvested at different time of manufacturing, CD8+ T cells obtained from 3 donors (Donor 1, Donor 2, and Donor 3) were harvested on Day 4 (expansion for 3 days), 7 (expansion for 6 days) and 10 (expansion for 9 days) of manufacturing followed by T cell memory phenotyping analysis.

Figure 33:
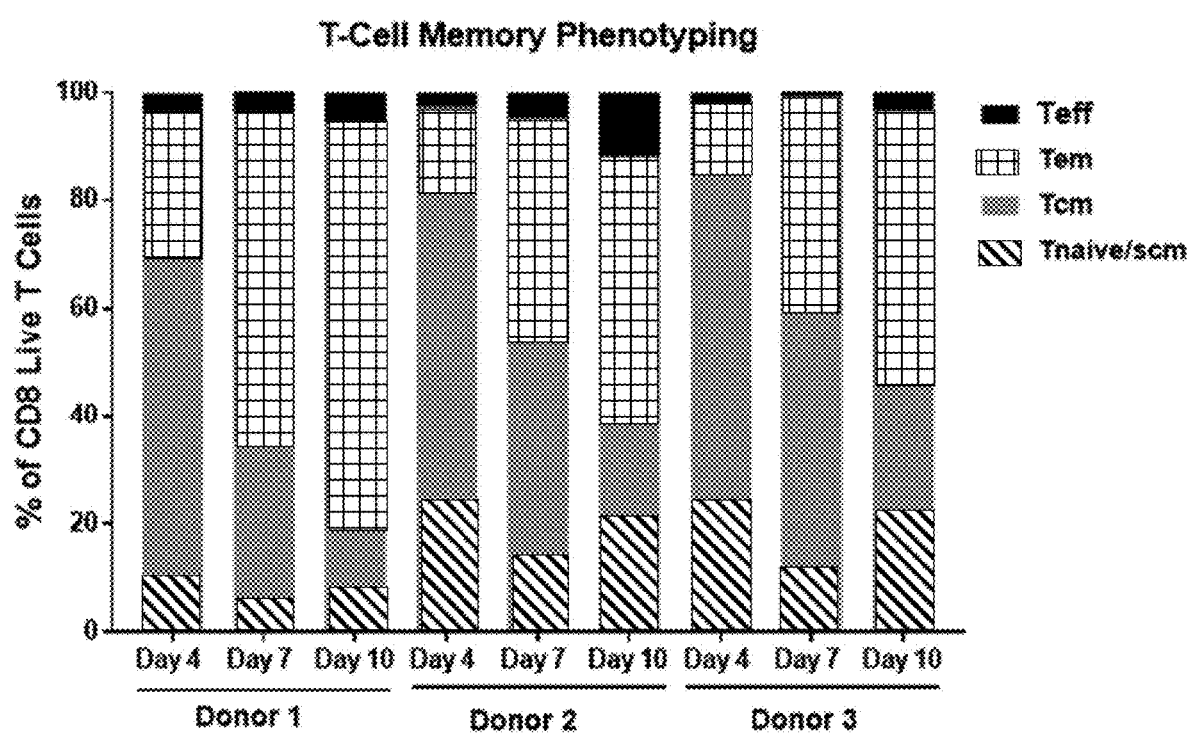
FIG. 33 shows T cell memory phenotyping of T cells produced by a manufacturing process in accordance with one embodiment of the present disclosure.

FIG. 33 shows the amount of CD8+ T cells exhibiting the less differentiated phenotypes, e.g., $T_{n/scm}$-CD45RA+CCR7+ and $T_{cm}$-CD45RO+CCR7+, decreases in an expansion time-dependent manner, i.e., Day 4>Day 7>Day 10. Conversely, the amount of CD8+ T cells exhibiting the more differentiated phenotypes, e.g., $T_{em}$-CD45RO+CCR7- and $T_{eff}$-CD45RA+CCR7-, increases in an expansion time-dependent manner, i.e., Day 4<Day 7<Day 10, indicating more less differentiated phenotypes of Day 4 expanded cells than that of Day 7 and Day 10 expanded cells. These results suggest the shorter the T cells expand, the more the T cells exhibit less differentiated memory phenotypes, thus, with greater therapeutic efficacy.

CD27 and CD28 co-stimulation may be required during primary CD8+ T cell responses. This co-stimulation may provide proliferation and survival cues to naive CD8+ T cells. To evaluate the CD27 and CD28 co-stimulation potentials of T cell products harvested at different time of manufacturing, CD8+ T cells obtained from 3 donors (Donor 1, Donor 2, and Donor 3) were harvested on Day 4, 7 and 10 of manufacturing followed by CD27 and CD28 expression analysis.

Figure 34:
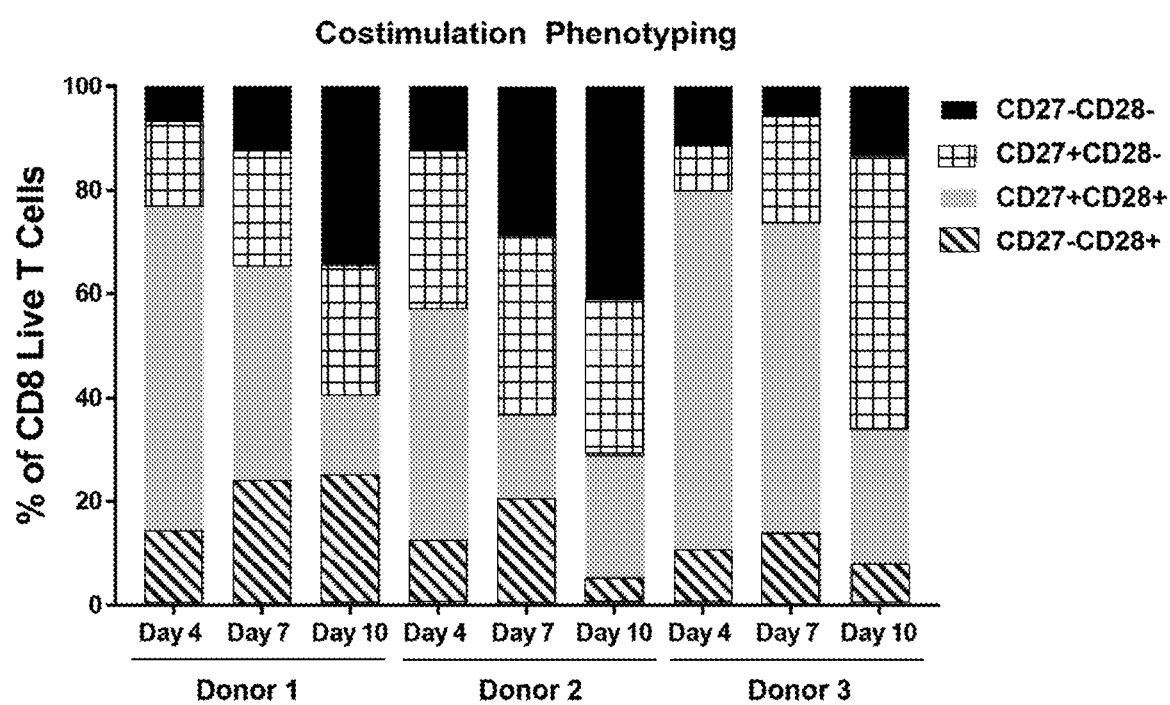
FIG. 34 shows CD27 and CD28 co-stimulation phenotyping of T cells produced by a manufacturing process in accordance with one embodiment of the present disclosure.

FIG. 34 shows the amount of CD8+ T cells exhibiting the CD27+CD28+ co-stimulation phenotypes decreases in an expansion time-dependent manner, i.e., Day 4>Day 7>Day 10, indicating superior CD27 and CD28 co-stimulation of Day 4 expanded cells to that of Day 7 and Day 10 expanded cells. These results suggest, in general, the shorter the T cells expand, the more the T cells express both CD27 and CD28.

To evaluate the replicative potentials of T cell products harvested at different time of manufacturing, T cells were harvested on Day 4, 7 and 10 of manufacturing and monitored for growth in response to relevant cytokines, e.g., IL-7, IL-15, or IL-2 in cytokine sensitivity assay.

Figure 35:
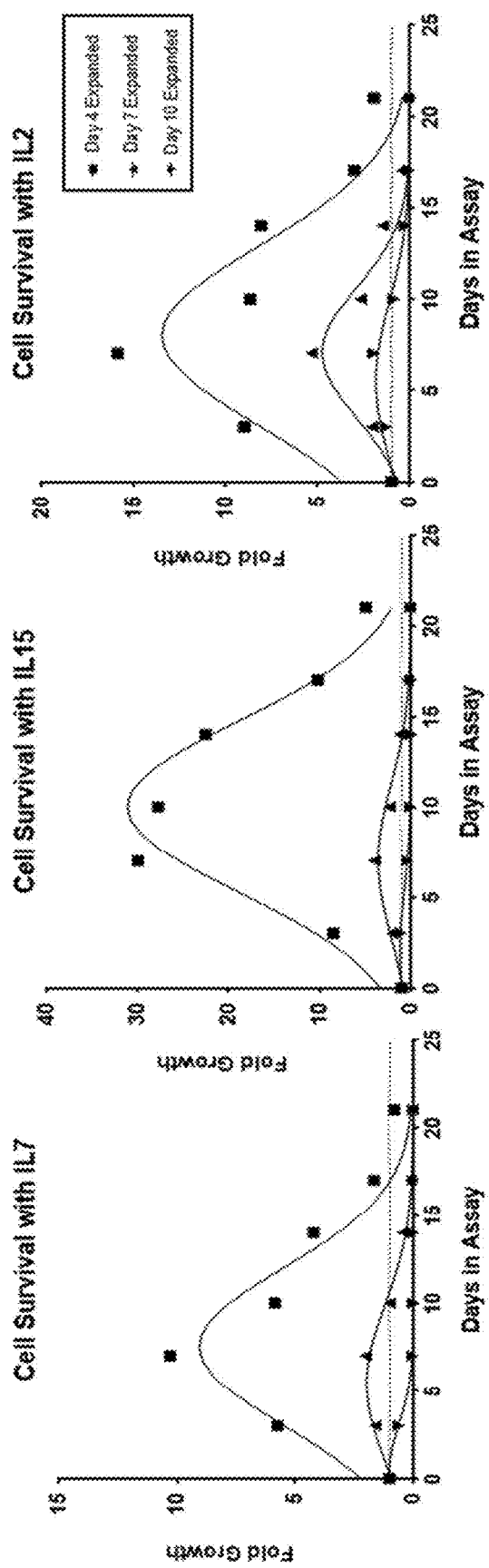
FIG. 35 shows T cell growth induced by IL-7, IL-15, or IL-2 decreases in an expansion time-dependent manner in accordance with one embodiment of the present disclosure.

FIG. 35 shows T cell growth induced by IL-7, IL-15, or IL-2 for about 21 days decreases in an expansion time-dependent manner, i.e., Day 4>Day 7>Day 10, indicating superior replicative potentials of Day 4 expanded cells to that of Day 7 and Day 10 expanded cells. These results suggest the shorter the T cells expand, the more the T cells respond to cytokines for proliferation.

To evaluate the anti-tumor activity of T cell products harvested at different time of manufacturing, T cell products obtained from 4 donors (Donor 1, Donor 2, Donor 3, and Donor 4) were harvested on Day 5, 7 and 9 of manufacturing followed by interferon-gamma (IFN-γ) release assays in response to exposure to target positive cell line.

Figure 36:
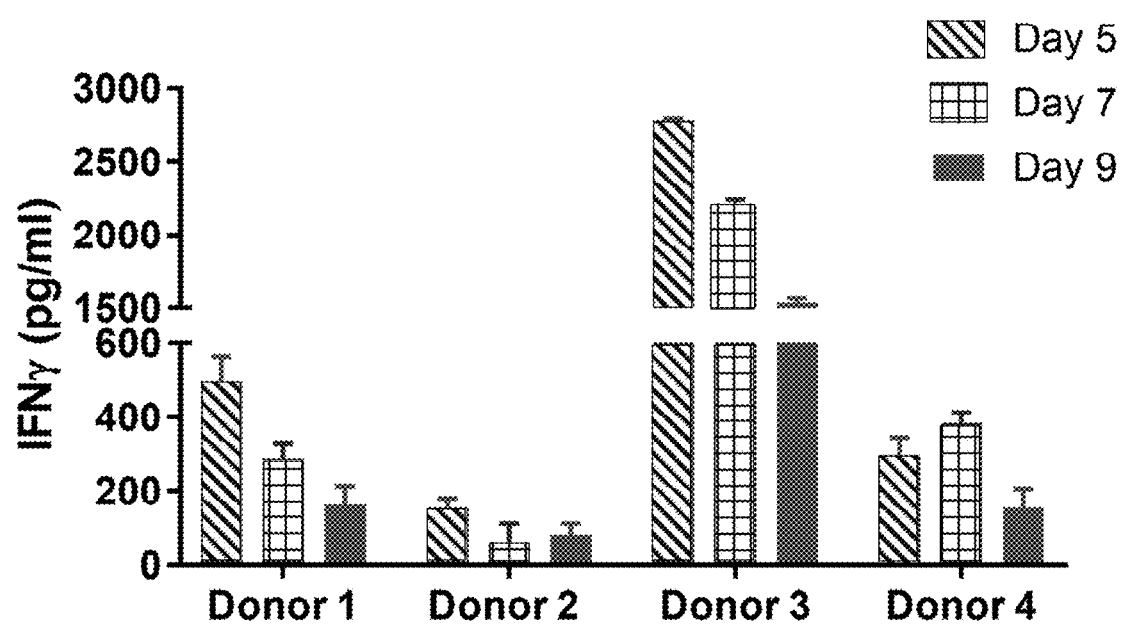
FIG. 36 shows IFN-γ secretion decreases in an expansion time-dependent manner in accordance with one embodiment of the present disclosure.

FIG. 36 shows IFN-γ secretion decreases in an expansion time-dependent manner, i.e., Day 5>Day 7>Day 9, indicating, in general, superior anti-tumor activity of Day 5 expanded cells to that of Day 7 and Day 9 expanded cells. These results suggest, in general, the shorter the T cells expand, the more the T cells secret IFN-γ.

To further evaluate the cytotoxic activity of T cell products harvested at different time of manufacturing, $EC_{50}$ based on IFN-γ response against T2 cells pulsed with decreasing concentrations of the cognate peptide was determined.

Figure 37:
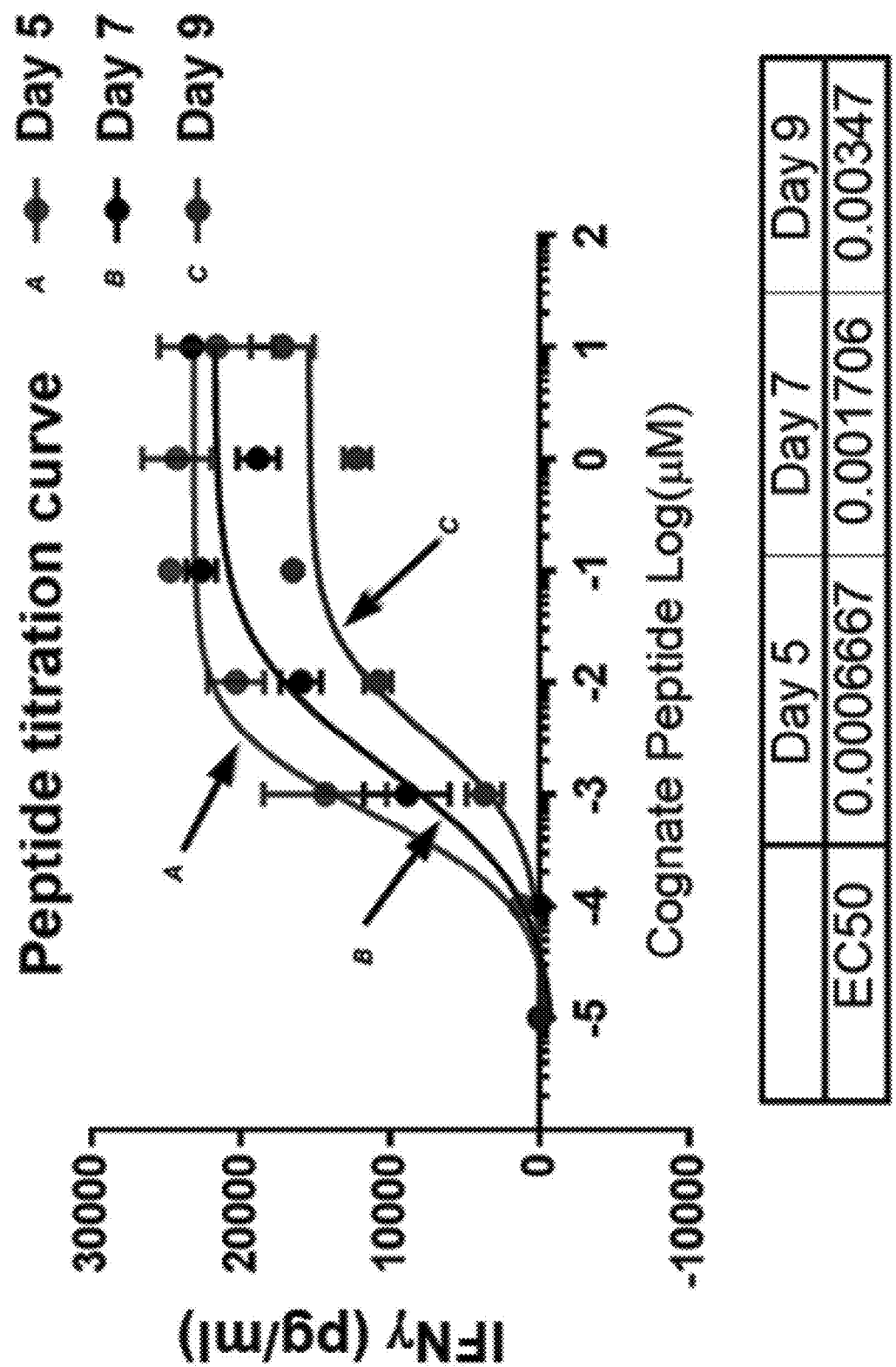
FIG. 37 shows $EC_{50}$ increases in an expansion time-dependent manner in accordance with one embodiment of the present disclosure.

FIG. 37 shows $EC_{50}$ increases in an expansion time-dependent manner, i.e., Day 5>Day 7>Day 9, indicating superior peptide-specific cytotoxic activity of Day 5 expanded cells to that of Day 7 and Day 9 expanded cells.

T Cell Product #3 GMP Manufacturing

Characterization of products manufactured with final T Cell Product #3 process

Figure 38:
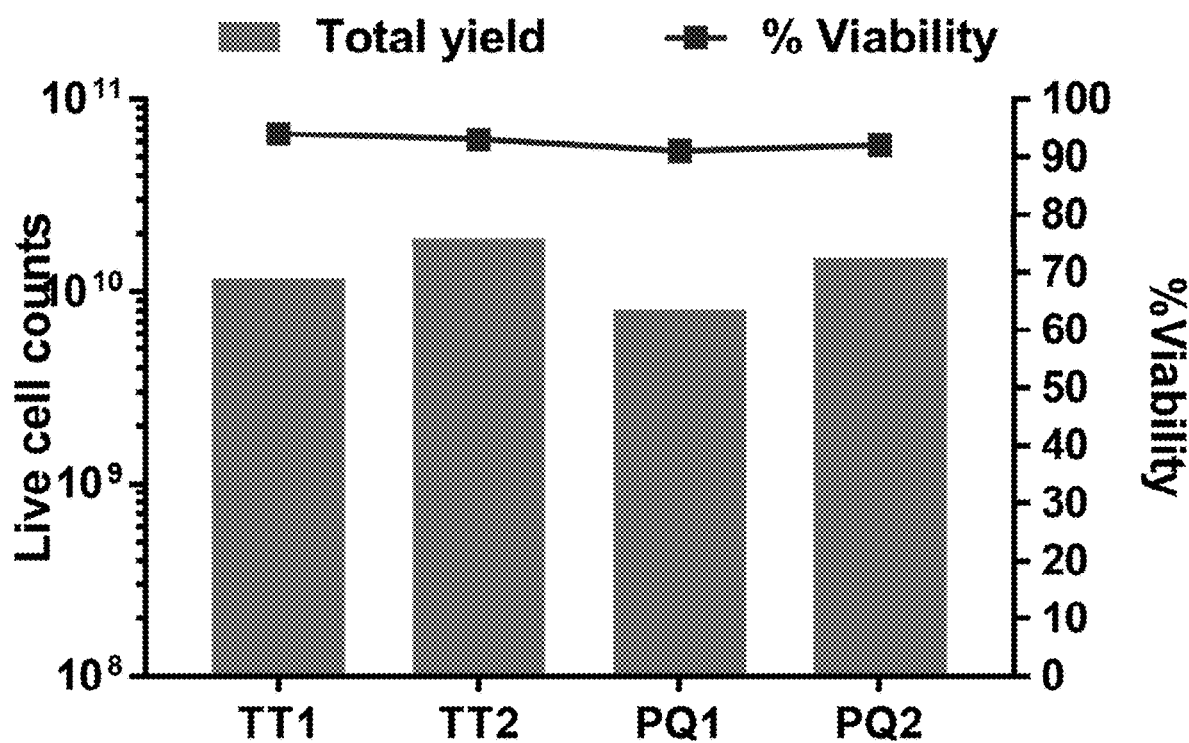
FIG. 38 shows expansion metrics in accordance with one embodiment of the present disclosure.

FIG. 38 shows expansion metrics. In two Technology Transfer (TT) manufacturing runs and two Process Qualification (PQ) manufacturing runs (n=4), an average of 1.3× $10^{10}$ cells was harvested with >90% viability following short expansion, e.g., about 6 days.

Figure 39:
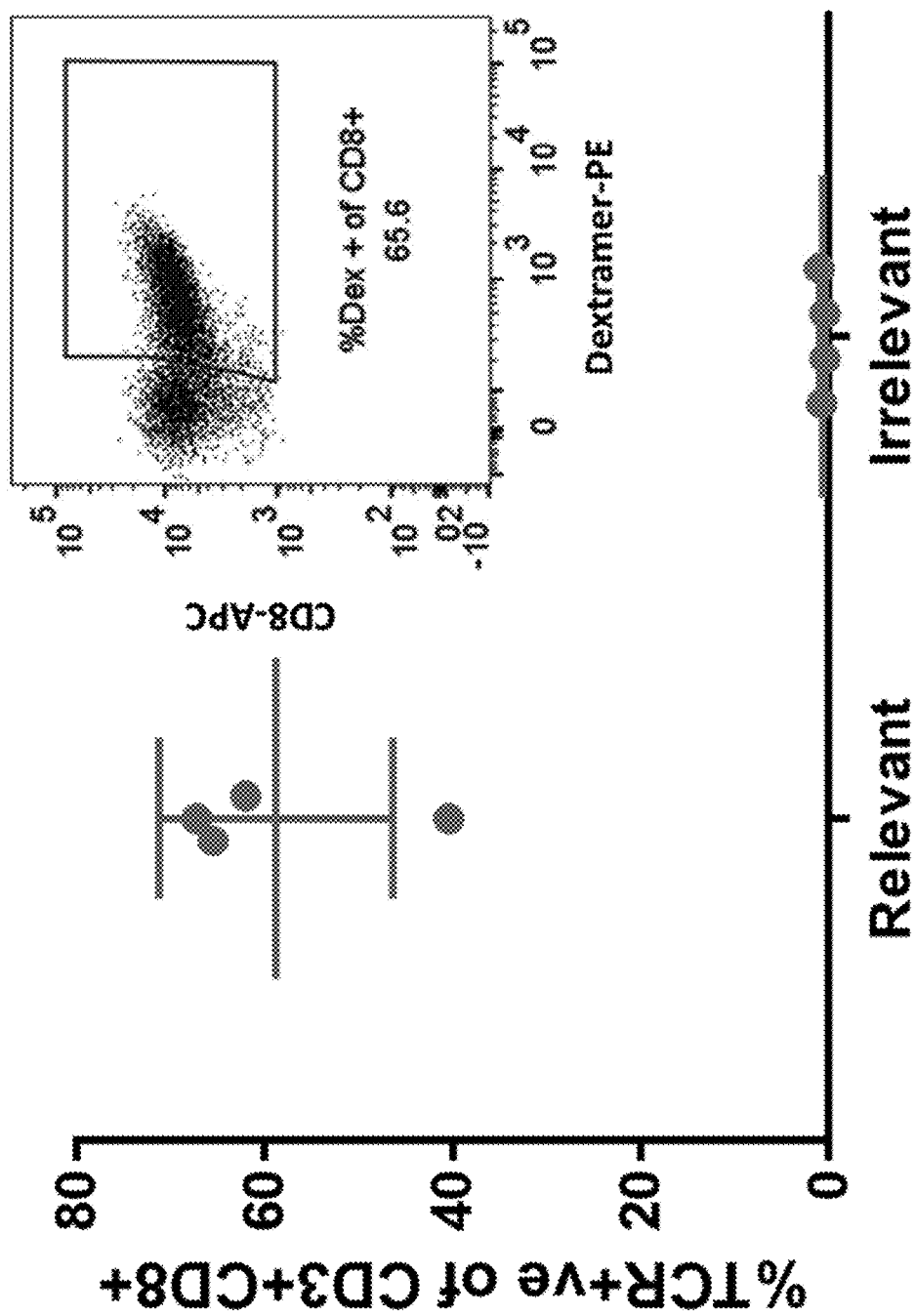
FIG. 39 shows surface expression of TCR in accordance with one embodiment of the present disclosure.

FIG. 39 shows surface expression of T Cell Product #3 TCR detected by flow cytometry using a TCR specific HLA-dextramer. A representative FACS plot and combined data (Mean±SD) are shown from Technology Transfer (TT)

and Process Qualification (PQ) manufacturing runs (n=4) performed using leukapheresis products from healthy donors.

Figure 40:
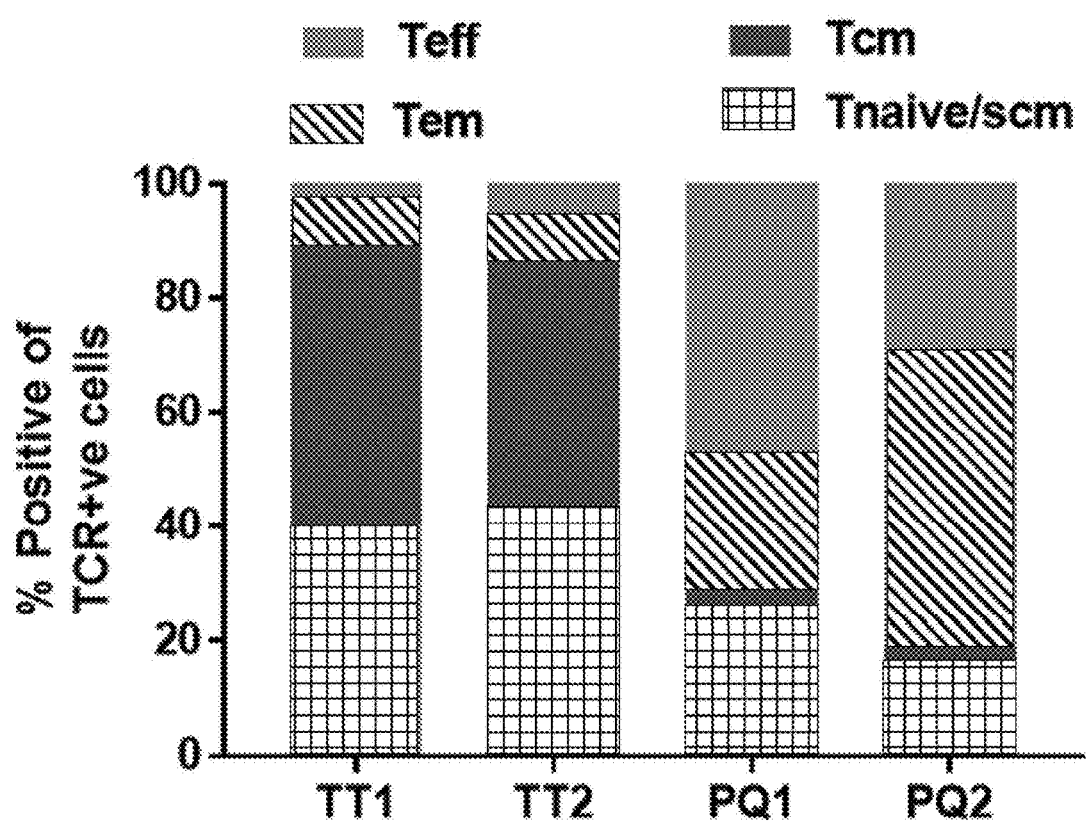
FIG. 40 shows T-cell memory phenotype of the final products in accordance with one embodiment of the present disclosure.

FIG. 40 shows T-cell memory phenotype of the final T Cell Product #3, in which T cells produced by Technology Transfer (TT1, TT2) and Process Qualification (PQ1, PQ2) manufacturing runs preserve less differentiated phenotype in donors representing highly variable memory phenotype of T cell populations in PBMC used for manufacturing (n=4) ($T_{n/scm}$-17.9%, 19.2%, 11.2%, 35.0% $T_{cm}$-23.4%, 15.7%, 0.9%, 2.4% $T_{em}$-34.8%, 27.0%, 25.9%, 43% $T_{eff}$-23.8%, 38.2%, 62.0%, 16.1% respectively)

Figure 41:
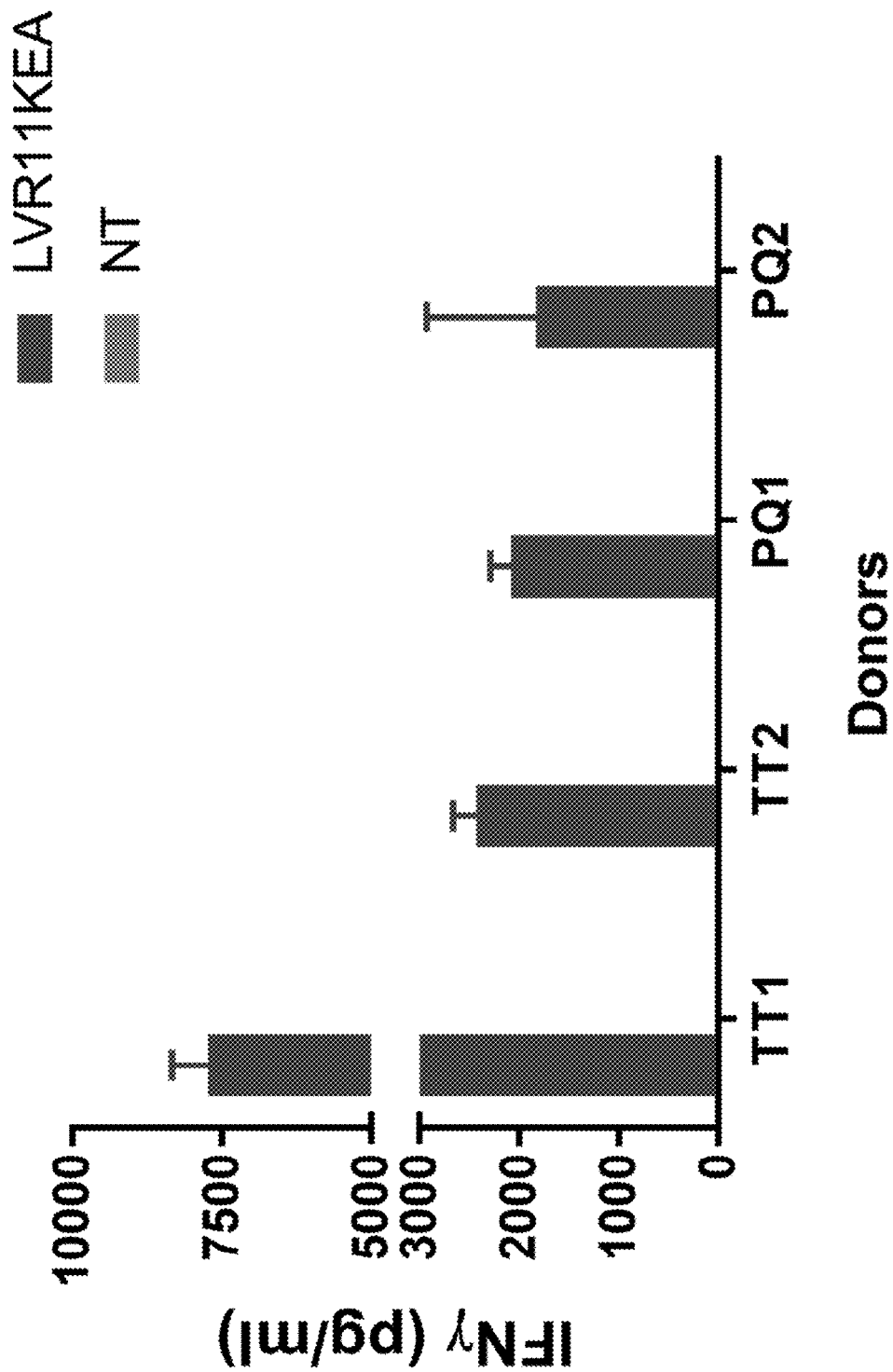
FIG. 41 shows IFN-γ release in response to exposure to target cells in accordance with one embodiment of the present disclosure.

FIG. 41 shows IFN-γ release in response to exposure to target positive (LVR11KEA) and negative (NT) cell lines. T cells produced by Technology Transfer (TT) and Process Qualification (PQ) manufacturing runs show specific cytotoxic activity, e.g., IFN-γ release, against the target positive cells. No IFN-γ release was detected against the negative control cells.

Figure 42:
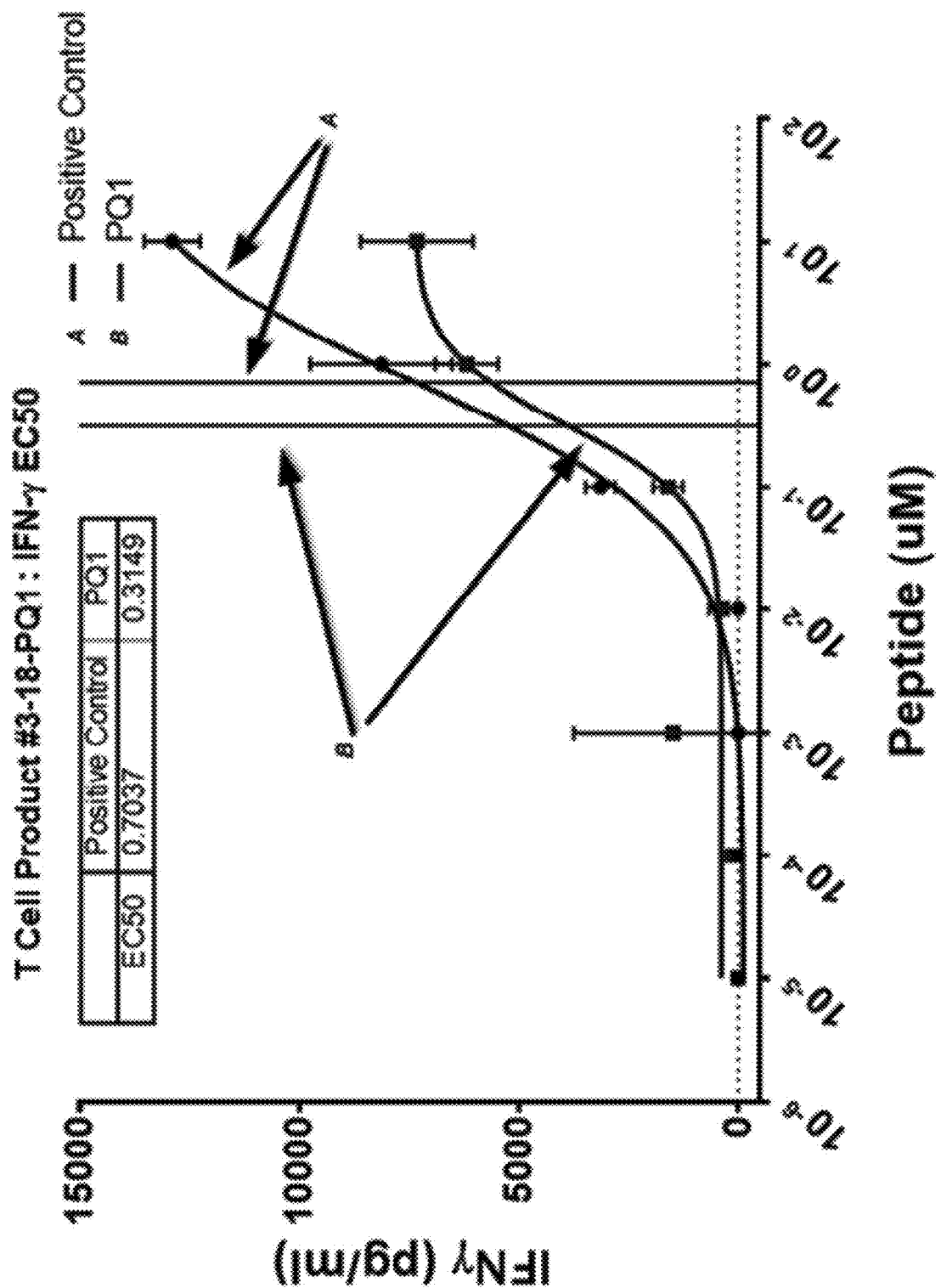
FIG. 42 shows $EC_{50}$ determination in accordance with one embodiment of the present disclosure.

FIG. 42 shows $EC_{50}$ determination based on IFN-γ response against target cells pulsed with decreasing concentrations of the cognate peptide. The results show T cells produced by Process Qualification (PQ1) manufacturing run exhibit anti-tumor activity ($EC_{50}$=0.3149) comparable to that produced by the positive control in the assay ($EC_{50}$=0.7037).

Figure 43:
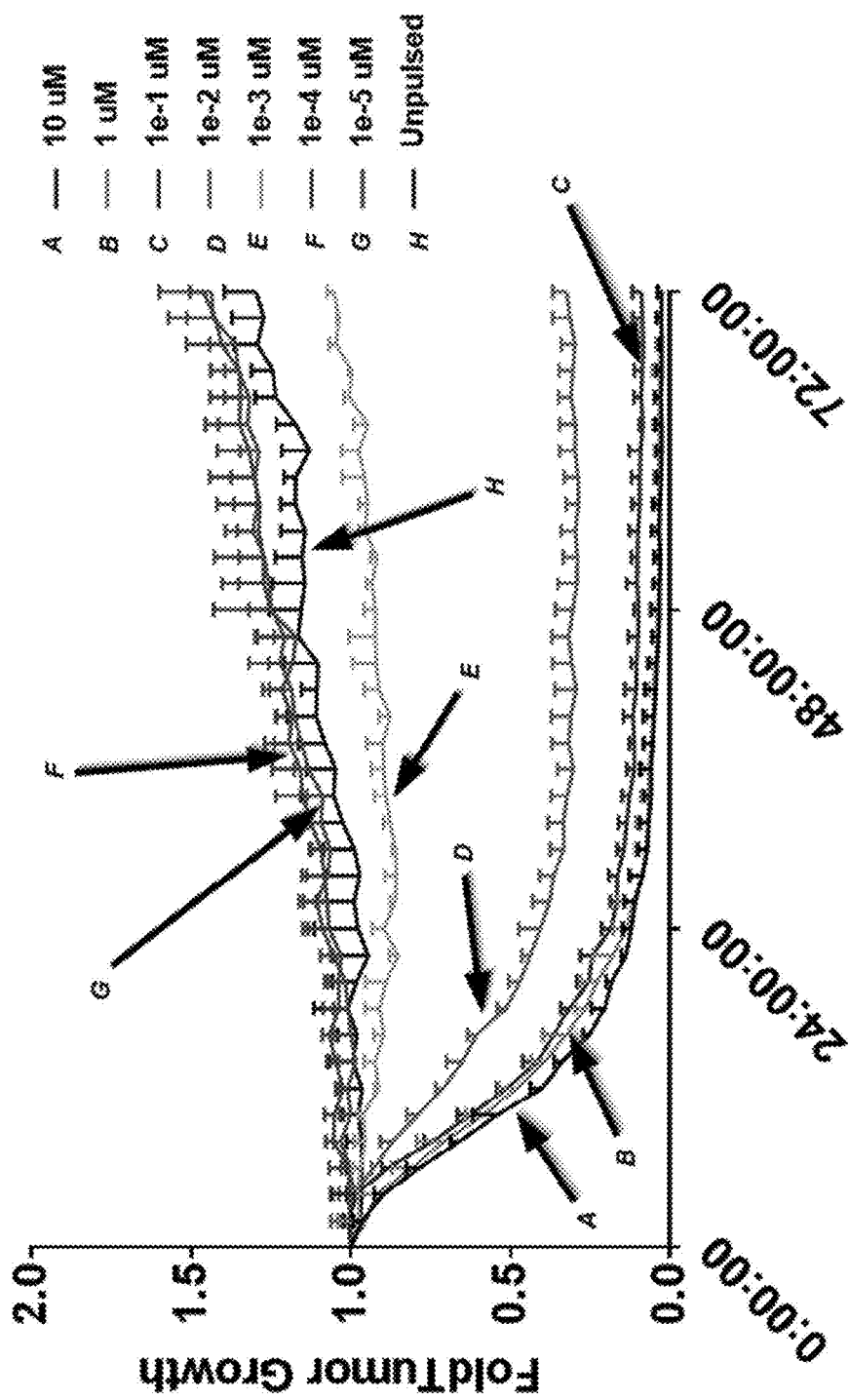
FIG. 43 shows cytotoxic potential of T cells in accordance with one embodiment of the present disclosure.

FIG. 43 shows a representative figure of cytotoxic potential of T Cell Product #3 in the Incucyte® killing assay. Data is presented as fold tumor growth in the presence of T Cell Product #3 over 72 h co-culturing period with a target negative cell line pulsed with decreasing concentration of the relevant peptide. The results show a peptide dose dependent killing of target cells by T cells produced by Process Qualification (PQ1) manufacturing run.

In sum, shorter ex-vivo expansion and overall "turn-around time" can have a substantial impact not only on the quality of the cell product but also clinical applicability of cellular immunotherapies. The process development efforts to shorten the expansion phase during GMP manufacturing of TCR engineered T cells were completed with the development of a robust, 5-6 day long, semi-closed T cell manufacturing process for T Cell Product #3. The Technology Transfer (TT) and Process Qualification (PQ) runs for T Cell Product #3 manufacturing in GMP environment cleanroom confirmed the reproducibility and feasibility of the manufacturing process with shortened expansion phase. All the release, phenotype, and functionality testing of the TCR engineered T cells were confirmed for the GMP manufactured T cell products.

Example 7

Manufacturing and Functionality of T Cell Products Generated from Cancer Patients As noted above, T Cell Product #3 generated from healthy donors show T-cell memory phenotype and cytotoxic potentials. As shown below, similar characteristics were observed in T Cell Product #3 generated from cancer patients, when compared with that of T Cell Product #3 generated from healthy donors.

Patient and Donor Characteristics

| Patient (PT)/ Donor (D) | Primary diagnosis | Age | Gender | Race | Clinical Stage | Disease Status/Chemo Treatment Status | Treatment Status: Treatment Notes |
|---|---|---|---|---|---|---|---|
| PT1 | Ovarian Cancer | 78 | Female | W | IV | Stable/Active Treatment | Cisplatin/Gemzar |
| PT2 | Ovarian Cancer | 69 | Female | W | III-C | Stable/Active Treatment | Doxil |
| PT3 | Ovarian Cancer | 73 | Female | W | III-B | Stable/Active Treatment | Carboplatin/Gemzar |
| PT4 | Endometria 1 Cancer | 72 | Female | AI | III-A | Unknown/ Pre-treatment | Taxol/Carboplatin |
| D1 | Normal | 69 | Male | W | N/A | Unknown | N/A |
| D2 | Normal | 70 | Male | W | N/A | Unknown | N/A |
| D3 | Normal | 62 | Male | W | N/A | Unknown | N/A |
| D4 | Normal | 52 | Female | H | N/A | Unknown | N/A |

W = White;
AI = American Indian;
H = Hispanic

T Cell Product #3 were manufactured in small scale using PBMC obtained from cancer patients and healthy donors. Briefly, on Day 0, cryopreserved PBMC isolated from leukapheresis products of 4 cancer patients and 4 healthy donors were thawed and rested in the presence of IL-7 for about 4-6 hours, followed by activation in NTC 24-well plates and incubation for about 16-24 hours. On Day 1, cells transduced with viral vector expressing recombinant TCR, e.g., R11KEA TCR, at 5 μl/$10^6$ cells. Non-transduced (NT)) cells were included as controls. Transduced and non-transduced cells were seeded at a minimum of 1.0×$10^6$ cells/ml, e.g., 2.0×$10^6$ cells/ml. On Day 2, Transduced and non-transduced cells were expanded in TexMACS complete medium with IL-7 and IL-15. On Day 6, i.e., expansion for 4 days, expanded cells were harvested followed by flow cytometry analysis and functional assays to determine, e.g., recovery, viability, phenotypes, integrated DNA copy numbers, and functionality.

Figure 44:
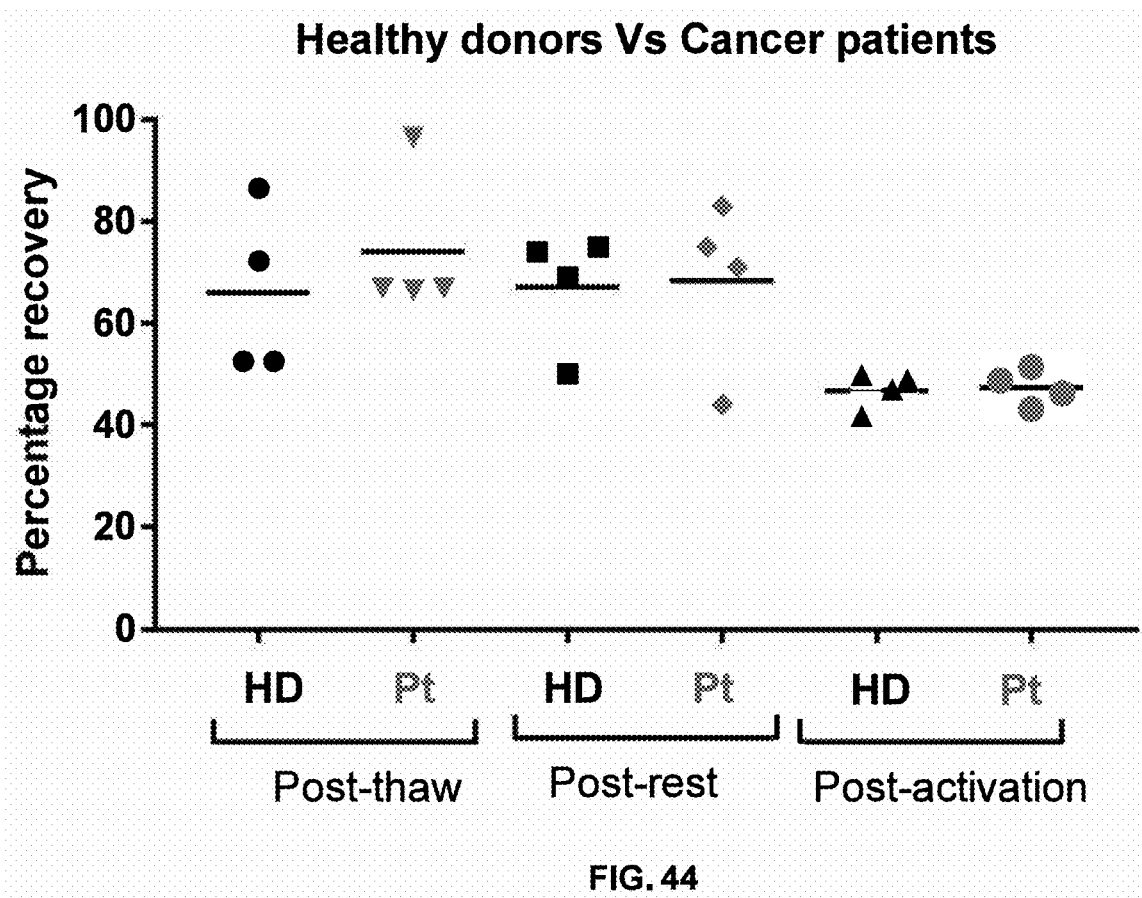
FIG. 44 shows a comparison in cell recovery between T cell products obtained from healthy donors and cancer patients in accordance with an embodiment of the present disclosure.

FIG. 44 shows comparable recoveries of T cells obtained from cancer patients (Pt) and healthy donors (HD) at post-thawing, post-resting, and post-activation.

Figure 45:
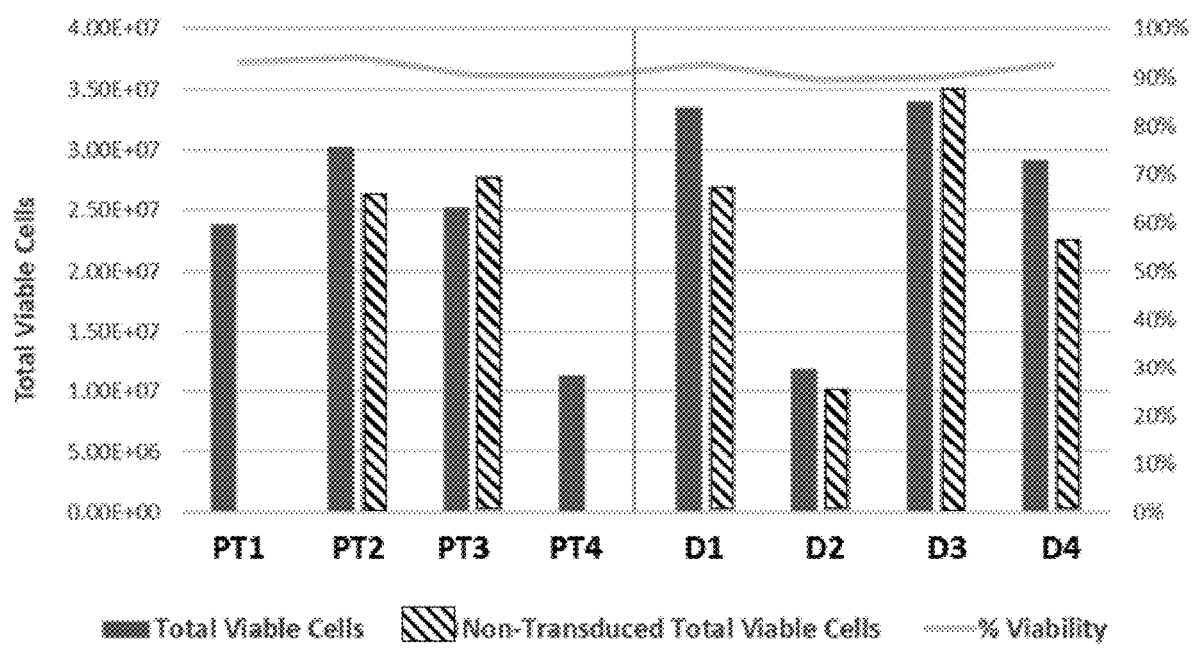
FIG. 45 shows a comparison in cell viability between T cell products obtained from healthy donors and cancer patients in accordance with an embodiment of the present disclosure.

FIG. 45 shows comparable total viable cells and % viability of T Cell Product #3 on Day 6, i.e., expansion for 4 days, in transduced and non-transduced cells within each individual, except PT1 and PT4, in which all cells were transduced.

Figure 46:
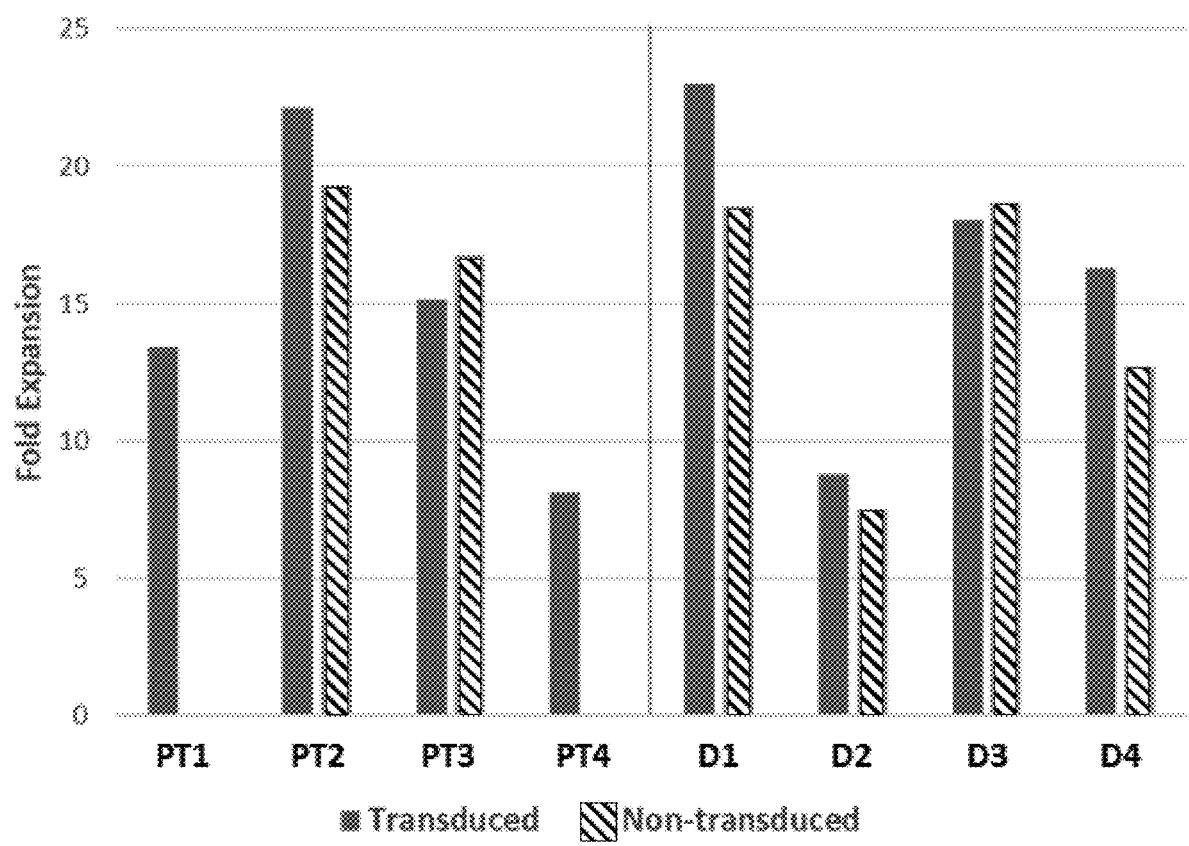
FIG. 46 shows a comparison in fold expansion between T cell products obtained from healthy donors and cancer patients in accordance with an embodiment of the present disclosure.

FIG. 46 shows comparable fold-expansion of T Cell Product #3 on Day 6, i.e., expansion for 4 days, in transduced and non-transduced cells within each individual, except PT1 and PT4, in which all cells were transduced.

Phenotype Analysis

Figure 47:
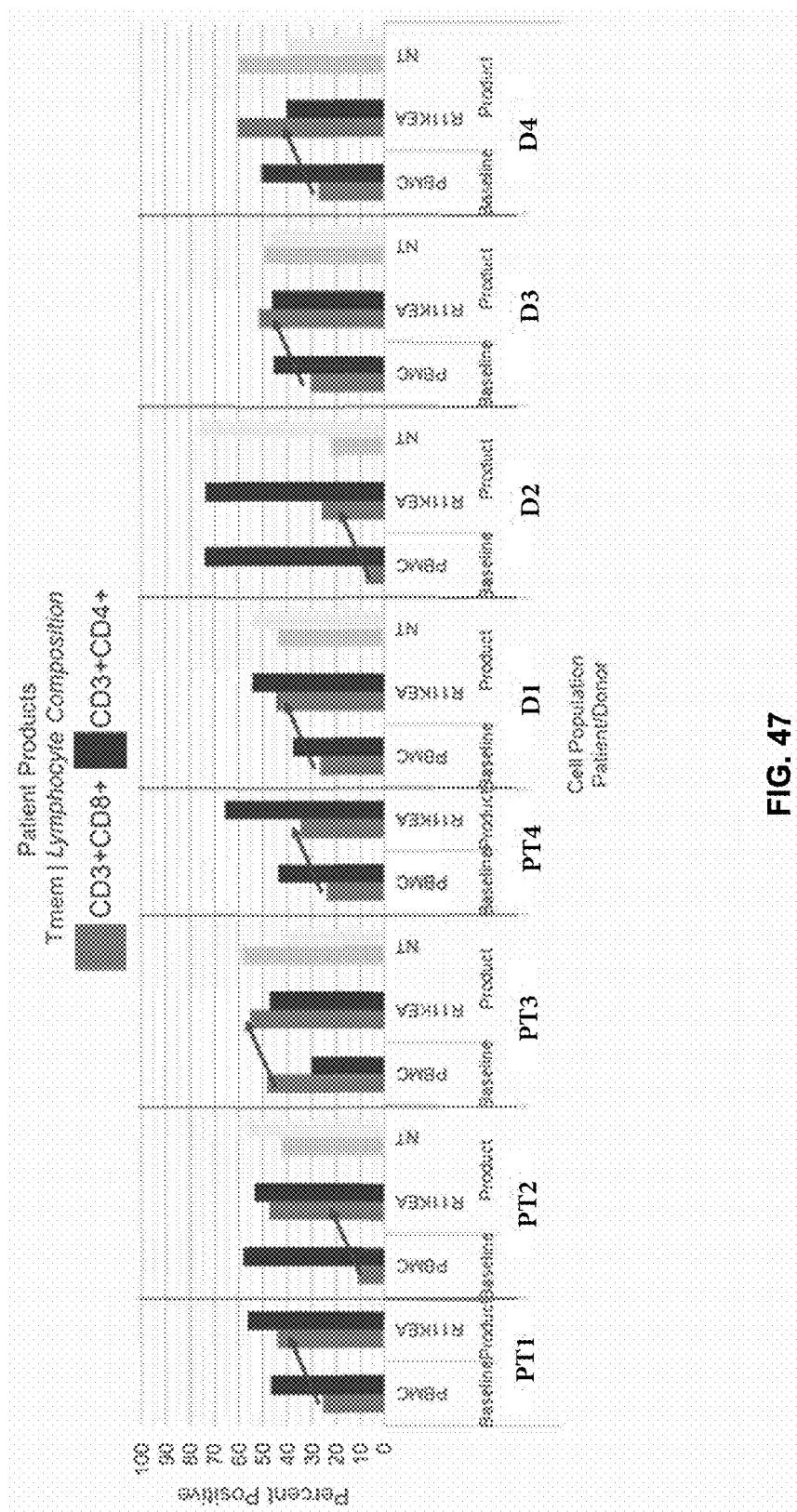
FIG. 47 shows a comparison in cell phenotype between T cell products obtained from healthy donors and cancer patients in accordance with an embodiment of the present disclosure.

FIG. 47 shows preferential expansion of CD3+CD8+ cells (as indicated by arrows), as compared with that of CD3+

CD4+ cells, in PBMCs obtained from cancer patients (PT1-PT4) and healthy donors (D1-D4).

Figure 48:
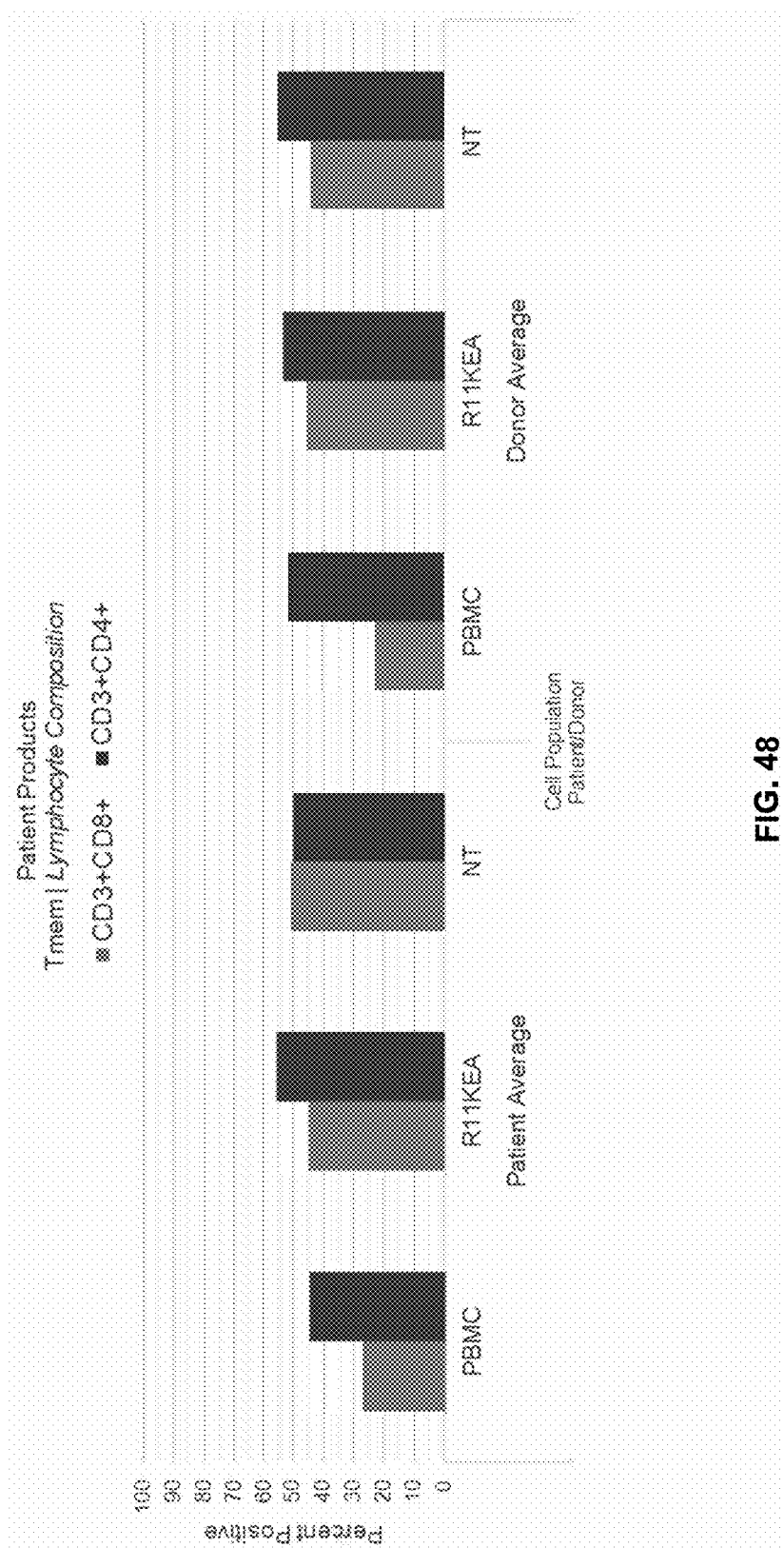
FIG. 48 shows a comparison in cell phenotype between T cell products obtained from healthy donors and cancer patients in accordance with an embodiment of the present disclosure.

FIG. 48 shows comparable overall averages of the CD3+ CD8+ cells and the CD3+CD4+ cells in T Cell Product #3 and non-transduced cells (NT) obtained from patients (PT1-PT4) and healthy donors (D1-D4).

Figure 49:
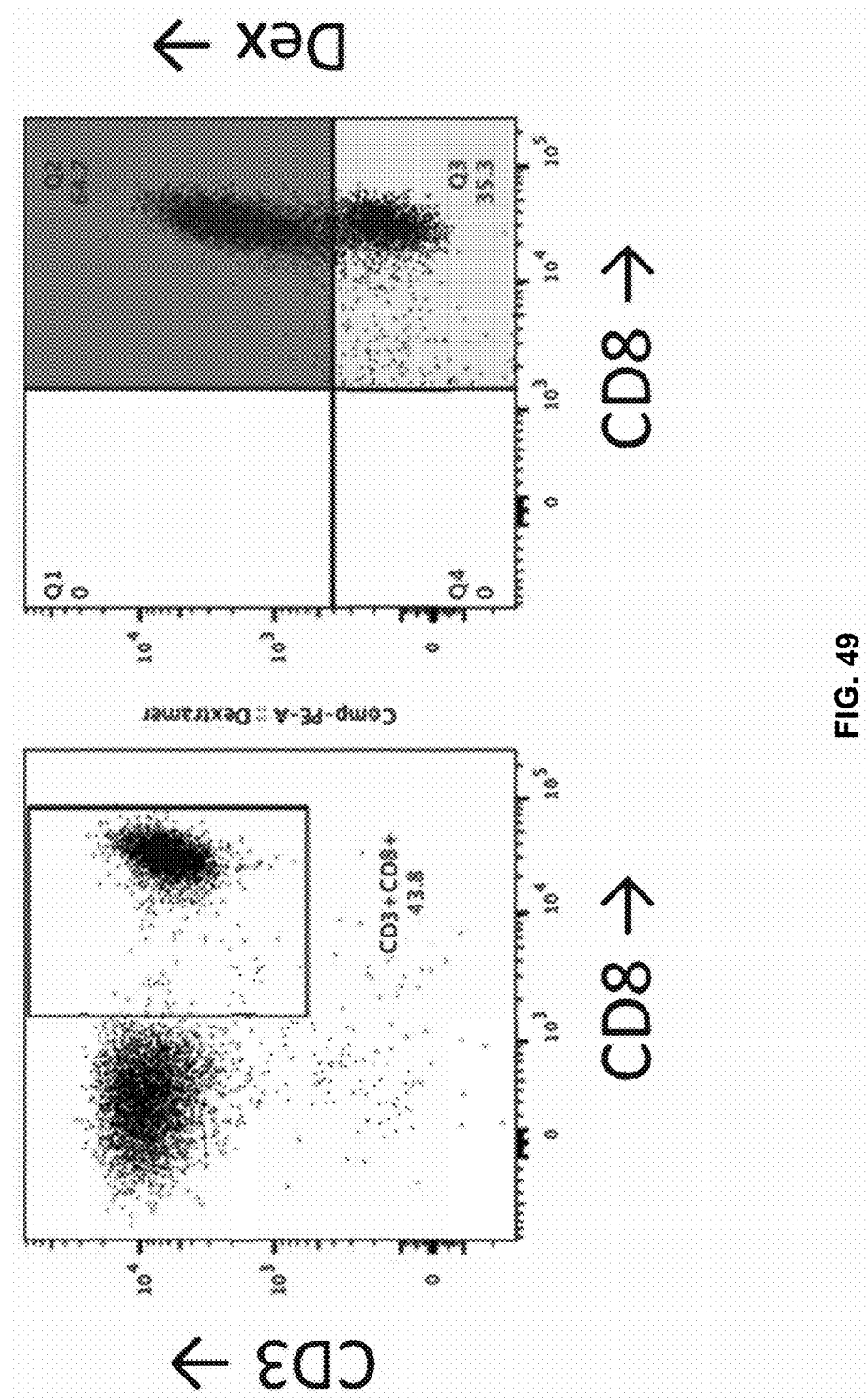
FIG. 49 shows TCR expression of T cell products in accordance with an embodiment of the present disclosure.

FIG. 49 shows an example of flow cytometry analysis of T Cell Product #3. The results indicate 43.8% of T Cell Product #3 contain CD3+CD8+ cells, in which 64.7% of the cells expressing R11KEA TCR, as indicated by peptide/MHC dextramer (Dex) staining, and 35.3% of the cells that do not express R11KEA TCR.

Figure 50:
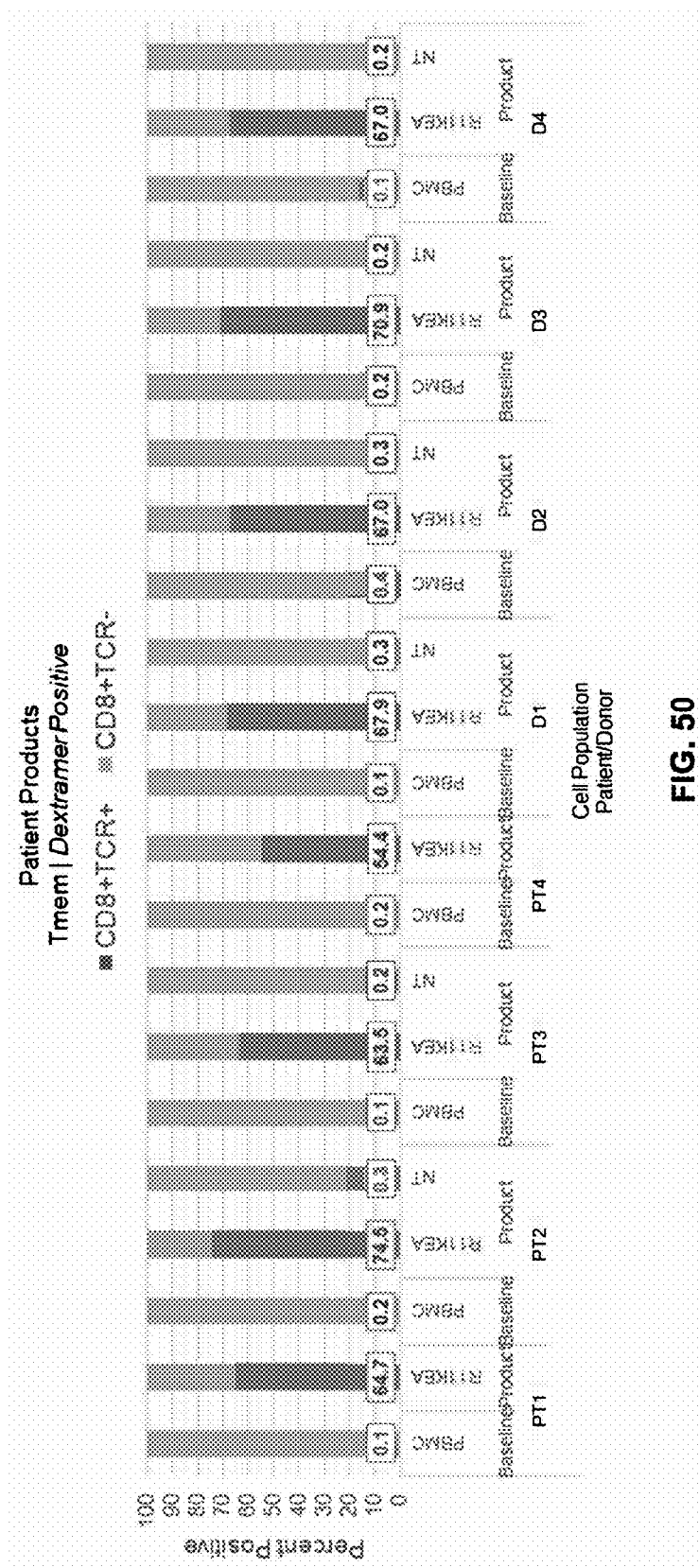
FIG. 50 shows a comparison in TCR expression between T cell products obtained from healthy donors and cancer patients in accordance with an embodiment of the present disclosure.

FIG. 50 shows comparable R11KEA TCR expression in CD8+ T Cell Product #3 generated from cancer patients (PT1-PT4) and healthy donors (D1-D4).

Figure 51:
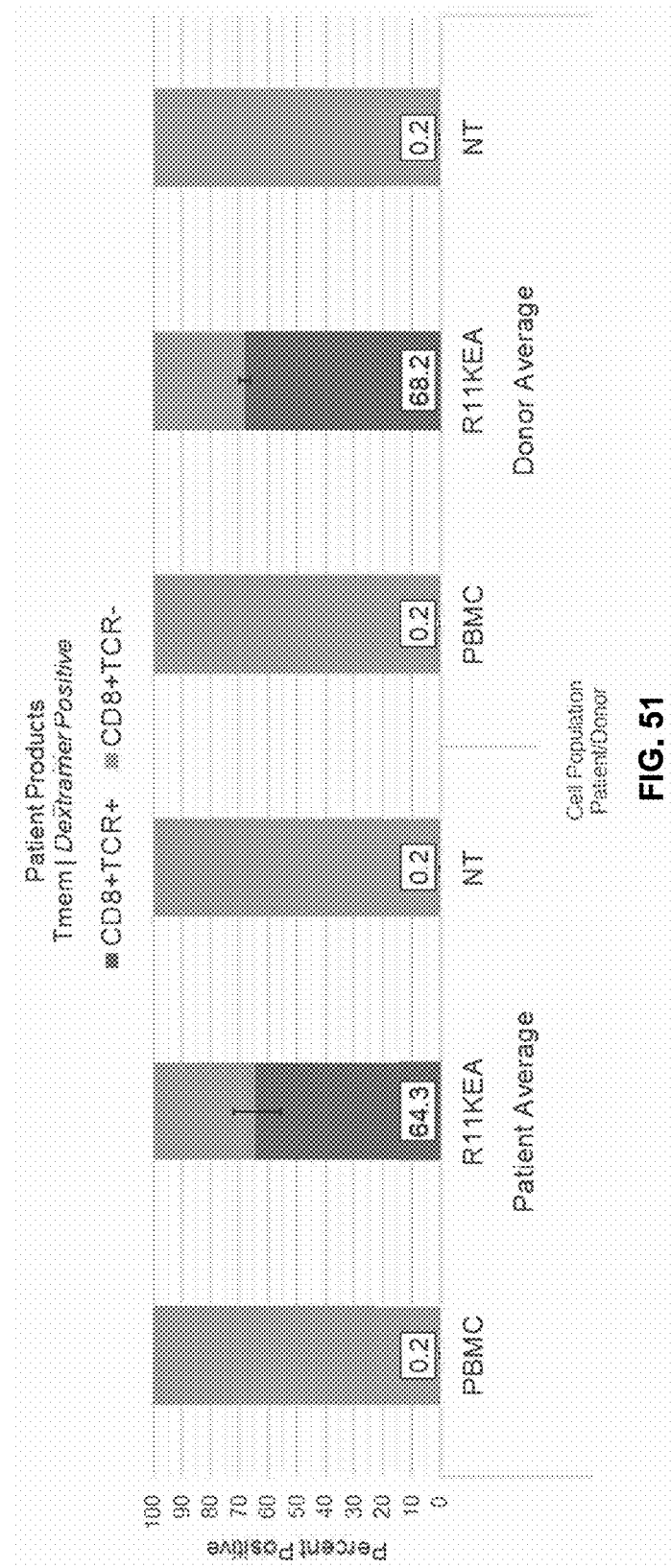
FIG. 51 shows a comparison in TCR expression between T cell products obtained from healthy donors and cancer patients in accordance with an embodiment of the present disclosure.

FIG. 51 also shows comparable average R11KEA TCR expression in CD8+ T Cell Product #3 generated from cancer patients (PT1-PT4) (e.g., 64.3%) and healthy donors (D1-D4) (e.g., 68.2%).

Figure 52:
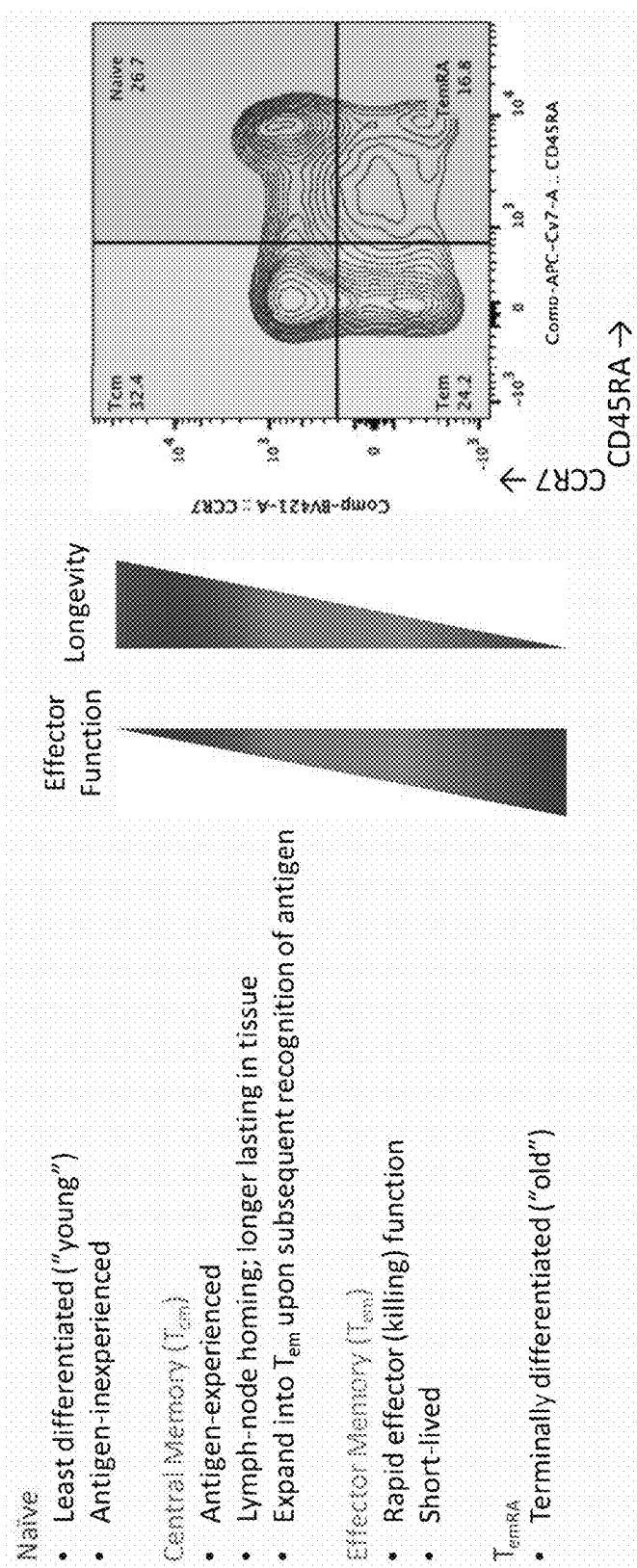
FIG. 52 shows gating scheme and $T_{memory}$ subsets in accordance with an embodiment of the present disclosure.

FIG. 52 shows gating scheme to determine T cell memory ($T_{memory}$) phenotype of T Cell Product #3. For example, by gating for CD45RA and CCR7, naïve "young" T cells (CD45RA+CCR7+), terminally differentiated "old" T cells (TemRA) (CD45RA+CCR7−), effector memory T cells (Tem) (CD45RA−CCR7−), and central memory T cell (Tcm) (CD45RA−CCR7+) can be identified.

Figure 53:
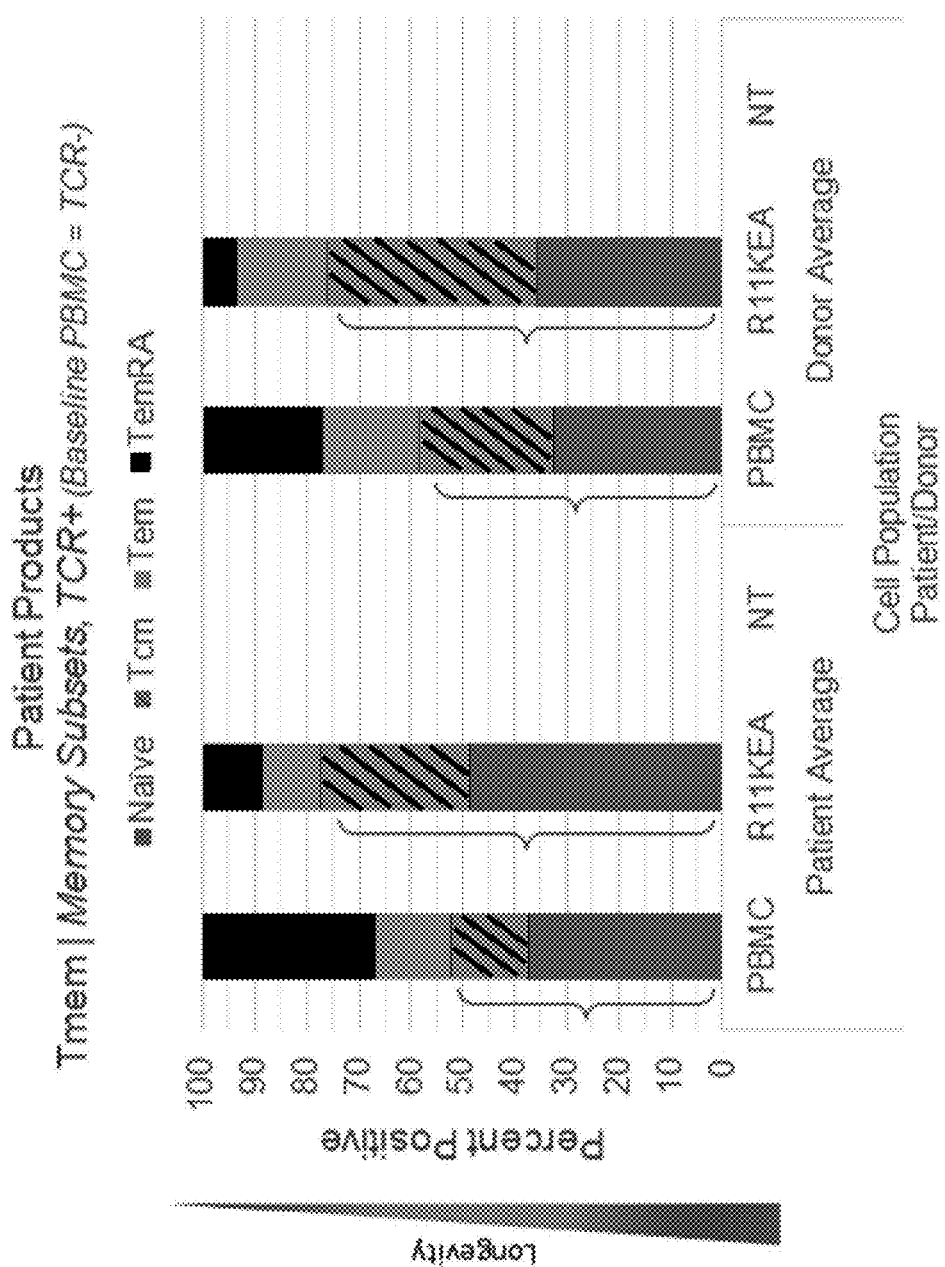
FIG. 53 shows a comparison in cell phenotype between T cell products obtained from healthy donors and cancer patients in accordance with an embodiment of the present disclosure.

FIG. 53 shows notable average increases in both desirable naive and Tcm compartments of T Cell Product #3 generated from both patients (PT1-PT4) and healthy donors (D1-D4). These results suggest that transduced cells may possess greater ability to persist after infusion and produce longer lasting responses in vivo.

Functional Assays

To determine the functionality of T Cell Product #3, cells may be stimulated with relevant peptide (e.g., 1 μg/ml) that specifically binds R11KEA TCR or irrelevant peptide (e.g., 1 μg/ml), which does not bind R11KEA TCR, as a control. Stimulation with PMA and ionomycin, which activate all lymphocytes, serves as positive control; and non-stimulation serves as negative control. After 2 hours of stimulation, protein transport inhibitors were added. At 6 hours after stimulation, expression of cytokines and signalling molecules, e.g., CD107a, IFN-γ, TNF-α, IL-2, and macrophage inflammatory protein-1-beta (MIP-1β), in CD3+CD8+ cells were evaluated by intracellular staining (ICS).

Figure 54:
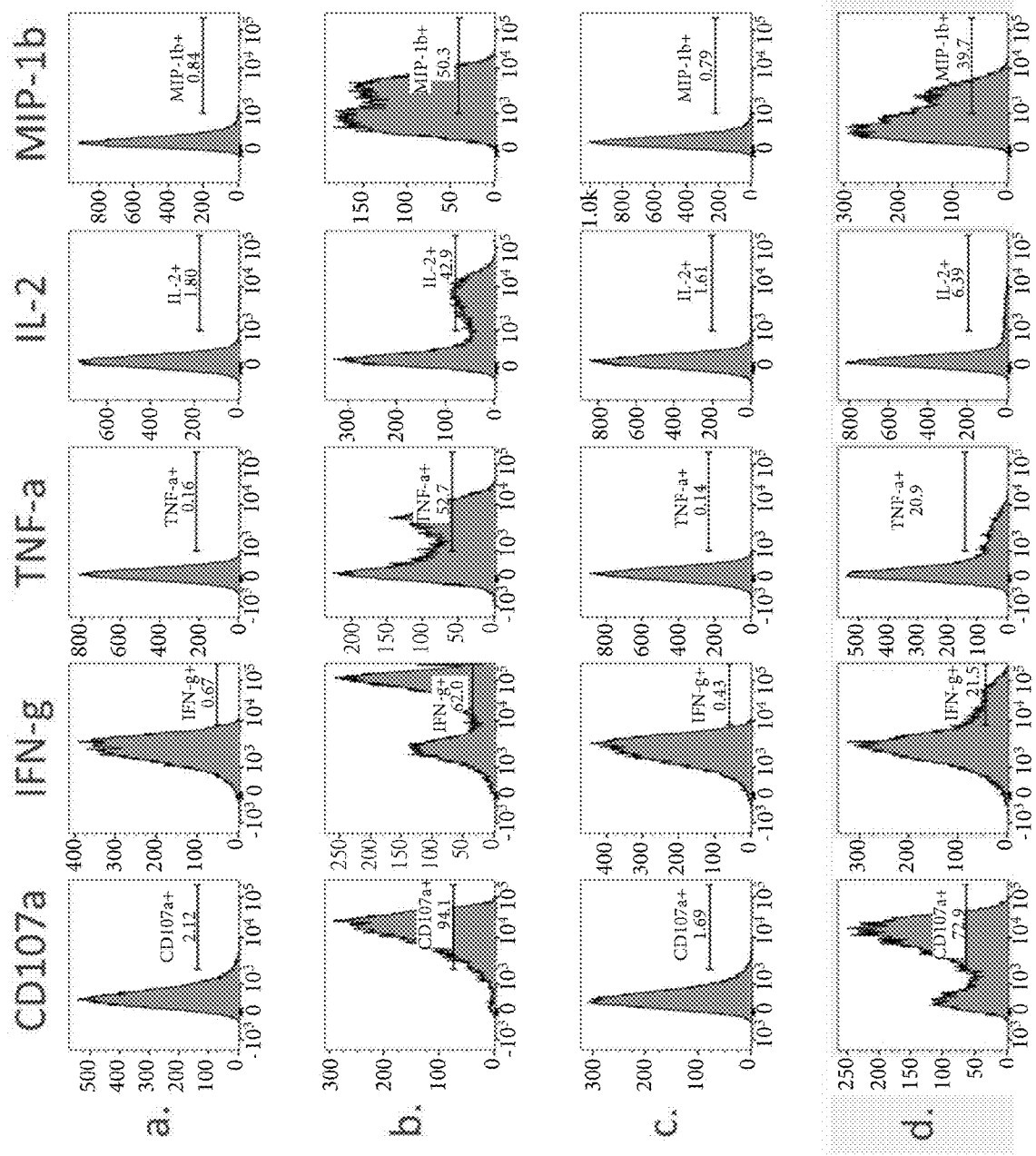
FIG. 54 shows cytokine expression in T cell products in accordance with an embodiment of the present disclosure.

FIG. 54 shows an example of T Cell Product #3, after stimulation with the relevant peptide (d), the expression levels of CD107a, IFN-γ, TNF-α, IL-2, and MIP-1β in T Cell Product #3 increase as compared with that of stimulation with the irrelevant peptide (c). Stimulation with PMA and ionomycin, which activate all lymphocytes, serves as positive control (b); and non-stimulation serves as negative control (a).

Figure 55:
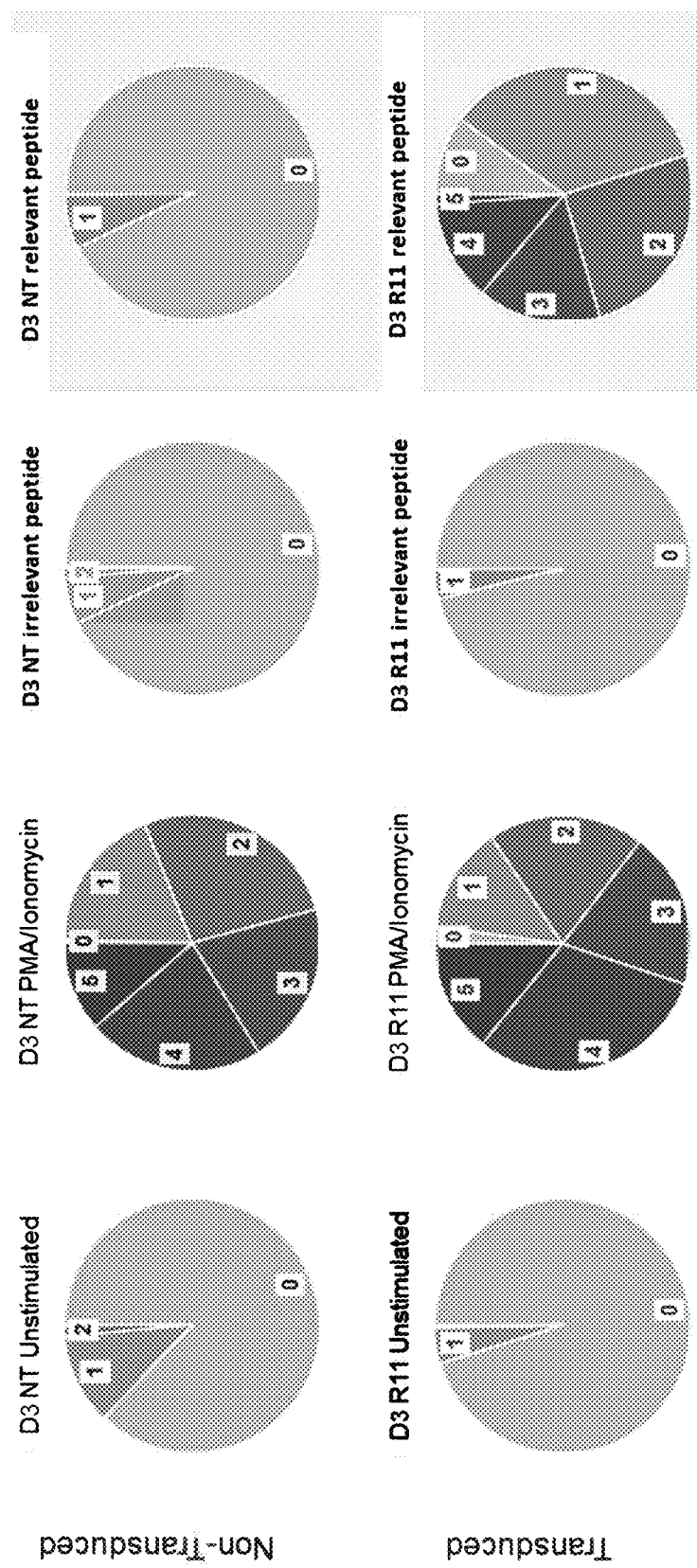
FIG. 55 shows cytokine expression in T cell products obtained from healthy donor in accordance with an embodiment of the present disclosure.

FIG. 55 shows polyfunctionality of T Cell Product #3. The numbers 0, 1, 2, 3, 4, and 5 denote, respectively, the portion of T Cell Product #3 express none, any one, any two, any three, any four, and all five of CD107a, IFN-γ, TN F-α, IL-2, and MIP-1β. For example, after stimulation with relevant peptide, more than 50% of the T Cell Product #3 obtained from healthy donor (D3) transduced with R11KEA TCR (R11) express at least 2 cytokines from CD107a, IFN-γ, TNF-α, IL-2, and MIP-1β, as compared with that of stimulation with irrelevant peptide, i.e., 0% of cells express at least 2 cytokines. In contrast, there is no significant difference in cytokine expression in non-transduced (NT) cells between stimulation with relevant peptide and irrelevant peptide. These results show T Cell Product #3 generated from healthy donors and transduced with R11KEA TCR is polyfunctional. The positive controls, i.e., T cells stimulated with PMA/ionomycin, exhibit polyfunctionality with or without TCR transduction. The negative controls, i.e., T cells without stimulation, exhibit poor functionality with or without TCR transduction.

Figure 56:
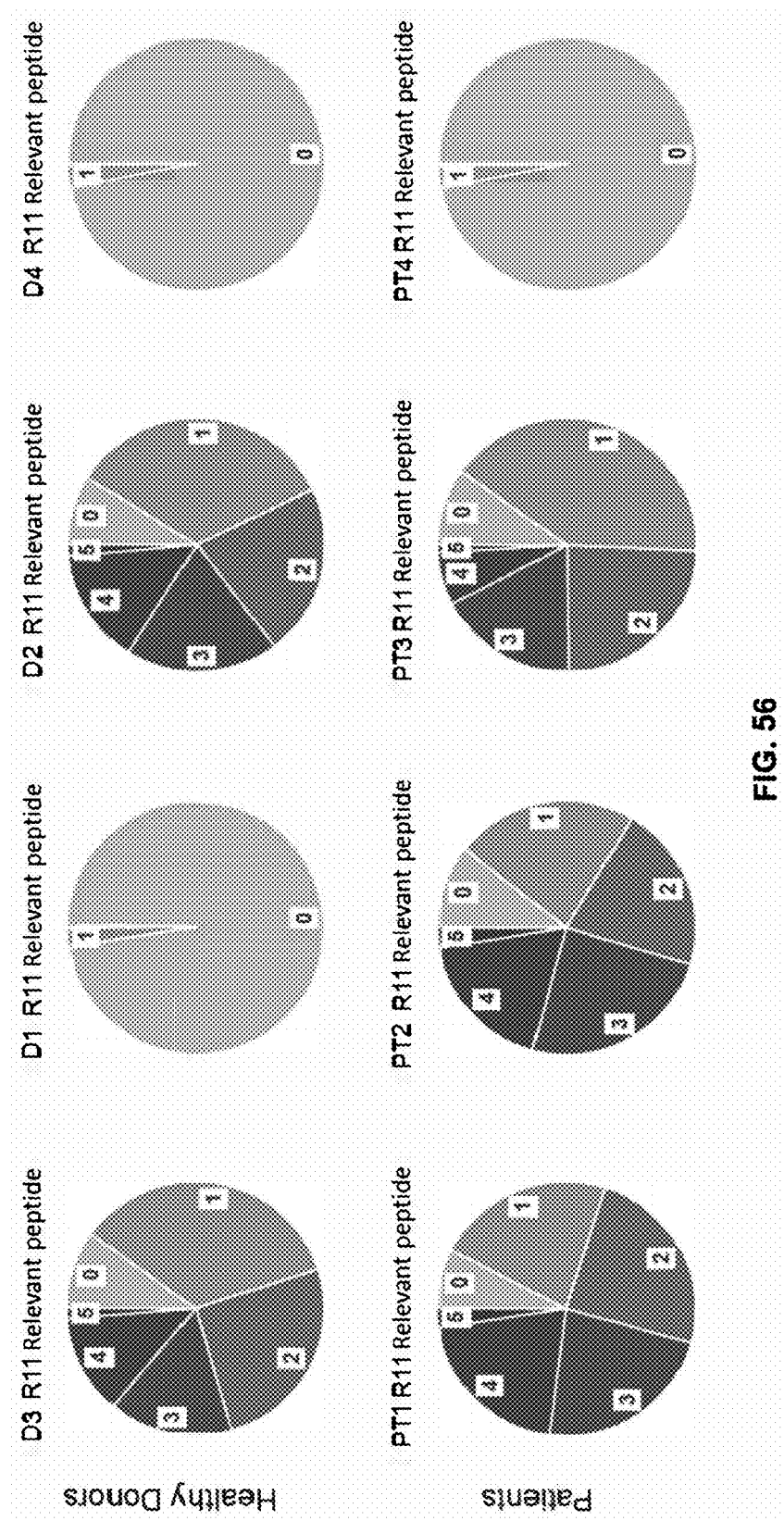
FIG. 56 shows a comparison in cytokine expression between T cell products obtained from healthy donors and cancer patients in accordance with an embodiment of the present disclosure.

FIG. 56 shows, after stimulation with relevant peptide, polyfunctionality of the R11KEA TCR+(CD8+Vb8+) T Cell Product #3 generated from healthy donors, e.g., D3 and D2, and from cancer patients, e.g., PT1, PT2, and PT3. T cells generated from D1, D4, and PT4 may not appear polyfunctional as determined by these functional assays. As shown below, T cells generated from D1, D4, and PT4, however, still have cytotoxic activity against target cells.

Figure 57:
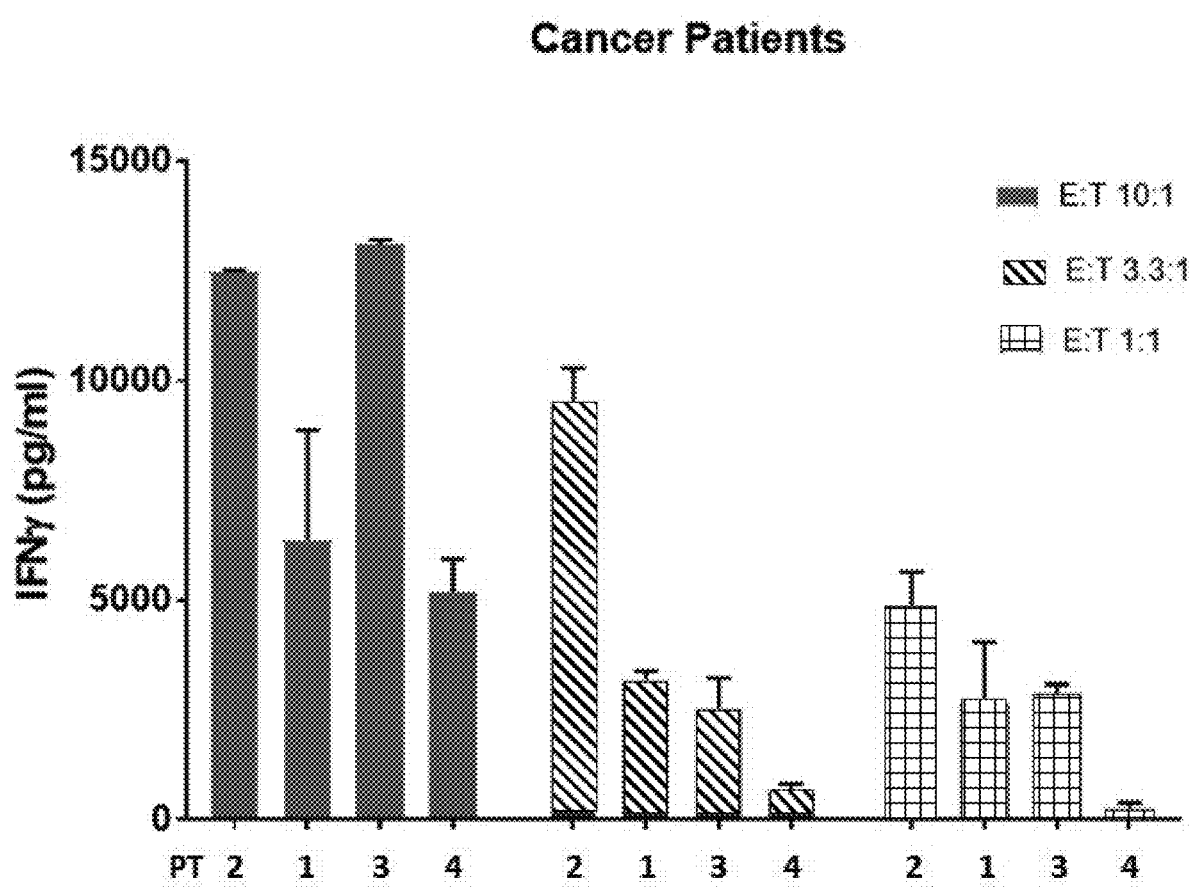
FIG. 57 shows IFN-γ release from T cell products obtained from cancer patients in accordance with an embodiment of the present disclosure.

FIG. 57 shows IFN-γ release from T Cell Product #3 generated from cancer patients, e.g., PT1-PT4, when these cells were in contact with a high target cell line, which has about 1,000 copies/cell of the relevant peptide presented on the cell surface, in E:T ratio-dependent manner, e.g., 10:1>3.3:1>1:1. Note that T cells generated from PT4, which may not appear polyfunctional in FIG. 56, also show IFN-γ release in E:T ratio-dependent manner.

Figure 58:
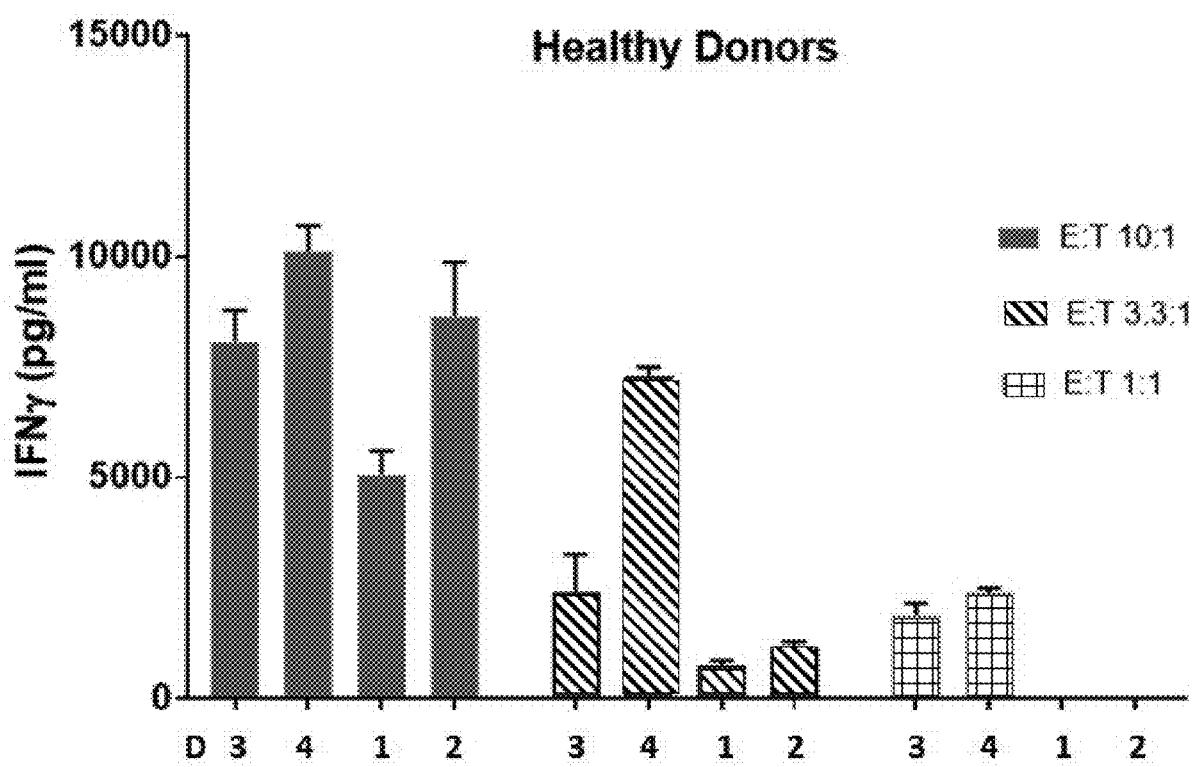
FIG. 58 shows IFN-γ release from T cell products obtained from healthy donors in accordance with an embodiment of the present disclosure.

FIG. 58 shows IFN-γ release from T Cell Product #3 generated from healthy donors, e.g., D1-D4, when these cells were in contact with a high target cell line, which has about 1,000 copies/cell of the relevant peptide presented on the cell surface in E:T ratio-dependent manner, e.g., 10:1>3.3:1>1:1. Note that T cells generated from D1 and D4, which may not appear polyfunctional in FIG. 56, also show IFN-γ release in E:T ratio-dependent manner.

Figure 59:
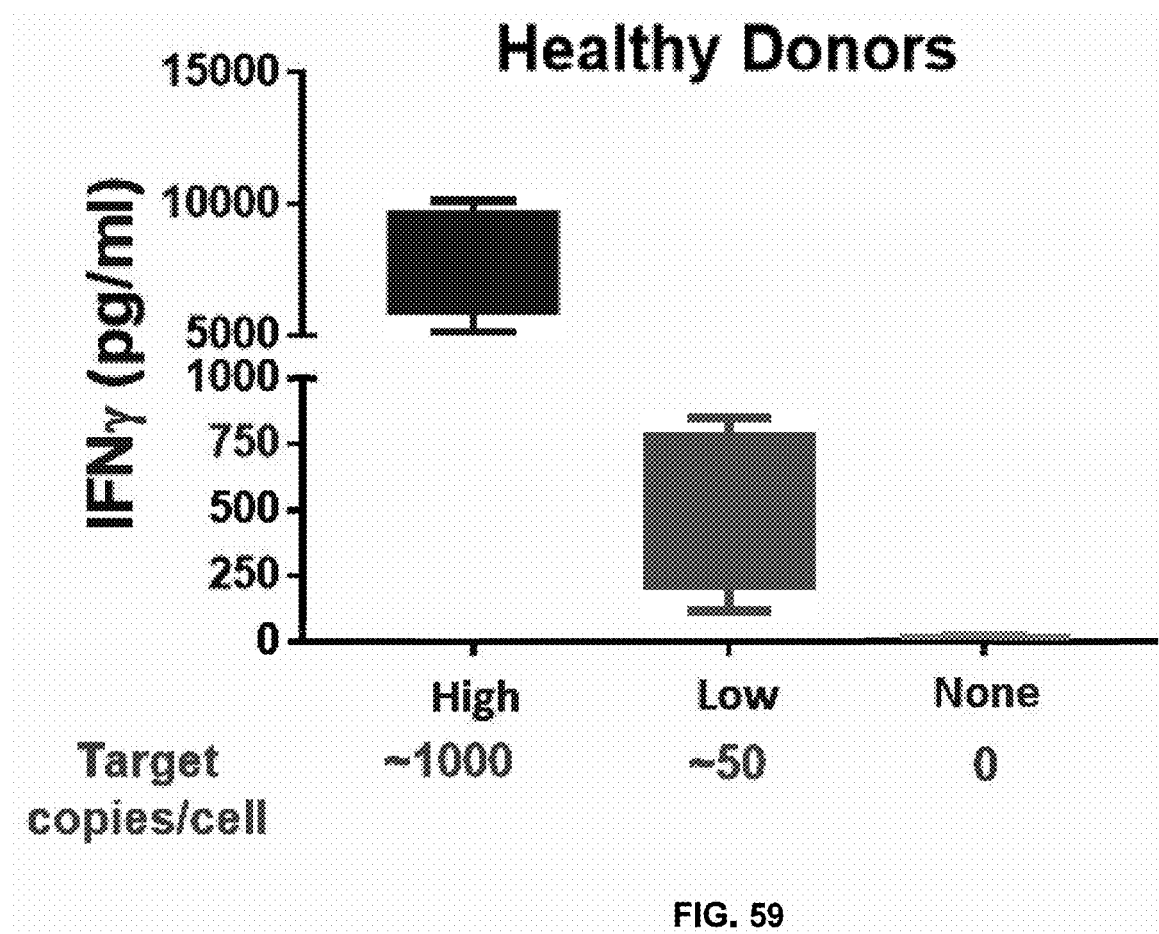
FIG. 59 shows IFN-γ release from T cell products obtained from healthy donors in accordance with an embodiment of the present disclosure.

FIG. 59 shows average IFN-γ release from T Cell Product #3 generated from healthy donors (D1-D4), when these cells were in contact with cells with different levels of relevant peptide presented on the cell surface, e.g., high-target cell line that has about 1,000 copies/cell of the relevant peptide presented on the cell surface, low-target cell line that has about 50 copies/cell of the relevant peptide presented on the cell surface, and none-target cell line that does not have the relevant peptide presented on the cell surface, in peptide presentation level-dependent manner, i.e., high-target>low-target>none-target.

Figure 60:
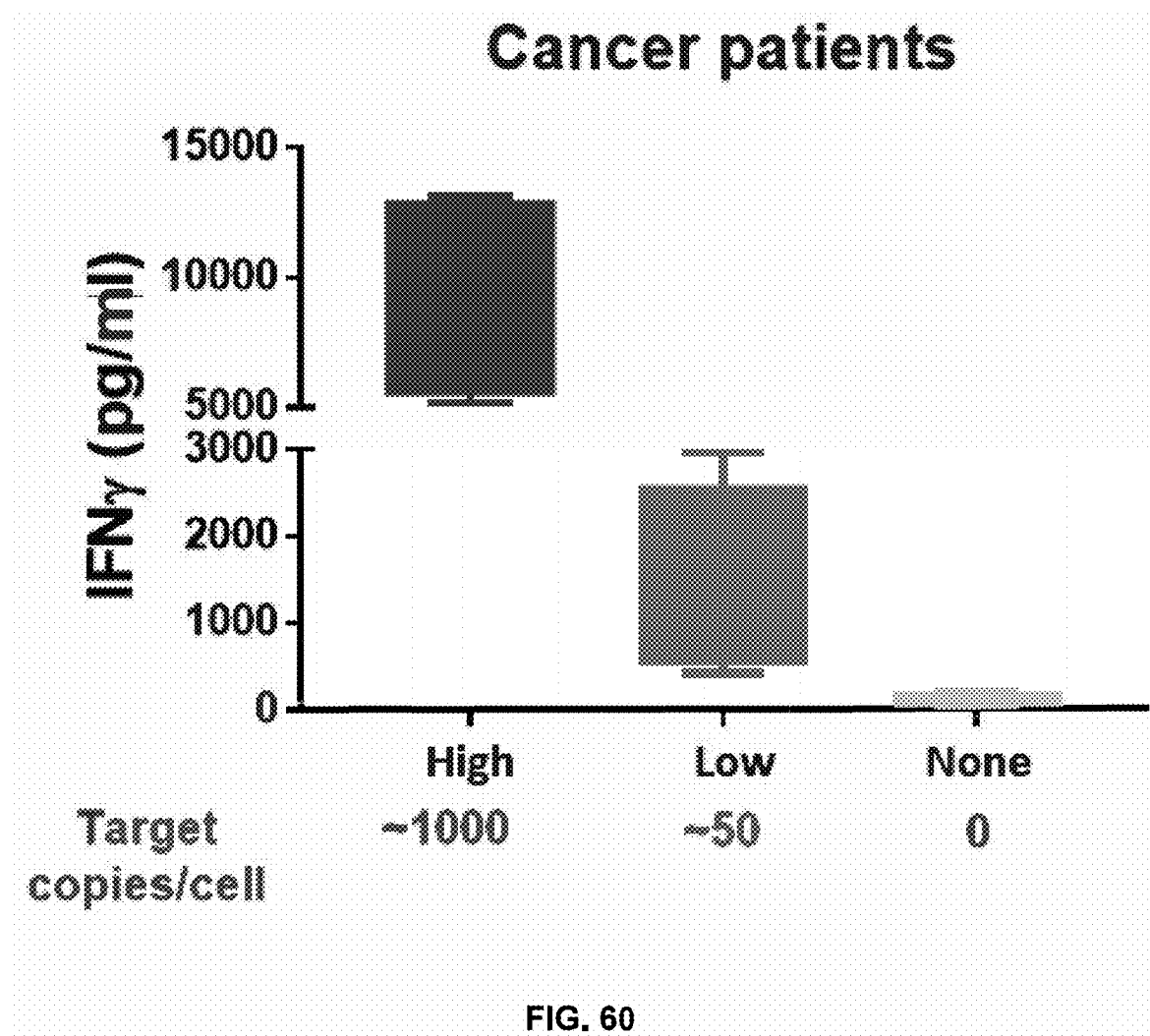
FIG. 60 shows IFN-γ release from T cell products obtained from cancer patients in accordance with an embodiment of the present disclosure.

FIG. 60 shows, similarly, average IFN-γ release from T Cell Product #3 generated from cancer patients (PT1-PT4), when these cells were in contact with high-target cell line, low-target cell line, and none-target cell line, in peptide presentation level-dependent manner, e.g., high-target>low-target>none-target.

Figure 61:
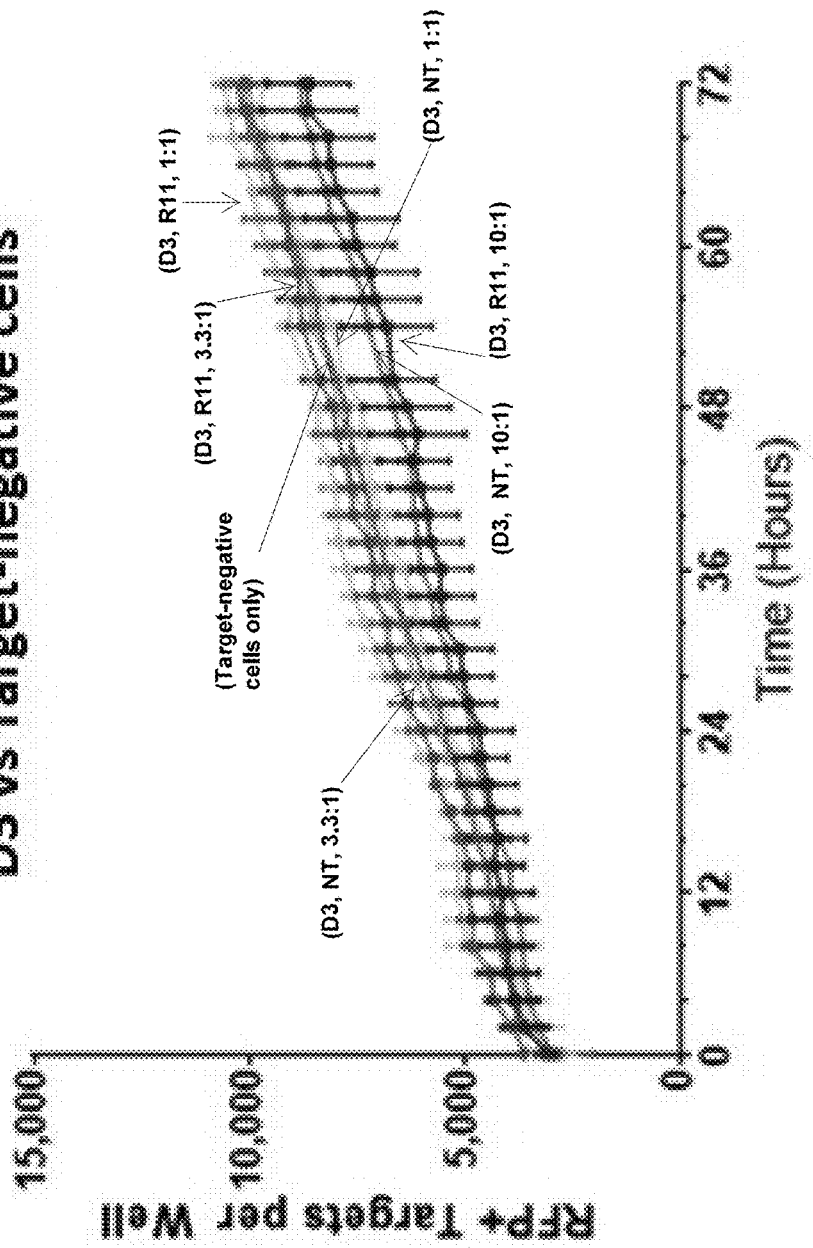
FIG. 61 shows cell killing activity of T cell products obtained from healthy donors in accordance with an embodiment of the present disclosure.
Figure 61:
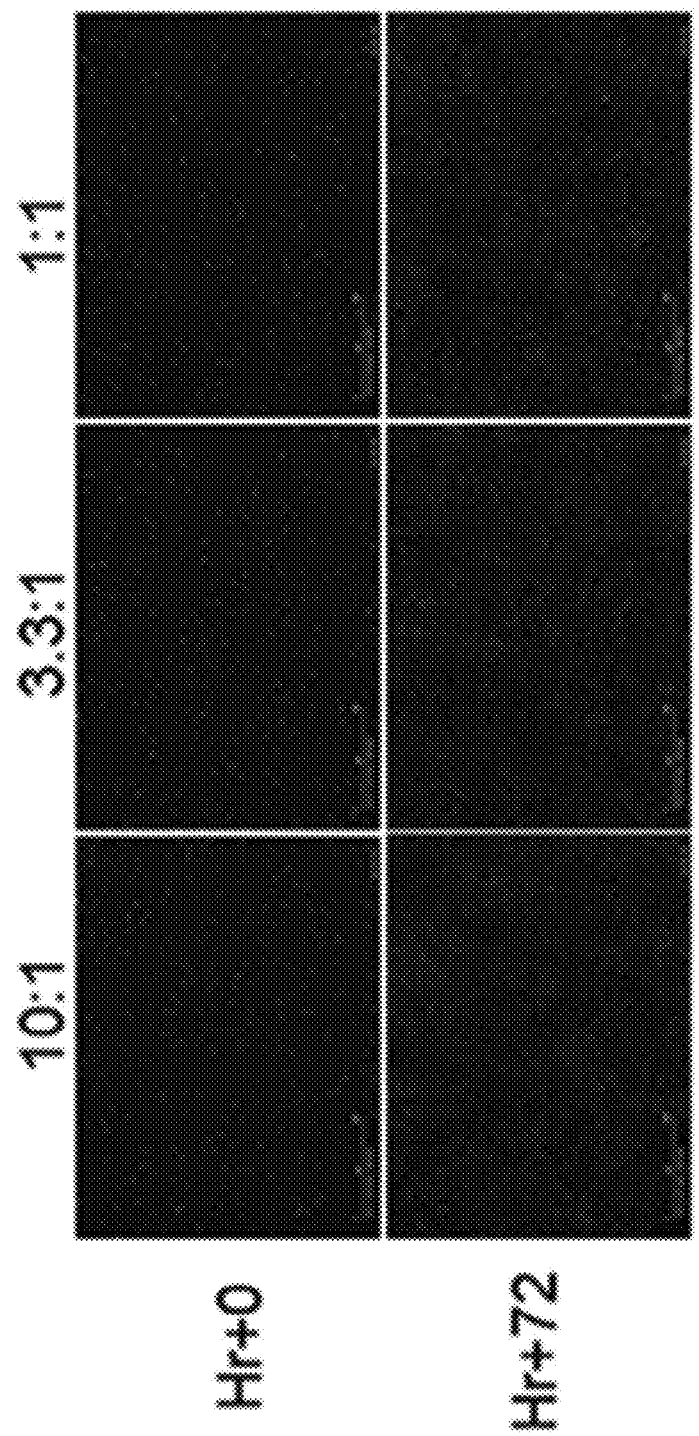

FIG. 61 shows lack of killing activity of T Cell Product #3 generated from healthy donor, e.g., D3, in contact with target-negative cell line, in which the relevant peptide is not presented on the cell surface. Briefly, T cells generated from D3 transduced with R11KEA TCR (R11) or without transduction (NT) were co-cultured with target-negative cell line at E:T ratios of 10:1, 3.3:1, and 1:1. Cell killing activity was measured by using IncuCyte Killing Assay. These results show no significant difference in cell killing against target-negative cell line between T cells with (R11) and without (NT) TCR transduction.

Figure 62:
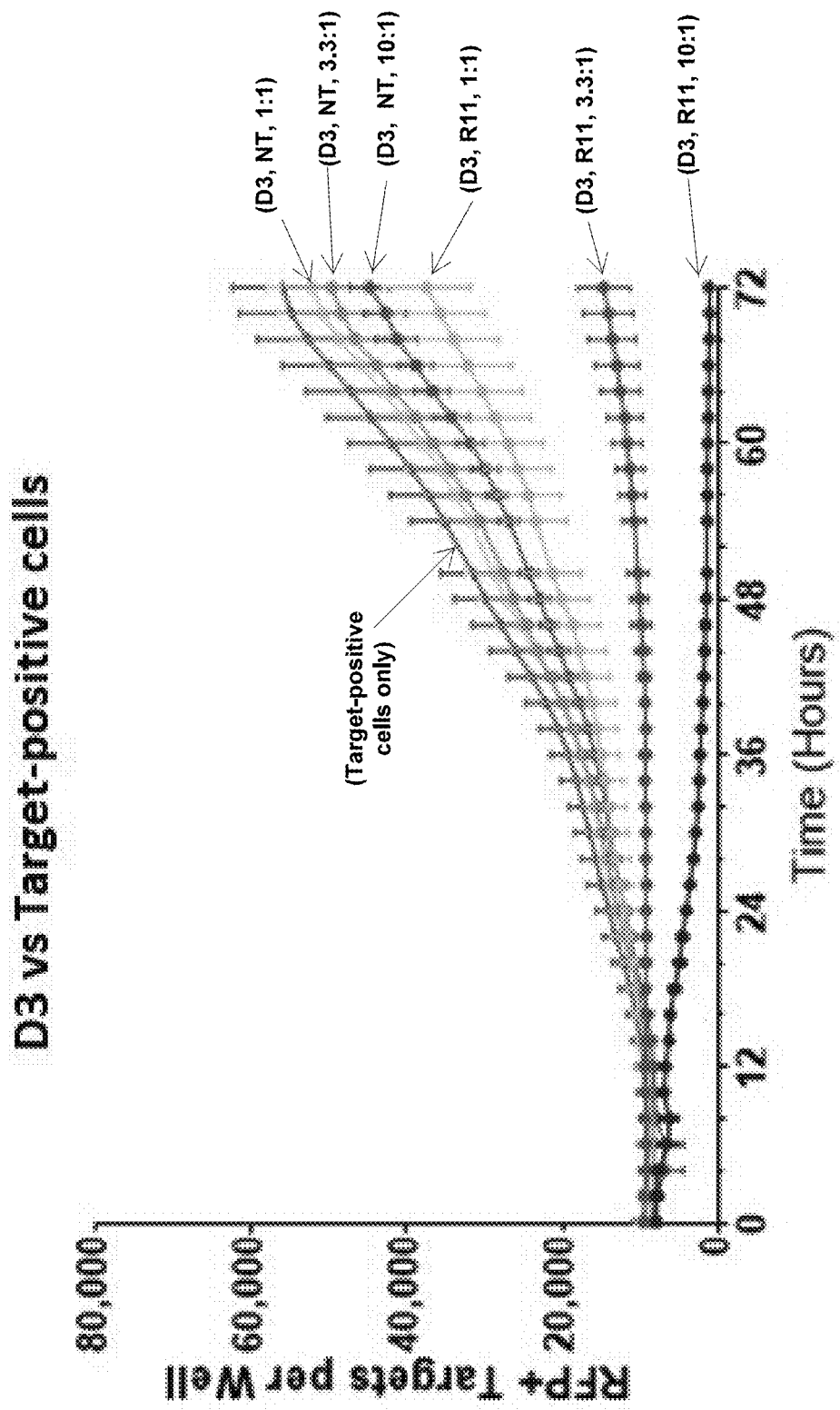
FIG. 62 shows cell killing activity of T cell products obtained from healthy donors in accordance with an embodiment of the present disclosure.
Figure 62:
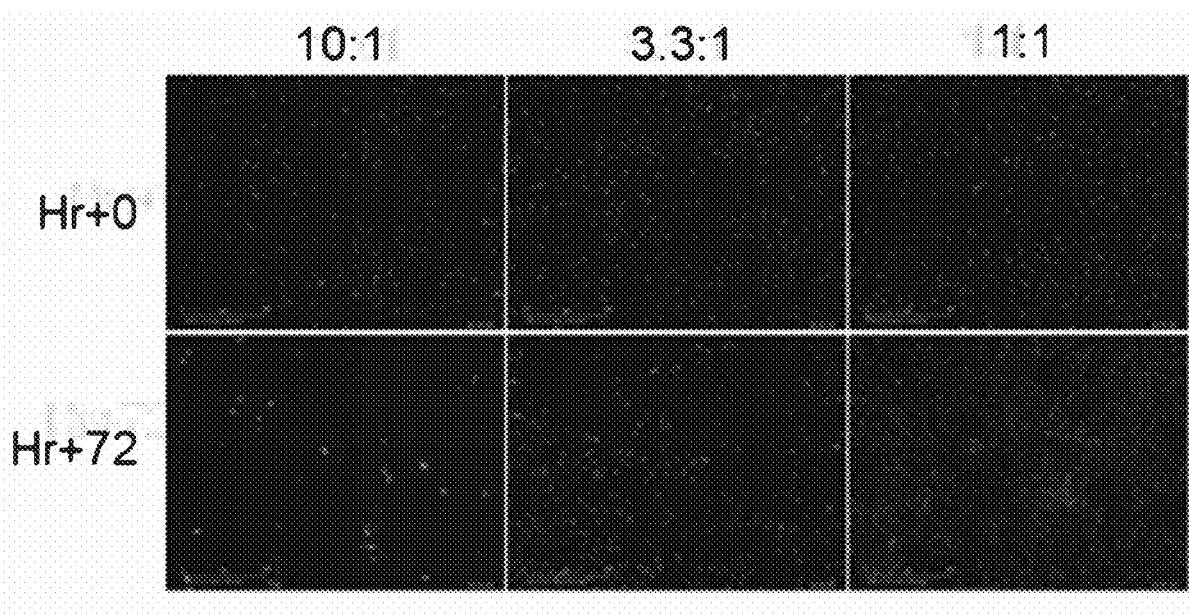

In contrast, FIG. 62 shows TCR-specific killing activity of T Cell Product #3 generated from healthy donor, e.g., D3, in contact with target-positive cell line, in which the relevant peptide is presented on the cell surface. That is, R11KEA TCR-expressing T cells kill the target-positive cells in E:T ratio-dependent manner, e.g., 10:1>3.3:1>1:1. In contrast, there is no significant difference in cell killing between T cells without transduction (NT) at different E:T ratios.

Figure 63A:
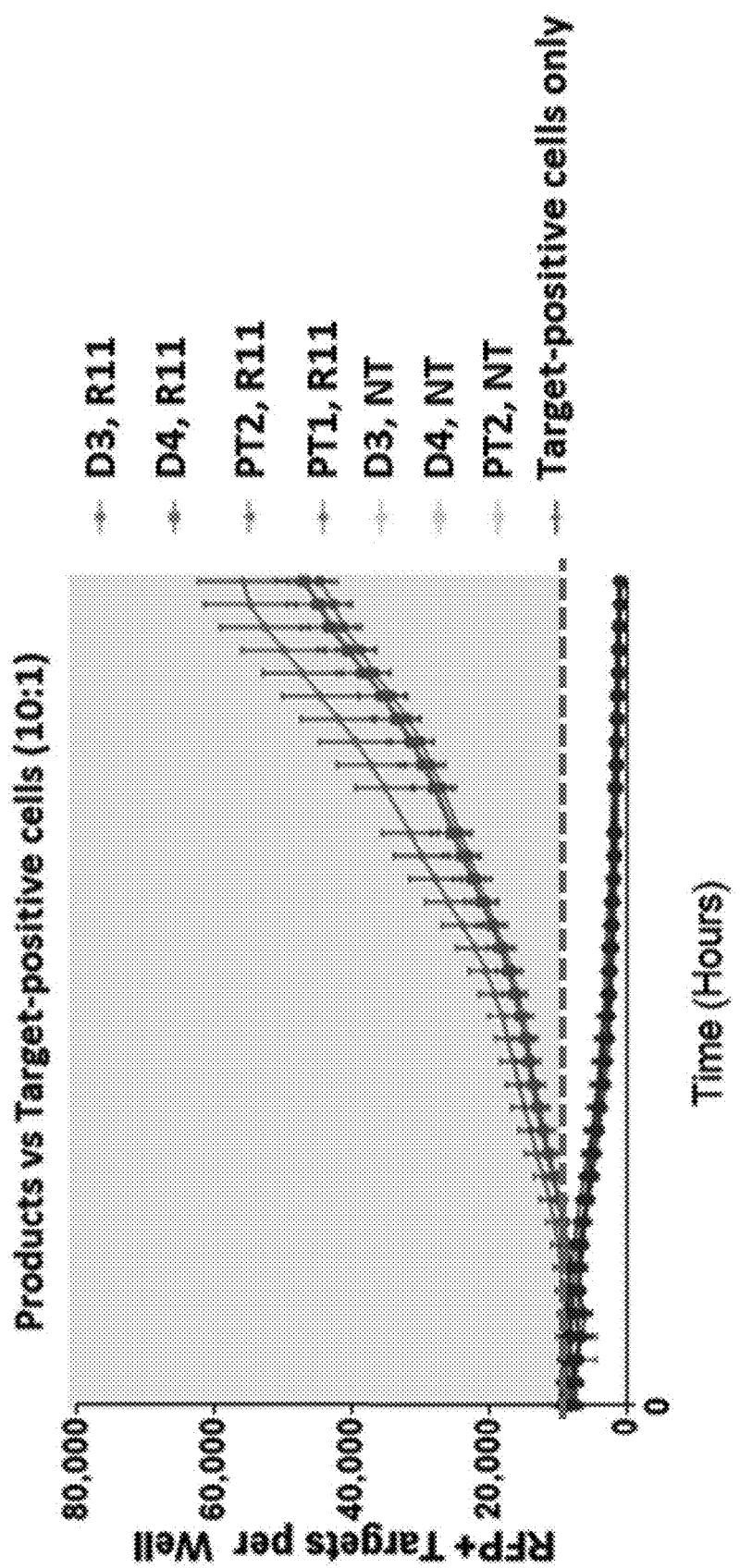
FIG. 63A shows a comparison in cell killing between T cell products obtained from healthy donors and cancer patients in accordance with an embodiment of the present disclosure.
Figure 63B:
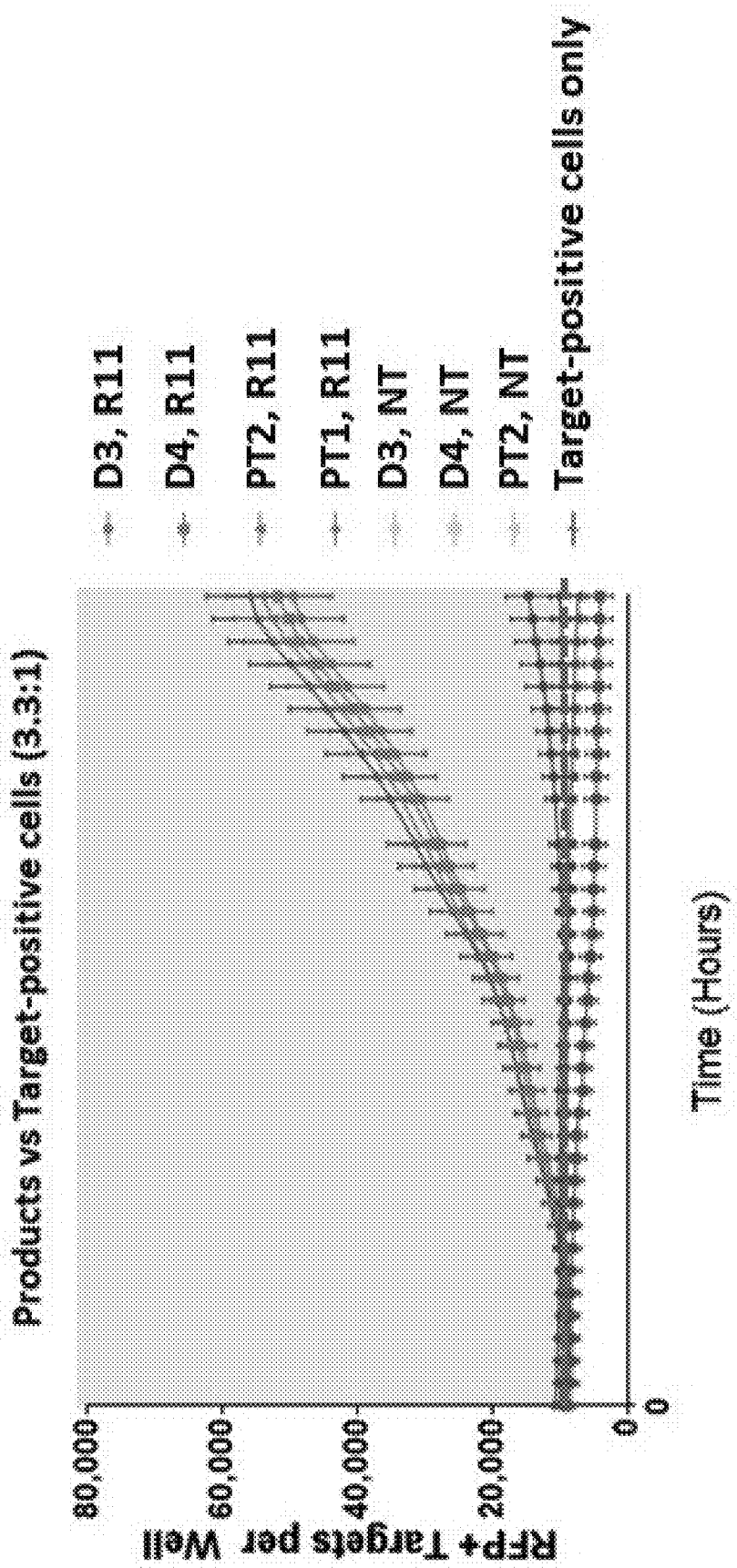
FIG. 63B shows a comparison in cell killing between T cell products obtained from healthy donors and cancer patients in accordance with an embodiment of the present disclosure.
Figure 63C:
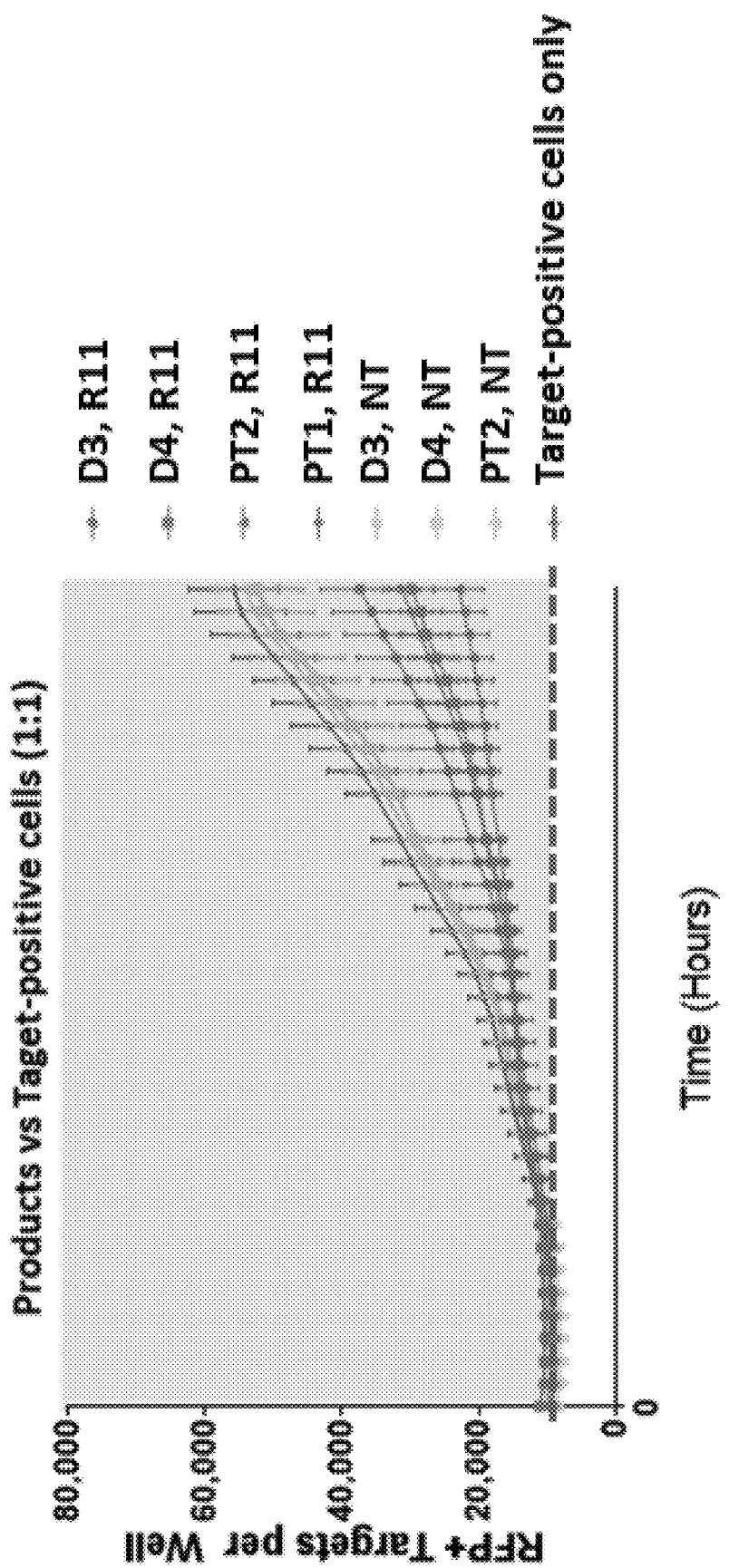
FIG. 63C shows a comparison in cell killing between T cell products obtained from healthy donors and cancer patients in accordance with an embodiment of the present disclosure.

FIGS. 63A-63C show TCR-specific killing activity of T Cell Product #3 transduced with R11KEA TCR (R11) generated from healthy donors, e.g., D3 and D4, and from cancer patients, e.g., PT1 and PT2, in contact with target-positive cell line, in which the relevant peptide is presented on the cell surface. R11KEA TCR (R11)-expressing T cells generated from D3, D4, PT1, and PT2 kill the target-positive cells in E:T ratio-dependent manner, e.g., 10:1 (FIG. 63A) >3.3:1 (FIG. 63B)>1:1 (FIG. 63C). In contrast, there is no significant difference in cell killing between T cells without R11KEA TCR transduction (NT) at different E:T ratios.

In sum, these results show T Cell Product #3 process may generate T cell products expressing TCR transgene with target specificity. This process works as well with starting material obtained from cancer patients as from healthy donors. T Cell Product #3 process takes shorter time than that for preparing T Cell Products #1 and #2 and yet generates products with large numbers of naïve and Tcm cells. T Cell Product #3 may be polyfunctional and secrete IFN-γ in response to target-positive tumor cell lines. T Cell Product #3 may also exhibit good effector function in cell line killing assays.

Advantages of the present disclosure may include autologous T cell manufacturing processes that may shorten resting time to, e.g., 4-6 hours, activation time to, e.g., 16-20 hours, transduction time to, e.g., 24 hours, and expansion phase to, e.g., 5-7 days, for clinical manufacturing of engineered TCR T cell products. Critical parameters influencing each step may be systematically evaluated and may be optimized to yield over 10 billion young, tumor-reactive T cells with a strong ability to recognize and efficiently kill target expressing tumor cells. In addition to improving the quality of T cell products, these optimizations may also result in reducing the cost of manufacturing by 30%. Further, autologous T cell manufacturing processes of the present disclosure may be scaled up using flask bound and/or bag bound anti-CD3 and anti-CD28 antibodies for activating T cells to yield comparable levels of activation, transducibility, and expansion and these scale-up processes may be faster than processes using plate bound antibodies.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A method of transducing a T cell, comprising
   thawing frozen peripheral blood mononuclear cells (PBMC),
   resting the thawed PBMC for about 4 to about 6 hours,
   activating the T cell in the rested PBMC with an anti-CD3 antibody and an anti-CD28 antibody,
   transducing the activated T cell with a viral vector,
   expanding the transduced T cell, and
   obtaining the expanded T cell.

2. The method of claim 1, wherein the activating step comprises immobilizing the T cell in the rested PBMC with the anti-CD3 antibody and the anti-CD28 antibody on a solid phase support.

3. The method of claim 1, wherein the resting is carried out in the presence of at least one cytokine.

4. The method of claim 3, wherein the at least one cytokine comprises interleukin 7 (IL-7) and/or interleukin 15 (IL-15).

5. The method of claim 1, wherein the activation is carried out within a period of time from about 1 hour to about 120 hours.

6. The method of claim 2, wherein the solid phase support comprises a surface of a bead, a plate, a flask, or a bag.

7. The method of claim 1, wherein the transducing is carried out within a period of time from about 1 hour to about 72 hours.

8. The method of claim 1, wherein the viral vector comprises a retroviral vector expressing a T cell receptor (TCR).

9. The method of claim 1, wherein the viral vector comprises a lentiviral vector expressing a TCR.

10. The method of claim 1, wherein the transducing is carried out in the presence of at least one cytokine.

11. The method of claim 10, wherein the at least one cytokine comprises IL-7 and/or IL-15.

12. The method of claim 1, wherein the expanding is carried out in the presence of at least one cytokine selected from the group consisting of IL-2, IL-7, IL-12, IL-15, and IL-21.

13. The method of claim 12, wherein the at least one cytokine comprises IL-2.

14. The method of claim 12, wherein the at least one cytokine comprises IL-7 and IL-15.

15. The method of claim 1, wherein the obtained T cell comprises a $CD3^+CD8^+$T cell.

16. The method of claim 1, wherein the thawing, the resting, the activating, the transducing, the expanding, and the obtaining are performed in a closed system.

17. The method of claim 1, wherein number of obtained T cells with a resting time of about 4 hours to about 6 hours is about 1.5-fold to about 2.0-fold greater than that of the obtained T cells prepared under identical conditions with a resting time of about 16 hours to 20 hours.

18. The method of claim 4, wherein the at least one cytokine is IL-7.

19. The method of claim 4, wherein the at least one cytokine is IL-15.

20. The method of claim 4, wherein the at least one cytokine is IL-7 and IL-15.

* * * * *